US008344029B2

(12) United States Patent
Aoki et al.

(10) Patent No.: US 8,344,029 B2
(45) Date of Patent: Jan. 1, 2013

(54) SUBSTITUTED PROPANAMIDE DERIVATIVE AND PHARMACEUTICAL COMPOSITION CONTAINING THE SAME

(75) Inventors: Kazumasa Aoki, Tokyo (JP); Koji Suda, Tokyo (JP); Kentoku Gotanda, Tokyo (JP); Tomio Kimura, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 1038 days.

(21) Appl. No.: 11/996,268

(22) PCT Filed: Jul. 18, 2006

(86) PCT No.: PCT/JP2006/314144

§ 371 (c)(1), (2), (4) Date: Dec. 10, 2008

(87) PCT Pub. No.: WO2007/010885

PCT Pub. Date: Jan. 25, 2007

(65) Prior Publication Data

US 2009/0292024 A1 Nov. 26, 2009

(30) Foreign Application Priority Data

Jul. 19, 2005 (JP) ................................ 2005-208036

(51) Int. Cl.

| | |
|---|---|
| ***A01N 37/18*** | (2006.01) |
| ***A01N 33/02*** | (2006.01) |
| ***A01N 33/18*** | (2006.01) |
| ***A01N 33/24*** | (2006.01) |
| ***A61K 31/165*** | (2006.01) |
| ***A61K 31/135*** | (2006.01) |
| ***A61K 31/04*** | (2006.01) |

(52) U.S. Cl. ......................... 514/617; 514/646; 514/741

(58) Field of Classification Search ........................ None
See application file for complete search history.

(56) References Cited

U.S. PATENT DOCUMENTS

| | | | | |
|---|---|---|---|---|
| 3,996,288 | A | 12/1976 | Yukata et al. | |
| 4,004,008 | A | 1/1977 | Makovec et al. | |
| 4,621,092 | A | 11/1986 | Natarajan et al. | |
| 2006/0094708 | A1 * | 5/2006 | Qian et al. | 514/215 |

FOREIGN PATENT DOCUMENTS

| | | | |
|---|---|---|---|
| DE | 25 03 992 | | 8/1975 |
| EP | 0 217 286 | A1 | 4/1987 |
| WO | WO 98/25949 | | 6/1998 |
| WO | WO 98/34115 | A1 | 8/1998 |
| WO | WO 99/24460 | | 5/1999 |
| WO | WO 00/06535 | | 2/2000 |
| WO | WO 00/39077 | A2 | 7/2000 |
| WO | WO 03/066576 | | 8/2003 |
| WO | WO 03/075836 | | 9/2003 |
| WO | WO 2004/026851 | | 4/2004 |
| WO | WO 2004/052921 | | 6/2004 |
| WO | WO 2004/074238 | | 9/2004 |
| WO | WO 2004/084842 | | 10/2004 |
| WO | WO 2004/110983 | | 12/2004 |
| WO | WO 2005/061440 | A1 | 7/2005 |
| WO | WO 2005/097103 | | 10/2005 |
| WO | WO 2005/107762 | | 11/2005 |

OTHER PUBLICATIONS

Iqbal et al. "Osteroporosis: A Review", Missouri Medicine, vol. 99, No. 1: pp. 19-24, Jan. 2002.
International Search Report for PCT/JP2006/314144 dated Sep. 21, 2006.
International Preliminary Report on Patentability for PCT/JP2006/314144 dated Jan. 22, 2008.
Viewig, H., et al., "Synthesis of N.alpha.-(4-methylbenzoyl)-4-amidinophenylalaninamides and ester," Pharmazie, 38(3), 1983, pp. 170-171.
Katunuma, N., et al., "Structure-Based Development of Pyridoxal Propionate Derivatives as Specific Inhibitors of Cathepsin K in Vitro and in Vivo," Biochemical and Biophysical Research Communications, vol. 267, No. 3, Jan. 1, 2000, pp. 850-854.
Chemical Abstracts Service, Columbus, Ohio, US, Nov. 16, 1984, XP002672779, retrieved from STN accession No. 57227-85-7.
Chemical Abstracts Service, Columbus, Ohio, US, Nov. 16, 1984, XP002672780, retrieved from STN accession No. 57227-83-5.

* cited by examiner

*Primary Examiner* — James D Anderson
*Assistant Examiner* — Stephanie Springer
(74) *Attorney, Agent, or Firm* — Dorsey & Whitney LLP

(57) ABSTRACT

It is an object of the present invention to provide a substituted propanamide derivative or a pharmacologically acceptable salt thereof that is useful as a prophylactic or therapeutic agent for a bone metabolic disease. The present invention relates to a pharmaceutical composition comprising a compound having General Formula (I) or a pharmacologically acceptable salt thereof as an active ingredient:

(I)

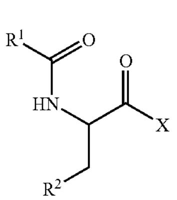

[wherein, $R^1$ represents a $C_6$-$C_{10}$ aryl group that may be substituted by a group selected from Substituent Group α, for example; $R^2$ represents a $C_6$-$C_{10}$ aryl group that may be substituted by a group selected from Substituent Group α, for example; and X represents a hydroxyl group or a $C_1$-$C_6$ alkoxy group, for example].

15 Claims, No Drawings

SUBSTITUTED PROPANAMIDE DERIVATIVE AND PHARMACEUTICAL COMPOSITION CONTAINING THE SAME

RELATED APPLICATION DATA

This application is a national phase application filed pursuant to 35 CFR §371 of International Patent Application Serial No. PCT/JP2006/314144, filed Jul. 18, 2006, entitled SUBSTITUTED PROPANAMIDE DERIVATIVE AND PHARMACEUTICAL COMPOSITION CONTAINING THE SAME, which application claims priority to Japanese Patent Application Serial No. 2005-208036, filed Jul. 19, 2005, entitled SUBSTITUTED PROPANAMIDE DERIVATIVE AND PHARMACEUTICAL COMPOSITION CONTAINING THE SAME, which applications are incorporated herein by reference in their entireties.

TECHNICAL FIELD

The present invention relates to a substituted propanamide derivative or a pharmacologically acceptable salt thereof that is useful for prophylaxis or treatment of a bone metabolic disease such as osteoporosis, hypercalcemia, bone metastasis of cancer, periodontal disease, bone Paget's disease, or osteoarthrosis.

BACKGROUND ART

In general, in normal bone metabolism, bone resorption by osteoclasts is balanced with bone formation by osteoblasts to maintain homeostasis. It is thought that an imbalance between the bone resorption and the bone formation causes bone metabolic diseases. Bones retain about 99% of the total calcium in a living body and play an important role in maintaining a constant blood calcium concentration by bone formation and bone resorption. If osteoclasts, which are mainly responsible for bone resorption, are abnormally formed or activated, bone resorption is accelerated to increase blood calcium concentration, and thereby bone metabolic diseases, such as hypercalcemia, are caused.

Conventionally, for bone metabolic diseases, hormone replacement therapy using estrogen or the like has been conducted or a therapeutic agent such as a bisphosphonate or a calcitonin that suppresses osteoclast activity has been administered (refer to Non-Patent Document 1). However, none of these existing agents can be satisfactory for essentially treating hypercalcemia or bone metabolic diseases, and therefore development of agents having high therapeutic efficacy is desired.

The following substituted propanamide derivatives are known hitherto.

(1) Patent Document 1 discloses phenylalanine derivatives shown in Table 1 having an analgesic effect and a vasodilating effect and are expected to have therapeutic effects on, for example, cerebral palsy syndromes. However, the document does not mention a bone resorption-suppressing activity at all (refer to Patent Document 1).

TABLE 1

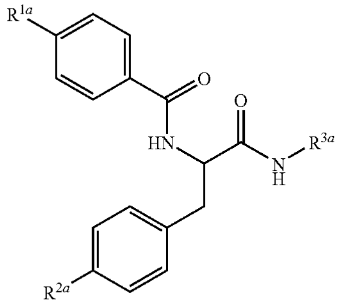

(a)

| No. | $R^{1a}$ | $R^{2a}$ | $R^{3a}$ |
|---|---|---|---|
| 1 | H | 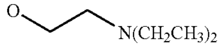 | $(CH_2)_3CH_3$ |
| 2 | H | H | $(CH_2)_2OH$ |
| 3 | H | OH | $(CH_2)_2CH_3$ |
| 4 | H | OH | $(CH_2)_3CH_3$ |
| 5 | H | OH | $(CH_2)_5CH_3$ |
| 6 | H | $OCOC_6H_5$ | $(CH_2)_2CH_3$ |
| 7 | H | $OCOC_6H_5$ | $(CH_2)_3CH_3$ |
| 8 | H | $OCOC_6H_5$ | $(CH_2)_5CH_3$ |
| 9 | $CH_3$ | 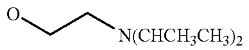 | $(CH_2)_3CH_3$ |
| 10 | $CH_3$ | OH | $(CH_2)_3CH_3$ |
| 11 | $CH_3$ | OH | $(CH_2)_5CH_3$ |
| 12 | $CH_3$ | $OCOC_6H_5$ | $(CH_2)_3CH_3$ |
| 13 | $CH_3$ | $OCOC_6H_5$ | $(CH_2)_5CH_3$ |
| 14 | Cl | 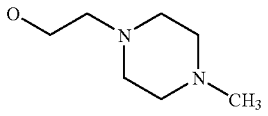 | $(CH_2)_3CH_3$ |
| 15 | Cl | 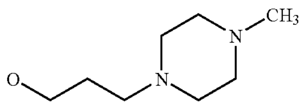 | $(CH_2)_3CH_3$ |
| 16 | Cl | 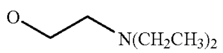 | $(CH_2)_3CH_3$ |
| 17 | Cl | OH | $(CH_2)_3CH_3$ |
| 18 | Cl | $OCO(p\text{-}Cl—C_6H_5)$ | $(CH_2)_3CH_3$ |

(2) Patent Document 2 discloses phenylalanine derivatives shown in Table 2 having a cathepsin B inhibitory activity, but does not mention a bone resorption-suppressing activity at all (refer to Patent Document 2).

TABLE 2

(b)

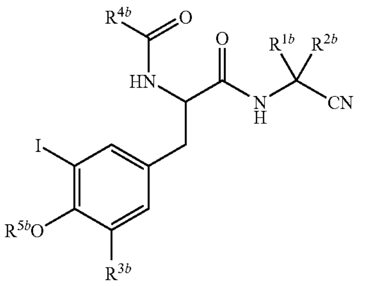

| No. | $R^{1b}$ | $R^{2b}$ | $R^{1b} + R^{2b}$ | $R^{3b}$ | $R^{4b}$ | $R^{5b}$ |
|---|---|---|---|---|---|---|
| 1 | H | H | | I | 4-(2-pyridin-4-yl-amino-thiazol-4-yl)phenyl | H |
| 2 | H | H | | I | (4-morpholin-4-yl)phenyl | H |
| 3 | H | H | | I | morpholin-4-yl | H |
| 4 | | | cyclopropyl | I | (4-morpholin-4-yl)phenyl | H |
| 5 | H | H | | I | (4-morpholin-4-yl)phenyl | $CH_3$ |
| 6 | H | H | | I | 4-[2-(4-methylpiperazin-1-yl)-thiazol-4-yl]phenyl | H |
| 7 | H | H | | $CH_3$ | (4-morpholin-4-yl)phenyl | H |
| 8 | H | H | | $CH_2CH_3$ | (4-morpholin-4-yl)phenyl | H |

(3) Patent Document 3 discloses phenylalanine derivatives shown in Table 3 having a cathepsin S inhibitory activity, but does not mention a bone resorption-suppressing activity at all (refer to Patent Document 3).

TABLE 3

(c)

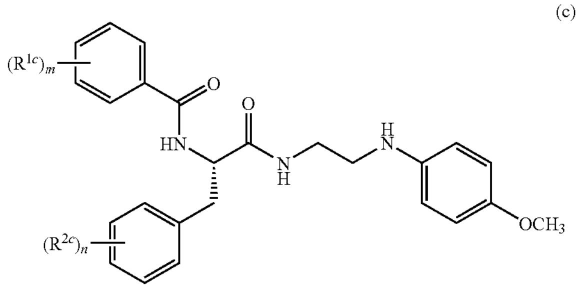

| No. | $(R^{1c})_m$ | $(R^{2c})_n$ |
|---|---|---|
| 1 | 3,4-dichloro | 3-methyl |
| 2 | H | 3-bromo |
| 3 | 2-tolyloxy | 3-methyl |
| 4 | 3-(2-methylthiazol-4-yl) | H |
| 5 | 3-cyano | H |
| 6 | 4-methyl | 3-methyl |
| 7 | 3-methyl | 4-(4-dimethylaminophenyl) |
| 8 | 2,4,5-trimethyl | H |
| 9 | 3-bromo-4-methyl | H |
| 10 | 4-methoxy-3,5-dimethyl | H |
| 11 | 4-benzoyloxy-3,5-dimethyl | H |
| 12 | 3,5-dichloro | 3-methyl |
| 13 | 2-chloro-3-methyl | H |
| 14 | 2,3-dimethyl | 3-methyl |
| 15 | 3,5-dimethyl | 3-methyl |
| 16 | 3-chloro | 3-methyl |
| 17 | 3-methyl | 4-methoxy |
| 18 | 3-methyl | 4-phenoxy |
| 19 | 3-methyl | 4-(4-chlorophenoxy) |
| 20 | 3-methyl | 4-(2-methoxypyridin-5-yl) |
| 21 | 3-methyl | 4-(2,4-dimethoxypyridin-5-yl) |
| 22 | 3-methyl | 4-(3-acetylphenyl) |
| 23 | 3-methyl | 4-(4-hydroxyphenyl) |
| 24 | 3-methyl | 4-(2-acetylphenyl) |

TABLE 3-continued (c)

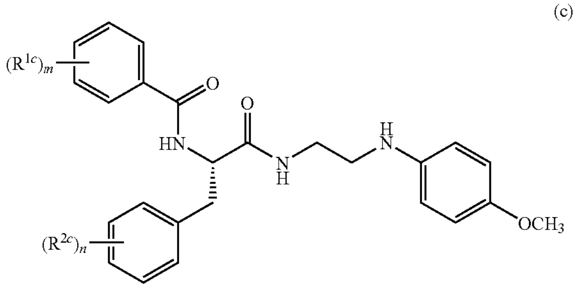

| No. | $(R^{1c})_m$ | $(R^{2c})_n$ |
|---|---|---|
| 25 | 3-methyl | 4-(2,5-dichlorophenyl) |
| 26 | 3-methyl | 4-(2,4-dimethoxyphenyl) |
| 27 | 3-methyl | 4-(3-hydroxymethylphenyl) |
| 28 | 3-methyl | 4-(5-fluoro-2-methylphenyl) |
| 29 | 3-methyl | 4-(4-hydroxymethylphenyl) |
| 30 | 3-methyl | 4-(3,4-dimethoxyphenyl) |
| 31 | 3-methyl | 4-(3-aminophenyl) |
| 32 | 3-methyl | 4-(2,3-dimethoxyphenyl) |
| 33 | 3-methyl | 4-(4-chlorophenyl) |
| 34 | 3-methyl | 4-(pyridin-4-yl) |
| 35 | 3-methyl | 4-(4-cyanophenyl) |
| 36 | 3-methyl | 4-(thiophen-3-yl) |
| 37 | 3-methyl | 4-(pyridin-3-yl) |
| 38 | 3-methyl | 4-(3-nitrophenyl) |
| 39 | 3-methyl | 4-(2-nitrophenyl) |
| 40 | 3-methyl | 4-phenyl |
| 41 | 3-methyl | 4-(3-methylphenoxy) |
| 42 | 3-methyl | 4-t-butyl |
| 43 | 3-methyl | 4-trifluoromethyl |
| 44 | 3-methyl | 3-trifluoromethyl |
| 45 | 3-methyl | 4-benzyloxy |
| 46 | 3-methyl | 4-fluoro |
| 47 | 3-methyl | 4-nitro |
| 48 | 3-methyl | 4-chloro |
| 49 | 3-methyl | 4-bromo |
| 50 | 3-methyl | 4-cyano |
| 51 | 3-methyl | 2-trifluoromethyl |
| 52 | 3-methyl | 3-methyl |
| 53 | 3-methyl | 3,4-difluoro |
| 54 | 3-methyl | 3-fluoro |
| 55 | 3-methyl | 4-methyl |

TABLE 3-continued (c)

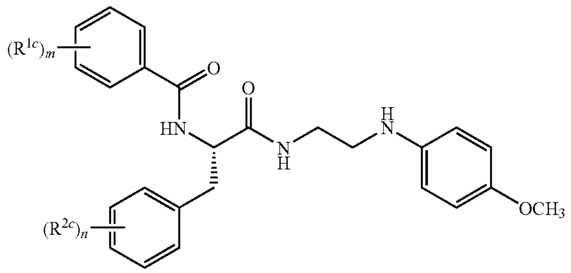

| No. | $(R^{1c})_m$ | $(R^{2c})_n$ |
|---|---|---|
| 56 | 3-methyl | 4-acetamido |
| 57 | 3-methyl | 3,4-dichloro |
| 58 | 3-methyl | 3,5-difluoro |
| 59 | 3-methyl | 3,5-dichloro |
| 60 | 3-methyl | 4-hydroxy |
| 61 | 3-methyl | 4-t-butoxy |
| 62 | 3-methyl | 4-iodo |
| 63 | H | 3-methoxy |

[Patent Document 1] U.S. Pat. No. 4,004,008

[Patent Document 2] International Publication No. WO 2004/026851

[Patent Document 3] International Publication No. WO 2004/084842

[Non-Patent Document 1] Mohammad M. Iqbal, et al., Missouri Medicine, 2002, vol. 99, p. 19.

DISCLOSURE OF THE INVENTION

An object of the present invention is to provide a substituted propanamide derivative or a pharmacologically acceptable salt thereof that is useful for prophylaxis or treatment of a bone metabolic disease such as osteoporosis, hypercalcemia, bone metastasis of cancer, periodontal disease, bone Paget's disease, or osteoarthrosis.

The present inventors have conducted intensive studies on compounds having an excellent blood calcium concentration-decreasing activity and a bone mass decrease-suppressing activity, and as a result, have found the fact that a substituted propanamide derivative having General Formula (I) (hereinafter referred to as a compound of the present invention) has low toxicity, shows favorable pharmacokinetics, has an excellent bone resorption-suppressing activity and a blood calcium concentration-decreasing activity and a bone mass decrease-suppressing activity associated therewith, and is useful for prophylaxis or treatment for a bone metabolic disease such as osteoporosis, hypercalcemia, bone metastasis of cancer, periodontal disease, bone Paget's disease, or osteoarthrosis. Thus, the present invention has been completed. The present invention will now be described below.

The present invention provides (1) a pharmaceutical composition comprising a compound having General Formula (I) or a pharmacologically acceptable salt thereof as an active ingredient for use as a bone resorption suppressant:

(I)

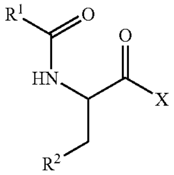

[wherein, $R^1$ represents a $C_6$-$C_{10}$ aryl group that may be substituted by a group selected from Substituent Group α, or a 5- to 10-membered heteroaryl group that may be substituted by a group selected from Substituent Group α;

$R^2$ represents a $C_6$-$C_{10}$ aryl group that may be substituted by a group selected from Substituent Group α, 5- to 10-membered heteroaryl groups that may be substituted by a group selected from Substituent Group α, or 3- to 6-membered heterocyclyl groups that may be substituted by a group selected from Substituent Group α; and X represents a hydroxyl group, a $C_1$-$C_6$ alkoxy group, a $C_1$-$C_6$ alkoxy group that is substituted by a hydroxyl group, or a group having the formula $N(R^3)R^4$ (wherein, $R^3$ and $R^4$ are the same or different and each independently represents a hydrogen atom, a $C_1$-$C_6$ alkyl group that may be substituted by a group selected from Substituent Group β, a $C_1$-$C_6$ haloalkyl group, a $C_1$-$C_6$ hydroxyalkyl group that may be protected by a hydroxyl protecting group, a $C_1$-$C_6$ alkoxy group that may be substituted by a hydroxyl group, a $C_3$-$C_6$ cycloalkyl group that may be substituted by a group selected from Substituent Group α, a $C_2$-$C_6$ alkenyl group that may be substituted by a group selected from Substituent Group α, a $C_6$-$C_{10}$ aryl group that may be substituted by a group selected from Substituent Group α, or a 5- to 10-membered heteroaryl group that may be substituted by a group selected from Substituent Group α; or $R^3$ and $R^4$, together with the nitrogen atom to which $R^3$ and $R^4$ are bound, form a 3- to 6-membered heterocyclyl group that may be substituted by a group selected from Substituent Group β), wherein, Substituent Group α is a group consisting of hydroxyl groups, nitro groups, cyano groups, amino groups, $C_1$-$C_6$ alkylamino groups, $C_1$-$C_6$ dialkylamino groups, $C_3$-$C_6$ cycloalkylamino groups, acetamido groups, halogen atoms, $C_1$-$C_6$ alkyl groups that may be substituted by a group selected from Substituent Group β, $C_1$-$C_6$ haloalkyl groups, $C_3$-$C_6$ cycloalkyl groups, 3- to 6-membered heterocyclyl groups, $C_3$-$C_6$ cycloalkenyl groups, $C_6$-$C_{10}$ aryl groups that may be substituted by a group selected from Substituent Group γ, 5- to 10-membered heteroaryl groups that may be substituted by a group selected from Substituent Group γ, $C_1$-$C_6$ alkoxy groups that may be substituted by a group selected from Substituent Group β, $C_1$-$C_6$ haloalkoxy groups, $C_1$-$C_6$ alkoxy-$C_1$-$C_6$ alkoxy groups that may be substituted by a group selected from Substituent Group β, $C_2$-$C_6$ alkenyloxy groups that may be substituted by a group selected from Substituent Group β, $C_2$-$C_6$ alkynyloxy groups that may be substituted by a group selected from Substituent Group β, $C_3$-$C_6$ cycloalkyloxy groups, 3- to 6-membered heterocyclyloxy groups, $C_6$-$C_{10}$ aryloxy groups that may be substituted by a group selected from Substituent Group γ, $C_1$-$C_6$ alkyleneoxy groups, $C_1$-$C_6$ alkylenedioxy groups, $C_1$-$C_6$ alkylthio groups that may be substituted by a group selected from Substituent Group β, $C_1$-$C_6$ haloalkylthio groups, $C_1$-$C_6$ alkylsulfonyl groups that may be substituted by a group selected from Substituent Group β, $C_1$-$C_6$ haloalkylsulfonyl groups, $C_1$-$C_6$ alkylcarbonyl groups that may be substituted by a group selected from Substituent Group β, $C_1$-$C_6$ haloalkylcarbonyl groups, and $C_6$-$C_{10}$ arylcarbonyl groups that may be substituted by a group selected from Substituent Group γ;

Substituent Group β is a group consisting of carboxyl groups, $C_1$-$C_6$ alkoxycarbonyl groups, carbamoyl groups, cyano groups, amino groups, thiol groups, $C_1$-$C_6$ alkylthio groups, $C_2$-$C_6$ acyl groups, acetamido groups, N—$C_6$-$C_{10}$ arylacetamido groups, $C_1$-$C_6$ alkoxycarbonylamido groups, urea groups, $C_3$-$C_6$ cycloalkyl groups that may be substituted by a group selected from Substituent Group γ, $C_3$-$C_6$ cycloalkenyl groups, 3- to 6-membered heterocyclyl groups, $C_2$-$C_6$ alkenyl groups that may be substituted by a group selected from Substituent Group γ, $C_2$-$C_6$ alkynyl groups that may be substituted by a group selected from Substituent Group γ, $C_6$-$C_{10}$ aryl groups that may be substituted by a group selected from Substituent Group γ, 5- to 10-membered heteroaryl groups that may be substituted by a group selected from Substituent Group γ, $C_1$-$C_6$ alkoxy groups, $C_6$-$C_{10}$ aryloxy groups that may be substituted by a group selected from Substituent Group γ, $C_3$-$C_6$ cycloalkyloxy groups, and an oxime group that may be substituted by a group selected from Substituent Group γ; and Substituent Group γ is a group consisting of hydrogen atoms, hydroxyl groups, cyano groups, amino groups, $C_1$-$C_6$ alkylamino groups, $C_1$-$C_6$ dialkylamino groups, $C_2$-$C_6$ cyclic amino groups, halogen atoms, $C_1$-$C_6$ alkyl groups, $C_3$-$C_6$ cycloalkyl groups, $C_1$-$C_6$ haloalkyl groups, $C_1$-$C_6$ alkoxy groups, $C_2$-$C_6$ acyloxy groups, $C_1$-$C_6$ haloalkoxy groups, $C_3$-$C_6$ cycloalkyloxy groups, $C_1$-$C_6$ alkylenedioxy groups, and phenyl groups].

Preferable examples of the aforementioned composition are:

(2) the composition according to the above (1), wherein, $R^1$ is a phenyl group that may be substituted by a group selected from Substituent Group α or a pyridyl group that may be substituted by a group selected from Substituent Group α;

(3) the composition according to the above (1), wherein, $R^1$ is a phenyl group that may be substituted by a group selected from Substituent Group α;

(4) the composition according to the above (1), wherein, $R^1$ is a phenyl group that may be substituted by a group selected from the group consisting of $C_1$-$C_6$ alkoxy groups that may be substituted by a group selected from Substituent Group β, $C_1$-$C_6$ haloalkoxy groups, $C_2$-$C_6$ alkenyloxy groups, and $C_6$-$C_{10}$ aryloxy groups that may be substituted by a group selected from Substituent Group γ;

(5) the composition according to the above (1), wherein, $R^1$ is a 4-(propoxy)phenyl, 4-(isobutyloxy)phenyl, 4-[(cyclopropyl)methoxy]phenyl, 4-[2-(cyclopropyl)ethoxy]phenyl, 4-[3-(cyclopropyl)propoxy]phenyl, 4-[(cyclobutyl)methoxy]phenyl, 4-[(cyclopentyl)methoxy]phenyl, 4-[2-(cyclopentyl)ethoxy]phenyl, 4-[2-(phenyl)ethoxy]phenyl, 4-[2-(4-methoxyphenyl)ethoxy]phenyl, 4-[2-(4-chlorophenyl)ethoxy]phenyl, 4-[(2,2-difluorocyclopropan-1-yl)methoxy]phenyl, 4-(2,2-difluoroethoxy)phenyl, 4-(2,2,2-trifluoroethoxy)phenyl, 4-(3,3,3-trifluoropropoxy)phenyl, 4-(4,4,4-trifluorobutoxy)phenyl, 4-[((E)-buten-2-yl)oxy]phenyl, 4-[4-(trifluoromethyl)phenoxy]phenyl, 4-(4-methoxyphenoxy)phenyl, 4-(4-chlorophenoxy)phenyl, or 4-(4-fluorophenoxy)phenyl group;

(6) the composition according to any one selected from the above (1) to (5), wherein, $R^2$ is a $C_6$-$C_{10}$ aryl group that may be substituted by a group selected from Substituent Group α;

(7) the composition according to any one selected from the above (1) to (5), wherein, $R^2$ is a phenyl group that may be substituted by a group selected from Substituent Group α;

(8) the composition according to any one selected from the above (1) to (5), wherein, $R^2$ is a phenyl group that may be substituted by a group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_1$-$C_6$ haloalkoxy groups, $C_1$-$C_6$ alkylthio groups, $C_1$-$C_6$ haloalkylthio groups, and 5- to 10-membered heteroaryl groups;

(9) the composition according to any one selected from the above (1) to (5), wherein, $R^2$ is a 4-fluorophenyl, 4-chlorophenyl, 4-(ethyl)phenyl, 4-(propyl)phenyl, 4-(isopropyl)phenyl, 4-(trifluoromethyl)phenyl, 4-(cyclopropyl)phenyl, 4-methoxyphenyl, 4-(ethoxy)phenyl, 4-(isopropyloxy)phenyl, 4-(cyclopropyloxy)phenyl, 4-(difluoromethoxy)phenyl, 4-(trifluoromethoxy)phenyl, 4-(2,2-difluoroethoxy)phenyl, 4-(2,2,2-trifluoroethoxy)phenyl, 4-methylthiophenyl, 4-trifluoromethylthiophenyl, or 4-(1-pyrrolyl)phenyl group;

(10) the composition according to any one selected from the above (1) to (5), wherein, $R^2$ is a 4-(ethyl)phenyl, 4-(propyl)phenyl, 4-(trifluoromethyl)phenyl, 4-(cyclopropyl)phenyl, 4-(ethoxy)phenyl, 4-(isopropyloxy)phenyl, 4-(cyclopropyloxy)phenyl, 4-(difluoromethoxy)phenyl, 4-(trifluoromethoxy)phenyl, 4-(2,2-difluoroethoxy)phenyl, 4-(2,2,2-trifluoroethoxy)phenyl, 4-methylthiophenyl, or 4-(1-pyrrolyl)phenyl group;

(11) the composition according to any one selected from the above (1) to (10), wherein, X is a group having the formula $N(R^3)R^4$ (wherein, $R^3$ represents a $C_1$-$C_6$ haloalkyl group, a $C_1$-$C_6$ alkyl group that may be substituted by groups selected from Substituent Group β3, or a $C_1$-$C_6$ hydroxyalkyl group that may be protected by a hydroxyl protecting group, and $R^4$ represents a hydrogen atom);

(12) the pharmaceutical composition according to the above (11), wherein, $R^3$ is a $C_1$-$C_6$ haloalkyl group, a $C_1$-$C_6$ hydroxyalkyl group that may be protected by a hydroxyl protecting group, a $C_1$-$C_5$ alkyl-methyl group that may be substituted by a group selected from Substituent Group β, a $C_6$-$C_{10}$ aryl-methyl group that may be substituted by a group selected from Substituent Group β, or a $C_3$-$C_6$ cycloalkyl-methyl group that may be substituted by a group selected from Substituent Group β;

(13) the pharmaceutical composition according to the above (11), wherein, $R^3$ is a $C_1$-$C_6$ hydroxyalkyl group that may be protected by a hydroxyl protecting group or a $C_3$-$C_6$ cycloalkyl-$C_1$-$C_6$ alkyl group that may be substituted by a hydroxyl group;

(14) the pharmaceutical composition according to the above (11), wherein, $R^3$ is a $C_2$-$C_4$ hydroxyalkyl group that may be protected by a hydroxyl protecting group or a $C_3$-$C_6$ cycloalkyl-$C_2$-$C_4$ alkyl group that may be substituted by a hydroxyl group;

(15) the pharmaceutical composition according to the above (11), wherein, $R^3$ is a (1-hydroxycyclopropyl)methyl, 2-hydroxyethyl, 3-hydroxypropyl, 2-acetoxyethyl, 2-(morpholin-4-ylacetoxy)ethyl, or 2-(3-carboxypropionyloxy)ethyl group; and

(16) the pharmaceutical composition according to any one selected from the above (1) to (15), wherein, General Formula (I) is General Formula (I-a):

(I-a)

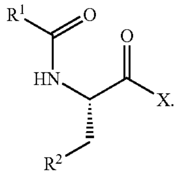

Furthermore, the present invention provides

(17) a compound having General Formula (I') or a pharmacologically acceptable salt thereof:

(I')

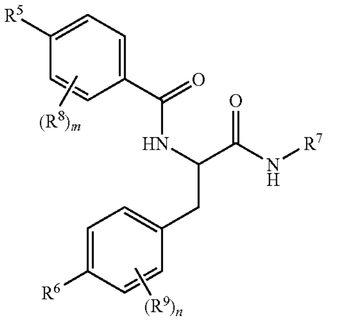

[wherein, $R^5$ and $R^6$ are the same or different and each independently represents a group selected from the group consisting of nitro groups, cyano groups, amino groups, $C_1$-$C_6$ alkylamino groups, $C_1$-$C_6$ dialkylamino groups, $C_3$-$C_6$ cycloalkylamino groups, acetamido groups, halogen atoms, $C_1$-$C_6$ alkyl groups that may be substituted by a group selected from Substituent Group β, $C_1$-$C_6$ haloalkyl groups, $C_3$-$C_6$ cycloalkyl groups, 3- to 6-membered heterocyclyl groups, $C_3$-$C_6$ cycloalkenyl groups, $C_6$-$C_{10}$ aryl groups that may be substituted by a group selected from Substituent Group γ, 5- to 10-membered heteroaryl groups that may be substituted by a group selected from Substituent Group γ, $C_1$-$C_6$ alkoxy groups that may be substituted by a group selected from Substituent Group β, $C_1$-$C_6$ haloalkoxy groups, $C_1$-$C_6$ alkoxy-$C_1$-$C_6$ alkoxy groups that may be substituted by a group selected from Substituent Group β, $C_2$-$C_6$ alkenyloxy groups that may be substituted by a group selected from Substituent Group β, $C_2$-$C_6$ alkynyloxy groups that may be substituted by a group selected from Substituent Group β, $C_3$-$C_6$ cycloalkyloxy groups, 3- to 6-membered heterocyclyloxy groups, $C_6$-$C_{10}$ aryloxy groups that may be substituted by a group selected from Substituent Group γ, $C_1$-$C_6$ alkyleneoxy groups, $C_1$-$C_6$ alkylenedioxy groups, $C_1$-$C_6$ alkylthio groups that may be substituted by groups selected from Substituent Group β, $C_1$-$C_6$ haloalkylthio groups, $C_1$-$C_6$ alkylsulfonyl groups that may be substituted by a group selected from Substituent Group β, $C_1$-$C_6$ haloalkylsulfonyl groups, $C_1$-$C_6$ alkylcarbonyl groups that may be substituted by a group selected from Substituent Group β, $C_1$-$C_6$ haloalkylcarbonyl groups, and $C_6$-$C_{10}$ arylcarbonyl groups that may be substituted by a group selected from Substituent Group γ;

$R^7$ represents a hydrogen atom, a $C_1$-$C_6$ alkyl group, a $C_1$-$C_6$ alkoxy-$C_1$-$C_6$ alkyl group, a $C_1$-$C_6$ haloalkyl group, a $C_1$-$C_6$ hydroxyalkyl group that may be protected by a hydroxyl protecting group, or a $C_3$-$C_6$ cycloalkyl-$C_1$-$C_6$ alkyl group that may be substituted by a hydroxyl group;

$R^8$ and $R^9$ are the same or different and each independently represents a group selected from the group consisting of halogen atoms, $C_1$-$C_3$ alkyl groups, $C_1$-$C_3$ haloalkyl groups, and $C_1$-$C_3$ alkoxy groups;

m represents an integer of 0 to 4;

n represents an integer of 0 to 4;

Substituent Group β is a group consisting of carboxyl groups, $C_1$-$C_6$ alkoxycarbonyl groups, carbamoyl groups, cyano groups, amino groups, thiol groups, $C_1$-$C_6$ alkylthio groups, $C_2$-$C_6$ acyl groups, acetamido groups, N—$C_6$-$C_{10}$ arylacetamido groups, $C_1$-$C_6$ alkoxycarbonylamido groups, urea groups, $C_3$-$C_6$ cycloalkyl groups that may be substituted by groups selected from Substituent Group γ, $C_3$-$C_6$ cycloalkenyl groups, 3- to 6-membered heterocyclyl groups, $C_2$-$C_6$ alkenyl groups that may be substituted by groups selected from Substituent Group γ, $C_2$-$C_6$ alkynyl groups that may be substituted by groups selected from Substituent Group γ, $C_6$-$C_{10}$ aryl groups that may be substituted by groups selected from Substituent Group γ, 5- to 10-membered heteroaryl groups that may be substituted by groups selected from Substituent Group γ, $C_1$-$C_6$ alkoxy groups, $C_6$-$C_{10}$ aryloxy groups that may be substituted by groups selected from Substituent Group γ, $C_3$-$C_6$ cycloalkyloxy groups, and an oxime group that may be substituted by groups selected from Substituent Group γ; and Substituent Group γ is a group consisting of hydrogen atoms, hydroxyl groups, cyano groups, amino groups, $C_1$-$C_6$ alkylamino groups, $C_1$-$C_6$ dialkylamino groups, $C_2$-$C_6$ cyclic amino groups, halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_2$-$C_6$ acyloxy groups, $C_1$-$C_6$ haloalkoxy groups, $C_3$-$C_6$ cycloalkyloxy groups, $C_1$-$C_6$ alkylenedioxy groups, and phenyl groups].

Preferable examples of the aforementioned compound or a pharmacologically acceptable salt thereof are:

(18) the compound or a pharmacologically acceptable salt thereof according to the above (17), wherein, $R^5$ represents a halogen atom, a $C_1$-$C_6$ alkyl group that may be substituted by a group selected from Substituent Group β, a $C_1$-$C_6$ haloalkyl group, a $C_3$-$C_6$ cycloalkyl group, a $C_1$-$C_6$ alkoxy group that may be substituted by a group selected from Substituent Group β, a $C_1$-$C_6$ haloalkoxy group, a $C_3$-$C_6$ cycloalkyloxy group, a $C_2$-$C_6$ alkenyloxy group, or a $C_6$-$C_{10}$ aryloxy group that may be substituted by a group selected from Substituent Group γ;

(19) the compound or a pharmacologically acceptable salt thereof according to the above (17), wherein, $R^5$ represents a $C_1$-$C_6$ alkoxy group that may be substituted by a group selected from Substituent Group β, a $C_1$-$C_6$ haloalkoxy group, a $C_2$-$C_6$ alkenyloxy group, or a $C_6$-$C_{10}$ aryloxy group that may be substituted by a group selected from Substituent Group γ;

(20) the compound or a pharmacologically acceptable salt thereof according to the above (17), wherein, $R^5$ is a propoxy, isobutyloxy, (cyclopropyl)methoxy, 2-(cyclopropyl)ethoxy, 3-(cyclopropyl)propoxy, (cyclobutyl)methoxy, (cyclopentyl) methoxy, 2-(cyclopentyl)ethoxy, 2-(phenyl)ethoxy, 2-(4-methoxyphenyl)ethoxy, 2-(4-chlorophenyl)ethoxy, (2,2-difluorocyclopropan-1-yl)methoxy, 2,2-difluoroethoxy, 2,2,2-trifluoroethoxy, 3,3,3-trifluoropropoxy, 4,4,4- trifluorobutoxy, ((E)-buten-2-yl)oxy, 4-(trifluoromethyl) phenoxy, 4-methoxyphenoxy, 4-chlorophenoxy, or 4-fluorophenoxy group;

(21) the compound or a pharmacologically acceptable salt thereof according to any one selected from the above (17) to (20), wherein, $R^6$ is a group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_1$-$C_6$ haloalkoxy groups, $C_1$-$C_6$ alkylthio groups, $C_1$-$C_6$ haloalkylthio groups, and 5- to 10-membered heteroaryl groups;

(22) the compound or a pharmacologically acceptable salt thereof according to any one selected from the above (17) to (20), wherein, $R^6$ is a fluorine or chlorine atom, or an ethyl, propyl, isopropyl, trifluoromethyl, cyclopropyl, methoxy, ethoxy, isopropyloxy, cyclopropyloxy, difluoromethoxy, trifluoromethoxy, 2,2-difluoroethoxy, 2,2,2-trifluoroethoxy, methylthio, trifluoromethylthio, or pyrrolyl group;

(23) the compound or a pharmacologically acceptable salt thereof according to any one selected from the above (17) to (20), wherein, $R^6$ is an ethyl, propyl, trifluoromethyl, cyclopropyl, ethoxy, isopropyloxy, cyclopropyloxy, difluoromethoxy, trifluoromethoxy, or 2,2-difluoroethoxy group;

(24) the compound or a pharmacologically acceptable salt thereof according to any one selected from the above (17) to (23), wherein, $R^7$ is a $C_1$-$C_3$ alkyl group, a $C_1$-$C_3$ alkoxy-$C_2$-$C_4$ alkyl group, a $C_2$-$C_4$ haloalkyl group, a $C_2$-$C_4$ hydroxyalkyl group that may be protected by a hydroxyl protecting group, or a $C_3$-$C_6$ cylcoalkyl-$C_2$-$C_4$ alkyl group that may be substituted by a hydroxyl group;

(25) the compound or a pharmacologically acceptable salt thereof according to any one selected from the above (17) to (23), wherein, $R^7$ is a $C_2$-$C_4$ hydroxyalkyl group that may be protected by a hydroxyl protecting group or a $C_3$-$C_6$ cylcoalkyl-$C_2$-$C_4$ alkyl group that may be substituted by a hydroxyl group;

(26) the compound or a pharmacologically acceptable salt thereof according to any one selected from the above (17) to (23), wherein, $R^7$ is a (1-hydroxycyclopropyl)methyl, 2-hydroxyethyl, 3-hydroxypropyl, 2-acetoxyethyl, 2-(morpholin-4-ylacetoxy)ethyl, or 2-(3-carboxypropionyloxy)ethyl group;

(27) the compound or a pharmacologically acceptable salt thereof according to any one selected from the above (17) to (26), wherein, $R^8$ is a chlorine atom, a fluorine atom, or a methyl group;

(28) the compound or a pharmacologically acceptable salt thereof according to any one selected from the above (17) to (26), wherein, $R^8$ is a fluorine atom;

(29) the compound or a pharmacologically acceptable salt thereof according to any one selected from the above (17) to (28), wherein, $R^9$ is a chlorine atom, a fluorine atom, or a methyl group;

(30) the compound or a pharmacologically acceptable salt thereof according to any one selected from the above (17) to (28), wherein, $R^9$ is a fluorine atom;

(31) the compound or a pharmacologically acceptable salt thereof according to any one selected from the above (17) to (30), wherein, m is 0 or 1;

(32) the compound or a pharmacologically acceptable salt thereof according to any one selected from the above (17) to (31), wherein, n is 0 or 1;

(33) the compound or a pharmacologically acceptable salt thereof according to any one selected from the above (17) to (32), wherein, General Formula (I') is General Formula (I'-a):

(I'-a)

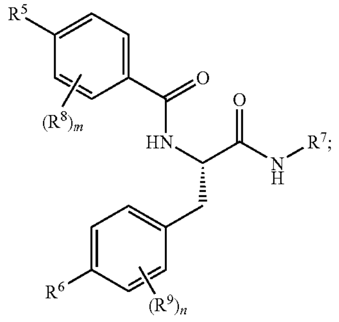

(34) the compound or a pharmacologically acceptable salt thereof according to the above (17), wherein, the compound having General Formula (I') is any one of the following compounds:

4-(cyclopropylmethoxy)-N-{1-[4-(cyclopropyloxy)benzyl]-2-[(2-hydroxyethyl)amino]-2-oxoethyl}benzamide, N-{1-(4-cyclopropylbenzyl)-2-[(2-hydroxyethyl)amino]-2-oxoethyl}-4-(cyclopropylmethoxy)benzamide, 4-(cyclopropylmethoxy)-N-{1-[4-(difluoromethoxy)benzyl]-2-[(2-hydroxyethyl)amino]-2-oxo ethyl}benzamide, 4-(cyclopropylmethoxy)-N-{2-[(2-hydroxyethyl)amino]-2-oxo-1-[4-(trifluoromethoxy)benzyl]ethyl}benzamide, 4-(cyclopropylmethoxy)-N-{2-[(2-hydroxyethyl)amino]-2-oxo-1-[4-(trifluoromethyl)benzyl]ethyl}benzamide, 4-(2-cyclopropylethoxy)-N-{1-[4-(difluoromethoxy)benzyl]-2-[(2-hydroxyethyl)amino]-2-oxoethyl}benzamide, 4-(2-cyclopropylethoxy)-N-{2-[(2-hydroxyethyl)amino]-2-oxo-1-[4-(trifluoromethoxy)benzyl]ethyl}benzamide, 4-(2-cyclopropylethoxy)-N-{2-[(2-hydroxyethyl)amino]-2-oxo-1-[4-(trifluoromethyl)benzyl]ethyl}benzamide, 4-(3-cyclopropylpropoxy)-N-{2-[(2-hydroxyethyl)amino]-2-oxo-1-[4-(trifluoromethoxy)benzyl]ethyl}benzamide, N-{1-[4-(difluoromethoxy)benzyl]-2-[(2-hydroxyethyl) amino]-2-oxoethyl}-4-(3,3,3-trifluoropropoxy)benzamide, N-{2-[(2-hydroxyethyl)amino]-2-oxo-1-[4-(trifluoromethoxy)benzyl]ethyl}-4-(3,3,3-trifluoropropoxy)benzamide, N-{2-[(2-hydroxyethyl)amino]-2-oxo-1-[4-(trifluoromethyl)benzyl]ethyl}-4-(3,3,3-trifluoropropoxy)benzamide, 4-(2,2-difluoroethoxy)-N-{2-[(2-hydroxyethyl)amino]-2-oxo-1-[4-(trifluoromethoxy)benzyl]ethyl}benzamide, 4-[(2,2-difluorocyclopropyl)methoxy]-N-{2-[(2-hydroxyethyl)amino]-2-oxo-1-[4-(trifluoromethoxy)benzyl] ethyl}benzamide, N-{1-[4-(difluoromethoxy)benzyl]-2-[(2-hydroxyethyl) amino]-2-oxoethyl}-4-[4-(trifluoromethyl)phenoxy]benzamide, N-{2-[(2-hydroxyethyl)amino]-2-oxo-1-[4-(trifluoromethoxy)benzyl]ethyl}-4-[4-(trifluoromethyl)phenoxy]benzamide, N-{2-[(2-hydroxyethyl)amino]-2-oxo-1-[4-(trifluoromethyl)benzyl]ethyl}-4-[4-(trifluoromethyl)phenoxy]benzamide, N-{2-(methylamino)-2-oxo-1-[4-(trifluoromethoxy)benzyl] ethyl}-4-(3,3,3-trifluoropropoxy)benzamide, N-{2-{[(2R)-2-hydroxypropyl]amino}-2-oxo-1-[4-(trifluoromethoxy)benzyl]ethyl}-4-(3,3,3-trifluoropropoxy)benzamide, N-{2-[(2-fluoroethyl)amino]-2-oxo-1-[4-(trifluoromethoxy)benzyl]ethyl}-4-(3,3,3-trifluoropropoxy)benzamide, N-{2-amino-2-oxo-1-[4-(trifluoromethoxy)benzyl]ethyl}-4-(3,3,3-trifluoropropoxy)benzamide, N-{2-[(2-hydroxyethyl)amino]-2-oxo-1-[4-(trifluoromethoxy)benzyl]ethyl}-4-(4,4,4-trifluorobutoxy)benzamide, and N-{2-[(2-hydroxyethyl)amino]-2-oxo-1-[4-(trifluoromethoxy)benzyl]ethyl}-4-(2,2,2-trifluoroethoxy)benzamide; and

(35) the compound or a pharmacologically acceptable salt thereof according to the above (34), wherein, the absolute configuration is S.

Furthermore, the present invention provides:

(36) a pharmaceutical composition comprising a compound or a pharmacologically acceptable salt thereof according to any one selected from the above (17) to (35) as an active ingredient;

(37) a pharmaceutical composition according to the above (36), for use as a bone resorption suppressant;

(38) a pharmaceutical composition according to any one selected from the above (1) to (16), and (36) to (37), for use in decreasing blood calcium concentration;

(39) a pharmaceutical composition according to any one selected from the above (1) to (16), and (36) to (37), for use in suppressing a decrease in bone mass; and

(40) a pharmaceutical composition according to any one selected from the above (1) to (16), and (36) to (37), for use in improving bone metabolism.

Furthermore, the present invention provides:

(41) a pharmaceutical composition according to any one selected from the above (1) to (16), and (36) to (37), for use in prophylaxis or treatment of a bone metabolic disease;

(42) the pharmaceutical composition according to the above (41), wherein, the bone metabolic disease is osteoporosis;

(43) the pharmaceutical composition according to the above (41), wherein, the bone metabolic disease is hypercalcemia; and

(44) a pharmaceutical composition according to any one selected from the above (1) to (16), and (36) to (37), for use in for suppressing bone metastasis of cancer.

Furthermore, the present invention provides:

(45) a method for improving bone metabolism by administering an effective amount of the pharmaceutical composition according to any one selected from the above (1) to (16), and (36) to (37) to a mammal;

(46) a method for prophylaxis of treatment for a bone metabolic disease, wherein an effective amount of the pharmaceutical composition according to any one selected from the above (1) to (16), and (36) to (37) is administered to a mammal;

(47) a method for prophylaxis or treatment for osteoporosis, wherein an effective amount of the pharmaceutical composition according to any one selected from the above (1) to (16), and (36) to (37) is administered to a mammal; and

(48) use of the compound or a pharmacologically acceptable salt thereof according to any one selected from the above (17) to (35) for manufacturing a pharmaceutical composition for suppressing bone resorption.

(Definition, Preferable Groups and so on)

Among the aforementioned Substituent Group α, those in the group consisting of halogen atoms, $C_1$-$C_6$ alkyl groups that may be substituted by a group selected from Substituent Group β, $C_1$-$C_6$ haloalkyl groups, $C_3$-$C_6$ cycloalkyl groups, $C_6$-$C_{10}$ aryl groups that may be substituted by a group selected from Substituent Group γ, $C_1$-$C_6$ alkoxy groups that may be substituted by a group selected from Substituent Group β, $C_1$-$C_6$ haloalkoxy groups, $C_2$-$C_6$ alkenyloxy groups that may be substituted by a group selected from Substituent Group β, $C_3$-$C_6$ cycloalkyloxy groups, $C_6$-$C_{10}$ aryloxy groups that may be substituted by a group selected from Substituent Group γ, $C_1$-$C_6$ alkylthio groups that may be substituted by a group selected from Substituent Group β, and $C_1$-$C_6$ haloalkylthio groups are preferable.

Among the aforementioned Substituent Group β, those in the group consisting of $C_3$-$C_6$ cycloalkyl groups that may be substituted by a group selected from Substituent Group γ, $C_3$-$C_6$ cycloalkenyl groups, $C_6$-$C_{10}$ aryl groups that may be substituted by a group selected from Substituent Group γ, $C_1$-$C_6$ alkoxy groups, $C_6$-$C_{10}$ aryloxy groups that may be substituted by a group selected from Substituent Group γ, and $C_3$-$C_6$ cycloalkyloxy groups are preferable.

Among the aforementioned Substituent Group γ, those in the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_1$-$C_6$ haloalkyloxy groups, and $C_3$-$C_6$ cycloalkyloxy groups are preferable.

The aforementioned $R^x$ is preferably a phenyl group that may be substituted by a group selected from Substituent Group α; more preferably a phenyl group that may be substituted by a group selected from the group consisting of $C_1$-$C_6$ alkoxy groups that may be substituted by a group selected from Substituent Group β, $C_1$-$C_6$ haloalkoxy groups, $C_2$-$C_6$ alkenyloxy groups, and $C_6$-$C_{10}$ aryloxy groups that may be substituted by a group selected from Substituent Group γ; and still more preferably a 4-(propoxy)phenyl, 4-(isobutyloxy)phenyl, 4-[(cyclopropyl)methoxy]phenyl, 4-[2-(cyclopropyl)ethoxy]phenyl, 4-[3-(cyclopropyl)propoxy]phenyl, 4-[(cyclobutyl)methoxy]phenyl, 4-[(cyclopentyl)methoxy]phenyl, 4-[2-(cyclopentyl)ethoxy]phenyl, 4-[2-(phenyl)ethoxy]phenyl, 4-[2-(4-methoxyphenyl)ethoxy]phenyl, 4-[2-(4-chlorophenyl)ethoxy]phenyl, 4-[(2,2-difluorocyclopropan-1-yl)methoxy]phenyl, 4-(2,2-difluoroethoxy)phenyl, 4-(2,2,2-trifluoroethoxy)phenyl, 4-(3,3,3-trifluoropropoxy)phenyl, 4-(4,4,4-trifluorobutoxy)phenyl, 4-[((E)-buten-2-yl)oxy]phenyl, 4-[4-(trifluoromethyl)phenoxy]phenyl, 4-(4-methoxyphenoxy)phenyl, 4-(4-chlorophenoxy)phenyl, or 4-(4-fluorophenoxy)phenyl group.

The aforementioned $R^2$ is preferably a phenyl group that may be substituted by a group selected from Substituent Group α; more preferably a phenyl group that may be substituted by a group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_1$-$C_6$ haloalkoxy groups, $C_1$-$C_6$ alkylthio groups, $C_1$-$C_6$ haloalkylthio groups, and 5- to 10-membered heteroaryl groups; and still more preferably a 4-fluorophenyl, 4-chlorophenyl, 4-(ethyl)phenyl, 4-(propyl)phenyl, 4-(isopropyl)phenyl, 4-(trifluoromethyl)phenyl, 4-(cyclopropyl)phenyl, 4-methoxyphenyl, 4-(ethoxy)phenyl, 4-(isopropyloxy)phenyl, 4-(cyclopropyloxy)phenyl, 4-(difluoromethoxy)phenyl, 4-(trifluoromethoxy)phenyl, 4-(2,2-difluoroethoxy)phenyl, 4-(2,2,2-trifluoroethoxy)phenyl, 4-methylthiophenyl, 4-trifluoromethylthiophenyl, or 4-(1-pyrrolyl)phenyl group; and particularly more preferably a 4-(ethyl)phenyl, 4-(propyl)phenyl, 4-(trifluoromethyl)phenyl, 4-(cyclopropyl)phenyl, 4-(ethoxy)phenyl, 4-(isopropyloxy)phenyl, 4-(cyclopropyloxy)phenyl, 4-(difluoromethoxy)phenyl, 4-(trifluoromethoxy)phenyl, or 4-(2,2-difluoroethoxy)phenyl group.

The aforementioned $R^3$ is preferably a $C_1$-$C_6$ haloalkyl group, a $C_1$-$C_6$ alkyl group that may be substituted by a group selected from Substituent Group β, or a $C_1$-$C_6$ hydroxyalkyl group that may be protected by a hydroxyl protecting group; more preferably a $C_1$-$C_6$ haloalkyl group, a $C_1$-$C_6$ hydroxyalkyl group that may be protected by a hydroxyl protecting group, a $C_1$-$C_5$ alkyl-methyl group that may be substituted by a group selected from Substituent Group β, a $C_6$-$C_{10}$ arylmethyl group that may be substituted by a group selected from Substituent Group β, or a $C_3$-$C_6$ cycloalkyl-methyl group that may be substituted by a group selected from Substituent Group β; still more preferably a $C_1$-$C_6$ hydroxyalkyl group that may be protected by a hydroxyl protecting group or a $C_3$-$C_6$ cycloalkyl-$C_1$-$C_6$ alkyl group that may be substituted by a hydroxyl group; and particularly more preferably a $C_2$-$C_4$ hydroxyalkyl group that may be protected by a hydroxyl protecting group or a $C_3$-$C_6$ cycloalkyl-$C_2$-$C_4$ alkyl group that may be substituted by a hydroxyl group; and particularly more preferably a (1-hydroxycyclopropyl)methyl, 2-hydroxyethyl, 3-hydroxypropyl, 2-acetoxyethyl, 2-(morpholin-4-ylacetoxy)ethyl, or 2-(3-carboxypropionyloxy)ethyl group.

The aforementioned $R^4$ is preferably a hydrogen atom.

The aforementioned $R^5$ and $R^6$ are each preferably selected from a group consisting of halogen atoms, $C_1$-$C_6$ alkyl groups that may be substituted by groups selected from Substituent Group β, $C_1$-$C_6$ haloalkyl groups, $C_3$-$C_6$ cycloalkyl groups, $C_6$-$C_{10}$ aryl groups that may be substituted by groups selected from Substituent Group γ, $C_1$-$C_6$ alkoxy groups that may be substituted by groups selected from Substituent Group β, $C_1$-$C_6$ haloalkoxy groups, $C_2$-$C_6$ alkenyloxy groups that may be substituted by groups selected from Substituent Group β, $C_3$-$C_6$ cycloalkyloxy groups, $C_6$-$C_{10}$ aryloxy groups that may be substituted by groups selected from Substituent Group γ, $C_1$-$C_6$ alkylthio groups that may be substituted by groups selected from Substituent Group β, and $C_1$-$C_6$ haloalkylthio groups.

The aforementioned $R^5$ is preferably a halogen atom, a $C_1$-$C_6$ alkyl group that may be substituted by groups selected from Substituent Group β, a $C_1$-$C_6$ haloalkyl group, a $C_3$-$C_6$ cycloalkyl group, a $C_1$-$C_6$ alkoxy group that may be substituted by a group selected from Substituent Group β, a $C_1$-$C_6$ haloalkoxy group, a $C_3$-$C_6$ cycloalkyloxy group, a $C_2$-$C_6$ alkenyloxy group, or a $C_6$-$C_{10}$ aryloxy group that may be substituted by a group selected from Substituent Group γ; more preferably a $C_1$-$C_6$ alkoxy group that may be substituted by a group selected from Substituent Group β, a $C_1$-$C_6$ haloalkoxy group, a $C_2$-$C_6$ alkenyloxy group, or a $C_6$-$C_{10}$ aryloxy group that may be substituted by a group selected from Substituent Group γ; and more preferably a propoxy, isobutyloxy, (cyclopropyl)methoxy, 2-(cyclopropyl)ethoxy, 3-(cyclopropyl)propoxy, (cyclobutyl)methoxy, (cyclopentyl)methoxy, 2-(cyclopentyl)ethoxy, 2-(phenyl)ethoxy, 2-(4-methoxyphenyl)ethoxy, 2-(4-chlorophenyl)ethoxy, (2,2-difluorocyclopropan-1-yl)methoxy, 2,2-difluoroethoxy, 2,2,2-trifluoroethoxy, 3,3,3-trifluoropropoxy, 4,4,4-trifluorobutoxy, ((E)-buten-2-yl)oxy, 4-(trifluoromethyl)phenoxy, 4-methoxyphenoxy, 4-chlorophenoxy, or 4-fluorophenoxy group.

The aforementioned $R^6$ is preferably a group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_1$-$C_6$ haloalkoxy groups, $C_1$-$C_6$ alkylthio groups, $C_1$-$C_6$ haloalkylthio groups, and 5- to 10-membered heteroaryl groups; more preferably a fluorine or chlorine atom, or an ethyl, propyl, isopropyl, trifluoromethyl, cyclopropyl, methoxy, ethoxy, isopropyloxy, cyclopropyloxy, difluoromethoxy, trifluoromethoxy, 2,2-difluoroethoxy, 2,2,2-trifluoroethoxy, methylthio, trifluoromethylthio, or pyrrolyl group; still more preferably an ethyl, propyl, trifluoromethyl, cyclopropyl, ethoxy, isopropyloxy, cyclopropyloxy, difluoromethoxy, trifluoromethoxy, or 2,2-difluoroethoxy group; and particularly more preferably a trifluoromethyl, cyclopropyl, cyclopropyloxy, difluoromethoxy, or trifluoromethoxy group.

The aforementioned $R^7$ is preferably a $C_1$-$C_3$ alkyl group, a $C_1$-$C_3$ alkoxy-$C_2$-$C_4$ alkyl group, a $C_2$-$C_4$ haloalkyl group, a $C_2$-$C_4$ hydroxyalkyl group that may be protected by a hydroxyl protecting group, or a $C_3$-$C_6$ cycloalkyl-$C_2$-$C_4$ alkyl group that may be substituted by a hydroxyl group; more preferably a $C_2$-$C_4$ hydroxyalkyl group that may be protected by a hydroxyl protecting group or a cyclopropyl-$C_2$-$C_4$ alkyl group that may be substituted by a hydroxyl group; and still more preferably a (1-hydroxycyclopropyl)methyl, 2-hydroxyethyl, 3-hydroxypropyl, 2-acetoxyethyl, 2-(morpholin-4-ylacetoxy)ethyl, or 2-(3-carboxypropionyloxy)ethyl group.

The aforementioned $R^8$ is preferably a fluorine or chlorine atom, or a methyl, ethyl, fluoromethyl, difluoromethyl, trifluoromethyl, methoxy, or ethoxy group; more preferably a fluorine atom, a chlorine atom, or a methyl group; and more preferably a fluorine atom.

The aforementioned $R^9$ is preferably a fluorine or chlorine atom, or a methyl, ethyl, fluoromethyl, difluoromethyl, trifluoromethyl, methoxy, or ethoxy group; more preferably a fluorine atom, a chlorine atom, or a methyl group; and more preferably a fluorine atom.

The aforementioned m is preferably 0 or 1.

The aforementioned n is preferably 0 or 1.

Among the compounds having General Formula (I), preferable combination of substituents is:

$R^1$ is a phenyl group that may be substituted by groups selected from Substituent Group α;

$R^2$ is a phenyl group that may be substituted by groups selected from Substituent Group α;

X is a group having the formula $N(R^3)R^4$;

$R^3$ is a $C_1$-$C_6$ haloalkyl group, a $C_1$-$C_6$ alkyl group that may be substituted by a group selected from Substituent Group β, or a $C_1$-$C_6$ hydroxyalkyl group that may be protected by a hydroxyl protecting group; and $R^4$ is a hydrogen atom.

A more preferable combination of substituents is:

$R^1$ is a phenyl group that may be substituted by a $C_1$-$C_6$ alkoxy group that may be substituted by a group selected from Substituent Group β, a phenyl group that may be substituted by a $C_1$-$C_6$ haloalkoxy group, a phenyl group that may be substituted by a $C_2$-$C_6$ alkenyloxy group, or a phenyl group that may be substituted by a $C_6$-$C_{10}$ aryloxy group that may be substituted by a group selected from Substituent Group γ;

$R^2$ is a phenyl group that may be substituted by a halogen atom, a phenyl group that may be substituted by a $C_1$-$C_6$ alkyl group, a phenyl group that may be substituted by a $C_1$-$C_6$ haloalkyl group, a phenyl group that may be substituted by a $C_3$-$C_6$ cycloalkyl group, a phenyl group that may be substituted by a $C_1$-$C_6$ alkoxy group, a phenyl group that may be substituted by a $C_3$-$C_6$ cycloalkyloxy group, a phenyl group that may be substituted by a $C_1$-$C_6$ haloalkoxy group, a phenyl group that may be substituted by a $C_1$-$C_6$ alkylthio group, a phenyl group that may be substituted by a $C_1$-$C_6$ haloalkylthio group, or a phenyl group that may be substituted by a 5- to 10-membered heteroaryl group;

X is a group having the formula $N(R^3)R^4$;

$R^3$ is a $C_1$-$C_6$ haloalkyl group, a $C_1$-$C_6$ hydroxyalkyl group that may be protected by a hydroxyl protecting group, a $C_1$-$C_5$ alkyl-methyl group that may be substituted by a group selected from Substituent Group β, a $C_6$-$C_{10}$ aryl-methyl group that may be substituted by a group selected from Substituent Group β, or a $C_3$-$C_6$ cycloalkyl-methyl group that may be substituted by a group selected from Substituent Group β; and $R^4$ is a hydrogen atom.

A still more preferable combination of substituents is:

$R^1$ is a 4-(propoxy)phenyl, 4-(isobutyloxy)phenyl, 4-[(cyclopropyl)methoxy]phenyl, 4-[2-(cyclopropyl)ethoxy]phenyl, 4-[3-(cyclopropyl)propoxy]phenyl, 4-[(cyclobutyl)methoxy]phenyl, 4-[(cyclopentyl)methoxy]phenyl, 4-[2-(cyclopentyl)ethoxy]phenyl, 4-[2-(phenyl)ethoxy]phenyl, 4-[2-(4-methoxyphenyl)ethoxy]phenyl, 4-[2-(4-chlorophenyl)ethoxy]phenyl, 4-[(2,2-difluorocyclopropan-1-yl)methoxy]phenyl, 4-(2,2-difluoroethoxy)phenyl, 4-(2,2,2-trifluoroethoxy)phenyl, 4-(3,3,3-trifluoropropoxy)phenyl, 4-(4,4,4-trifluorobutoxy)phenyl, 4-[((E)-buten-2-yl)oxy]phenyl, 4-[4-(trifluoromethyl)phenoxy]phenyl, 4-(4-methoxyphenoxy)phenyl, 4-(4-chlorophenoxy)phenyl, or 4-(4-fluorophenoxy)phenyl group;

$R^2$ is a 4-(ethyl)phenyl, 4-(propyl)phenyl, 4-(trifluoromethyl)phenyl, 4-(cyclopropyl)phenyl, 4-(ethoxy)phenyl, 4-(isopropyloxy)phenyl, 4-(cyclopropyloxy)phenyl, 4-(difluoromethoxy)phenyl, 4-(trifluoromethoxy)phenyl, or 4-(2,2-difluoroethoxy)phenyl group;

X is a group having the formula $N(R^3)R^4$;

$R^3$ is a (1-hydroxycyclopropyl)methyl, 2-hydroxyethyl, 3-hydroxypropyl, 2-acetoxyethyl, 2-(morpholin-4-ylacetoxy)ethyl, or 2-(3-carboxypropionyloxy)ethyl group; and $R^4$ is a hydrogen atom.

In addition, the compounds having General Formula (I) are preferably the compounds having General Formula (I'). Among the compounds having General Formula (I'), a preferable combination of substituents is:

$R^5$ is a halogen atom, a $C_1$-$C_6$ alkyl group that may be substituted by a group selected from Substituent Group β, a $C_1$-$C_6$ haloalkyl group, a $C_3$-$C_6$ cycloalkyl group, a $C_1$-$C_6$ alkoxy group that may be substituted by a group selected from Substituent Group β, a $C_1$-$C_6$ haloalkoxy group, a $C_3$-$C_6$ cycloalkyloxy group, a $C_2$-$C_6$ alkenyloxy group, or a $C_6$-$C_{10}$ aryloxy group that may be substituted by a group selected from Substituent Group γ;

$R^6$ is a halogen atom, a $C_1$-$C_6$ alkyl group, a $C_1$-$C_6$ haloalkyl group, a $C_3$-$C_6$ cycloalkyl group, a $C_1$-$C_6$ alkoxy group, a $C_3$-$C_6$ cycloalkyloxy group, a $C_1$-$C_6$ haloalkoxy group, a $C_1$-$C_6$ alkylthio group, a $C_1$-$C_6$ haloalkylthio group, or a 5- to 10-membered heteroaryl group;

$R^7$ is a $C_1$-$C_3$ alkyl group, a $C_1$-$C_3$ alkoxy-$C_2$-$C_4$ alkyl group, a $C_2$-$C_4$ haloalkyl group, a $C_2$-$C_4$ hydroxyalkyl group that may be protected by a hydroxyl protecting group, or a $C_3$-$C_6$ cycloalkyl-$C_2$-$C_4$ alkyl group that may be substituted by a hydroxyl group; $R^8$ is a chlorine atom, a fluorine atom, or a methyl group; $R^9$ is a chlorine atom, a fluorine atom, or a methyl group; m is 0 or 1; and n is 0 or 1.

More preferably, $R^5$ is a $C_1$-$C_6$ alkoxy group that may be substituted by a group selected from Substituent Group β, a $C_1$-$C_6$ haloalkoxy group, a $C_2$-$C_6$ alkenyloxy group, or a $C_6$-$C_{10}$ aryloxy group that may be substituted by a group selected from Substituent Group γ;

$R^6$ is a fluorine or chlorine atom, or an ethyl, propyl, isopropyl, trifluoromethyl, cyclopropyl, methoxy, ethoxy, isopropyloxy, cyclopropyloxy, difluoromethoxy, trifluoromethoxy, 2,2-difluoroethoxy, 2,2,2-trifluoroethoxy, methylthio, trifluoromethylthio, or pyrrolyl group;

$R^7$ is a $C_2$-$C_4$ hydroxyalkyl group that may be protected by a hydroxyl protecting group or a cyclopropyl-$C_2$-$C_4$ alkyl group that may be substituted by a hydroxyl group; $R^8$ is a fluorine atom; $R^9$ is a fluorine atom; m is 0 or 1; and n is 0 or 1.

Still more preferably, $R^5$ is a propoxy, isobutyloxy, (cyclopropyl)methoxy, 2-(cyclopropyl)ethoxy, 3-(cyclopropyl)propoxy, (cyclobutyl)methoxy, (cyclopentyl)methoxy, 2-(cyclopentyl)ethoxy, 2-(phenyl)ethoxy, 2-(4-methoxyphenyl)ethoxy, 2-(4-chlorophenyl)ethoxy, (2,2-difluorocyclopropan-1-yl)methoxy, 2,2-difluoroethoxy, 2,2,2-trifluoroethoxy, 3,3,3-trifluoropropoxy, 4,4,4-trifluorobutoxy, ((E)-buten-2-yl)oxy, 4-(trifluoromethyl)phenoxy, 4-methoxyphenoxy, 4-chlorophenoxy, or 4-fluorophenoxy group;

$R^6$ is an ethyl, propyl, trifluoromethyl, cyclopropyl, ethoxy, isopropyloxy, cyclopropyloxy, difluoromethoxy, trifluoromethoxy, or 2,2-difluoroethoxy group;

$R^7$ is a (1-hydroxycyclopropyl)methyl, 2-hydroxyethyl, 3-hydroxypropyl, 2-acetoxyethyl, 2-(morpholin-4-ylacetoxy)ethyl, or 2-(3-carboxypropionyloxy)ethyl group;

m is 0; and n is 0.

Furthermore, preferable examples of the compound having General Formula (I') are as follows:

4-(cyclopropylmethoxy)-N-{1-[4-(cyclopropyloxy)benzyl]-2-[(2-hydroxyethyl)amino]-2-oxoethyl}benzamide, N-{1-(4-cyclopropylbenzyl)-2-[(2-hydroxyethyl)amino]-2-oxoethyl}-4-(cyclopropylmethoxy)benzamide, 4-(cyclopropylmethoxy)-N-{1-[4-(difluoromethoxy)benzyl]-2-[(2-hydroxyethyl)amino]-2-oxoethyl}benzamide, 4-(cyclopropylmethoxy)-N-{2-[(2-hydroxyethyl)amino]-2-oxo-1-[4-(trifluoromethoxy)benzyl]ethyl}benzamide, 4-(cyclopropylmethoxy)-N-{2-[(2-hydroxyethyl)amino]-2-oxo-1-[4-(trifluoromethyl)benzyl]ethyl}benzamide, 4-(2-cyclopropylethoxy)-N-{1-[4-(difluoromethoxy)benzyl]-2-[(2-hydroxyethyl)amino]-2-oxoethyl}benzamide, 4-(2-cyclopropylethoxy)-N-{2-[(2-hydroxyethyl)amino]-2-oxo-1-[4-(trifluoromethoxy)benzyl]ethyl}benzamide, 4-(2-cyclopropylethoxy)-N-{2-[(2-hydroxyethyl)amino]-2-oxo-1-[4-(trifluoromethyl)benzyl]ethyl}benzamide, 4-(3-cyclopropylpropoxy)-N-{2-[(2-hydroxyethyl)amino]-2-oxo-1-[4-(trifluoromethoxy)benzyl]ethyl}benzamide, N-{1-[4-(difluoromethoxy)benzyl]-2-[(2-hydroxyethyl)amino]-2-oxoethyl}-4-(3,3,3-trifluoropropoxy)benzamide, N-{2-[(2-hydroxyethyl)amino]-2-oxo-1-[4-(trifluoromethoxy)benzyl]ethyl}-4-(3,3,3-trifluoropropoxy)benzamide, N-{2-[(2-hydroxyethyl)amino]-2-oxo-1-[4-(trifluoromethyl)benzyl]ethyl}-4-(3,3,3-trifluoropropoxy)benzamide, 4-(2,2-difluoroethoxy)-N-{2-[(2-hydroxyethyl)amino]-2-oxo-1-[4-(trifluoromethoxy)benzyl]ethyl}benzamide, 4-[(2,2-difluorocyclopropyl)methoxy]-N-{2-[(2-hydroxyethyl)amino]-2-oxo-1-[4-(trifluoromethoxy)benzyl]ethyl}benzamide, N-{1-[4-(difluoromethoxy)benzyl]-2-[(2-hydroxyethyl)amino]-2-oxoethyl}-4-[4-(trifluoromethyl)phenoxy]benzamide, N-{2-[(2-hydroxyethyl)amino]-2-oxo-1-[4-(trifluoromethoxy)benzyl]ethyl}-4-[4-(trifluoromethyl)phenoxy]benzamide, N-{2-[(2-hydroxyethyl)amino]-2-oxo-1-[4-(trifluoromethyl)benzyl]ethyl}-4-[4-(trifluoromethyl)phenoxy]benzamide, N-{2-(methylamino)-2-oxo-1-[4-(trifluoromethoxy)benzyl]ethyl}-4-(3,3,3-trifluoropropoxy)benzamide, N-{2-{[(2R)-2-hydroxypropyl]amino}-2-oxo-1-[4-(trifluoromethoxy)benzyl]ethyl}-4-(3,3,3-trifluoropropoxy)benzamide, N-{2-[(2-fluoroethyl)amino]-2-oxo-1-[4-(trifluoromethoxy)benzyl]ethyl}-4-(3,3,3-trifluoropropoxy)benzamide, N-{2-amino-2-oxo-1-[4-(trifluoromethoxy)benzyl]ethyl}-4-(3,3,3-trifluoropropoxy)benzamide, N-{2-[(2-hydroxyethyl)amino]-2-oxo-1-[4-(trifluoromethoxy)benzyl]ethyl}-4-(4,4,4-trifluorobutoxy)benzamide, and N-{2-[(2-hydroxyethyl)amino]-2-oxo-1-[4-(trifluoromethoxy)benzyl]ethyl}-4-(2,2,2-trifluoroethoxy)benzamide.

The $C_6$-$C_{10}$ aryl group of the aforementioned "$C_6$-$C_{10}$ aryl group that may be substituted by a group selected from Substituent Group α" and "$C_6$-$C_{10}$ aryl group that may be substituted by a group selected from Substituent Group γ" is, for example, a phenyl group, an indenyl group, or a naphthyl group and is preferably a phenyl group.

The term "may be substituted" of the aforementioned "$C_6$-$C_{10}$ aryl group that may be substituted by a group selected from Substituent Group α" preferably means mono- or di-substituted; and the term "may be substituted" of the "$C_6$-$C_{10}$ aryl group that may be substituted by a group selected from Substituent Group γ" preferably means unsubstituted or monosubstituted.

The 5- to 10 membered heteroaryl group of the aforementioned "5- to 10 membered heteroaryl group that may be substituted by a group selected from Substituent Group α" and "5- to 10 membered heteroaryl group that may be substituted by a group selected from Substituent Group γ" is a cyclic group composed of three to six carbon atoms and a nitrogen, oxygen, and/or sulfur atom, and examples thereof include a furyl group, a thienyl group, a pyrrolyl group, a pyrazolyl group, an imidazolyl group, an oxazolyl group, an isoxazolyl group, a thiazolyl group, an isothiazolyl group, a triazolyl group, a tetrazolyl group, a pyranyl group, a pyridyl group, a pyridazinyl group, a pyrimidinyl group, and a pyrazinyl group. Among them, 5- or 6-membered heteroaryl groups are preferred. The above-mentioned "5- to 10-membered heteroaryl group" may be fused with another cyclic group, and such groups are, for example, an indolyl group, a benzofuranyl group, a benzothienyl group, a quinolyl group, an isoquinolyl group, a quinazolinyl group, a tetrahydroquinolyl group, and a tetrahydroisoquinolyl group. For $R^1$, a pyridyl group is preferred; for $R^2$, a pyridyl group, a triazolyl group, and a pyrrolyl group are preferred; for $R^3$ and $R^4$, a pyridyl group is preferred; and for Substituent Group β, a benzothiazoyl group, a pyridyl group, and a pyrrolyl group are preferred.

The term "may be substituted" of the aforementioned "5- to 10 membered heteroaryl group that may be substituted by a group selected from Substituent Group α" preferably means mono- or di-substituted; and the term "may be substituted" of the "5- to 10 membered heteroaryl group that may be substituted by a group selected from Substituent Group γ" preferably means unsubstituted or mono-substituted.

The 3- to 6-membered heterocyclyl group of the aforementioned "3- to 6-membered heterocyclyl group that may be substituted by a group selected from Substituent Group α", "3- to 6-membered heterocyclyl group that may be substituted by a group selected from Substituent Group β", and "3- to 6-membered heterocyclyl group" can be, for example, an azetidinyl group, a pyrrolidinyl group, a pyrrolinyl group, an imidazolidinyl group, an imidazolinyl group, a pyrazolidinyl group, a pyrazolinyl group, an oxazolidinyl group, a thiazolidinyl group, a piperidyl group, a tetrahydropyridyl group, a dihydropyridyl group, a piperazinyl group, a morpholinyl group, a thiomorpholinyl group, a homopiperidyl group, a tetrahydrofuryl group, or a tetrahydropyranyl group. For Substituent Group β, a pyrrolidinyl group, a piperidyl group, a morpholinyl group, and a tetrahydrofuryl group are preferred.

The $C_1$-$C_6$ alkoxy group of the aforementioned "$C_1$-$C_6$ alkoxy group", "$C_1$-$C_6$ alkoxy group substituted by a hydroxyl group", "$C_1$-$C_6$ alkoxy group that may be substituted by a hydroxyl group", and "$C_1$-$C_6$ alkoxy group that may be substituted by a group selected from Substituent Group β" is, for example, a linear or branched alkoxy group having one to six carbon atoms and is preferably a methoxy group, an ethoxy group, a propoxy group, an isopropoxy group, a butoxy group, or an isobutoxy group.

The term "substituted" in the aforementioned "$C_1$-$C_6$ alkoxy group that may be substituted by a hydroxyl group" means mono- to tri-substituted and preferably mono- or di-substituted.

The $C_1$-$C_6$ alkyl group in the definition of the aforementioned "$C_1$-$C_6$ alkyl group" and "$C_1$-$C_6$ alkyl group that may be substituted by a group selected from Substituent Group β" can be, for example, a linear or branched alkyl group having one to six carbon atoms and is preferably a methyl group, an ethyl group, a propyl group, an isopropyl group, or a butyl group.

The term "may be substituted" of the "$C_1$-$C_6$ alkyl group that may be substituted by a group selected from Substituent Group β" preferably means mono- or di-substituted.

The aforementioned "hydroxyl protecting group" can be, for example, an "aliphatic acyl group" including an alkylcarbonyl group such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl, and henicosanoyl; an aminated alkylcarbonyl group, in which the aforementioned alkylcarbonyl group is substituted by an amino group, such as morpholin-4-ylacetyl, piperidin-1-ylacetyl, and pyrrolidin-1-ylacetyl; a carboxylated alkylcarbonyl group such as succinoyl, glutaroyl, and azipoyl; a halogeno $C_1$-$C_6$ alkylcarbonyl group such as chloroacetyl, dichloroacetyl, trichloroacetyl, and trifluoroacetyl; a $C_1$-$C_6$ alkoxy $C_1$-$C_6$ alkylcarbonyl group such as methoxyacetyl; and a unsaturated alkylcarbonyl group such as (E)-2-methyl-2-butenoyl; an "aromatic acyl group" including an arylcarbonyl group such as benzoyl, α-naphthoyl, and β-naphthoyl; a halogeno arylcarbonyl group such as 2-bromobenzoyl and 4-chlorobenzoyl; a lower-alkylated arylcarbonyl group such as 2,4,6-trimethylbenzoyl and 4-toluoyl; a lower-alkoxylated arylcarbonyl group such as 4-anisoyl; a carboxylated arylcarbonyl group such as 2-carboxybenzoyl, 3-carboxybenzoyl, and 4-carboxybenzoyl; a nitrated arylcarbonyl group such as 4-nitrobenzoyl and 2-nitrobenzoyl; a lower alkoxycarbonylated arylcarbonyl group such as 2-(methoxycarbonyl)benzoyl; and an arylated arylcarbonyl group such as 4-phenylbenzoyl; a "tetrahydropyranyl or tetrahydrothiopyranyl group" such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl; a "tetrahydrofuranyl or tetrahydrothiofuranyl group" such as tetrahydrofuran-2-yl and tetrahydrothiofuran-2-yl; a "silyl group" including a tri(lower alkyl)silyl group such as trimethylsilyl, triethylsilyl, isopropyldimethylsilyl, t-butyldimethylsilyl, methyldiisopropylsilyl, methyldi-t-butylsilyl, and triisopropylsilyl; and a tri(lower alkyl)silyl group substituted by one or two aryl groups, such as diphenylmethylsilyl, diphenylbutylsilyl, diphenylisopropylsilyl, and phenyldiisopropylsilyl; an "alkoxymethyl group" including a lower alkoxymethyl group such as methoxymethyl, 1,1-dimethyl-1-methoxymethyl, ethoxymethyl, propoxymethyl, isopropoxymethyl, butoxymethyl, and t-butoxymethyl; a lower alkoxylated lower alkoxymethyl group such as 2-methoxyethoxymethyl; and a halogeno lower alkoxy methyl group such as 2,2,2-trichloroethoxymethyl and bis(2-chloroethoxy)methyl; a "substituted ethyl group" including a lower alkoxylated ethyl group such as 1-ethoxyethyl and 1-(isopropoxy)ethyl; and a halogenated ethyl group such as 2,2,2-trichloroethyl; an "aralkyl group" including a lower alkyl group substituted by one to three aryl groups, such as benzyl, α-naphthylmethyl, β-naphthylmethyl, diphenylmethyl, triphenylmethyl, α-naphthyldiphenylmethyl, and 9-anthrylmethyl; and a lower alkyl group substituted by one to three aryl groups of which aryl ring is substituted by a lower alkyl, lower alkoxy, halogen, or cyano group, such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, methyl, and piperonyl; an "alkoxycarbonyl group" including a lower alkoxycarbonyl group such as methoxycarbonyl, ethoxycarbonyl, t-butoxycarbonyl, and isobutoxycarbonyl; and a lower alkoxycarbonyl group substituted by a halogen or tri(lower alkyl)silyl group, such as 2,2,2-trichloroethoxycarbonyl and 2-trimethylsilylethoxycarbonyl; an "alkenyloxycarbonyl group" such as vinyloxycarbonyl and allyloxycarbonyl; or an "aralkyloxycarbonyl group in which the aryl ring may be substituted by one or two lower alkoxy or nitro groups" such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl, and is preferably an aliphatic acyl group, more preferably an alkylcarbonyl group, an aminated alkylcarbonyl group, or a carboxylated alkylcarbonyl group and more preferably an acetyl, morpholin-4-ylacetyl, or succinoyl group.

The $C_1$-$C_6$ hydroxyalkyl group of the aforementioned "$C_1$-$C_6$ hydroxyalkyl group that may be protected by a hydroxyl protecting group" is a group in which the aforementioned $C_1$-$C_6$ alkyl group is substituted by a hydroxyl group that is protected or not protected by a hydroxyl protecting group and is, for example, a hydroxymethyl, 1-hydroxyethyl, 2-hydroxyethyl, 3-hydroxypropyl, 2-hydroxypropyl, 1-hydroxypropyl, 1-hydroxy-1-methylethyl, 4-hydroxybutyl, 3-hydroxybutyl, 2-hydroxybutyl, 1-hydroxybutyl, 1-hydroxy-1-methylpropyl, 2-hydroxy-2-methylpropyl, 4-hydroxybutyl, 5-hydroxypentyl, 6-hydroxyhexyl, or 5-hydroxyhexyl group and preferably a hydroxymethyl, 2-hydroxyethyl, 3-hydroxypropyl, or 4-hydroxybutyl group.

The $C_3$-$C_6$ cycloalkyl-$C_1$-$C_6$ alkyl group of the aforementioned "$C_3$-$C_6$ cycloalkyl-$C_1$-$C_6$ alkyl group that may be substituted by a hydroxyl group" is, for example, a $C_1$-$C_6$ alkyl group substituted by a $C_3$-$C_6$ cycloalkyl group, such as a cyclopropylmethyl, 2-cyclopropylethyl, 3-cyclopropylpropyl, 4-cyclopropylbutyl, 5-cyclopropylpentyl, 6-cyclopropylhexyl, cyclobutylmethyl, 2-cyclobutylethyl, 3-cyclobutylpropyl, cyclopentylmethyl, 2-cyclopentylethyl, cyclohexylmethyl, and 2-cyclohexylethyl, or a $C_1$-$C_6$ alkyl group comprising a $C_3$-$C_6$ cycloalkyl, such as (1-methylcyclopropyl)methyl, (1-methylcyclopropyl)ethyl, (1-ethylcyclopropyl)methyl, (1-ethylcyclopropyl)ethyl, (1-methylcyclohexyl)methyl, and (1-methylcyclohexyl)ethyl, and is preferably cyclopropylmethyl or 2-cyclopropylethyl. The aforementioned "$C_3$-$C_6$ cycloalkyl-$C_1$-$C_6$ alkyl group that may be substituted by a hydroxyl group" is preferably a (cyclopropyl)methyl, (1-hydroxycyclopropyl)methyl, or 2-(1-hydroxycyclopropyl)ethyl group.

The $C_3$-$C_6$ cycloalkyl group of the aforementioned "$C_3$-$C_6$ cycloalkyl group that may be substituted by a group selected from Substituent Group α", "$C_3$-$C_6$ cycloalkyl group", and "$C_3$-$C_6$ cycloalkyl group that may be substituted by a group selected from Substituent Group γ" is, for example, a cyclopropyl group, a cyclobutyl group, a cyclopentyl group, or a cyclohexyl group.

The term "may be substituted" in the aforementioned "$C_3$-$C_6$ cycloalkyl group that may be substituted by a group selected from Substituent Group α" and "$C_3$-$C_6$ cycloalkyl group that may be substituted by a group selected from Substituent Group γ" means unsubstituted or mono- to tri-substituted.

The aforementioned "$C_1$-$C_6$ alkylamino group" is an amino group monosubstituted by the aforementioned $C_1$-$C_6$ alkyl group and is, for example, an amino group monosubstituted by a linear or branched alkyl group having one to six carbon atoms, and is preferably a methylamino group, an ethylamino group, a propylamino group, an isopropylamino group, or a butylamino group and more preferably a methylamino group, an ethylamino group, or a propylamino group.

The aforementioned "$C_1$-$C_6$ dialkylamino group" is an amino group disubstituted by the aforementioned $C_1$-$C_6$ alkyl group(s) and is, for example, an amino group disubstituted by a linear or branched alkyl group(s) having one to six carbon atoms, and is preferably a dimethylamino group, a diethylamino group, a dipropylamino group, a diisopropylamino group, or a dibutylamino group and more preferably a dimethylamino group or a diethylamino group.

The aforementioned "$C_3$-$C_6$ cycloalkylamino group" is, for example, a cyclopropylamino group, a cyclobutylamino group, a cyclopentylamino group, or a cyclohexylamino group, and is preferably a cyclopentylamino group or a cyclohexylamino group.

The aforementioned "$C_1$-$C_6$ haloalkyl group" is a group in which the aforementioned $C_1$-$C_6$ alkyl group is substituted by a halogen atom(s) and is, for example, a fluoromethyl group, a difluoromethyl group, a trifluoromethyl group, a fluoroethyl group, a difluoroethyl group, a trifluoroethyl group, a fluoropropyl group, a difluoropropyl group, a trifluoropropyl group, a fluorobutyl group, a difluorobutyl group, a trifluorobutyl group, a fluoropentyl group, a difluoropentyl group, a trifluoropentyl group, a fluorohexyl group, a difluorohexyl group, a trifluorohexyl group, a pentafluoroethyl group, a hexafluoropropyl group, a nonafluorobutyl group, a chloromethyl group, a dichloromethyl group, a trichloromethyl group, a chloroethyl group, a dichloroethyl group, a trichloroethyl group, a chloropropyl group, a dichloropropyl group, a trichloropropyl group, a chlorobutyl group, a dichlorobutyl group, a trichlorobutyl group, a chloropentyl group, a dichloropentyl group, a trichloropentyl group, a chlorohexyl group, a dichlorohexyl group, a trichlorohexyl group, a pentachloroethyl group, a hexachloropropyl group, or a nonachlorobutyl group; and is preferably a fluoromethyl group, a difluoromethyl group, a trifluoromethyl group, a fluoroethyl group, a difluoroethyl group, a trifluoroethyl group, a fluoropropyl group, a difluoropropyl group, or a trifluoropropyl group and more preferably a fluoromethyl group, a difluoromethyl group, a trifluoromethyl group, a fluoroethyl group, a difluoroethyl group, or a trifluoroethyl group.

The aforementioned "$C_3$-$C_6$ cycloalkenyl group" is, for example, a cyclopropenyl group, a cyclobutenyl group, a cyclopentenyl group, or a cyclohexyl group, and is preferably a cyclopentenyl group or a cyclohexyl group.

The aforementioned "$C_1$-$C_6$ haloalkoxy group" is a group in which the aforementioned $C_1$-$C_6$ haloalkyl group is substituted by an oxygen atom at the alkyl terminus and is, for example, a fluoromethoxy group, a difluoromethoxy group, a trifluoromethoxy group, a fluoroethoxy group, a difluoroethoxy group, a trifluoroethoxy group, a fluoropropoxy group, a difluoropropoxy group, a trifluoropropoxy group, a fluorobutoxy group, a difluorobutoxy group, a trifluorobutoxy group, a fluoropentyloxy group, a difluoropentyloxy group, a trifluoropentyloxy group, a fluorohexyloxy group, a difluorohexyloxy group, a trifluorohexyloxy group, a pentafluoroethoxy group, a hexafluoropropoxy group, a nonafluorobutoxy group, a chloromethoxy group, a dichloromethoxy group, a trichloromethoxy group, a chloroethoxy group, a dichloroethoxy group, a trichloroethoxy group, a chloropropoxy group, a dichloropropoxy group, a trichloropropoxy group, a chlorobutoxy group, a dichlorobutoxy group, a trichlorobutoxy group, a chloropentyloxy group, a dichloropentyloxy group, a trichloropentyloxy group, a chlorohexyloxy group, a dichlorohexyloxy group, a trichlorohexyloxy group, a pentachloroethoxy group, a hexachloropropoxy group, or a nonachlorobutoxy group; and is preferably a fluoromethoxy group, a difluoromethoxy group, a trifluoromethoxy group, a fluoroethoxy group, a difluoroethoxy group, a trifluoroethoxy group, a fluoropropoxy group, a difluoropropoxy group, or a trifluoropropoxy group and more preferably a fluoromethoxy group, a difluoromethoxy group, a trifluoromethoxy group, a fluoroethoxy group, a difluoroethoxy group, or a trifluoroethoxy group.

The $C_1$-$C_6$ alkoxy-$C_1$-$C_6$ alkoxy group in the definition of the aforementioned "$C_1$-$C_6$ alkoxy-$C_1$-$C_6$ alkoxy group that may be substituted by a group selected from Substituent Group β" is the aforementioned $C_1$-$C_6$ alkoxy group monosubstituted by the aforementioned $C_1$-$C_6$ alkoxy group and is, for example, a methoxymethoxy group, a 2-methoxyethoxy group, a 3-methoxypropoxy group, a 4-methoxybutoxy group, a 5-methoxypentyloxy group, a 6-methoxyhexyloxy group, an ethoxymethoxy group, a 2-ethoxyethoxy group, a 3-ethoxypropoxy group, a 4-ethoxybutoxy group, a 5-ethoxypentyloxy group, or a 6-ethoxyhexyloxy group; and is preferably a 2-methoxyethoxy group, a 3-methoxypropoxy group, a 4-methoxybutoxy group, or a 5-methoxypentyloxy group.

The aforementioned "$C_1$-$C_6$ alkoxy-$C_1$-$C_6$ alkyl group" is a group in which the aforementioned $C_1$-$C_6$ alkyl group is monosubstituted by the aforementioned $C_1$-$C_6$ alkoxy group and is, for example, a methoxymethyl group, a 2-methoxyethyl group, a 3-methoxypropyl group, a 4-methoxybutyl group, a 5-methoxypentyl group, a 6-methoxyhexyl group, an ethoxymethyl group, a 2-ethoxyethyl group, a 3-ethoxypropyl group, a 4-ethoxybutyl group, a 5-ethoxypentyl group, or a 6-ethoxyhexyl group; and is preferably a 2-methoxyethyl group, a 3-methoxypropyl group, a 4-methoxybutyl group, or a 5-methoxypentyl group.

The $C_2$-$C_6$ alkenyl group in the definition of the aforementioned "$C_2$-$C_6$ alkenyl group that may be substituted by a group selected from Substituent Group α" and "$C_2$-$C_6$ alkenyl group that may be substituted by a group selected from Substituent Group γ" is, for example, a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, or a 5-hexenyl group; and is preferably a 1-propenyl group, a 2-propenyl group, a 1-butenyl group, a 2-butenyl group, or a 3-butenyl group.

The $C_2$-$C_6$ alkenyloxy group in the definition of the aforementioned "$C_2$-$C_6$ alkenyloxy group" and "$C_2$-$C_6$ alkenyloxy group that may be substituted by a group selected from Substituent Group β" is, for example, a vinyloxy group, a 1-propenyloxy group, a 2-propenyloxy group, a 1-butenyloxy group, a 2-butenyloxy group, a 3-butenyloxy group, a 1-pentenyloxy group, a 2-pentenyloxy group, a 3-pentenyloxy group, a 4-pentenyloxy group, a 1-hexenyloxy group, a 2-hexenyloxy group, a 3-hexenyloxy group, a 4-hexenyloxy group, or a 5-hexenyloxy group; and is preferably a 1-propenyloxy group, a 2-propenyloxy group, a 1-butenyloxy group, a 2-butenyloxy group, or a 3-butenyloxy group.

The $C_2$-$C_6$ alkynyl group in the definition of the aforementioned "$C_2$-$C_6$ alkynyl group that may be substituted by a group selected from Substituent Group γ" is an acetylene group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, or a 5-hexynyl group; and is preferably a 1-propynyl group, a 2-propynyl group, a 1-butynyl group, a 2-butynyl group, or a 3-butynyl group.

The $C_2$-$C_6$ alkynyloxy group in the definition of the aforementioned "$C_2$-$C_6$ alkynyloxy group that may be substituted by groups selected from Substituent Group β" is, for example, a 1-propynyloxy group, a 2-propynyloxy group, a 1-butynyloxy group, a 2-butynyloxy group, a 3-butynyloxy group, a 1-pentynyloxy group, a 2-pentynyloxy group, a 3-pentynyloxy group, a 4-pentynyloxy group, a 1-hexynyloxy group, a 2-hexynyloxy group, a 3-hexynyloxy group, a 4-hexynyloxy group, or a 5-hexynyloxy group; and is preferably a 1-propynyloxy group, a 2-propynyloxy group, a 1-butynyloxy group, a 2-butynyloxy group, or a 3-butynyloxy group.

The term "may be substituted" in the aforementioned "$C_1$-$C_6$ alkoxy-$C_1$-$C_6$ alkoxy group that may be substituted by a group selected from Substituent Group β", "$C_2$-$C_6$ alkenyloxy group that may be substituted by a group selected from Substituent Group β", and "$C_2$-$C_6$ alkynyloxy group that may be substituted by a group selected from Substituent Group β" means unsubstituted or mono- to tri-substituted.

The aforementioned "$C_3$-$C_6$ cycloalkyloxy group" is a group in which an oxygen atom is bound to the aforementioned $C_3$-$C_6$ cycloalkyl group and is, a cyclopropoxy group, a cyclobutoxy group, a cyclopentyloxy group, or a cyclohexyloxy group; and is preferably a cyclopropoxy group, a cyclobutoxy group, or a cyclopentyloxy group.

The aforementioned "halogen atom" is, for example, a fluorine atom, a chlorine atom, a bromine atom, or an iodine atom and is preferably a fluorine atom or a chlorine atom.

The aforementioned "$C_1$-$C_3$ alkyl group" is, for example, a methyl group, an ethyl group, or a propyl group and is preferably a methyl group.

The aforementioned "$C_1$-$C_3$ haloalkyl group" is, for example, a fluoromethyl group, a difluoromethyl group, or a trifluoromethyl group and is preferably a trifluoromethyl group.

The aforementioned "$C_1$-$C_3$ alkoxy group" is, for example, a methoxy group, an ethoxy group, or a propoxy group and is preferably a methoxy group.

The aforementioned "3- to 6-membered heterocyclyloxy group" is a group in which an oxygen atom is bound to a cyclic group composed of three to six carbon atoms and a nitrogen atom, an oxygen atom, and/or a sulfur atom and is, for example, an aziridinyloxy group, an azetidinyloxy group, a pyrrodinyloxy group, a piperidinyloxy group, a thiranyloxy group, a thienyloxy group, a tetrahydrothienyloxy group, a tetrahydrothiopyranyloxy group, an oxiranyloxy group, an oxetanyloxy group, a tetrahydrofuryloxy group, or a tetrahydropyranyloxy group; and is preferably a tetrahydrofuryloxy group or a tetrahydropyranyloxy group.

The $C_6$-$C_{10}$ aryloxy group of the aforementioned "$C_6$-$C_{10}$ aryloxy group that may be substituted by a group selected from Substituent Group γ" is a group in which an oxygen atom is bound to the aforementioned $C_6$-$C_{10}$ aryl group and is, for example, a phenoxy group, an indenyloxy group, or a naphthyloxy group; and is preferably a phenoxy group.

The term "may be substituted" in the "$C_6$-$C_{10}$ aryloxy group that may be substituted by a group selected from Substituent Group γ" means unsubstituted or mono- to tri-substituted.

The aforementioned "$C_1$-$C_6$ alkyleneoxy group" is, for example, an ethyleneoxy group, a trimethyleneoxy group, a tetramethyleneoxy group, a pentamethyleneoxy group, or a hexamethyleneoxy group and is preferably an ethyleneoxy group or a trimethyleneoxy group.

The aforementioned "$C_1$-$C_6$ alkylenedioxy group" is, for example, a methylenedioxy group, an ethylenedioxy group, a trimethylenedioxy group, a tetramethylenedioxy group, a pentamethylenedioxy group, or a hexamethylenedioxy group and is preferably a methylenedioxy group or an ethylenedioxy group.

The aforementioned $C_1$-$C_6$ alkylthio group in the definition of the aforementioned "$C_1$-$C_6$ alkylthio group" and "$C_1$-$C_6$ alkylthio group that may be substituted by a group selected from Substituent Group β" is a group in which a sulfur atom is bound to the aforementioned $C_1$-$C_6$ alkyl group and is preferably a methylthio group, an ethylthio group, a propylthio group, an isopropylthio group, or a butylthio group and more preferably a methylthio group or an ethylthio group.

The term "may be substituted" in the aforementioned "$C_1$-$C_6$ alkylthio group that may be substituted by a group selected from Substituent Group β" means unsubstituted or mono- to tri-substituted.

The aforementioned "$C_1$-$C_6$ haloalkylthio group" is a group in which the aforementioned $C_1$-$C_6$ alkylthio group is substituted by a halogen atom(s) and is, for example, a fluoromethylthio group, a difluoromethylthio group, a trifluoromethylthio group, a fluoroethylthio group, a difluoroethylthio group, a trifluoroethylthio group, a fluoropropylthio group, a difluoropropylthio group, a trifluoropropylthio group, a fluorobutylthio group, a difluorobutylthio group, a trifluorobutylthio group, a fluoropentylthio group, a difluoropentylthio group, a trifluoropentylthio group, a fluorohexylthio group, a difluorohexylthio group, a trifluorohexylthio group, a pentafluoroethylthio group, a hexafluoropropylthio group, a nonafluorobutylthio group, a chloromethylthio group, a dichloromethylthio group, a trichloromethylthio group, a chloroethylthio group, a dichloroethylthio group, a trichloroethylthio group, a chloropropylthio group, a dichloropropylthio group, a trichloropropylthio group, a chlorobutylthio group, a dichlorobutylthio group, a trichlorobutylthio group, a chloropentylthio group, a dichloropentylthio group, a trichloropentylthio group, a chlorohexylthio group, a dichlorohexylthio group, a trichlorohexylthio group, a pentachloroethylthio group, a hexachloropropylthio group, or a nonachlorobutylthio group; and is preferably a fluoromethylthio group, a difluoromethylthio group, a trifluoromethylthio group, a fluoroethylthio group, a difluoroethylthio group, a trifluoroethylthio group, a fluoropropylthio group, a difluoropropylthio group, or a trifluoropropylthio group.

The $C_1$-$C_6$ alkylsulfonyl group in the definition of the aforementioned "$C_1$-$C_6$ alkylsulfonyl group that may be substituted by a group selected from Substituent Group β" is a group in which a sulfonyl group is bound to the aforementioned $C_1$-$C_6$ alkyl group and is preferably a methylsulfonyl group, an ethylsulfonyl group, a propylsulfonyl group, an isopropylsulfonyl group, or a butylsulfonyl group and more preferably a methylsulfonyl group or an ethylsulfonyl group.

The term "may be substituted" in the aforementioned "$C_1$-$C_6$ alkylsulfonyl group that may be substituted by a group selected from Substituent Group β" means unsubstituted or mono- to tri-substituted.

The aforementioned "$C_1$-$C_6$ haloalkylsulfonyl group" is a group in which the aforementioned $C_1$-$C_6$ alkylsulfonyl group is substituted by a halogen atom(s) and is, for example, a fluoromethylsulfonyl group, a difluoromethylsulfonyl group, a trifluoromethylsulfonyl group, a fluoroethylsulfonyl group, a difluoroethylsulfonyl group, a trifluoroethylsulfonyl group, a fluoropropylsulfonyl group, a difluoropropylsulfonyl group, a trifluoropropylsulfonyl group, a fluorobutylsulfonyl group, a difluorobutylsulfonyl group, a trifluorobutylsulfonyl group, a fluoropentylsulfonyl group, a difluoropentylsulfonyl group, a trifluoropentylsulfonyl group, a fluorohexylsulfonyl group, a difluorohexylsulfonyl group, a trifluorohexylsulfonyl group, a pentafluoroethylsulfonyl group, a hexafluoropropylsulfonyl group, a nonafluorobutylsulfonyl group, a chloromethylsulfonyl group, a dichloromethylsulfonyl group, a trichloromethylsulfonyl group, a chloroethylsulfonyl group, a dichloroethylsulfonyl group, a trichloroethylsulfonyl group, a chloropropylsulfonyl group, a dichloropropylsulfonyl group, a trichloropropylsulfonyl group, a chlorobutylsulfonyl group, a dichlorobutylsulfonyl group, a trichlorobutylsulfonyl group, a chloropentylsulfonyl group, a dichloropentylsulfonyl group, a trichloropentylsulfonyl group, a chlorohexylsulfonyl group, a dichlorohexylsulfonyl group, a trichlorohexylsulfonyl group, a pentachloroethylsulfonyl group, a hexachloropropylsulfonyl group, or a nonachlorobutylsulfonyl group; and is preferably a fluoromethylsulfonyl group, a difluoromethylsulfonyl group, a trifluoromethylsulfonyl group, a fluoroethylsulfonyl group, a difluoroethylsulfonyl group, a trifluoroethylsulfonyl group, a fluoropropylsulfonyl group, a difluoropropylsulfonyl group, or a trifluoropropylsulfonyl group.

The $C_1$-$C_6$ alkylcarbonyl group in the definition of the aforementioned "$C_1$-$C_6$ alkylcarbonyl group that may be substituted by a group selected from Substituent Group β" is a group in which a carbonyl group is bound to the aforementioned $C_1$-$C_6$ alkyl group and is, for example, an acetyl group, an ethylcarbonyl group, a propylcarbonyl group, a butylcarbonyl group, a pentylcarbonyl group, or a hexylcarbonyl group; and is preferably an acetyl group, an ethylcarbonyl group, or a propylcarbonyl group.

The term "may be substituted" in the aforementioned "$C_1$-$C_6$ alkylcarbonyl group that may be substituted by a group selected from Substituent Group β" means unsubstituted or mono- to tri-substituted.

The aforementioned "$C_1$-$C_6$ haloalkylcarbonyl group" is a group in which a carbonyl group is bound to the aforementioned $C_1$-$C_6$ haloalkyl group and is, for example, a fluoromethylcarbonyl group, a difluoromethylcarbonyl group, a trifluoromethylcarbonyl group, a fluoroethylcarbonyl group, a difluoroethylcarbonyl group, a trifluoroethylcarbonyl group, a fluoropropylcarbonyl group, a difluoropropylcarbonyl group, a trifluoropropylcarbonyl group, a fluorobutylcarbonyl group, a difluorobutylcarbonyl group, a trifluorobutylcarbonyl group, a fluoropentylcarbonyl group, a difluoropentylcarbonyl group, a trifluoropentylcarbonyl group, a fluorohexylcarbonyl group, a difluorohexylcarbonyl group, a trifluorohexylcarbonyl group, a pentafluoroethylcarbonyl group, a hexafluoropropylcarbonyl group, a nonafluorobutylcarbonyl group, a chloromethylcarbonyl group, a dichloromethylcarbonyl group, a trichloromethylcarbonyl group, a chloroethylcarbonyl group, a dichloroethylcarbonyl group, a trichloroethylcarbonyl group, a chloropropylcarbonyl group, a dichloropropylcarbonyl group, a trichloropropylcarbonyl group, a chlorobutylcarbonyl group, a dichlorobutylcarbonyl group, a trichlorobutylcarbonyl group, a chloropentylcarbonyl group, a dichloropentylcarbonyl group, a trichloropentylcarbonyl group, a chlorohexylcarbonyl group, a dichlorohexylcarbonyl group, a trichlorohexylcarbonyl group, a pentachloroethylcarbonyl group, a hexachloropropylcarbonyl group, or a nonachlorobutylcarbonyl group; and is preferably a fluoromethylcarbonyl group, a difluoromethylcarbonyl group, a trifluoromethylcarbonyl group, a fluoroethylcarbonyl group, a difluoroethylcarbonyl group, a trifluoroethylcarbonyl group, a fluoropropylcarbonyl group, a difluoropropylcarbonyl group, or a trifluoropropylcarbonyl group.

The $C_6$-$C_{10}$ arylcarbonyl group of the aforementioned "$C_6$-$C_{10}$ arylcarbonyl group that may be substituted by a group selected from Substituent Group γ" is a group in which a carbonyl group is bound to the aforementioned $C_6$-$C_{10}$ aryl group and is, for example, a benzoyl group, an indenylcarbonyl group, or a naphthylcarbonyl group; and is preferably a benzoyl group.

The term "may be substituted" in the aforementioned "$C_6$-$C_{10}$ arylcarbonyl group that may be substituted by a group selected from Substituent Group γ" means unsubstituted or mono- to tri-substituted.

The aforementioned "$C_1$-$C_6$ alkoxycarbonyl group" is a group in which a carbonyl group is bound to the aforementioned $C_1$-$C_6$ alkoxy group and is, for example, a linear or branched alkoxycarbonyl group having one to six carbon atoms; and is preferably a methoxycarbonyl group, an ethoxycarbonyl group, a propoxycarbonyl group, an isopropoxycarbonyl group, or a butoxycarbonyl group and more preferably a methoxycarbonyl group or an ethoxycarbonyl group.

The aforementioned "$C_2$-$C_6$ acyl group" is, for example, an acetyl group, a propanoyl group, a butanoyl group, a pentanoyl group, or a hexanoyl group and preferably an acetyl group.

The aforementioned "N—$C_6$-$C_{10}$ arylacetamido group" is an acetamido group substituted by the aforementioned $C_6$-$C_{10}$ aryl group on the nitrogen atom and is, for example, an N-phenylacetamido group, an N-indenylacetamido group, or an N-naphthylacetamido group; and is preferably an N-phenylacetamido group.

The aforementioned "$C_1$-$C_6$ alkoxycarbonylamido group" is a group in which an amino group is bound to the carbonyl group of the aforementioned $C_1$-$C_6$ alkoxycarbonyl group, and is, for example, a linear or branched alkoxycarbonylamido group having one to six carbon atoms and is preferably a methoxycarbonylamido group, an ethoxycarbonylamido group, a propoxycarbonylamido group, an isopropoxycarbonylamido group, or a butoxycarbonylamido group and more preferably a methoxycarbonylamido group or an ethoxycarbonylamido group.

The aforementioned "$C_2$-$C_6$ cyclic amino group" is, for example, an aziridine group, an azetidine group, a pyrrolidine group, or a piperidine group and preferably a pyrrolidine group or a piperidine group.

The oxime group of the aforementioned "oxime group that may be substituted by groups selected from Substituent Group γ" is a group in which the carbonyl oxygen atom of an aldehyde or ketone is substituted by an oximino group ($=NO^-$).

The aforementioned "$C_2$-$C_6$ acyloxy group" is, for example, an acetoxy group, a propanoyloxy group, a butanoyloxy group, a pentanoyloxy group, or a hexanoyloxy group and is preferably an acetoxy group.

The aforementioned term "bone metabolic disease" means a disease characterized by a substantial decrease in bone mass or an increase in blood calcium concentration or a disease that requires suppression of bone resorption or the rate of bone resorption for their prophylaxis or treatment.

Examples of such bone metabolic disease include osteoporosis, hypercalcemia, bone metastasis of cancer, periodontal diseases, bone Paget's disease, and osteoarthrosis.

The aforementioned "osteoporosis" is, for example, postmenopausal osteoporosis, senile osteoporosis, secondary osteoporosis caused by steroid or immunosuppressive agent use, osteoclasis or osteopenia in rheumatoid arthritis, or osteopenia due to artificial joint replacement.

The aforementioned term "treating" means to cure or improve a disease or a symptom or to suppress a symptom.

The term "pharmacologically acceptable salt" means a basic salt or an acid salt produced by a reaction of a compound having General Formula (I) of the present invention with a base or an acid, when the compound has an acidic group or a basic group.

The pharmacologically acceptable "basic salt" of the compound having General Formula (I) of the present invention is preferably an alkali metal salt such as a sodium salt, a potassium salt, or a lithium salt; an alkaline-earth metal salt such as a magnesium salt or a calcium salt; an organic basic salt such as an N-methylmorpholine salt, a triethylamine salt, a tributylamine salt, a diisopropylethylamine salt, a dicyclohexylamine salt, an N-methylpiperidine salt, a pyridine salt, a 4-pyrrolidinopyridine salt, or a picoline salt; or an amino acid salt such as a glycine salt, a lysine salt, an arginine salt, an ornithine salt, a glutamate, or an aspartate, and preferably an alkali metal salt.

The pharmacologically acceptable "acid salt" of the compound having General Formula (I) of the present invention is preferably an inorganic acid salt, for example, a hydrohalide such as hydrofluoride, hydrochloride, hydrobromide, or hydroiodide, nitrate, perchlorate, sulfate, or phosphate; an organic acid salt, for example, a lower alkanesulfonate such as methanesulfonate, trifluoromethanesulfonate, or ethanesulfonate, an arylsulfonate such as benzenesulfonate or p-toluenesulfonate, acetate, malate, fumarate, succinate, citrate, ascorbate, tartrate, oxalate, or maleate; and an amino acid salt such as a glycine salt, a lysine salt, an arginine salt, an ornithine salt, a glutamate, or an aspartate, and more preferably a hydrohalide.

The compound having General Formula (I) or a pharmacologically acceptable salt thereof according to the present invention may become a hydrate by absorbing moisture or being attached with water when left in the air or recrystallized, and such a hydrate is included in the present invention.

The compound having General Formula (I) or the pharmacologically acceptable salt thereof according to the present invention has an asymmetric carbon atom due to the α-substituted α-amino acid in the central structure of the molecule and thereby has optical isomers. In the compound according to the present invention, all optical isomers and mixtures thereof are represented by a single formula, namely, General Formula (I). Therefore, the present invention includes all these optical isomers and mixtures comprising the optical isomers at any proportion. However, an optical isomer of which the absolute configuration of the asymmetric carbon is S configuration is preferred. A mixture of these isomers can be separated by a known separation method.

The present invention also includes the compounds having General Formula (I) and being labeled with an isotope (for example, $^{3}H$, $^{14}C$, or $^{35}S$).

Preferable examples of the compound having General Formula (I) of the present invention are, for example, compounds having Formula (I-1) described in the following Table 4, but the present invention is not limited to these compounds.

In the Table, substituents are denoted by the following abbreviations. Some substituents are represented by a combination of an abbreviation(s) and an atomic symbol(s). For example, (1-Me-cPr)CH2O denotes a [1-methyl(cyclopropyl)]methoxy group. In addition, (R) denotes that the absolute configuration of an asymmetric carbon of a substituent is R, and (S) denotes that the absolute configuration of an asymmetric carbon of a substituent is S.

di di
c cyclo
iso
Me methyl group
Et ethyl group
Pr propyl group
Bu butyl group
Pn pentyl group
Ph phenyl group
Ac acetyl group
HO hydroxyl group
1-pyrr pyrrol-1-yl group
CH2 methylene group
CHCH vinylene group
CHF2 difluoromethyl group
CF3 trifluoromethyl group

TABLE 4

Exemplary compound table 1

(I-1)

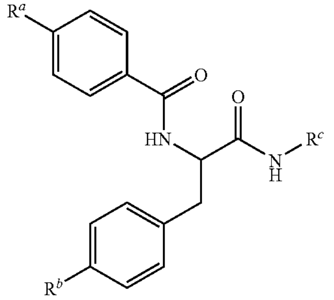

| Compound No. | $R^a$ | $R^b$ | $R^c$ |
|---|---|---|---|
| 1 | cPnO | cPrO | CH2CH2OH |
| 2 | cPnO | cPr | CH2CH2OH |
| 3 | cPnO | CHF2O | CH2CH2OH |
| 4 | cPnO | CF3O | CH2CH2OH |
| 5 | cPnO | CF3 | CH2CH2OH |
| 6 | iBuO | cPrO | CH2CH2OH |
| 7 | iBuO | iPrO | CH2CH2OH |
| 8 | iBuO | CHF2O | CH2CH2OH |
| 9 | iBuO | CF3O | CH2CH2OH |
| 10 | iBuO | CF3 | CH2CH2OH |
| 11 | cBuCH2O | cPrO | CH2CH2OH |
| 12 | cBuCH2O | cPr | CH2CH2OH |
| 13 | cBuCH2O | CHF2O | CH2CH2OH |
| 14 | cBuCH2O | CF3O | CH2CH2OH |
| 15 | cBuCH2O | CF3 | CH2CH2OH |
| 16 | cPrCH2O | cPrO | CH2CH2OH |
| 17 | cPrCH2O | cPr | CH2CH2OH |
| 18 | cPrCH2O | CHF2O | CH2CH2OH |
| 19 | cPrCH2O | CF3O | CH2CH2OH |
| 20 | cPrCH2O | CF3 | CH2CH2OH |
| 21 | cPrCH2O | iPrO | CH2CH2OH |
| 22 | cPrCH2O | iPr | CH2CH2OH |
| 23 | cPrCH2O | CHF2CH2O | CH2CH2OH |
| 24 | cPrCH2O | CF3CH2O | CH2CH2OH |
| 25 | cPrCH2O | EtO | CH2CH2OH |
| 26 | cPrCH2O | Et | CH2CH2OH |
| 27 | cPrCH2O | Pr | CH2CH2OH |
| 28 | cPrCH2O | MeS | CH2CH2OH |
| 29 | cPrCH2O | CF3S | CH2CH2OH |
| 30 | cPrCH2O | 1-pyrr | CH2CH2OH |
| 31 | (1-Me-cPr)CH2O | cPrO | CH2CH2OH |
| 32 | (1-Me-cPr)CH2O | cPr | CH2CH2OH |
| 33 | (1-Me-cPr)CH2O | CHF2O | CH2CH2OH |
| 34 | (1-Me-cPr)CH2O | CF3O | CH2CH2OH |
| 35 | (1-Me-cPr)CH2O | CF3 | CH2CH2OH |
| 36 | cPrCH2CH2O | cPrO | CH2CH2OH |
| 37 | cPrCH2CH2O | cPr | CH2CH2OH |
| 38 | cPrCH2CH2O | CHF2O | CH2CH2OH |

TABLE 4-continued

Exemplary compound table 1

(I-1)

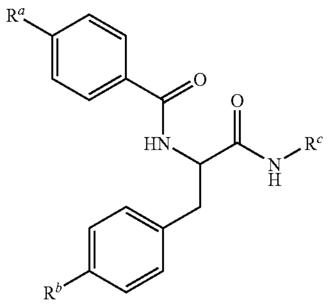

| Compound No. | $R^a$ | $R^b$ | $R^c$ |
|---|---|---|---|
| 39 | cPrCH2CH2O | CF3O | CH2CH2OH |
| 40 | cPrCH2CH2O | CF3 | CH2CH2OH |
| 41 | cPrCH2CH2O | iPrO | CH2CH2OH |
| 42 | cPrCH2CH2O | iPr | CH2CH2OH |
| 43 | cPrCH2CH2O | CHF2CH2O | CH2CH2OH |
| 44 | cPrCH2CH2O | CF3CH2O | CH2CH2OH |
| 45 | cPrCH2CH2O | EtO | CH2CH2OH |
| 46 | cPrCH2CH2O | Et | CH2CH2OH |
| 47 | cPrCH2CH2O | Pr | CH2CH2OH |
| 48 | cPrCH2CH2O | MeS | CH2CH2OH |
| 49 | cPrCH2CH2O | CF3S | CH2CH2OH |
| 50 | cPrCH2CH2O | 1-pyrr | CH2CH2OH |
| 51 | cPrCH2CH2CH2O | cPrO | CH2CH2OH |
| 52 | cPrCH2CH2CH2O | cPr | CH2CH2OH |
| 53 | cPrCH2CH2CH2O | CHF2O | CH2CH2OH |
| 54 | cPrCH2CH2CH2O | CF3O | CH2CH2OH |
| 55 | cPrCH2CH2CH2O | CF3 | CH2CH2OH |
| 56 | cPrCH2CH2CH2O | iPrO | CH2CH2OH |
| 57 | cPrCH2CH2CH2O | iPr | CH2CH2OH |
| 58 | cPrCH2CH2CH2O | CHF2CH2O | CH2CH2OH |
| 59 | cPrCH2CH2CH2O | CF3CH2O | CH2CH2OH |
| 60 | cPrCH2CH2CH2O | EtO | CH2CH2OH |
| 61 | cPrCH2CH2CH2O | Et | CH2CH2OH |
| 62 | cPrCH2CH2CH2O | Pr | CH2CH2OH |
| 63 | cPrCH2CH2CH2O | MeS | CH2CH2OH |
| 64 | cPrCH2CH2CH2O | CF3S | CH2CH2OH |
| 65 | cPrCH2CH2CH2O | 1-pyrr | CH2CH2OH |
| 66 | cPnCH2O | cPrO | CH2CH2OH |
| 67 | cPnCH2O | cPr | CH2CH2OH |
| 68 | cPnCH2O | CHF2O | CH2CH2OH |
| 69 | cPnCH2O | CF3O | CH2CH2OH |
| 70 | cPnCH2O | CF3 | CH2CH2OH |
| 71 | cPnCH2CH2O | cPrO | CH2CH2OH |
| 72 | cPnCH2CH2O | cPr | CH2CH2OH |
| 73 | cPnCH2CH2O | CHF2O | CH2CH2OH |
| 74 | cPnCH2CH2O | CF3O | CH2CH2OH |
| 75 | cPnCH2CH2O | CF3 | CH2CH2OH |
| 76 | PhCH2CH2O | cPrO | CH2CH2OH |
| 77 | PhCH2CH2O | cPr | CH2CH2OH |
| 78 | PhCH2CH2O | CHF2O | CH2CH2OH |
| 79 | PhCH2CH2O | CF3O | CH2CH2OH |
| 80 | PhCH2CH2O | CF3 | CH2CH2OH |
| 81 | 4-MeO-PhCH2CH2O | cPrO | CH2CH2OH |
| 82 | 4-MeO-PhCH2CH2O | CHF2CH2O | CH2CH2OH |
| 83 | 4-MeO-PhCH2CH2O | CHF2O | CH2CH2OH |
| 84 | 4-MeO-PhCH2CH2O | CF3O | CH2CH2OH |
| 85 | 4-MeO-PhCH2CH2O | CF3 | CH2CH2OH |
| 86 | 4-Cl-PhCH2CH2O | cPrO | CH2CH2OH |
| 87 | 4-Cl-PhCH2CH2O | cPr | CH2CH2OH |
| 88 | 4-Cl-PhCH2CH2O | CHF2O | CH2CH2OH |
| 89 | 4-Cl-PhCH2CH2O | CF3O | CH2CH2OH |
| 90 | 4-Cl-PhCH2CH2O | CF3 | CH2CH2OH |
| 91 | CF3CH2CH2O | cPrO | CH2CH2OH |
| 92 | CF3CH2CH2O | cPr | CH2CH2OH |
| 93 | CF3CH2CH2O | CHF2O | CH2CH2OH |
| 94 | CF3CH2CH2O | CF3O | CH2CH2OH |
| 95 | CF3CH2CH2O | CF3 | CH2CH2OH |
| 96 | CF3CH2CH2O | iPrO | CH2CH2OH |
| 97 | CF3CH2CH2O | iPr | CH2CH2OH |

TABLE 4-continued

Exemplary compound table 1

(I-1)

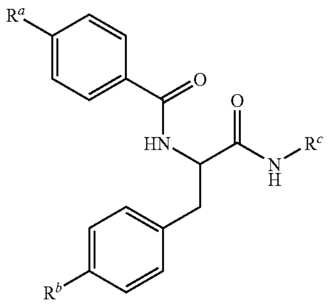

| Compound No. | $R^a$ | $R^b$ | $R^c$ |
|---|---|---|---|
| 98 | CF3CH2CH2O | CHF2CH2O | CH2CH2OH |
| 99 | CF3CH2CH2O | CF3CH2O | CH2CH2OH |
| 100 | CF3CH2CH2O | EtO | CH2CH2OH |
| 101 | CF3CH2CH2O | Et | CH2CH2OH |
| 102 | CF3CH2CH2O | Pr | CH2CH2OH |
| 103 | CF3CH2CH2O | MeS | CH2CH2OH |
| 104 | CF3CH2CH2O | CF3S | CH2CH2OH |
| 105 | CF3CH2CH2O | 1-pyrr | CH2CH2OH |
| 106 | CHF2CH2O | cPrO | CH2CH2OH |
| 107 | CHF2CH2O | cPr | CH2CH2OH |
| 108 | CHF2CH2O | CHF2O | CH2CH2OH |
| 109 | CHF2CH2O | CF3O | CH2CH2OH |
| 110 | CHF2CH2O | CF3 | CH2CH2OH |
| 111 | CHF2CH2O | iPrO | CH2CH2OH |
| 112 | CHF2CH2O | iPr | CH2CH2OH |
| 113 | CHF2CH2O | CHF2CH2O | CH2CH2OH |
| 114 | CHF2CH2O | CF3CH2O | CH2CH2OH |
| 115 | CHF2CH2O | EtO | CH2CH2OH |
| 116 | CHF2CH2O | Et | CH2CH2OH |
| 117 | CHF2CH2O | Pr | CH2CH2OH |
| 118 | CHF2CH2O | MeS | CH2CH2OH |
| 119 | CHF2CH2O | CF3S | CH2CH2OH |
| 120 | CHF2CH2O | 1-pyrr | CH2CH2OH |
| 121 | (E)-MeCHCHCH2O | cPrO | CH2CH2OH |
| 122 | (E)-MeCHCHCH2O | cPr | CH2CH2OH |
| 123 | (E)-MeCHCHCH2O | CHF2O | CH2CH2OH |
| 124 | (E)-MeCHCHCH2O | CF3O | CH2CH2OH |
| 125 | (E)-MeCHCHCH2O | CF3 | CH2CH2OH |
| 126 | (2,2-diF-cPr)CH2O | cPrO | CH2CH2OH |
| 127 | (2,2-diF-cPr)CH2O | cPr | CH2CH2OH |
| 128 | (2,2-diF-cPr)CH2O | CHF2O | CH2CH2OH |
| 129 | (2,2-diF-cPr)CH2O | CF3O | CH2CH2OH |
| 130 | (2,2-diF-cPr)CH2O | CF3 | CH2CH2OH |
| 131 | (2,2-diF-cPr)CH2O | iPrO | CH2CH2OH |
| 132 | (2,2-diF-cPr)CH2O | iPr | CH2CH2OH |
| 133 | (2,2-diF-cPr)CH2O | CHF2CH2O | CH2CH2OH |
| 134 | (2,2-diF-cPr)CH2O | CF3CH2O | CH2CH2OH |
| 135 | (2,2-diF-cPr)CH2O | EtO | CH2CH2OH |
| 136 | (2,2-diF-cPr)CH2O | Et | CH2CH2OH |
| 137 | (2,2-diF-cPr)CH2O | Pr | CH2CH2OH |
| 138 | (2,2-diF-cPr)CH2O | MeS | CH2CH2OH |
| 139 | (2,2-diF-cPr)CH2O | CF3S | CH2CH2OH |
| 140 | (2,2-diF-cPr)CH2O | 1-pyrr | CH2CH2OH |
| 141 | PrO | cPrO | CH2CH2OH |
| 142 | PrO | cPr | CH2CH2OH |
| 143 | PrO | CHF2O | CH2CH2OH |
| 144 | PrO | CF3O | CH2CH2OH |
| 145 | PrO | CF3 | CH2CH2OH |
| 146 | 4-CF3PhO | cPrO | CH2CH2OH |
| 147 | 4-CF3PhO | cPr | CH2CH2OH |
| 148 | 4-CF3PhO | CHF2O | CH2CH2OH |
| 149 | 4-CF3PhO | CF3O | CH2CH2OH |
| 150 | 4-CF3PhO | CF3 | CH2CH2OH |
| 151 | 4-CF3PhO | iPrO | CH2CH2OH |
| 152 | 4-CF3PhO | iPr | CH2CH2OH |
| 153 | 4-CF3PhO | CHF2CH2O | CH2CH2OH |
| 154 | 4-CF3PhO | CF3CH2O | CH2CH2OH |
| 155 | 4-CF3PhO | EtO | CH2CH2OH |
| 156 | 4-CF3PhO | Et | CH2CH2OH |

TABLE 4-continued

Exemplary compound table 1

(I-1)

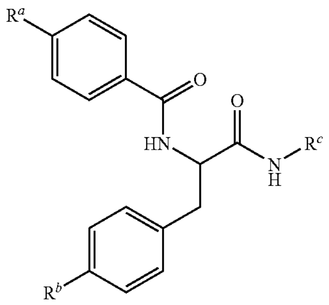

| Compound No. | $R^a$ | $R^b$ | $R^c$ |
|---|---|---|---|
| 157 | 4-CF3PhO | Pr | CH2CH2OH |
| 158 | 4-CF3PhO | MeS | CH2CH2OH |
| 159 | 4-CF3PhO | CF3S | CH2CH2OH |
| 160 | 4-CF3PhO | 1-pyrr | CH2CH2OH |
| 161 | 4-ClPhO | cPrO | CH2CH2OH |
| 162 | 4-ClPhO | cPr | CH2CH2OH |
| 163 | 4-ClPhO | CHF2O | CH2CH2OH |
| 164 | 4-ClPhO | CF3O | CH2CH2OH |
| 165 | 4-ClPhO | CF3 | CH2CH2OH |
| 166 | 3-ClPhO | cPrO | CH2CH2OH |
| 167 | 3-ClPhO | cPr | CH2CH2OH |
| 168 | 3-ClPhO | CHF2O | CH2CH2OH |
| 169 | 3-ClPhO | CF3O | CH2CH2OH |
| 170 | 3-ClPhO | CF3 | CH2CH2OH |
| 171 | 4-FPhO | cPrO | CH2CH2OH |
| 172 | 4-FPhO | cPr | CH2CH2OH |
| 173 | 4-FPhO | CHF2O | CH2CH2OH |
| 174 | 4-FPhO | CF3O | CH2CH2OH |
| 175 | 4-FPhO | CF3 | CH2CH2OH |
| 176 | 4-MeOPhO | cPrO | CH2CH2OH |
| 177 | 4-MeOPhO | cPr | CH2CH2OH |
| 178 | 4-MeOPhO | CHF2O | CH2CH2OH |
| 179 | 4-MeOPhO | CF3O | CH2CH2OH |
| 180 | 4-MeOPhO | CF3 | CH2CH2OH |
| 181 | cPnO | cPrO | CH2CH2CH2OH |
| 182 | cPnO | cPr | CH2CH2CH2OH |
| 183 | cPnO | CHF2O | CH2CH2CH2OH |
| 184 | cPnO | CF3O | CH2CH2CH2OH |
| 185 | cPnO | CF3 | CH2CH2CH2OH |
| 186 | iBuO | cPrO | CH2CH2CH2OH |
| 187 | iBuO | cPr | CH2CH2CH2OH |
| 188 | iBuO | CHF2O | CH2CH2CH2OH |
| 189 | iBuO | CF3O | CH2CH2CH2OH |
| 190 | iBuO | CF3 | CH2CH2CH2OH |
| 191 | cBuCH2O | cPrO | CH2CH2CH2OH |
| 192 | cBuCH2O | cPr | CH2CH2CH2OH |
| 193 | cBuCH2O | CHF2O | CH2CH2CH2OH |
| 194 | cBuCH2O | CF3O | CH2CH2CH2OH |
| 195 | cBuCH2O | CF3 | CH2CH2CH2OH |
| 196 | cPrCH2O | cPrO | CH2CH2CH2OH |
| 197 | cPrCH2O | cPr | CH2CH2CH2OH |
| 198 | cPrCH2O | CHF2O | CH2CH2CH2OH |
| 199 | cPrCH2O | CF3O | CH2CH2CH2OH |
| 200 | cPrCH2O | CF3 | CH2CH2CH2OH |
| 201 | cPrCH2O | iPrO | CH2CH2CH2OH |
| 202 | cPrCH2O | iPr | CH2CH2CH2OH |
| 203 | cPrCH2O | CHF2CH2O | CH2CH2CH2OH |
| 204 | cPrCH2O | CF3CH2O | CH2CH2CH2OH |
| 205 | cPrCH2O | EtO | CH2CH2CH2OH |
| 206 | cPrCH2O | Et | CH2CH2CH2OH |
| 207 | cPrCH2O | Pr | CH2CH2CH2OH |
| 208 | cPrCH2O | MeS | CH2CH2CH2OH |
| 209 | cPrCH2O | CF3S | CH2CH2CH2OH |
| 210 | cPrCH2O | 1-pyrr | CH2CH2CH2OH |
| 211 | (1-Me-cPr)CH2O | cPrO | CH2CH2CH2OH |
| 212 | (1-Me-cPr)CH2O | cPr | CH2CH2CH2OH |
| 213 | (1-Me-cPr)CH2O | CHF2O | CH2CH2CH2OH |
| 214 | (1-Me-cPr)CH2O | CF3O | CH2CH2CH2OH |
| 215 | (1-Me-cPr)CH2O | CF3 | CH2CH2CH2OH |

TABLE 4-continued

Exemplary compound table 1

(I-1)

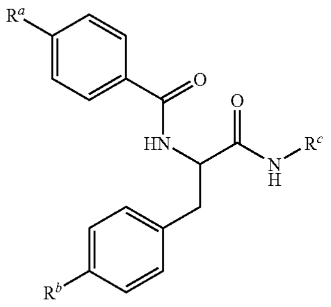

| Compound No. | $R^a$ | $R^b$ | $R^c$ |
|---|---|---|---|
| 216 | cPrCH2CH2O | cPrO | CH2CH2CH2OH |
| 217 | cPrCH2CH2O | cPr | CH2CH2CH2OH |
| 218 | cPrCH2CH2O | CHF2O | CH2CH2CH2OH |
| 219 | cPrCH2CH2O | CF3O | CH2CH2CH2OH |
| 220 | cPrCH2CH2O | CF3 | CH2CH2CH2OH |
| 221 | cPrCH2CH2O | iPrO | CH2CH2CH2OH |
| 222 | cPrCH2CH2O | iPr | CH2CH2CH2OH |
| 223 | cPrCH2CH2O | CHF2CH2O | CH2CH2CH2OH |
| 224 | cPrCH2CH2O | CF3CH2O | CH2CH2CH2OH |
| 225 | cPrCH2CH2O | EtO | CH2CH2CH2OH |
| 226 | cPrCH2CH2O | Et | CH2CH2CH2OH |
| 227 | cPrCH2CH2O | Pr | CH2CH2CH2OH |
| 228 | cPrCH2CH2O | MeS | CH2CH2CH2OH |
| 229 | cPrCH2CH2O | CF3S | CH2CH2CH2OH |
| 230 | cPrCH2CH2O | 1-pyrr | CH2CH2CH2OH |
| 231 | cPrCH2CH2CH2O | cPrO | CH2CH2CH2OH |
| 232 | cPrCH2CH2CH2O | cPr | CH2CH2CH2OH |
| 233 | cPrCH2CH2CH2O | CHF2O | CH2CH2CH2OH |
| 234 | cPrCH2CH2CH2O | CF3O | CH2CH2CH2OH |
| 235 | cPrCH2CH2CH2O | CF3 | CH2CH2CH2OH |
| 236 | cPrCH2CH2CH2O | iPrO | CH2CH2CH2OH |
| 237 | cPrCH2CH2CH2O | iPr | CH2CH2CH2OH |
| 238 | cPrCH2CH2CH2O | CHF2CH2O | CH2CH2CH2OH |
| 239 | cPrCH2CH2CH2O | CF3CH2O | CH2CH2CH2OH |
| 240 | cPrCH2CH2CH2O | EtO | CH2CH2CH2OH |
| 241 | cPrCH2CH2CH2O | Et | CH2CH2CH2OH |
| 242 | cPrCH2CH2CH2O | Pr | CH2CH2CH2OH |
| 243 | cPrCH2CH2CH2O | MeS | CH2CH2CH2OH |
| 244 | cPrCH2CH2CH2O | CF3S | CH2CH2CH2OH |
| 245 | cPrCH2CH2CH2O | 1-pyrr | CH2CH2CH2OH |
| 246 | cPnCH2O | cPrO | CH2CH2CH2OH |
| 247 | cPnCH2O | cPr | CH2CH2CH2OH |
| 248 | cPnCH2O | CHF2O | CH2CH2CH2OH |
| 249 | cPnCH2O | CF3O | CH2CH2CH2OH |
| 250 | cPnCH2O | CF3 | CH2CH2CH2OH |
| 251 | cPnCH2CH2O | cPrO | CH2CH2CH2OH |
| 252 | cPnCH2CH2O | cPr | CH2CH2CH2OH |
| 253 | cPnCH2CH2O | CHF2O | CH2CH2CH2OH |
| 254 | cPnCH2CH2O | CF3O | CH2CH2CH2OH |
| 255 | cPnCH2CH2O | CF3 | CH2CH2CH2OH |
| 256 | PhCH2CH2O | cPrO | CH2CH2CH2OH |
| 257 | PhCH2CH2O | cPr | CH2CH2CH2OH |
| 258 | PhCH2CH2O | CHF2O | CH2CH2CH2OH |
| 259 | PhCH2CH2O | CF3O | CH2CH2CH2OH |
| 260 | PhCH2CH2O | CF3 | CH2CH2CH2OH |
| 261 | 4-MeO-PhCH2CH2O | cPrO | CH2CH2CH2OH |
| 262 | 4-MeO-PhCH2CH2O | cPr | CH2CH2CH2OH |
| 263 | 4-MeO-PhCH2CH2O | CHF2O | CH2CH2CH2OH |
| 264 | 4-MeO-PhCH2CH2O | CF3O | CH2CH2CH2OH |
| 265 | 4-MeO-PhCH2CH2O | CF3 | CH2CH2CH2OH |
| 266 | 4-Cl-PhCH2CH2O | cPrO | CH2CH2CH2OH |
| 267 | 4-Cl-PhCH2CH2O | cPr | CH2CH2CH2OH |
| 268 | 4-Cl-PhCH2CH2O | CHF2O | CH2CH2CH2OH |
| 269 | 4-Cl-PhCH2CH2O | CF3O | CH2CH2CH2OH |
| 270 | 4-Cl-PhCH2CH2O | CF3 | CH2CH2CH2OH |
| 271 | CF3CH2CH2O | cPrO | CH2CH2CH2OH |
| 272 | CF3CH2CH2O | cPr | CH2CH2CH2OH |
| 273 | CF3CH2CH2O | CHF2O | CH2CH2CH2OH |
| 274 | CF3CH2CH2O | CF3O | CH2CH2CH2OH |

TABLE 4-continued

Exemplary compound table 1

(I-1)

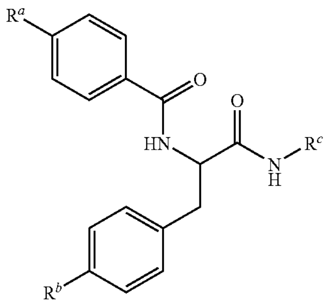

| Compound No. | $R^a$ | $R^b$ | $R^c$ |
|---|---|---|---|
| 275 | CF3CH2CH2O | CF3 | CH2CH2CH2OH |
| 276 | CF3CH2CH2O | iPrO | CH2CH2CH2OH |
| 277 | CF3CH2CH2O | iPr | CH2CH2CH2OH |
| 278 | CF3CH2CH2O | CHF2CH2O | CH2CH2CH2OH |
| 279 | CF3CH2CH2O | CF3CH2O | CH2CH2CH2OH |
| 280 | CF3CH2CH2O | EtO | CH2CH2CH2OH |
| 281 | CF3CH2CH2O | Et | CH2CH2CH2OH |
| 282 | CF3CH2CH2O | Pr | CH2CH2CH2OH |
| 283 | CF3CH2CH2O | MeS | CH2CH2CH2OH |
| 284 | CF3CH2CH2O | CF3S | CH2CH2CH2OH |
| 285 | CF3CH2CH2O | 1-pyrr | CH2CH2CH2OH |
| 286 | CHF2CH2O | cPrO | CH2CH2CH2OH |
| 287 | CHF2CH2O | cPr | CH2CH2CH2OH |
| 288 | CHF2CH2O | CHF2O | CH2CH2CH2OH |
| 289 | CHF2CH2O | CF3O | CH2CH2CH2OH |
| 290 | CHF2CH2O | CF3 | CH2CH2CH2OH |
| 291 | CHF2CH2O | iPrO | CH2CH2CH2OH |
| 292 | CHF2CH2O | iPr | CH2CH2CH2OH |
| 293 | CHF2CH2O | CHF2CH2O | CH2CH2CH2OH |
| 294 | CHF2CH2O | CF3CH2O | CH2CH2CH2OH |
| 295 | CHF2CH2O | EtO | CH2CH2CH2OH |
| 296 | CHF2CH2O | Et | CH2CH2CH2OH |
| 297 | CHF2CH2O | Pr | CH2CH2CH2OH |
| 298 | CHF2CH2O | MeS | CH2CH2CH2OH |
| 299 | CHF2CH2O | CF3S | CH2CH2CH2OH |
| 300 | CHF2CH2O | 1-pyrr | CH2CH2CH2OH |
| 301 | (E)-MeCHCHCH2O | cPrO | CH2CH2CH2OH |
| 302 | (E)-MeCHCHCH2O | cPr | CH2CH2CH2OH |
| 303 | (E)-MeCHCHCH2O | CHF2O | CH2CH2CH2OH |
| 304 | (E)-MeCHCHCH2O | CF3O | CH2CH2CH2OH |
| 305 | (E)-MeCHCHCH2O | CF3 | CH2CH2CH2OH |
| 306 | (2,2-diF-cPr)CH2O | cPrO | CH2CH2CH2OH |
| 307 | (2,2-diF-cPr)CH2O | cPr | CH2CH2CH2OH |
| 308 | (2,2-diF-cPr)CH2O | CHF2O | CH2CH2CH2OH |
| 309 | (2,2-diF-cPr)CH2O | CF3O | CH2CH2CH2OH |
| 310 | (2,2-diF-cPr)CH2O | CF3 | CH2CH2CH2OH |
| 311 | (2,2-diF-cPr)CH2O | iPrO | CH2CH2CH2OH |
| 312 | (2,2-diF-cPr)CH2O | iPr | CH2CH2CH2OH |
| 313 | (2,2-diF-cPr)CH2O | CHF2CH2O | CH2CH2CH2OH |
| 314 | (2,2-diF-cPr)CH2O | CF3CH2O | CH2CH2CH2OH |
| 315 | (2,2-diF-cPr)CH2O | EtO | CH2CH2CH2OH |
| 316 | (2,2-diF-cPr)CH2O | Et | CH2CH2CH2OH |
| 317 | (2,2-diF-cPr)CH2O | Pr | CH2CH2CH2OH |
| 318 | (2,2-diF-cPr)CH2O | MeS | CH2CH2CH2OH |
| 319 | (2,2-diF-cPr)CH2O | CF3S | CH2CH2CH2OH |
| 320 | (2,2-diF-cPr)CH2O | 1-pyrr | CH2CH2CH2OH |
| 321 | PrO | cPrO | CH2CH2CH2OH |
| 322 | PrO | cPr | CH2CH2CH2OH |
| 323 | PrO | CHF2O | CH2CH2CH2OH |
| 324 | PrO | CF3O | CH2CH2CH2OH |
| 325 | PrO | CF3 | CH2CH2CH2OH |
| 326 | 4-CF3PhO | cPrO | CH2CH2CH2OH |
| 327 | 4-CF3PhO | cPr | CH2CH2CH2OH |
| 328 | 4-CF3PhO | CHF2O | CH2CH2CH2OH |
| 329 | 4-CF3PhO | CF3O | CH2CH2CH2OH |
| 330 | 4-CF3PhO | CF3 | CH2CH2CH2OH |
| 331 | 4-CF3PhO | iPrO | CH2CH2CH2OH |
| 332 | 4-CF3PhO | iPr | CH2CH2CH2OH |
| 333 | 4-CF3PhO | CHF2CH2O | CH2CH2CH2OH |

TABLE 4-continued

Exemplary compound table 1

(I-1)

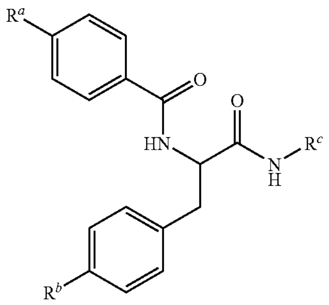

| Compound No. | $R^a$ | $R^b$ | $R^c$ |
|---|---|---|---|
| 334 | 4-CF3PhO | CF3CH2O | CH2CH2CH2OH |
| 335 | 4-CF3PhO | EtO | CH2CH2CH2OH |
| 336 | 4-CF3PhO | Et | CH2CH2CH2OH |
| 337 | 4-CF3PhO | Pr | CH2CH2CH2OH |
| 338 | 4-CF3PhO | MeS | CH2CH2CH2OH |
| 339 | 4-CF3PhO | CF3S | CH2CH2CH2OH |
| 340 | 4-CF3PhO | 1-pyrr | CH2CH2CH2OH |
| 341 | 4-ClPhO | cPrO | CH2CH2CH2OH |
| 342 | 4-ClPhO | cPr | CH2CH2CH2OH |
| 343 | 4-ClPhO | CHF2O | CH2CH2CH2OH |
| 344 | 4-ClPhO | CF3O | CH2CH2CH2OH |
| 345 | 4-ClPhO | CF3 | CH2CH2CH2OH |
| 346 | 3-ClPhO | cPrO | CH2CH2CH2OH |
| 347 | 3-ClPhO | cPr | CH2CH2CH2OH |
| 348 | 3-ClPhO | CHF2O | CH2CH2CH2OH |
| 349 | 3-ClPhO | CF3O | CH2CH2CH2OH |
| 350 | 3-ClPhO | CF3 | CH2CH2CH2OH |
| 351 | 4-FPhO | cPrO | CH2CH2CH2OH |
| 352 | 4-FPhO | cPr | CH2CH2CH2OH |
| 353 | 4-FPhO | CHF2O | CH2CH2CH2OH |
| 354 | 4-FPhO | CF3O | CH2CH2CH2OH |
| 355 | 4-FPhO | CF3 | CH2CH2CH2OH |
| 356 | 4-MeOPhO | cPrO | CH2CH2CH2OH |
| 357 | 4-MeOPhO | cPr | CH2CH2CH2OH |
| 358 | 4-MeOPhO | CHF2O | CH2CH2CH2OH |
| 359 | 4-MeOPhO | CF3O | CH2CH2CH2OH |
| 360 | 4-MeOPhO | CF3 | CH2CH2CH2OH |
| 361 | cPnO | cPrO | CH2-(1-HO-cPr) |
| 362 | cPnO | cPr | CH2-(1-HO-cPr) |
| 363 | cPnO | CHF2O | CH2-(1-HO-cPr) |
| 364 | cPnO | CF3O | CH2-(1-HO-cPr) |
| 365 | cPnO | CF3 | CH2-(1-HO-cPr) |
| 366 | iBuO | cPrO | CH2-(1-HO-cPr) |
| 367 | iBuO | cPr | CH2-(1-HO-cPr) |
| 368 | iBuO | CHF2O | CH2-(1-HO-cPr) |
| 369 | iBuO | CF3O | CH2-(1-HO-cPr) |
| 370 | iBuO | CF3 | CH2-(1-HO-cPr) |
| 371 | cBuCH2O | cPrO | CH2-(1-HO-cPr) |
| 372 | cBuCH2O | cPr | CH2-(1-HO-cPr) |
| 373 | cBuCH2O | CHF2O | CH2-(1-HO-cPr) |
| 374 | cBuCH2O | CF3O | CH2-(1-HO-cPr) |
| 375 | cBuCH2O | CF3 | CH2-(1-HO-cPr) |
| 376 | cPrCH2O | cPrO | CH2-(1-HO-cPr) |
| 377 | cPrCH2O | cPr | CH2-(1-HO-cPr) |
| 378 | cPrCH2O | CHF2O | CH2-(1-HO-cPr) |
| 379 | cPrCH2O | CF3O | CH2-(1-HO-cPr) |
| 380 | cPrCH2O | CF3 | CH2-(1-HO-cPr) |
| 381 | cPrCH2O | iPrO | CH2-(1-HO-cPr) |
| 382 | cPrCH2O | iPr | CH2-(1-HO-cPr) |
| 383 | cPrCH2O | CHF2CH2O | CH2-(1-HO-cPr) |
| 384 | cPrCH2O | CF3CH2O | CH2-(1-HO-cPr) |
| 385 | cPrCH2O | EtO | CH2-(1-HO-cPr) |
| 386 | cPrCH2O | Et | CH2-(1-HO-cPr) |
| 387 | cPrCH2O | Pr | CH2-(1-HO-cPr) |
| 388 | cPrCH2O | MeS | CH2-(1-HO-cPr) |
| 389 | cPrCH2O | CF3S | CH2-(1-HO-cPr) |
| 390 | cPrCH2O | 1-pyrr | CH2-(1-HO-cPr) |
| 391 | (1-Me-cPr)CH2O | cPrO | CH2-(1-HO-cPr) |
| 392 | (1-Me-cPr)CH2O | cPr | CH2-(1-HO-cPr) |

TABLE 4-continued

Exemplary compound table 1

(I-1)

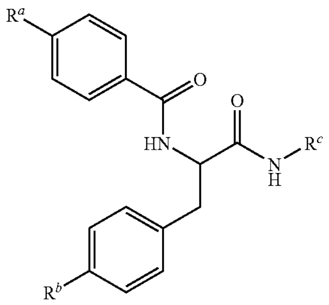

| Compound No. | $R^a$ | $R^b$ | $R^c$ |
|---|---|---|---|
| 393 | (1-Me-cPr)CH2O | CHF2O | CH2-(1-HO-cPr) |
| 394 | (1-Me-cPr)CH2O | CF3O | CH2-(1-HO-cPr) |
| 395 | (1-Me-cPr)CH2O | CF3 | CH2-(1-HO-cPr) |
| 396 | cPrCH2CH2O | cPrO | CH2-(1-HO-cPr) |
| 397 | cPrCH2CH2O | cPr | CH2-(1-HO-cPr) |
| 398 | cPrCH2CH2O | CHF2O | CH2-(1-HO-cPr) |
| 399 | cPrCH2CH2O | CF3O | CH2-(1-HO-cPr) |
| 400 | cPrCH2CH2O | CF3 | CH2-(1-HO-cPr) |
| 401 | cPrCH2CH2O | iPrO | CH2-(1-HO-cPr) |
| 402 | cPrCH2CH2O | iPr | CH2-(1-HO-cPr) |
| 403 | cPrCH2CH2O | CHF2CH2O | CH2-(1-HO-cPr) |
| 404 | cPrCH2CH2O | CF3CH2O | CH2-(1-HO-cPr) |
| 405 | cPrCH2CH2O | EtO | CH2-(1-HO-cPr) |
| 406 | cPrCH2CH2O | Et | CH2-(1-HO-cPr) |
| 407 | cPrCH2CH2O | Pr | CH2-(1-HO-cPr) |
| 408 | cPrCH2CH2O | MeS | CH2-(1-HO-cPr) |
| 409 | cPrCH2CH2O | CF3S | CH2-(1-HO-cPr) |
| 410 | cPrCH2CH2O | 1-pyrr | CH2-(1-HO-cPr) |
| 411 | cPrCH2CH2CH2O | cPrO | CH2-(1-HO-cPr) |
| 412 | cPrCH2CH2CH2O | cPr | CH2-(1-HO-cPr) |
| 413 | cPrCH2CH2CH2O | CHF2O | CH2-(1-HO-cPr) |
| 414 | cPrCH2CH2CH2O | CF3O | CH2-(1-HO-cPr) |
| 415 | cPrCH2CH2CH2O | CF3 | CH2-(1-HO-cPr) |
| 416 | cPrCH2CH2CH2O | iPrO | CH2-(1-HO-cPr) |
| 417 | cPrCH2CH2CH2O | iPr | CH2-(1-HO-cPr) |
| 418 | cPrCH2CH2CH2O | CHF2CH2O | CH2-(1-HO-cPr) |
| 419 | cPrCH2CH2CH2O | CF3CH2O | CH2-(1-HO-cPr) |
| 420 | cPrCH2CH2CH2O | EtO | CH2-(1-HO-cPr) |
| 421 | cPrCH2CH2CH2O | Et | CH2-(1-HO-cPr) |
| 422 | cPrCH2CH2CH2O | Pr | CH2-(1-HO-cPr) |
| 423 | cPrCH2CH2CH2O | MeS | CH2-(1-HO-cPr) |
| 424 | cPrCH2CH2CH2O | CF3S | CH2-(1-HO-cPr) |
| 425 | cPrCH2CH2CH2O | 1-pyrr | CH2-(1-HO-cPr) |
| 426 | cPnCH2O | cPrO | CH2-(1-HO-cPr) |
| 427 | cPnCH2O | cPr | CH2-(1-HO-cPr) |
| 428 | cPnCH2O | CHF2O | CH2-(1-HO-cPr) |
| 429 | cPnCH2O | CF3O | CH2-(1-HO-cPr) |
| 430 | cPnCH2O | CF3 | CH2-(1-HO-cPr) |
| 431 | cPnCH2CH2O | cPrO | CH2-(1-HO-cPr) |
| 432 | cPnCH2CH2O | cPr | CH2-(1-HO-cPr) |
| 433 | cPnCH2CH2O | CHF2O | CH2-(1-HO-cPr) |
| 434 | cPnCH2CH2O | CF3O | CH2-(1-HO-cPr) |
| 435 | cPnCH2CH2O | CF3 | CH2-(1-HO-cPr) |
| 436 | PhCH2CH2O | cPrO | CH2-(1-HO-cPr) |
| 437 | PhCH2CH2O | cPr | CH2-(1-HO-cPr) |
| 438 | PhCH2CH2O | CHF2O | CH2-(1-HO-cPr) |
| 439 | PhCH2CH2O | CF3O | CH2-(1-HO-cPr) |
| 440 | PhCH2CH2O | CF3 | CH2-(1-HO-cPr) |
| 441 | 4-MeO-PhCH2CH2O | cPrO | CH2-(1-HO-cPr) |
| 442 | 4-MeO-PhCH2CH2O | cPr | CH2-(1-HO-cPr) |
| 443 | 4-MeO-PhCH2CH2O | CHF2O | CH2-(1-HO-cPr) |
| 444 | 4-MeO-PhCH2CH2O | CF3O | CH2-(1-HO-cPr) |
| 445 | 4-MeO-PhCH2CH2O | CF3 | CH2-(1-HO-cPr) |
| 446 | 4-Cl-PhCH2CH2O | cPrO | CH2-(1-HO-cPr) |
| 447 | 4-Cl-PhCH2CH2O | cPr | CH2-(1-HO-cPr) |
| 448 | 4-Cl-PhCH2CH2O | CHF2O | CH2-(1-HO-cPr) |
| 449 | 4-Cl-PhCH2CH2O | CF3O | CH2-(1-HO-cPr) |
| 450 | 4-Cl-PhCH2CH2O | CF3 | CH2-(1-HO-cPr) |
| 451 | CF3CH2CH2O | cPrO | CH2-(1-HO-cPr) |

TABLE 4-continued

Exemplary compound table 1

(I-1)

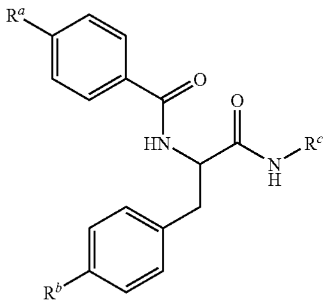

| Compound No. | $R^a$ | $R^b$ | $R^c$ |
|---|---|---|---|
| 452 | CF3CH2CH2O | cPr | CH2-(1-HO-cPr) |
| 453 | CF3CH2CH2O | CHF2O | CH2-(1-HO-cPr) |
| 454 | CF3CH2CH2O | CF3O | CH2-(1-HO-cPr) |
| 455 | CF3CH2CH2O | CF3 | CH2-(1-HO-cPr) |
| 456 | CF3CH2CH2O | iPrO | CH2-(1-HO-cPr) |
| 457 | CF3CH2CH2O | iPr | CH2-(1-HO-cPr) |
| 458 | CF3CH2CH2O | CHF2CH2O | CH2-(1-HO-cPr) |
| 459 | CF3CH2CH2O | CF3CH2O | CH2-(1-HO-cPr) |
| 460 | CF3CH2CH2O | EtO | CH2-(1-HO-cPr) |
| 461 | CF3CH2CH2O | Et | CH2-(1-HO-cPr) |
| 462 | CF3CH2CH2O | Pr | CH2-(1-HO-cPr) |
| 463 | CF3CH2CH2O | MeS | CH2-(1-HO-cPr) |
| 464 | CF3CH2CH2O | CF3S | CH2-(1-HO-cPr) |
| 465 | CF3CH2CH2O | 1-pyrr | CH2-(1-HO-cPr) |
| 466 | CHF2CH2O | cPrO | CH2-(1-HO-cPr) |
| 467 | CHF2CH2O | cPr | CH2-(1-HO-cPr) |
| 468 | CHF2CH2O | CHF2O | CH2-(1-HO-cPr) |
| 469 | CHF2CH2O | CF3O | CH2-(1-HO-cPr) |
| 470 | CHF2CH2O | CF3 | CH2-(1-HO-cPr) |
| 471 | CHF2CH2O | iPrO | CH2-(1-HO-cPr) |
| 472 | CHF2CH2O | iPr | CH2-(1-HO-cPr) |
| 473 | CHF2CH2O | CHF2CH2O | CH2-(1-HO-cPr) |
| 474 | CHF2CH2O | CF3CH2O | CH2-(1-HO-cPr) |
| 475 | CHF2CH2O | EtO | CH2-(1-HO-cPr) |
| 476 | CHF2CH2O | Et | CH2-(1-HO-cPr) |
| 477 | CHF2CH2O | Pr | CH2-(1-HO-cPr) |
| 478 | CHF2CH2O | MeS | CH2-(1-HO-cPr) |
| 479 | CHF2CH2O | CF3S | CH2-(1-HO-cPr) |
| 480 | CHF2CH2O | 1-pyrr | CH2-(1-HO-cPr) |
| 481 | (E)-MeCHCHCH2O | cPrO | CH2-(1-HO-cPr) |
| 482 | (E)-MeCHCHCH2O | cPr | CH2-(1-HO-cPr) |
| 483 | (E)-MeCHCHCH2O | CHF2O | CH2-(1-HO-cPr) |
| 484 | (E)-MeCHCHCH2O | CF3O | CH2-(1-HO-cPr) |
| 485 | (E)-MeCHCHCH2O | CF3 | CH2-(1-HO-cPr) |
| 486 | (2,2-diF-cPr)CH2O | cPrO | CH2-(1-HO-cPr) |
| 487 | (2,2-diF-cPr)CH2O | cPr | CH2-(1-HO-cPr) |
| 488 | (2,2-diF-cPr)CH2O | CHF2O | CH2-(1-HO-cPr) |
| 489 | (2,2-diF-cPr)CH2O | CF3O | CH2-(1-HO-cPr) |
| 490 | (2,2-diF-cPr)CH2O | CF3 | CH2-(1-HO-cPr) |
| 491 | (2,2-diF-cPr)CH2O | iPrO | CH2-(1-HO-cPr) |
| 492 | (2,2-diF-cPr)CH2O | iPr | CH2-(1-HO-cPr) |
| 493 | (2,2-diF-cPr)CH2O | CHF2CH2O | CH2-(1-HO-cPr) |
| 494 | (2,2-diF-cPr)CH2O | CF3CH2O | CH2-(1-HO-cPr) |
| 495 | (2,2-diF-cPr)CH2O | EtO | CH2-(1-HO-cPr) |
| 496 | (2,2-diF-cPr)CH2O | Et | CH2-(1-HO-cPr) |
| 497 | (2,2-diF-cPr)CH2O | Pr | CH2-(1-HO-cPr) |
| 498 | (2,2-diF-cPr)CH2O | MeS | CH2-(1-HO-cPr) |
| 499 | (2,2-diF-cPr)CH2O | CF3S | CH2-(1-HO-cPr) |
| 500 | (2,2-diF-cPr)CH2O | 1-pyrr | CH2-(1-HO-cPr) |
| 501 | PrO | cPrO | CH2-(1-HO-cPr) |
| 502 | PrO | cPr | CH2-(1-HO-cPr) |
| 503 | PrO | CHF2O | CH2-(1-HO-cPr) |
| 504 | PrO | CF3O | CH2-(1-HO-cPr) |
| 505 | PrO | CF3 | CH2-(1-HO-cPr) |
| 506 | 4-CF3PhO | cPrO | CH2-(1-HO-cPr) |
| 507 | 4-CF3PhO | cPr | CH2-(1-HO-cPr) |
| 508 | 4-CF3PhO | CHF2O | CH2-(1-HO-cPr) |
| 509 | 4-CF3PhO | CF3O | CH2-(1-HO-cPr) |
| 510 | 4-CF3PhO | CF3 | CH2-(1-HO-cPr) |

TABLE 4-continued

Exemplary compound table 1

(I-1)

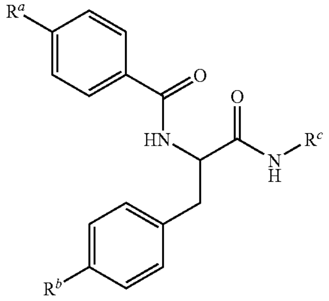

| Compound No. | $R^a$ | $R^b$ | $R^c$ |
|---|---|---|---|
| 511 | 4-CF3PhO | iPrO | CH2-(1-HO-cPr) |
| 512 | 4-CF3PhO | iPr | CH2-(1-HO-cPr) |
| 513 | 4-CF3PhO | CHF2CH2O | CH2-(1-HO-cPr) |
| 514 | 4-CF3PhO | CF3CH2O | CH2-(1-HO-cPr) |
| 515 | 4-CF3PhO | EtO | CH2-(1-HO-cPr) |
| 516 | 4-CF3PhO | Et | CH2-(1-HO-cPr) |
| 517 | 4-CF3PhO | Pr | CH2-(1-HO-cPr) |
| 518 | 4-CF3PhO | MeS | CH2-(1-HO-cPr) |
| 519 | 4-CF3PhO | CF3S | CH2-(1-HO-cPr) |
| 520 | 4-CF3PhO | 1-pyrr | CH2-(1-HO-cPr) |
| 521 | 4-ClPhO | cPrO | CH2-(1-HO-cPr) |
| 522 | 4-ClPhO | cPr | CH2-(1-HO-cPr) |
| 523 | 4-ClPhO | CHF2O | CH2-(1-HO-cPr) |
| 524 | 4-ClPhO | CF3O | CH2-(1-HO-cPr) |
| 525 | 4-ClPhO | CF3 | CH2-(1-HO-cPr) |
| 526 | 3-ClPhO | cPrO | CH2-(1-HO-cPr) |
| 527 | 3-ClPhO | cPr | CH2-(1-HO-cPr) |
| 528 | 3-ClPhO | CHF2O | CH2-(1-HO-cPr) |
| 529 | 3-ClPhO | CF3O | CH2-(1-HO-cPr) |
| 530 | 3-ClPhO | CF3 | CH2-(1-HO-cPr) |
| 531 | 4-FPhO | cPrO | CH2-(1-HO-cPr) |
| 532 | 4-FPhO | cPr | CH2-(1-HO-cPr) |
| 533 | 4-FPhO | CHF2O | CH2-(1-HO-cPr) |
| 534 | 4-FPhO | CF3O | CH2-(1-HO-cPr) |
| 535 | 4-FPhO | CF3 | CH2-(1-HO-cPr) |
| 536 | 4-MeOPhO | cPrO | CH2-(1-HO-cPr) |
| 537 | 4-MeOPhO | cPr | CH2-(1-HO-cPr) |
| 538 | 4-MeOPhO | CHF2O | CH2-(1-HO-cPr) |
| 539 | 4-MeOPhO | CF3O | CH2-(1-HO-cPr) |
| 540 | 4-MeOPhO | CF3 | CH2-(1-HO-cPr) |
| 541 | cPrCH2O | cPrO | CH2CH2OAc |
| 542 | cPrCH2O | cPr | CH2CH2OAc |
| 543 | cPrCH2O | CHF2O | CH2CH2OAc |
| 544 | cPrCH2O | CF3O | CH2CH2OAc |
| 545 | cPrCH2O | CF3 | CH2CH2OAc |
| 546 | cPrCH2O | iPrO | CH2CH2OAc |
| 547 | cPrCH2O | iPr | CH2CH2OAc |
| 548 | cPrCH2O | CHF2CH2O | CH2CH2OAc |
| 549 | cPrCH2O | CF3CH2O | CH2CH2OAc |
| 550 | cPrCH2O | EtO | CH2CH2OAc |
| 551 | cPrCH2O | Et | CH2CH2OAc |
| 552 | cPrCH2O | Pr | CH2CH2OAc |
| 553 | cPrCH2O | MeS | CH2CH2OAc |
| 554 | cPrCH2O | CF3S | CH2CH2OAc |
| 555 | cPrCH2O | 1-pyrr | CH2CH2OAc |
| 556 | cPrCH2CH2O | cPrO | CH2CH2OAc |
| 557 | cPrCH2CH2O | cPr | CH2CH2OAc |
| 558 | cPrCH2CH2O | CHF2O | CH2CH2OAc |
| 559 | cPrCH2CH2O | CF3O | CH2CH2OAc |
| 560 | cPrCH2CH2O | CF3 | CH2CH2OAc |
| 561 | cPrCH2CH2O | iPrO | CH2CH2OAc |
| 562 | cPrCH2CH2O | iPr | CH2CH2OAc |
| 563 | cPrCH2CH2O | CHF2CH2O | CH2CH2OAc |
| 564 | cPrCH2CH2O | CF3CH2O | CH2CH2OAc |
| 565 | cPrCH2CH2O | EtO | CH2CH2OAc |
| 566 | cPrCH2CH2O | Et | CH2CH2OAc |
| 567 | cPrCH2CH2O | Pr | CH2CH2OAc |
| 568 | cPrCH2CH2O | MeS | CH2CH2OAc |
| 569 | cPrCH2CH2O | CF3S | CH2CH2OAc |

TABLE 4-continued

Exemplary compound table 1

(I-1)

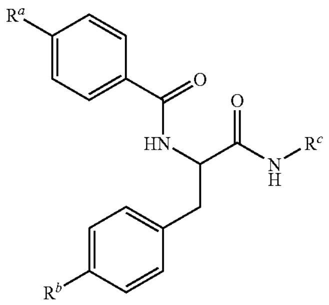

| Compound No. | $R^a$ | $R^b$ | $R^c$ |
|---|---|---|---|
| 570 | cPrCH2CH2O | 1-pyrr | CH2CH2OAc |
| 571 | cPrCH2CH2CH2O | cPrO | CH2CH2OAc |
| 572 | cPrCH2CH2CH2O | cPr | CH2CH2OAc |
| 573 | cPrCH2CH2CH2O | CHF2O | CH2CH2OAc |
| 574 | cPrCH2CH2CH2O | CF3O | CH2CH2OAc |
| 575 | cPrCH2CH2CH2O | CF3 | CH2CH2OAc |
| 576 | cPrCH2CH2CH2O | iPrO | CH2CH2OAc |
| 577 | cPrCH2CH2CH2O | iPr | CH2CH2OAc |
| 578 | cPrCH2CH2CH2O | CHF2CH2O | CH2CH2OAc |
| 579 | cPrCH2CH2CH2O | CF3CH2O | CH2CH2OAc |
| 580 | cPrCH2CH2CH2O | EtO | CH2CH2OAc |
| 581 | cPrCH2CH2CH2O | Et | CH2CH2OAc |
| 582 | cPrCH2CH2CH2O | Pr | CH2CH2OAc |
| 583 | cPrCH2CH2CH2O | MeS | CH2CH2OAc |
| 584 | cPrCH2CH2CH2O | CF3S | CH2CH2OAc |
| 585 | cPrCH2CH2CH2O | 1-pyrr | CH2CH2OAc |
| 586 | CF3CH2CH2O | cPrO | CH2CH2OAc |
| 587 | CF3CH2CH2O | cPr | CH2CH2OAc |
| 588 | CF3CH2CH2O | CHF2O | CH2CH2OAc |
| 589 | CF3CH2CH2O | CF3O | CH2CH2OAc |
| 590 | CF3CH2CH2O | CF3 | CH2CH2OAc |
| 591 | CF3CH2CH2O | iPrO | CH2CH2OAc |
| 592 | CF3CH2CH2O | iPr | CH2CH2OAc |
| 593 | CF3CH2CH2O | CHF2CH2O | CH2CH2OAc |
| 594 | CF3CH2CH2O | CF3CH2O | CH2CH2OAc |
| 595 | CF3CH2CH2O | EtO | CH2CH2OAc |
| 596 | CF3CH2CH2O | Et | CH2CH2OAc |
| 597 | CF3CH2CH2O | Pr | CH2CH2OAc |
| 598 | CF3CH2CH2O | MeS | CH2CH2OAc |
| 599 | CF3CH2CH2O | CF3S | CH2CH2OAc |
| 600 | CF3CH2CH2O | 1-pyrr | CH2CH2OAc |
| 601 | CHF2CH2O | cPrO | CH2CH2OAc |
| 602 | CHF2CH2O | cPr | CH2CH2OAc |
| 603 | CHF2CH2O | CHF2O | CH2CH2OAc |
| 604 | CHF2CH2O | CF3O | CH2CH2OAc |
| 605 | CHF2CH2O | CF3 | CH2CH2OAc |
| 606 | CHF2CH2O | iPrO | CH2CH2OAc |
| 607 | CHF2CH2O | iPr | CH2CH2OAc |
| 608 | CHF2CH2O | CHF2CH2O | CH2CH2OAc |
| 609 | CHF2CH2O | CF3CH2O | CH2CH2OAc |
| 610 | CHF2CH2O | EtO | CH2CH2OAc |
| 611 | CHF2CH2O | Et | CH2CH2OAc |
| 612 | CHF2CH2O | Pr | CH2CH2OAc |
| 613 | CHF2CH2O | MeS | CH2CH2OAc |
| 614 | CHF2CH2O | CF3S | CH2CH2OAc |
| 615 | CHF2CH2O | 1-pyrr | CH2CH2OAc |
| 616 | (2,2-diF-cPr)CH2O | cPrO | CH2CH2OAc |
| 617 | (2,2-diF-cPr)CH2O | cPr | CH2CH2OAc |
| 618 | (2,2-diF-cPr)CH2O | CHF2O | CH2CH2OAc |
| 619 | (2,2-diF-cPr)CH2O | CF3O | CH2CH2OAc |
| 620 | (2,2-diF-cPr)CH2O | CF3 | CH2CH2OAc |
| 621 | (2,2-diF-cPr)CH2O | iPrO | CH2CH2OAc |
| 622 | (2,2-diF-cPr)CH2O | iPr | CH2CH2OAc |
| 623 | (2,2-diF-cPr)CH2O | CHF2CH2O | CH2CH2OAc |
| 624 | (2,2-diF-cPr)CH2O | CF3CH2O | CH2CH2OAc |
| 625 | (2,2-diF-cPr)CH2O | EtO | CH2CH2OAc |
| 626 | (2,2-diF-cPr)CH2O | Et | CH2CH2OAc |
| 627 | (2,2-diF-cPr)CH2O | Pr | CH2CH2OAc |
| 628 | (2,2-diF-cPr)CH2O | MeS | CH2CH2OAc |

TABLE 4-continued

Exemplary compound table 1

(I-1)

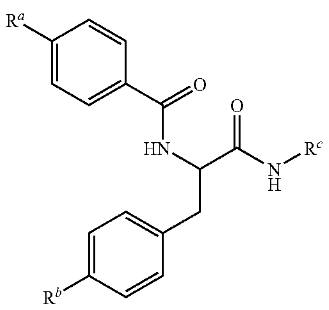

| Compound No. | $R^a$ | $R^b$ | $R^c$ |
|---|---|---|---|
| 629 | (2,2-diF-cPr)CH2O | CF3S | CH2CH2OAc |
| 630 | (2,2-diF-cPr)CH2O | 1-pyrr | CH2CH2OAc |
| 631 | 4-CF3PhO | cPrO | CH2CH2OAc |
| 632 | 4-CF3PhO | cPr | CH2CH2OAc |
| 633 | 4-CF3PhO | CHF2O | CH2CH2OAc |
| 634 | 4-CF3PhO | CF3O | CH2CH2OAc |
| 635 | 4-CF3PhO | CF3 | CH2CH2OAc |
| 636 | 4-CF3PhO | iPrO | CH2CH2OAc |
| 637 | 4-CF3PhO | iPr | CH2CH2OAc |
| 638 | 4-CF3PhO | CHF2CH2O | CH2CH2OAc |
| 639 | 4-CF3PhO | CF3CH2O | CH2CH2OAc |
| 640 | 4-CF3PhO | EtO | CH2CH2OAc |
| 641 | 4-CF3PhO | Et | CH2CH2OAc |
| 642 | 4-CF3PhO | Pr | CH2CH2OAc |
| 643 | 4-CF3PhO | MeS | CH2CH2OAc |
| 644 | 4-CF3PhO | CF3S | CH2CH2OAc |
| 645 | 4-CF3PhO | 1-pyrr | CH2CH2OAc |
| 646 | cPrCH2O | cPrO | CH2CH2OOCCH2CH2COOH |
| 647 | cPrCH2O | cPr | CH2CH2OOCCH2CH2COOH |
| 648 | cPrCH2O | CHF2O | CH2CH2OOCCH2CH2COOH |
| 649 | cPrCH2O | CF3O | CH2CH2OOCCH2CH2COOH |
| 650 | cPrCH2O | CF3 | CH2CH2OOCCH2CH2COOH |
| 651 | cPrCH2O | iPrO | CH2CH2OOCCH2CH2COOH |
| 652 | cPrCH2O | iPr | CH2CH2OOCCH2CH2COOH |
| 653 | cPrCH2O | CHF2CH2O | CH2CH2OOCCH2CH2COOH |
| 654 | cPrCH2O | CF3CH2O | CH2CH2OOCCH2CH2COOH |
| 655 | cPrCH2O | EtO | CH2CH2OOCCH2CH2COOH |
| 656 | cPrCH2O | Et | CH2CH2OOCCH2CH2COOH |
| 657 | cPrCH2O | Pr | CH2CH2OOCCH2CH2COOH |
| 658 | cPrCH2O | MeS | CH2CH2OOCCH2CH2COOH |
| 659 | cPrCH2O | CF3S | CH2CH2OOCCH2CH2COOH |
| 660 | cPrCH2O | 1-pyrr | CH2CH2OOCCH2CH2COOH |
| 661 | cPrCH2CH2O | cPrO | CH2CH2OOCCH2CH2COOH |
| 662 | cPrCH2CH2O | cPr | CH2CH2OOCCH2CH2COOH |
| 663 | cPrCH2CH2O | CHF2O | CH2CH2OOCCH2CH2COOH |
| 664 | cPrCH2CH2O | CF3O | CH2CH2OOCCH2CH2COOH |
| 665 | cPrCH2CH2O | CF3 | CH2CH2OOCCH2CH2COOH |
| 666 | cPrCH2CH2O | iPrO | CH2CH2OOCCH2CH2COOH |
| 667 | cPrCH2CH2O | iPr | CH2CH2OOCCH2CH2COOH |
| 668 | cPrCH2CH2O | CHF2CH2O | CH2CH2OOCCH2CH2COOH |
| 669 | cPrCH2CH2O | CF3CH2O | CH2CH2OOCCH2CH2COOH |
| 670 | cPrCH2CH2O | EtO | CH2CH2OOCCH2CH2COOH |
| 671 | cPrCH2CH2O | Et | CH2CH2OOCCH2CH2COOH |
| 672 | cPrCH2CH2O | Pr | CH2CH2OOCCH2CH2COOH |
| 673 | cPrCH2CH2O | MeS | CH2CH2OOCCH2CH2COOH |
| 674 | cPrCH2CH2O | CF3S | CH2CH2OOCCH2CH2COOH |
| 675 | cPrCH2CH2O | 1-pyrr | CH2CH2OOCCH2CH2COOH |
| 676 | cPrCH2CH2CH2O | cPrO | CH2CH2OOCCH2CH2COOH |
| 677 | cPrCH2CH2CH2O | cPr | CH2CH2OOCCH2CH2COOH |
| 678 | cPrCH2CH2CH2O | CHF2O | CH2CH2OOCCH2CH2COOH |
| 679 | cPrCH2CH2CH2O | CF3O | CH2CH2OOCCH2CH2COOH |
| 680 | cPrCH2CH2CH2O | CF3 | CH2CH2OOCCH2CH2COOH |
| 681 | cPrCH2CH2CH2O | iPrO | CH2CH2OOCCH2CH2COOH |
| 682 | cPrCH2CH2CH2O | iPr | CH2CH2OOCCH2CH2COOH |
| 683 | cPrCH2CH2CH2O | CHF2CH2O | CH2CH2OOCCH2CH2COOH |
| 684 | cPrCH2CH2CH2O | CF3CH2O | CH2CH2OOCCH2CH2COOH |
| 685 | cPrCH2CH2CH2O | EtO | CH2CH2OOCCH2CH2COOH |
| 686 | cPrCH2CH2CH2O | Et | CH2CH2OOCCH2CH2COOH |
| 687 | cPrCH2CH2CH2O | Pr | CH2CH2OOCCH2CH2COOH |

TABLE 4-continued

Exemplary compound table 1

(I-1)

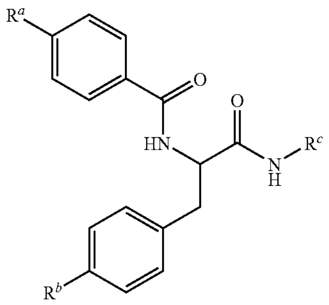

| Compound No. | $R^a$ | $R^b$ | $R^c$ |
|---|---|---|---|
| 688 | cPrCH2CH2CH2O | MeS | CH2CH2OOCCH2CH2COOH |
| 689 | cPrCH2CH2CH2O | CF3S | CH2CH2OOCCH2CH2COOH |
| 690 | cPrCH2CH2CH2O | 1-pyrr | CH2CH2OOCCH2CH2COOH |
| 691 | CF3CH2CH2O | cPrO | CH2CH2OOCCH2CH2COOH |
| 692 | CF3CH2CH2O | cPr | CH2CH2OOCCH2CH2COOH |
| 693 | CF3CH2CH2O | CHF2O | CH2CH2OOCCH2CH2COOH |
| 694 | CF3CH2CH2O | CF3O | CH2CH2OOCCH2CH2COOH |
| 695 | CF3CH2CH2O | CF3 | CH2CH2OOCCH2CH2COOH |
| 696 | CF3CH2CH2O | iPrO | CH2CH2OOCCH2CH2COOH |
| 697 | CF3CH2CH2O | iPr | CH2CH2OOCCH2CH2COOH |
| 698 | CF3CH2CH2O | CHF2CH2O | CH2CH2OOCCH2CH2COOH |
| 699 | CF3CH2CH2O | CF3CH2O | CH2CH2OOCCH2CH2COOH |
| 700 | CF3CH2CH2O | EtO | CH2CH2OOCCH2CH2COOH |
| 701 | CF3CH2CH2O | Et | CH2CH2OOCCH2CH2COOH |
| 702 | CF3CH2CH2O | Pr | CH2CH2OOCCH2CH2COOH |
| 703 | CF3CH2CH2O | MeS | CH2CH2OOCCH2CH2COOH |
| 704 | CF3CH2CH2O | CF3S | CH2CH2OOCCH2CH2COOH |
| 705 | CF3CH2CH2O | 1-pyrr | CH2CH2OOCCH2CH2COOH |
| 706 | CHF2CH2O | cPrO | CH2CH2OOCCH2CH2COOH |
| 707 | CHF2CH2O | cPr | CH2CH2OOCCH2CH2COOH |
| 708 | CHF2CH2O | CHF2O | CH2CH2OOCCH2CH2COOH |
| 709 | CHF2CH2O | CF3O | CH2CH2OOCCH2CH2COOH |
| 710 | CHF2CH2O | CF3 | CH2CH2OOCCH2CH2COOH |
| 711 | CHF2CH2O | iPrO | CH2CH2OOCCH2CH2COOH |
| 712 | CHF2CH2O | iPr | CH2CH2OOCCH2CH2COOH |
| 713 | CHF2CH2O | CHF2CH2O | CH2CH2OOCCH2CH2COOH |
| 714 | CHF2CH2O | CF3CH2O | CH2CH2OOCCH2CH2COOH |
| 715 | CHF2CH2O | EtO | CH2CH2OOCCH2CH2COOH |
| 716 | CHF2CH2O | Et | CH2CH2OOCCH2CH2COOH |
| 717 | CHF2CH2O | Pr | CH2CH2OOCCH2CH2COOH |
| 718 | CHF2CH2O | MeS | CH2CH2OOCCH2CH2COOH |
| 719 | CHF2CH2O | CF3S | CH2CH2OOCCH2CH2COOH |
| 720 | CHF2CH2O | 1-pyrr | CH2CH2OOCCH2CH2COOH |
| 721 | (2,2-diF-cPr)CH2O | cPrO | CH2CH2OOCCH2CH2COOH |
| 722 | (2,2-diF-cPr)CH2O | cPr | CH2CH2OOCCH2CH2COOH |
| 723 | (2,2-diF-cPr)CH2O | CHF2O | CH2CH2OOCCH2CH2COOH |
| 724 | (2,2-diF-cPr)CH2O | CF3O | CH2CH2OOCCH2CH2COOH |
| 725 | (2,2-diF-cPr)CH2O | CF3 | CH2CH2OOCCH2CH2COOH |
| 726 | (2,2-diF-cPr)CH2O | iPrO | CH2CH2OOCCH2CH2COOH |
| 727 | (2,2-diF-cPr)CH2O | iPr | CH2CH2OOCCH2CH2COOH |
| 728 | (2,2-diF-cPr)CH2O | CHF2CH2O | CH2CH2OOCCH2CH2COOH |
| 729 | (2,2-diF-cPr)CH2O | CF3CH2O | CH2CH2OOCCH2CH2COOH |
| 730 | (2,2-diF-cPr)CH2O | EtO | CH2CH2OOCCH2CH2COOH |
| 731 | (2,2-diF-cPr)CH2O | Et | CH2CH2OOCCH2CH2COOH |
| 732 | (2,2-diF-cPr)CH2O | Pr | CH2CH2OOCCH2CH2COOH |
| 733 | (2,2-diF-cPr)CH2O | MeS | CH2CH2OOCCH2CH2COOH |
| 734 | (2,2-diF-cPr)CH2O | CF3S | CH2CH2OOCCH2CH2COOH |
| 735 | (2,2-diF-cPr)CH2O | 1-pyrr | CH2CH2OOCCH2CH2COOH |
| 736 | 4-CF3PhO | cPrO | CH2CH2OOCCH2CH2COOH |
| 737 | 4-CF3PhO | cPr | CH2CH2OOCCH2CH2COOH |
| 738 | 4-CF3PhO | CHF2O | CH2CH2OOCCH2CH2COOH |
| 739 | 4-CF3PhO | CF3O | CH2CH2OOCCH2CH2COOH |
| 740 | 4-CF3PhO | CF3 | CH2CH2OOCCH2CH2COOH |
| 741 | 4-CF3PhO | iPrO | CH2CH2OOCCH2CH2COOH |
| 742 | 4-CF3PhO | iPr | CH2CH2OOCCH2CH2COOH |
| 743 | 4-CF3PhO | CHF2CH2O | CH2CH2OOCCH2CH2COOH |
| 744 | 4-CF3PhO | CF3CH2O | CH2CH2OOCCH2CH2COOH |
| 745 | 4-CF3PhO | EtO | CH2CH2OOCCH2CH2COOH |
| 746 | 4-CF3PhO | Et | CH2CH2OOCCH2CH2COOH |

TABLE 4-continued

Exemplary compound table 1

(I-1)

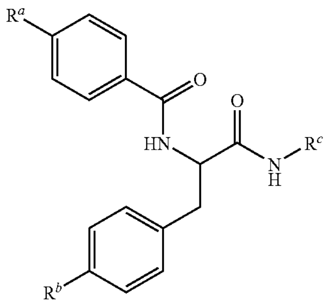

| Compound No. | $R^a$ | $R^b$ | $R^c$ |
|---|---|---|---|
| 747 | 4-CF3PhO | Pr | CH2CH2OOCCH2CH2COOH |
| 748 | 4-CF3PhO | MeS | CH2CH2OOCCH2CH2COOH |
| 749 | 4-CF3PhO | CF3S | CH2CH2OOCCH2CH2COOH |
| 750 | 4-CF3PhO | 1-pyrr | CH2CH2OOCCH2CH2COOH |
| 751 | CF3CH2O | cPrO | CH2CH2OH |
| 752 | CF3CH2O | cPr | CH2CH2OH |
| 753 | CF3CH2O | CHF2O | CH2CH2OH |
| 754 | CF3CH2O | CF3O | CH2CH2OH |
| 755 | CF3CH2O | CF3 | CH2CH2OH |
| 756 | CF3CH2O | cPrO | CH2CH2CH2OH |
| 757 | CF3CH2O | cPr | CH2CH2CH2OH |
| 758 | CF3CH2O | CHF2O | CH2CH2CH2OH |
| 759 | CF3CH2O | CF3O | CH2CH2CH2OH |
| 760 | CF3CH2O | CF3 | CH2CH2CH2OH |
| 761 | CF3CH2O | cPrO | CH2-(1-HO-cPr) |
| 762 | CF3CH2O | cPr | CH2-(1-HO-cPr) |
| 763 | CF3CH2O | CHF2O | CH2-(1-HO-cPr) |
| 764 | CF3CH2O | CF3O | CH2-(1-HO-cPr) |
| 765 | CF3CH2O | CF3 | CH2-(1-HO-cPr) |
| 766 | CF3CH2CH2CH2O | cPrO | CH2CH2OH |
| 767 | CF3CH2CH2CH2O | cPr | CH2CH2OH |
| 768 | CF3CH2CH2CH2O | CHF2O | CH2CH2OH |
| 769 | CF3CH2CH2CH2O | CF3O | CH2CH2OH |
| 770 | CF3CH2CH2CH2O | CF3 | CH2CH2OH |
| 771 | CF3CH2CH2CH2O | iPrO | CH2CH2OH |
| 772 | CF3CH2CH2CH2O | iPr | CH2CH2OH |
| 773 | CF3CH2CH2CH2O | CHF2CH2O | CH2CH2OH |
| 774 | CF3CH2CH2CH2O | CF3CH2O | CH2CH2OH |
| 775 | CF3CH2CH2CH2O | EtO | CH2CH2OH |
| 776 | CF3CH2CH2CH2O | Et | CH2CH2OH |
| 777 | CF3CH2CH2CH2O | Pr | CH2CH2OH |
| 778 | CF3CH2CH2CH2O | MeS | CH2CH2OH |
| 779 | CF3CH2CH2CH2O | CF3S | CH2CH2OH |
| 780 | CF3CH2CH2CH2O | 1-pyrr | CH2CH2OH |
| 781 | CF3CH2CH2CH2O | cPrO | CH2CH2CH2OH |
| 782 | CF3CH2CH2CH2O | cPr | CH2CH2CH2OH |
| 783 | CF3CH2CH2CH2O | CHF2O | CH2CH2CH2OH |
| 784 | CF3CH2CH2CH2O | CF3O | CH2CH2CH2OH |
| 785 | CF3CH2CH2CH2O | CF3 | CH2CH2CH2OH |
| 786 | CF3CH2CH2CH2O | iPrO | CH2CH2CH2OH |
| 787 | CF3CH2CH2CH2O | iPr | CH2CH2CH2OH |
| 788 | CF3CH2CH2CH2O | CHF2CH2O | CH2CH2CH2OH |
| 789 | CF3CH2CH2CH2O | CF3CH2O | CH2CH2CH2OH |
| 790 | CF3CH2CH2CH2O | EtO | CH2CH2CH2OH |
| 791 | CF3CH2CH2CH2O | Et | CH2CH2CH2OH |
| 792 | CF3CH2CH2CH2O | Pr | CH2CH2CH2OH |
| 793 | CF3CH2CH2CH2O | MeS | CH2CH2CH2OH |
| 794 | CF3CH2CH2CH2O | CF3S | CH2CH2CH2OH |
| 795 | CF3CH2CH2CH2O | 1-pyrr | CH2CH2CH2OH |
| 796 | CF3CH2CH2CH2O | cPrO | CH2-(1-HO-cPr) |
| 797 | CF3CH2CH2CH2O | cPr | CH2-(1-HO-cPr) |
| 798 | CF3CH2CH2CH2O | CHF2O | CH2-(1-HO-cPr) |
| 799 | CF3CH2CH2CH2O | CF3O | CH2-(1-HO-cPr) |
| 800 | CF3CH2CH2CH2O | CF3 | CH2-(1-HO-cPr) |
| 801 | CF3CH2CH2CH2O | iPrO | CH2-(1-HO-cPr) |
| 802 | CF3CH2CH2CH2O | iPr | CH2-(1-HO-cPr) |
| 803 | CF3CH2CH2CH2O | CHF2CH2O | CH2-(1-HO-cPr) |
| 804 | CF3CH2CH2CH2O | CF3CH2O | CH2-(1-HO-cPr) |
| 805 | CF3CH2CH2CH2O | EtO | CH2-(1-HO-cPr) |

TABLE 4-continued

Exemplary compound table 1

(I-1)

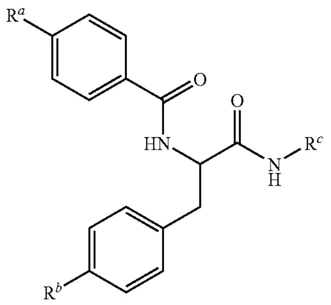

| Compound No. | $R^a$ | $R^b$ | $R^c$ |
|---|---|---|---|
| 806 | CF3CH2CH2CH2O | Et | CH2-(1-HO-cPr) |
| 807 | CF3CH2CH2CH2O | Pr | CH2-(1-HO-cPr) |
| 808 | CF3CH2CH2CH2O | MeS | CH2-(1-HO-cPr) |
| 809 | CF3CH2CH2CH2O | CF3S | CH2-(1-HO-cPr) |
| 810 | CF3CH2CH2CH2O | 1-pyrr | CH2-(1-HO-cPr) |
| 811 | CF3CH2CH2CH2O | cPrO | CH2CH2OAc |
| 812 | CF3CH2CH2CH2O | cPr | CH2CH2OAc |
| 813 | CF3CH2CH2CH2O | CHF2O | CH2CH2OAc |
| 814 | CF3CH2CH2CH2O | CF3O | CH2CH2OAc |
| 815 | CF3CH2CH2CH2O | CF3 | CH2CH2OAc |
| 816 | CF3CH2CH2CH2O | iPrO | CH2CH2OAc |
| 817 | CF3CH2CH2CH2O | iPr | CH2CH2OAc |
| 818 | CF3CH2CH2CH2O | CHF2CH2O | CH2CH2OAc |
| 819 | CF3CH2CH2CH2O | CF3CH2O | CH2CH2OAc |
| 820 | CF3CH2CH2CH2O | EtO | CH2CH2OAc |
| 821 | CF3CH2CH2CH2O | Et | CH2CH2OAc |
| 822 | CF3CH2CH2CH2O | Pr | CH2CH2OAc |
| 823 | CF3CH2CH2CH2O | MeS | CH2CH2OAc |
| 824 | CF3CH2CH2CH2O | CF3S | CH2CH2OAc |
| 825 | CF3CH2CH2CH2O | 1-pyrr | CH2CH2OAc |
| 826 | CF3CH2CH2CH2O | cPrO | CH2CH2OOCCH2CH2COOH |
| 827 | CF3CH2CH2CH2O | cPr | CH2CH2OOCCH2CH2COOH |
| 828 | CF3CH2CH2CH2O | CHF2O | CH2CH2OOCCH2CH2COOH |
| 829 | CF3CH2CH2CH2O | CF3O | CH2CH2OOCCH2CH2COOH |
| 830 | CF3CH2CH2CH2O | CF3 | CH2CH2OOCCH2CH2COOH |
| 831 | CF3CH2CH2CH2O | iPrO | CH2CH2OOCCH2CH2COOH |
| 832 | CF3CH2CH2CH2O | iPr | CH2CH2OOCCH2CH2COOH |
| 833 | CF3CH2CH2CH2O | CHF2CH2O | CH2CH2OOCCH2CH2COOH |
| 834 | CF3CH2CH2CH2O | CF3CH2O | CH2CH2OOCCH2CH2COOH |
| 835 | CF3CH2CH2CH2O | EtO | CH2CH2OOCCH2CH2COOH |
| 836 | CF3CH2CH2CH2O | Et | CH2CH2OOCCH2CH2COOH |
| 837 | CF3CH2CH2CH2O | Pr | CH2CH2OOCCH2CH2COOH |
| 838 | CF3CH2CH2CH2O | MeS | CH2CH2OOCCH2CH2COOH |
| 839 | CF3CH2CH2CH2O | CF3S | CH2CH2OOCCH2CH2COOH |
| 840 | CF3CH2CH2CH2O | 1-pyrr | CH2CH2OOCCH2CH2COOH |
| 841 | cPrCH2O | cPrO | H |
| 842 | cPrCH2O | cPr | H |
| 843 | cPrCH2O | CHF2O | H |
| 844 | cPrCH2O | CF3O | H |
| 845 | cPrCH2O | CF3 | H |
| 846 | cPrCH2O | cPrO | Me |
| 847 | cPrCH2O | cPr | Me |
| 848 | cPrCH2O | CHF2O | Me |
| 849 | cPrCH2O | CF3O | Me |
| 850 | cPrCH2O | CF3 | Me |
| 851 | cPrCH2O | cPrO | Et |
| 852 | cPrCH2O | cPr | Et |
| 853 | cPrCH2O | CHF2O | Et |
| 854 | cPrCH2O | CF3O | Et |
| 855 | cPrCH2O | CF3 | Et |
| 856 | cPrCH2O | cPrO | CH2CH2OMe |
| 857 | cPrCH2O | cPr | CH2CH2OMe |
| 858 | cPrCH2O | CHF2O | CH2CH2OMe |
| 859 | cPrCH2O | CF3O | CH2CH2OMe |
| 860 | cPrCH2O | CF3 | CH2CH2OMe |
| 861 | cPrCH2O | cPrO | CH2CCH |
| 862 | cPrCH2O | cPr | CH2CCH |
| 863 | cPrCH2O | CHF2O | CH2CCH |
| 864 | cPrCH2O | CF3O | CH2CCH |

TABLE 4-continued

Exemplary compound table 1

(I-1)

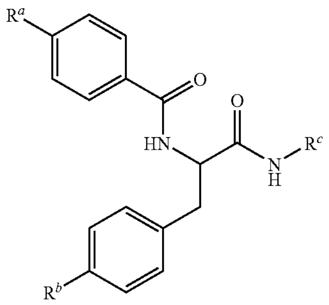

| Compound No. | $R^a$ | $R^b$ | $R^c$ |
|---|---|---|---|
| 865 | cPrCH2O | CF3 | CH2CCH |
| 866 | cPrCH2O | cPrO | (R)-CH2CH(OH)Me |
| 867 | cPrCH2O | cPr | (R)-CH2CH(OH)Me |
| 868 | cPrCH2O | CHF2O | (R)-CH2CH(OH)Me |
| 869 | cPrCH2O | CF3O | (R)-CH2CH(OH)Me |
| 870 | cPrCH2O | CF3 | (R)-CH2CH(OH)Me |
| 871 | cPrCH2O | cPrO | (S)-CH2CH(OH)Me |
| 872 | cPrCH2O | cPr | (S)-CH2CH(OH)Me |
| 873 | cPrCH2O | CHF2O | (S)-CH2CH(OH)Me |
| 874 | cPrCH2O | CF3O | (S)-CH2CH(OH)Me |
| 875 | cPrCH2O | CF3 | (S)-CH2CH(OH)Me |
| 876 | cPrCH2O | cPrO | CH2C(═O)Me |
| 877 | cPrCH2O | cPr | CH2C(═O)Me |
| 878 | cPrCH2O | CHF2O | CH2C(═O)Me |
| 879 | cPrCH2O | CF3O | CH2C(═O)Me |
| 880 | cPrCH2O | CF3 | CH2C(═O)Me |
| 881 | cPrCH2O | cPrO | CH2C(═NOH)Me |
| 882 | cPrCH2O | cPr | CH2C(═NOH)Me |
| 883 | cPrCH2O | CHF2O | CH2C(═NOH)Me |
| 884 | cPrCH2O | CF3O | CH2C(═NOH)Me |
| 885 | cPrCH2O | CF3 | CH2C(═NOH)Me |
| 886 | cPrCH2O | cPrO | CH2CH2F |
| 887 | cPrCH2O | cPr | CH2CH2F |
| 888 | cPrCH2O | CHF2O | CH2CH2F |
| 889 | cPrCH2O | CF3O | CH2CH2F |
| 890 | cPrCH2O | CF3 | CH2CH2F |
| 891 | cPrCH2O | cPrO | CH2CHF2 |
| 892 | cPrCH2O | cPr | CH2CHF2 |
| 893 | cPrCH2O | CHF2O | CH2CHF2 |
| 894 | cPrCH2O | CF3O | CH2CHF2 |
| 895 | cPrCH2O | CF3 | CH2CHF2 |
| 896 | cPrCH2CH2O | cPrO | H |
| 897 | cPrCH2CH2O | cPr | H |
| 898 | cPrCH2CH2O | CHF2O | H |
| 899 | cPrCH2CH2O | CF3O | H |
| 900 | cPrCH2CH2O | CF3 | H |
| 901 | cPrCH2CH2O | cPrO | Me |
| 902 | cPrCH2CH2O | cPr | Me |
| 903 | cPrCH2CH2O | CHF2O | Me |
| 904 | cPrCH2CH2O | CF3O | Me |
| 905 | cPrCH2CH2O | CF3 | Me |
| 906 | cPrCH2CH2O | cPrO | Et |
| 907 | cPrCH2CH2O | cPr | Et |
| 908 | cPrCH2CH2O | CHF2O | Et |
| 909 | cPrCH2CH2O | CF3O | Et |
| 910 | cPrCH2CH2O | CF3 | Et |
| 911 | cPrCH2CH2O | cPrO | CH2CH2OMe |
| 912 | cPrCH2CH2O | cPr | CH2CH2OMe |
| 913 | cPrCH2CH2O | CHF2O | CH2CH2OMe |
| 914 | cPrCH2CH2O | CF3O | CH2CH2OMe |
| 915 | cPrCH2CH2O | CF3 | CH2CH2OMe |
| 916 | cPrCH2CH2O | cPrO | CH2CCH |
| 917 | cPrCH2CH2O | cPr | CH2CCH |
| 918 | cPrCH2CH2O | CHF2O | CH2CCH |
| 919 | cPrCH2CH2O | CF3O | CH2CCH |
| 920 | cPrCH2CH2O | CF3 | CH2CCH |
| 921 | cPrCH2CH2O | cPrO | (R)-CH2CH(OH)Me |
| 922 | cPrCH2CH2O | cPr | (R)-CH2CH(OH)Me |
| 923 | cPrCH2CH2O | CHF2O | (R)-CH2CH(OH)Me |

TABLE 4-continued

Exemplary compound table 1

(I-1)

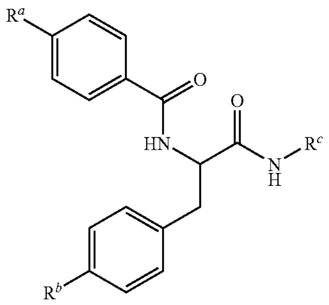

| Compound No. | $R^a$ | $R^b$ | $R^c$ |
|---|---|---|---|
| 924 | cPrCH2CH2O | CF3O | (R)-CH2CH(OH)Me |
| 925 | cPrCH2CH2O | CF3 | (R)-CH2CH(OH)Me |
| 926 | cPrCH2CH2O | cPrO | (S)-CH2CH(OH)Me |
| 927 | cPrCH2CH2O | cPr | (S)-CH2CH(OH)Me |
| 928 | cPrCH2CH2O | CHF2O | (S)-CH2CH(OH)Me |
| 929 | cPrCH2CH2O | CF3O | (S)-CH2CH(OH)Me |
| 930 | cPrCH2CH2O | CF3 | (S)-CH2CH(OH)Me |
| 931 | cPrCH2CH2O | cPrO | CH2C(═O)Me |
| 932 | cPrCH2CH2O | cPr | CH2C(═O)Me |
| 933 | cPrCH2CH2O | CHF2O | CH2C(═O)Me |
| 934 | cPrCH2CH2O | CF3O | CH2C(═O)Me |
| 935 | cPrCH2CH2O | CF3 | CH2C(═O)Me |
| 936 | cPrCH2CH2O | cPrO | CH2C(═NOH)Me |
| 937 | cPrCH2CH2O | cPr | CH2C(═NOH)Me |
| 938 | cPrCH2CH2O | CHF2O | CH2C(═NOH)Me |
| 939 | cPrCH2CH2O | CF3O | CH2C(═NOH)Me |
| 940 | cPrCH2CH2O | CF3 | CH2C(═NOH)Me |
| 941 | cPrCH2CH2O | cPrO | CH2CH2F |
| 942 | cPrCH2CH2O | cPr | CH2CH2F |
| 943 | cPrCH2CH2O | CHF2O | CH2CH2F |
| 944 | cPrCH2CH2O | CF3O | CH2CH2F |
| 945 | cPrCH2CH2O | CF3 | CH2CH2F |
| 946 | cPrCH2CH2O | cPrO | CH2CHF2 |
| 947 | cPrCH2CH2O | cPr | CH2CHF2 |
| 948 | cPrCH2CH2O | CHF2O | CH2CHF2 |
| 949 | cPrCH2CH2O | CF3O | CH2CHF2 |
| 950 | cPrCH2CH2O | CF3 | CH2CHF2 |
| 951 | CF3CH2CH2O | cPrO | H |
| 952 | CF3CH2CH2O | cPr | H |
| 953 | CF3CH2CH2O | CHF2O | H |
| 954 | CF3CH2CH2O | CF3O | H |
| 955 | CF3CH2CH2O | CF3 | H |
| 956 | CF3CH2CH2O | cPrO | Me |
| 957 | CF3CH2CH2O | cPr | Me |
| 958 | CF3CH2CH2O | CHF2O | Me |
| 959 | CF3CH2CH2O | CF3O | Me |
| 960 | CF3CH2CH2O | CF3 | Me |
| 961 | CF3CH2CH2O | cPrO | Et |
| 962 | CF3CH2CH2O | cPr | Et |
| 963 | CF3CH2CH2O | CHF2O | Et |
| 964 | CF3CH2CH2O | CF3O | Et |
| 965 | CF3CH2CH2O | CF3 | Et |
| 966 | CF3CH2CH2O | cPrO | CH2CH2OMe |
| 967 | CF3CH2CH2O | cPr | CH2CH2OMe |
| 968 | CF3CH2CH2O | CHF2O | CH2CH2OMe |
| 969 | CF3CH2CH2O | CF3O | CH2CH2OMe |
| 970 | CF3CH2CH2O | CF3 | CH2CH2OMe |
| 971 | CF3CH2CH2O | cPrO | CH2CCH |
| 972 | CF3CH2CH2O | cPr | CH2CCH |
| 973 | CF3CH2CH2O | CHF2O | CH2CCH |
| 974 | CF3CH2CH2O | CF3O | CH2CCH |
| 975 | CF3CH2CH2O | CF3 | CH2CCH |
| 976 | CF3CH2CH2O | cPrO | (R)-CH2CH(OH)Me |
| 977 | CF3CH2CH2O | cPr | (R)-CH2CH(OH)Me |
| 978 | CF3CH2CH2O | CHF2O | (R)-CH2CH(OH)Me |
| 979 | CF3CH2CH2O | CF3O | (R)-CH2CH(OH)Me |
| 980 | CF3CH2CH2O | CF3 | (R)-CH2CH(OH)Me |
| 981 | CF3CH2CH2O | cPrO | (S)-CH2CH(OH)Me |
| 982 | CF3CH2CH2O | cPr | (S)-CH2CH(OH)Me |

TABLE 4-continued

Exemplary compound table 1

(I-1)

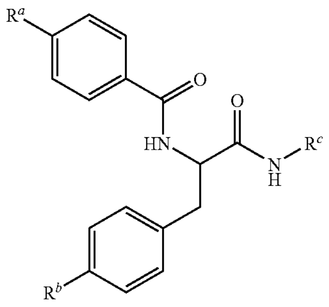

| Compound No. | $R^a$ | $R^b$ | $R^c$ |
|---|---|---|---|
| 983 | CF3CH2CH2O | CHF2O | (S)-CH2CH(OH)Me |
| 984 | CF3CH2CH2O | CF3O | (S)-CH2CH(OH)Me |
| 985 | CF3CH2CH2O | CF3 | (S)-CH2CH(OH)Me |
| 986 | CF3CH2CH2O | cPrO | CH2C(═O)Me |
| 987 | CF3CH2CH2O | cPr | CH2C(═O)Me |
| 988 | CF3CH2CH2O | CHF2O | CH2C(═O)Me |
| 989 | CF3CH2CH2O | CF3O | CH2C(═O)Me |
| 990 | CF3CH2CH2O | CF3 | CH2C(═O)Me |
| 991 | CF3CH2CH2O | cPrO | CH2C(═NOH)Me |
| 992 | CF3CH2CH2O | cPr | CH2C(═NOH)Me |
| 993 | CF3CH2CH2O | CHF2O | CH2C(═NOH)Me |
| 994 | CF3CH2CH2O | CF3O | CH2C(═NOH)Me |
| 995 | CF3CH2CH2O | CF3 | CH2C(═NOH)Me |
| 996 | CF3CH2CH2O | cPrO | CH2CH2F |
| 997 | CF3CH2CH2O | cPr | CH2CH2F |
| 998 | CF3CH2CH2O | CHF2O | CH2CH2F |
| 999 | CF3CH2CH2O | CF3O | CH2CH2F |
| 1000 | CF3CH2CH2O | CF3 | CH2CH2F |
| 1001 | CF3CH2CH2O | cPrO | CH2CHF2 |
| 1002 | CF3CH2CH2O | cPr | CH2CHF2 |
| 1003 | CF3CH2CH2O | CHF2O | CH2CHF2 |
| 1004 | CF3CH2CH2O | CF3O | CH2CHF2 |
| 1005 | CF3CH2CH2O | CF3 | CH2CHF2 |
| 1006 | CF3CH2CH2CH2O | cPrO | H |
| 1007 | CF3CH2CH2CH2O | cPr | H |
| 1008 | CF3CH2CH2CH2O | CHF2O | H |
| 1009 | CF3CH2CH2CH2O | CF3O | H |
| 1010 | CF3CH2CH2CH2O | CF3 | H |
| 1011 | CF3CH2CH2CH2O | cPrO | Me |
| 1012 | CF3CH2CH2CH2O | cPr | Me |
| 1013 | CF3CH2CH2CH2O | CHF2O | Me |
| 1014 | CF3CH2CH2CH2O | CF3O | Me |
| 1015 | CF3CH2CH2CH2O | CF3 | Me |
| 1016 | CF3CH2CH2CH2O | cPrO | Et |
| 1017 | CF3CH2CH2CH2O | cPr | Et |
| 1018 | CF3CH2CH2CH2O | CHF2O | Et |
| 1019 | CF3CH2CH2CH2O | CF3O | Et |
| 1020 | CF3CH2CH2CH2O | CF3 | Et |
| 1021 | CF3CH2CH2CH2O | cPrO | CH2CH2OMe |
| 1022 | CF3CH2CH2CH2O | cPr | CH2CH2OMe |
| 1023 | CF3CH2CH2CH2O | CHF2O | CH2CH2OMe |
| 1024 | CF3CH2CH2CH2O | CF3O | CH2CH2OMe |
| 1025 | CF3CH2CH2CH2O | CF3 | CH2CH2OMe |
| 1026 | CF3CH2CH2CH2O | cPrO | CH2CCH |
| 1027 | CF3CH2CH2CH2O | cPr | CH2CCH |
| 1028 | CF3CH2CH2CH2O | CHF2O | CH2CCH |
| 1029 | CF3CH2CH2CH2O | CF3O | CH2CCH |
| 1030 | CF3CH2CH2CH2O | CF3 | CH2CCH |
| 1031 | CF3CH2CH2CH2O | cPrO | (R)-CH2CH(OH)Me |
| 1032 | CF3CH2CH2CH2O | cPr | (R)-CH2CH(OH)Me |
| 1033 | CF3CH2CH2CH2O | CHF2O | (R)-CH2CH(OH)Me |
| 1034 | CF3CH2CH2CH2O | CF3O | (R)-CH2CH(OH)Me |
| 1035 | CF3CH2CH2CH2O | CF3 | (R)-CH2CH(OH)Me |
| 1036 | CF3CH2CH2CH2O | cPrO | (S)-CH2CH(OH)Me |
| 1037 | CF3CH2CH2CH2O | cPr | (S)-CH2CH(OH)Me |
| 1038 | CF3CH2CH2CH2O | CHF2O | (S)-CH2CH(OH)Me |
| 1039 | CF3CH2CH2CH2O | CF3O | (S)-CH2CH(OH)Me |
| 1040 | CF3CH2CH2CH2O | CF3 | (S)-CH2CH(OH)Me |
| 1041 | CF3CH2CH2CH2O | cPrO | CH2C(═O)Me |

TABLE 4-continued

Exemplary compound table 1

(I-1)

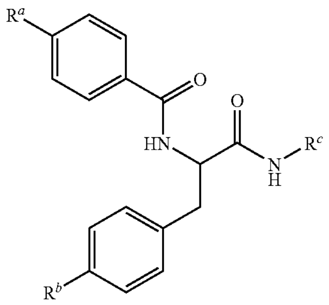

| Compound No. | $R^a$ | $R^b$ | $R^c$ |
|---|---|---|---|
| 1042 | CF3CH2CH2CH2O | cPr | CH2C(═O)Me |
| 1043 | CF3CH2CH2CH2O | CHF2O | CH2C(═O)Me |
| 1044 | CF3CH2CH2CH2O | CF3O | CH2C(═O)Me |
| 1045 | CF3CH2CH2CH2O | CF3 | CH2C(═O)Me |
| 1046 | CF3CH2CH2CH2O | cPrO | CH2C(═NOH)Me |
| 1047 | CF3CH2CH2CH2O | cPr | CH2C(═NOH)Me |
| 1048 | CF3CH2CH2CH2O | CHF2O | CH2C(═NCH)Me |
| 1049 | CF3CH2CH2CH2O | CF3O | CH2C(═NOH)Me |
| 1050 | CF3CH2CH2CH2O | CF3 | CH2C(═NOH)Me |
| 1051 | CF3CH2CH2CH2O | cPrO | CH2CH2F |
| 1052 | CF3CH2CH2CH2O | cPr | CH2CH2F |
| 1053 | CF3CH2CH2CH2O | CHF2O | CH2CH2F |
| 1054 | CF3CH2CH2CH2O | CF3O | CH2CH2F |
| 1055 | CF3CH2CH2CH2O | CF3 | CH2CH2F |
| 1056 | CF3CH2CH2CH2O | cPrO | CH2CHF2 |
| 1057 | CF3CH2CH2CH2O | cPr | CH2CHF2 |
| 1058 | CF3CH2CH2CH2O | CHF2O | CH2CHF2 |
| 1059 | CF3CH2CH2CH2O | CF3O | CH2CHF2 |
| 1060 | CF3CH2CH2CH2O | CF3 | CH2CHF2 |
| 1061 | 4-CF3PhO | cPrO | H |
| 1062 | 4-CF3PhO | cPr | H |
| 1063 | 4-CF3PhO | CHF2O | H |
| 1064 | 4-CF3PhO | CF3O | H |
| 1065 | 4-CF3PhO | CF3 | H |
| 1066 | 4-CF3PhO | cPrO | Me |
| 1067 | 4-CF3PhO | cPr | Me |
| 1068 | 4-CF3PhO | CHF2O | Me |
| 1069 | 4-CF3PhO | CF3O | Me |
| 1070 | 4-CF3PhO | CF3 | Me |
| 1071 | 4-CF3PhO | cPrO | Et |
| 1072 | 4-CF3PhO | cPr | Et |
| 1073 | 4-CF3PhO | CHF2O | Et |
| 1074 | 4-CF3PhO | CF3O | Et |
| 1075 | 4-CF3PhO | CF3 | Et |
| 1076 | 4-CF3PhO | cPrO | CH2CH2OMe |
| 1077 | 4-CF3PhO | cPr | CH2CH2OMe |
| 1078 | 4-CF3PhO | CHF2O | CH2CH2OMe |
| 1079 | 4-CF3PhO | CF3O | CH2CH2OMe |
| 1080 | 4-CF3PhO | CF3 | CH2CH2OMe |
| 1081 | 4-CF3PhO | cPrO | CH2CCH |
| 1082 | 4-CF3PhO | cPr | CH2CCH |
| 1083 | 4-CF3PhO | CHF2O | CH2CCH |
| 1084 | 4-CF3PhO | CF3O | CH2CCH |
| 1085 | 4-CF3PhO | CF3 | CH2CCH |
| 1086 | 4-CF3PhO | cPrO | (R)-CH2CH(OH)Me |
| 1087 | 4-CF3PhO | cPr | (R)-CH2CH(OH)Me |
| 1088 | 4-CF3PhO | CHF2O | (R)-CH2CH(OH)Me |
| 1089 | 4-CF3PhO | CF3O | (R)-CH2CH(OH)Me |
| 1090 | 4-CF3PhO | CF3 | (R)-CH2CH(OH)Me |
| 1091 | 4-CF3PhO | cPrO | (S)-CH2CH(OH)Me |
| 1092 | 4-CF3PhO | cPr | (S)-CH2CH(OH)Me |
| 1093 | 4-CF3PhO | CHF2O | (S)-CH2CH(OH)Me |
| 1094 | 4-CF3PhO | CF3O | (S)-CH2CH(OH)Me |
| 1095 | 4-CF3PhO | CF3 | (S)-CH2CH(OH)Me |
| 1096 | 4-CF3PhO | cPrO | CH2C(═O)Me |
| 1097 | 4-CF3PhO | cPr | CH2C(═O)Me |
| 1098 | 4-CF3FhO | CHF2O | CH2C(═O)Me |
| 1009 | 4-CF3PhO | CF3O | CH2C(═O)Me |
| 1100 | 4-CF3PhO | CF3 | CH2C(═O)Me |

TABLE 4-continued

Exemplary compound table 1

(I-1)

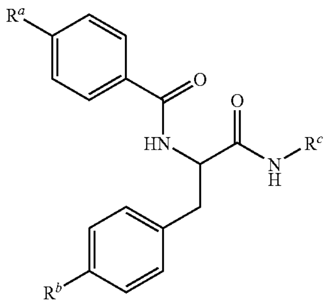

| Compound No. | $R^a$ | $R^b$ | $R^c$ |
|---|---|---|---|
| 1101 | 4-CF3PhO | cPrO | CH2C(=NOH)Me |
| 1102 | 4-CF3PhO | cPr | CH2C(=NOH)Me |
| 1103 | 4-CF3PhO | CHF2O | CH2C(=NOH)Me |
| 1104 | 4-CF3PhO | CF3O | CH2C(=NOH)Me |
| 1105 | 4-CF3PhO | CF3 | CH2C(=NOH)Me |
| 1106 | 4-CF3PhO | cPrO | CH2CH2F |
| 1107 | 4-CF3PhO | cPr | CH2CH2F |
| 1108 | 4-CF3PhO | CHF2O | CH2CH2F |
| 1109 | 4-CF3PhO | CF3O | CH2CH2F |
| 1110 | 4-CF3PhO | CF3 | CH2CH2F |
| 1111 | 4-CF3PhO | cPrO | CH2CHF2 |
| 1112 | 4-CF3PhO | cPr | CH2CHF2 |
| 1113 | 4-CF3PhO | CHF2O | CH2CHF2 |
| 1114 | 4-CF3PhO | CF3O | CH2CHF2 |
| 1115 | 4-CF3PhO | CF3 | CH2CHF2 |

In the above Table 4, preferable examples of the compound having General Formula (I-1) according to the present invention are Exemplary Compound Nos. 1 to 180, 196 to 210, 216 to 245, 271 to 300, 306 to 320, 326 to 340, 376 to 390, 396 to 425, 451 to 480, 486 to 500, 506 to 520, 541 to 645, 751 to 825, and 841 to 1115;

more preferable examples are Exemplary Compound Nos. 1 to 180, 751 to 755, 766 to 780, 841 to 850, 866 to 875, 886 to 905, 921 to 930, 941 to 960, 976 to 985, 996 to 1015, 1031 to 1040, 1051 to 1070, 1086 to 1095, and 1106 to 1115; and particularly preferable examples are Exemplary Compound No. 16: (Example 20) 4-(cyclopropylmethoxy)-N-{1-[4-(cyclopropyloxy)benzyl]-2-[(2-hydroxyethyl)amino]-2-oxoethyl}benzamide, Exemplary Compound No. 17: (Example 23) N-{1-(4-cyclopropylbenzyl)-2-[(2-hydroxyethyl)amino]-2-oxoethyl}-4-(cyclopropylmethoxy)benzamide, Exemplary Compound No. 18: (Example 18) 4-(cyclopropylmethoxy)-N-{1-[4-(difluoromethoxy)benzyl]-2-[(2-hydroxyethyl)amino]-2-oxoethyl}benzamide, Exemplary Compound No. 19: (Example 19) 4-(cyclopropylmethoxy)-N-{2-[(2-hydroxyethyl)amino]-2-oxo-1-[4-(trifluoromethoxy)benzyl]ethyl}benzamide, Exemplary Compound No. 20: (Example 22) 4-(cyclopropylmethoxy)-N-{2-[(2-hydroxyethyl)amino]-2-oxo-1-[4-(trifluoromethyl)benzyl]ethyl}benzamide, Exemplary Compound No. 38: (Example 3) 4-(2-cyclopropylethoxy)-N-{1-[4-(difluoromethoxy)benzyl]-2-[(2-hydroxyethyl)amino]-2-oxoethyl}benzamide, Exemplary Compound No. 39: (Example 4) 4-(2-cyclopropylethoxy)-N-{2-[(2-hydroxyethyl)amino]-2-oxo-1-[4-(trifluoromethoxy)benzyl]ethyl}benzamide, Exemplary Compound No. 40: (Example 7) 4-(2-cyclopropylethoxy)-N-{2-[(2-hydroxyethyl)amino]-2-oxo-1-[4-(trifluoromethyl)benzyl]ethyl}benzamide, Exemplary Compound No. 54: (Example 25) 4-(3-cyclopropylpropoxy)-N-{2-[(2-hydroxyethyl)amino]-2-oxo-1-[4-(trifluoromethoxy)benzyl]ethyl}benzamide, Exemplary Compound No. 93: (Example 33) N-{1-[4-(difluoromethoxy)benzyl]-2-[(2-hydroxyethyl)amino]-2-oxoethyl}-4-(3,3,3-trifluoropropoxy)benzamide, Exemplary Compound No. 94: (Example 34) N-{2-[(2-hydroxyethyl)amino]-2-oxo-1-[4-(trifluoromethoxy)benzyl]ethyl}-4-(3,3,3-trifluoropropoxy)benzamide, Exemplary Compound No. 95: (Example 37) N-{2-[(2-hydroxyethyl)amino]-2-oxo-1-[4-(trifluoromethyl)benzyl]ethyl}-4-(3,3,3-trifluoropropoxy)benzamide, Exemplary Compound No. 109: (Example 31) 4-(2,2-difluoroethoxy)-N-{2-[(2-hydroxyethyl)amino]-2-oxo-1-[4-(trifluoromethoxy)benzyl]ethyl}benzamide, Exemplary Compound No. 129: (Example 40) 4-[(2,2-difluorocyclopropyl)methoxy]-N-{2-[(2-hydroxyethyl)amino]-2-oxo-1-[4-(trifluoromethoxy)benzyl]ethyl}benzamide, Exemplary Compound No. 148: (Example 41) N-{1-[4-(difluoromethoxy)benzyl]-2-[(2-hydroxyethyl)amino]-2-oxoethyl}-4-[4-(trifluoromethyl)phenoxy]benzamide, Exemplary Compound No. 149: (Example 42) N-{2-[(2-hydroxyethyl)amino]-2-oxo-1-[4-(trifluoromethoxy)benzyl]ethyl}-4-[4-(trifluoromethyl)phenoxy]benzamide, Exemplary Compound No. 150: (Example 45) N-{2-[(2-hydroxyethyl)amino]-2-oxo-1-[4-(trifluoromethyl)benzyl]ethyl}-4-[4-(trifluoromethyl)phenoxy]benzamide, Exemplary Compound No. 754: (Example 85) N-{2-[(2-hydroxyethyl)amino]-2-oxo-1-[4-(trifluoromethoxy)benzyl]ethyl}-4-(2,2,2-trifluoroethoxy)benzamide, Exemplary Compound No. 769: (Example 81) N-{2-[(2-hydroxyethyl)amino]-2-oxo-1-[4-(trifluoromethoxy)benzyl]ethyl}-4-(4,4,4-trifluorobutoxy)benzamide, Exemplary Compound No. 954: (Example 80) N-{2-amino-2-oxo-1-[4-(trifluoromethoxy)benzyl]ethyl}-4-(3,3,3-trifluoropropoxy)benzamide, Exemplary Compound No. 959: (Example 69) N-{2-(methylamino)-2-oxo-1-[4-(trifluoromethoxy)benzyl]ethyl}-4-(3,3,3-trifluoropropoxy)benzamide, Exemplary Compound No. 979: (Example 74) N-{2-{[(2R)-2-hydroxypropyl]amino}-2-oxo-1-[4-(trifluoromethoxy)benzyl]ethyl}-4-(3,3,3-trifluoropropoxy)benzamide, and Exemplary Compound No. 999: (Example 78) N-{2-[(2-fluoroethyl)amino]-2-oxo-1-[4-(trifluoromethoxy)benzyl]ethyl}-4-(3,3,3-trifluoropropoxy)benzamide.

(Common Production Method)

The compound having General Formula (I) of the present invention can be produced according to the following methods:

The following production methods are usually conducted according to known methods described in, for example, "ORGANIC FUNCTIONAL GROUP PREPARATIONS", 2nd edition, ACADEMIC PRESS, INC., (1989) and "Comprehensive Organic Transformations", VCH Publishers Inc., (1989).

Because of production reasons, some functional groups require to be protected by suitable protecting groups in the stages of raw materials or intermediates. The protecting groups are groups that can be readily converted to the functional groups, and in such cases the desired compounds can be given by removing the protecting groups according to need.

Examples of such functional groups are a hydroxyl group, a carboxyl group, a carbonyl group, and an amino group, and the protecting groups for these functional groups are, for example, those described in Greene and Wuts, "Protective Groups in Organic Synthesis", 3rd edition, JOHN WILEY & SONS, INC., (1999). These protecting groups can be optionally used according to reaction conditions.

As the protecting group for a carboxyl group, for example, $C_1$-$C_6$ alkyl (example: methyl, ethyl, propyl, isopropyl, butyl, and t-butyl), $C_7$-$C_{11}$ aralkyl (example: benzyl), phenyl, trityl, silyl (example: trimethylsilyl, triethylsilyl, dimethylphenylsilyl, t-butyldimethylsilyl, and t-butyldiethylsilyl), and $C_2$-$C_6$ alkenyl (example: 1-allyl) groups are used. These groups may be mono- to tri-substituted by a halogen (example: fluorine, chlorine, bromine, and iodine) atom(s), a $C_1$-$C_6$ alkoxy (example: methoxy, ethoxy, and propoxy) group(s), or a nitro group(s), for example.

As the hydroxyl protecting group, for example, $C_1$-$C_6$ alkyl (example: methyl, ethyl, propyl, isopropyl, butyl, and t-butyl), phenyl, trityl, $C_7$-$C_{11}$ aralkyl (example: benzyl), formyl, $C_1$-$C_6$ alkylcarbonyl (example: acetyl and propionyl), benzoyl, $C_7$-$C_{11}$ aralkylcarbonyl (example: benzylcarbonyl), 2-tetrahydropyranyl, 2-tetrahydrofuranyl, silyl (example: trimethylsilyl, triethylsilyl, dimethylphenylsilyl, t-butyldimethylsilyl, and t-butyldiethylsilyl), and $C_2$-$C_6$ alkenyl (example: 1-allyl) groups are used. These groups may be mono- to tri-substituted by a halogen (example: fluorine, chlorine, bromine, and iodine) atom(s), a $C_1$-$C_6$ alkyl (example: methyl, ethyl, and propyl) group(s), a $C_1$-$C_6$ alkoxy (example: methoxy, ethoxy, and propoxy) group(s), or a nitro group(s), for example.

As the carbonyl protecting group, for example, cyclic acetal (example: 1,3-dioxane) and noncyclic acetal (example: di-$C_1$-$C_6$ alkylacetal) groups are used.

As the amino protecting group, for example, formyl, $C_1$-$C_6$ alkylcarbonyl (example: acetyl and propionyl), $C_1$-$C_6$ alkoxycarbonyl (example: methoxycarbonyl, ethoxycarbonyl, and t-butoxycarbonyl), benzoyl, $C_7$-$C_{11}$ aralkylcarbonyl (example: benzylcarbonyl), $C_7$-$C_{14}$ aralkyloxycarbonyl (example: benzyloxycarbonyl and 9-fluorenylmethoxycarbonyl), trityl, phthaloyl, N,N-dimethylaminomethylene, silyl (example: trimethylsilyl, triethylsilyl, dimethylphenylsilyl, t-butyldimethylsilyl, and t-butyldiethylsilyl), and $C_2$-$C_6$ alkenyl (example: 1-allyl) groups are used. These groups may be mono- to tri-substituted by a halogen (example: fluorine, chlorine, bromine, and iodine) atom(s), a $C_1$-$C_6$ alkoxy (example: methoxy, ethoxy, and propoxy) group(s), or a nitro group(s), for example.

The above protecting groups are removed by known methods, for example, a method using an acid, a base, ultraviolet light, hydrazine, phenylhydrazine, sodium N-methyldithiocarbamate, tetrabutylammonium fluoride, palladium acetate, or a trialkylsilyl halide (for example, trimethylsilyl iodide or trimethylsilyl bromide), or a method by reduction.

Method A is a method for producing a compound having General Formula (I).

Method A

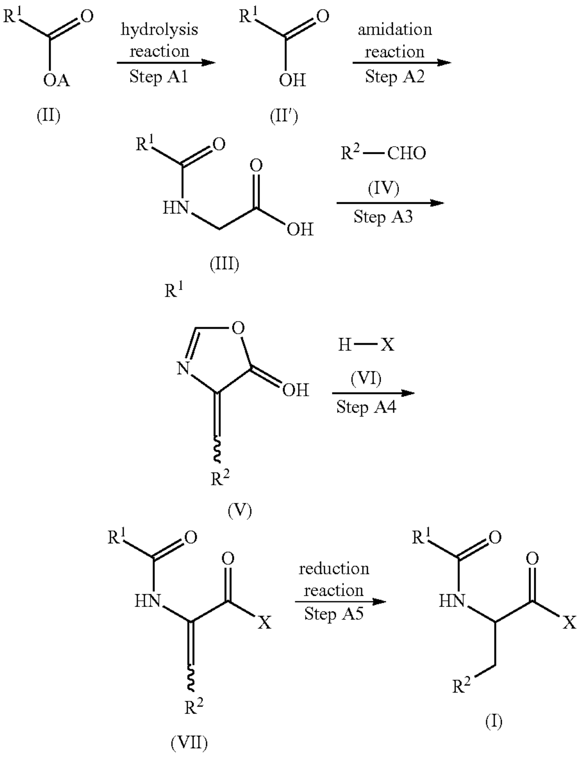

In the above formula, $R^1$, $R^2$, and X represent the same meanings as those described above, and A represents a protecting group for a carboxyl group.

Step A1 is a method for producing a compound having General Formula (II') and is conducted by a hydrolysis reaction of a compound having General Formula (II).

In the case that the reaction is conducted using a base, the base used is, for example, an alkali metal carbonate such as lithium carbonate, sodium carbonate, or potassium carbonate; an alkali metal bicarbonate such as lithium bicarbonate, sodium bicarbonate, or potassium bicarbonate; an alkali metal hydride such as lithium hydride, sodium hydride, or potassium hydride; an alkali metal hydroxide such as lithium hydroxide, sodium hydroxide, or potassium hydroxide; or an alkali metal alkoxide such as lithium methoxide, sodium methoxide, sodium ethoxide, or potassium t-butoxide. The base is preferably an alkali metal hydroxide or an alkali metal alkoxide, more preferably an alkali metal hydroxide, and particularly preferably lithium hydroxide, sodium hydroxide, or potassium hydroxide.

The solvent used in the above reaction is, for example, an ether such as diethyl ether, diisopropyl ether, tetrahydrofuran, dioxane, dimethoxyethane, or diethylene glycol dimethyl ether; a lower alkyl nitrile such as acetonitrile or propionitrile; an amide such as formamide, N,N-dimethylformamide, N,N-dimethylacetamide, or hexamethylphosphoric acid triamide; a lower alkyl alcohol such as methanol, ethanol, propanol, or butanol; or water. The solvent is preferably an alcohol, an ether, or water, more preferably an alcohol; and particularly preferably methanol or ethanol.

The reaction temperature varies depending on the raw compound, the reagent used, and the kind of the solvent, for example, and is usually 0° C. to 100° C. and preferably 25° C. to 80° C.

The reaction time varies depending on the reaction temperature, the raw compound, the reaction reagent, and the kind of the solvent used and is usually 10 minutes to 12 hours and preferably 2 to 3 hours.

In the case that the above reaction is conducted using an acid, the acid used is, for example, a Bronsted acid, e.g., an inorganic acid such as hydrochloric acid, hydrobromic acid, sulfuric acid, perchloric acid, or phosphoric acid or an organic acid such as acetic acid, formic acid, oxalic acid, methanesulfonic acid, p-toluenesulfonic acid, camphorsulfonic acid, trifluoroacetic acid, or trifluoromethanesulfonic acid; a Lewis acid such as zinc chloride, tin tetrachloride, boron trichloride, boron trifluoride, or boron tribromide; or an acidic ion-exchange resin. The acid is preferably an inorganic acid or an organic acid and more preferably trifluoroacetic acid.

The solvent used in the above reaction is, for example, an aliphatic hydrocarbon such as hexane, heptane, ligroin, or petroleum ether; an aromatic hydrocarbon such as toluene, benzene, or xylene; a halogenated hydrocarbon such as dichloromethane or 1,2-dichloroethane; an ether such as diethyl ether, diisopropyl ether, tetrahydrofuran, dioxane, dimethoxyethane, or diethylene glycol dimethyl ether; a lower alkyl nitrile such as acetonitrile or propionitrile; or an amide such as formamide, N,N-dimethylformamide, N,N-dimethylacetamide, or hexamethylphosphoric acid triamide. The solvent is preferably a halogenated hydrocarbon and more preferably dichloromethane.

The reaction temperature varies depending on the raw compound, the reagent used, and the kind of the solvent, for example, and is usually 0° C. to 100° C. and preferably 0° C. to 50° C.

The reaction time varies depending on the reaction temperature, the raw compound, the reaction reagent, and the kind of the solvent used and is usually 10 minutes to 6 hours and preferably 1 to 3 hours.

After completion of the reaction, the target compound of this step is collected from the reaction mixture according to a common method. For example, the reaction mixture is optionally neutralized or applied to filtration for removing insoluble substances, if present. Then, the reaction solution is extracted with an organic solvent that is not miscible with water, such as toluene, and is washed with water or the like. The organic layer containing the target compound is concentrated under reduced pressure to remove the solvent to give the target compound.

The obtained target compound can be separated and purified, according to need, by a common method such as recrystallization, reprecipitation, or a method that is widely used for separation and purification of organic compounds (for example, adsorption column chromatography using a carrier such as silica gel, alumina, or Florisil composed of magnesium-silica gel; partition column chromatography using a carrier such as Sephadex LH-20 (Pharmacia), Amberlite XAD-11 (Rohm and Haas), or Diaion HP-20 (Mitsubishi Chemical Company); ion-exchange chromatography; or normal-phase and reversed-phase column chromatography using silica gel or alkylated silica gel, and preferably silica-gel column chromatography).

Isomers can be separated, if necessary, by any of the aforementioned separation/purification means at an appropriate stage after the completion of the reaction of the above each step or the completion of a desired step.

In the case that a compound (I) is present as isomers such as position isomers, rotational isomers, or diastereomers, the isomers can be separated into their respective isometric forms, if desired, by the aforementioned separation and purification means. Furthermore, in the case that a compound (I) exists as a racemic mixture, the mixture can be separated to S-isomer and R-isomer by a usual optical resolution.

Step A2 is a step for producing a compound having General Formula (III) and is conducted by an amidation reaction of a compound having General Formula (II') and glycine.

This step, as shown below, is conducted by activating the carboxyl group of a compound having General Formula (II') (Step A2-1) and then subjecting it to a reaction with glycine (Step A2-2).

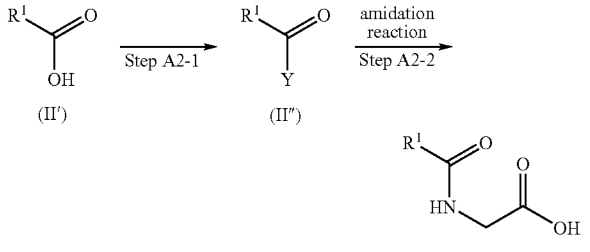

(II') (II") (III)

In the above formula, $R^1$ represents the same meaning as that described above, and Y represents a halogen atom or a group represented by the general formula —O—$S(O)_2R^C$ (wherein, $R^C$ represents a $C_1$-$C_6$ alkyl group that may be substituted by one to three halogen atoms, a methoxy group, or a phenyl group that may be mono- to tri-substituted by groups(s) selected from the group consisting of $C_1$-$C_6$ alkyl groups that may be mono- to tri-substituted by a halogen atom(s) and halogen atoms).

Step A2-1 is a method of producing a compound having General Formula (II").

The step is performed by the reaction of a compound having General Formula (II') and a halogenating agent or a sulfonylating agent in a solvent in the presence or absence of a base.

Any halogenating agent that is generally used for halogenating primary alcohols can be used in the above reaction without any limitation, and examples thereof include oxalyl chloride; thionyl halides such as thionyl chloride and thionyl bromide; phosphorus trihalides such as phosphorus trichloride and phosphorus tribromide; phosphorus pentahalides such as phosphorus pentachloride and phosphorus pentabromide; phosphorus oxyhalides such as phosphorus oxychloride and phosphorus oxybromide; Vilsmeier reagents such as N,N-dimethylchloro forminium chloride and N,N-dimethylbromo forminium bromide; combinations of a phosphine such as triphenylphosphine and a halogen or a methane tetrahalide; and combinations of a phosphine, an azodicarboxylic acid ester, and a metal halide such as a combination of triphenylphosphine, diethyl azodicarboxylate, and lithium bromide. The halogenating agent is preferably an oxalyl chloride or thionyl chloride and more preferably a catalytic amount of a combination of N,N-dimethylformamide and oxalyl chloride. The addition of N,N-dimethylformamide enhances the reaction rate.

Any sulfonylating agent that is generally used for sulfonylation can be used in the above reaction without any limitation, and examples thereof include sulfonyl halides such as methanesulfonyl chloride and p-toluenesulfonyl chloride, and sulfonic anhydride. The sulfonylating agent is preferably methanesulfonyl chloride or p-toluenesulfonyl chloride.

The base used in the above reaction varies depending on the reagent used, for example, and is not specifically limited. The base is, for example, an organic base such as imidazole, pyridine, triethylamine, or N-methylimidazole and is preferably imidazole, pyridine, or triethylamine.

The solvent used in the above reaction is, for example, an aliphatic hydrocarbon such as hexane or heptane; an aromatic hydrocarbon such as toluene or xylene; a halogenated hydrocarbon such as dichloromethane or 1,2-dichloroethane; an ester such as ethyl acetate or butyl acetate; an ether such as tetrahydrofuran, diethyl ether, or t-butylmethyl ether; or an amide such as 1-methyl-2-pyrrolidinone, N,N-dimethylformamide, or N,N-dimethylacetamide; preferably an aromatic hydrocarbon or a halogenated hydrocarbon; more preferably a halogenated hydrocarbon; and particularly preferably dichloromethane.

The reaction temperature varies depending on the raw compound, the reagent used, and the kind of the solvent, for example, and is usually −20° C. to 100° C. and preferably 0° C. to 25° C.

The reaction time varies depending on the reaction temperature, the raw compound, the reaction reagent, and the kind of the solvent used and is usually 10 minutes to 12 hours and preferably 2 to 3 hours.

Step A2-2 is a method for producing a compound having General Formula (III).

The step is performed by the reaction of a compound having General Formula (II") and glycine in a solvent in the presence of a base. This reaction is performed by (1) using an organic base in an organic solvent or (2) a Schotten-Baumann reaction.

Case Using Organic Base in Organic Solvent

The base used in the above reaction is, for example, an organic base such as imidazole, pyridine, triethylamine, N-methylimidazole, or diisopropylethylamine; and preferably diisopropylethylamine.

The solvent used in the above reaction is, for example, an aliphatic hydrocarbon such as hexane or heptane; an aromatic hydrocarbon such as toluene or xylene; a halogenated hydrocarbon such as dichloromethane or 1,2-dichloroethane; or an ether such as tetrahydrofuran, diethyl ether, or t-butylmethyl ether, and is preferably dichloromethane.

(2) Case of Schotten-Baumann Reaction

The base used in the above reaction is, for example, an alkali metal carbonate such as lithium carbonate, sodium carbonate, or potassium carbonate; an alkali metal bicarbonate such as lithium bicarbonate, sodium bicarbonate, or potassium bicarbonate; an alkali metal hydroxide such as lithium hydroxide, sodium hydroxide, or potassium hydroxide; an alkali metal alkoxide such as lithium methoxide, sodium methoxide, sodium ethoxide, or potassium t-butoxide; or an organic base such as imidazole, pyridine, triethylamine, N-methylimidazole, or diisopropylethylamine, preferably an alkali metal hydroxide, and more preferably sodium hydroxide.

The solvent used in the above reaction is, for example, an alcohol such as methanol, ethanol, n-propanol, isopropanol, n-butanol, isobutanol, t-butanol, isoamyl alcohol, diethylene glycol, glycerin, octanol, cyclohexanol, or methyl cellosolve; an ether such as diethyl ether, diisopropyl ether, tetrahydrofuran, dioxane, dimethoxyethane, or diethylene glycol dimethyl ether; water; or a solvent mixture of water and an organic solvent mentioned above, preferably a solvent mixture of an ether and water, and more preferably a solvent mixture of tetrahydrofuran and water.

The reaction temperature varies depending on the raw compound, the reagent used, and the kind of the solvent, for example, and is usually −20° C. to 100° C. and preferably 0° C. to 25° C.

The reaction time varies depending on the reaction temperature, the raw compound, the reaction reagent, and the kind of the solvent used and is usually 10 minutes to 24 hours and preferably 1 to 12 hours.

After completion of the reaction, the target compound of this step is collected from the reaction mixture according to a method similar to Step A1 of Method A.

Step A2' shown below is an alternate method of Step A2. This step is performed by condensing a compound having General Formula (II') and a compound having General Formula (L) by an amidation reaction (Step A2'-1) and then deprotecting the protecting group A (Step A2'-2).

Step A2'

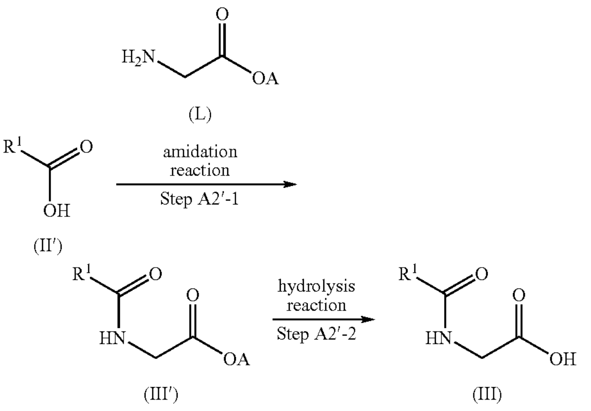

In the above formula, $R^1$ and A represent the same meanings as those described above.

Step A2'-1 is a method for producing a compound having General Formula (III') and is performed by the reaction of a compound having General Formula (II') and a compound having General Formula (L) in the presence of a condensing agent in a solvent in the presence or absence of a base.

The condensing agent used in the above reaction is, for example, an azodicarboxylic acid di-lower alkyl ester-triphenylphosphine such as azodicarboxylic acid diethyl ester-triphenylphosphine; a carbodiimide derivative such as N,N'-dicyclohexylcarbodiimide (DCC) or 1-ethyl-3-(3-dimethylaminopropyl)carbodiimide (EDCI); a 2-halo-1-lower alkylpyridinium halide such as 2-chloro-1-methylpyridinium iodide; a diarylphosphoryl azide such as diphenylphosphoryl azide (DPPA); a chloroformic acid ester such as ethyl chloroformate or isobutyl chloroformate; a phosphoryl chloride such as diethylphosphoryl chloride; an imidazole derivative such as N,N'-carbodiimidazole (CDI); a benzotriazole derivative such as O-(7-azabenzotriazol-1-yl)-N,N,N',N'-tetramethyluronium hexafluorophosphate (HATU) or (1H-benzotriazol-1-yloxy)tripyrrolidinophosphonium hexafluorophosphate (PyBOP); or 4-(4,6-dimethoxy-1,3,5-triazin-2-yl)-4-methylmorphorinium chloride (DMT-MM) and is preferably DMT-MM.

The base used in the above reaction varies depending on the reagent used, for example, and is not specifically limited. The base is, for example, an organic base such as imidazole, pyridine, triethylamine, N-methylimidazole, or diisopropylethylamine and is preferably triethylamine.

The solvent used in the above reaction is, for example, a halogenated hydrocarbon such as dichloromethane or 1,2-dichloroethane; an alcohol such as methanol, ethanol, n-propanol, isopropanol, n-butanol, isobutanol, t-butanol, isoamyl alcohol, diethylene glycol, glycerin, octanol, cyclohexanol, or methyl cellosolve; an ether such as diethyl ether, diisopropyl ether, tetrahydrofuran, dioxane, dimethoxyethane, or diethylene glycol dimethyl ether; an amide such as N,N-dimethylformamide; or water, and is preferably an amide or an alcohol and more preferably methanol or N,N-dimethylformamide.

The reaction temperature varies depending on the raw compound, the reagent used, and the kind of the solvent, for example, and is usually −20° C. to 100° C. and preferably 0° C. to 50° C.

The reaction time varies depending on the reaction temperature, the raw compound, the reaction reagent, and the kind of the solvent used and is usually 10 minutes to 24 hours and preferably 1 to 12 hours.

After completion of the reaction, the target compound of this step is collected from the reaction mixture according to a method similar to Step A1 of Method A.

Step A2'-2 is a step for producing a compound having General Formula (III) and is performed by hydrolyzing a compound having General Formula (III') in a solvent.

This step is performed using a base or an acid as in the hydrolysis reaction in Step A1.

Step A3 is a step of producing a compound having General Formula (V) and is performed by a reaction of a compound having General Formula (III) and a compound having General Formula (IV) in the presence of a base.

This step is performed in accordance with a method known as the Erlenmeyer method or the azlactone method (refer to Zikken Kagaku Koza (Experimental Methods of Chemistry), 4th ed., vol. 22. p. 202, ed. by The Chemical Society of Japan, Maruzen).

The base used in the above reaction is, for example, an organic acid alkali metal salt such as lithium acetate, sodium acetate, or potassium acetate; or an organic base such as imidazole, pyridine, diethylamine, triethylamine, ethyldiisopropylamine, or N-methylimidazole, and is preferably an organic acid alkali metal salt and more preferably sodium acetate.

The solvent used in the reaction is, for example, an aliphatic hydrocarbon such as hexane, heptane, ligroin, or petroleum ether; an aromatic hydrocarbon such as toluene, benzene, or xylene; an ether such as diethyl ether, diisopropyl ether, tetrahydrofuran, dioxane, dimethoxyethane, or diethylene glycol dimethyl ether; an amide such as N,N-dimethylacetamide or hexamethylphosphoric acid triamide; or an acid anhydride such as acetic anhydride, and is preferably an acid anhydride and more preferably acetic anhydride.

The reaction temperature varies depending on the raw compound, the solvent, and the kind of the base, for example, and is usually 25° C. to 200° C. and preferably 80° C. to 120° C.

The reaction time varies depending on the raw compound, the solvent, the base, and the reaction temperature, for example, and is usually 1 minute to 10 hours and preferably 10 minutes to 6 hours.

After completion of the reaction, the target compound of this step is collected from the reaction mixture according to a method similar to Step A1 of Method A.

Step A4 is a step for producing a compound having General Formula (VII) and is performed by the reaction of a compound having General Formula (V) and a compound having General Formula (VI).

The compound having General Formula (VI) used in the above reaction is, for example, a linear or branched primary or secondary aliphatic amine that may be substituted, such as methylamine, ethylamine, propylamine, isopropylamine, butylamine, isobutylamine, 2-fluoroethylamine, 2-methoxyethylamine, ethanolamine, ethoxyamine, aminoacetonitrile, 1-amino-2-propanol, 2-amino-2-methyl-1-propanol, 2-amino-1-propanol, 3-amino-1-propanol, N-acetylethylenediamine, benzylamine, furfurylamine, thiophene-2-methylamine, 2-(aminomethyl)pyridine, 1-phenylethylamine, 2-phenylethylamine, dimethylamine, diethylamine, pyrrolizine, piperidine, morpholine, piperazine, or 2-(methylamino)ethanol, or an aromatic amine such as aniline, 2-aminophenol, 3-aminophenol, 4-aminophenol, 4-fluoroaniline, 4-chloroaniline, or 4-methoxyaniline, and is preferably a linear or branched primary amine that may be substituted and more preferably an ethanolamine that may be substituted.

The solvent used in the above reaction is an aliphatic hydrocarbon such as hexane, heptane, ligroin, or petroleum ether; an aromatic hydrocarbon such as toluene, benzene, or xylene; an ether such as diethyl ether, diisopropyl ether, tetrahydrofuran, dioxane, dimethoxyethane, or diethylene glycol dimethyl ether; an amide such as N,N-dimethylacetamide or hexamethylphosphoric acid triamide; a lower-alkyl alcohol such as methanol, ethanol, propanol, or butanol, and is preferably an alcohol or an ether, more preferably an alcohol, and particularly preferably ethanol.

The reaction temperature varies depending on the raw compound, the solvent, and the kind of the base, for example, and is usually 0° C. to 200° C. and preferably 25° C. to 80° C.

The reaction time varies depending on the raw compound, the solvent, the base, and the reaction temperature, for example, and is usually 1 minute to 24 hours and preferably 10 minutes to 6 hours.

After completion of the reaction, the target compound of this step is collected from the reaction mixture according to a similar step to Step A1 of Method A.

Step A5 is a step for producing a compound having General Formula (I) and is performed by reducing a compound having General Formula (VII) and is preferably performed by reducing it with a metal catalyst under a hydrogen atmosphere.

Any metal catalyst that is generally used for a catalytic reduction reaction can be used in the above reaction without any limitation, and examples thereof include palladium catalysts such as palladium-carbon, palladium hydroxide, palladium-alumina, and palladium-zeolite; nickel catalysts such as Raney nickel; platinum catalysts such as platinum oxide and platinum-carbon; rhodium catalysts such as rhodium-aluminum oxide, rhodium-carbon, and tris(triphenylphosphine)-rhodium chloride; and other noble metal catalysts such as ruthenium-carbon. Among them, palladium catalysts and rhodium catalysts are preferred.

The hydrogen pressure of the above reaction is usually 0.1 to 50 atmospheres and preferably 1 to 10 atmospheres.

The solvent used in the above reaction is, for example, an aliphatic hydrocarbon such as hexane or heptane; an aromatic hydrocarbon such as toluene or xylene; a halogenated hydrocarbon such as dichloromethane or 1,2-dichloroethane; an ester such as ethyl acetate or butyl acetate; an ether such as tetrahydrofuran, diethyl ether, or t-butylmethyl ether; an amide such as 1-methyl-2-pyrrolidinone, N,N-dimethylformamide, or N,N-dimethylacetamide; an alcohol such as methanol, ethanol, or n-propanol; an organic acid such as formic acid or acetic acid; an inorganic acid aqueous solution such as a hydrochloric acid aqueous solution or a sulfuric acid aqueous solution; water; or a solvent mixture of a solvent mentioned above and water. In the case that a palladium catalyst is used as the metal catalyst, the solvent is preferably an ester, an alcohol, or an ether and more preferably methanol or a solvent mixture of methanol and tetrahydrofuran. In the case that a rhodium catalyst is used as the metal catalyst, the solvent is preferably an aromatic hydrocarbon, an alcohol, or an ether and more preferably methanol, ethanol or a solvent mixture of ethanol and tetrahydrofuran.

The reaction temperature varies depending on the raw compound, the reagent used, and the kind of the solvent, for example, and is usually −20° C. to 100° C. and preferably 0° C. to 70° C.

The reaction time varies depending on the reaction temperature, the raw compound, the reaction reagent, and the kind of the solvent used and is usually 5 minutes to 48 hours and preferably 30 minutes to 10 hours.

After completion of the reaction, the target compound of this step is collected from the reaction mixture according to a method similar to Step A1 of Method A.

Method B is an alternate method of Method A for producing a compound having General Formula (I).

Method B

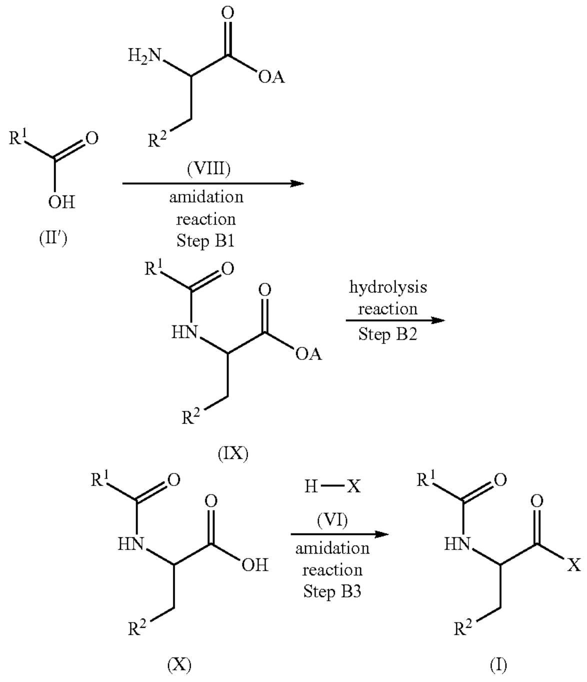

In the above formula, $R^1$, $R^2$, and X represent the same meanings as those described above. A represents a protecting group for a carboxyl group and is preferably a $C_1$-$C_6$ alkyl group and more preferably a t-butyl group. The compound having General Formula (VIII) is generally a compound that is commercially available or a known compound or a compound that can be readily synthesized by the above known method from a commercially available compound or a known compound.

Step B1 is a step for producing a compound having General Formula (IX) and is performed by amidating a compound having General Formula (II') and a compound having General Formula (VIII) by condensation.

The condensation reaction of this step is performed by a method similar to Step A2 of the above Method A.

Step B2 is a step for producing a compound having General Formula (X) and is performed by hydrolyzing a compound having General Formula (IX).

The hydrolysis reaction of this step is performed by a method similar to Step A1 of the above Method A.

Step B3 is a step for producing a compound having General Formula (I) and is performed by amidating a compound having General Formula (X) and a compound having General Formula (VI) by condensation.

The amidation reaction of this step is performed by a method similar to Step A2 of the above Method A.

Method C is an alternate method of Method A for producing a compound having General Formula (I) and is particularly a method used for producing an optically active compound having General Formula (I'). The following shows only a compound having General Formula (I'-s) that is an optically active S-isomer, but the corresponding R-isomer can be produced by a similar method by suitably selecting the starting material.

Method C

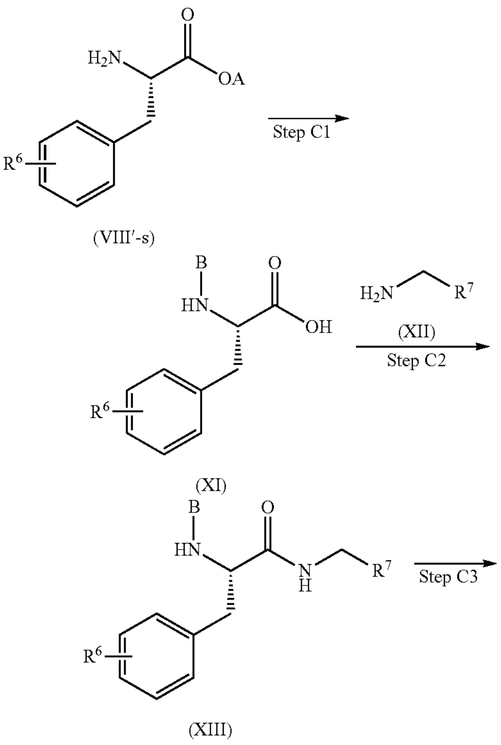

-continued

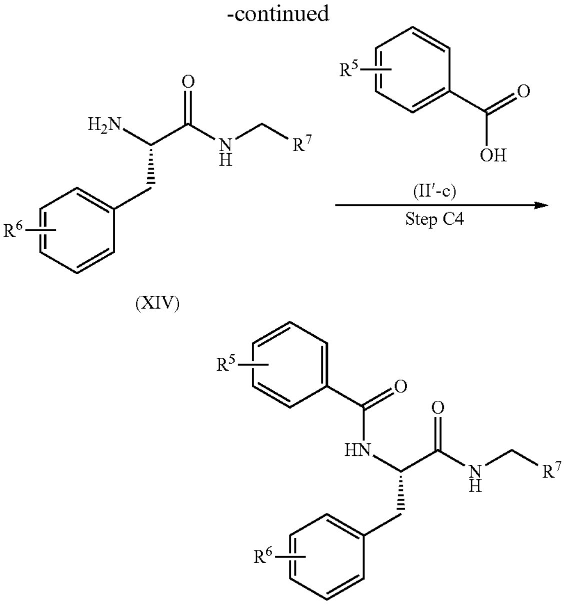

(XIV)

(I'-s)

In the above formula, $R^5$, $R^6$, and $R^7$ represent the same meanings as those described above, A represents a hydrogen atom, and B represents an amino protecting group.

Step C1 is a step for producing a compound having General Formula (XI) and for protecting the amino group of a compound having General Formula (VIII'-s) by a protecting group. The method of protecting an amino group is described in Greene and Wuts, "Protective Groups in Organic Synthesis", 3rd edition, JOHN WILEY & SONS, INC., (1999), pp. 494-653. In this step, the protecting group is preferably a benzyloxycarbonyl group.

The reaction conditions of this step are preferably the Schotten-Baumann reaction described in Step A2-2 of Method A.

The reagent used in this step is preferably benzyloxycarbonyl chloride or dibenzyl dicarbonate and more preferably benzyloxycarbonyl chloride.

The base used in this step is, for example, an alkali metal carbonate such as lithium carbonate, sodium carbonate, or potassium carbonate; an alkali metal bicarbonate such as lithium bicarbonate, sodium bicarbonate, or potassium bicarbonate; an alkali metal hydroxide such as lithium hydroxide, sodium hydroxide, or potassium hydroxide; an alkali metal alkoxide such as lithium methoxide, sodium methoxide, sodium ethoxide, or potassium t-butoxide; or an organic base such as imidazole, pyridine, triethylamine, N-methylimidazole, or diisopropylethylamine, and is preferably an alkali metal hydroxide and more preferably sodium hydroxide.

The solvent used in the above reaction is, for example, an alcohol such as methanol, ethanol, n-propanol, isopropanol, n-butanol, isobutanol, t-butanol, isoamyl alcohol, diethylene glycol, glycerin, octanol, cyclohexanol, or methyl cellosolve; an ether such as diethyl ether, diisopropyl ether, tetrahydrofuran, dioxane, dimethoxyethane, or diethylene glycol dimethyl ether; water; or a solvent mixture of water and an organic solvent mentioned above, and is preferably a solvent mixture of an ether and water and more preferably water.

The reaction temperature varies depending on the raw compound, the reagent used, and the kind of the solvent, for example, and is usually −20° C. to 100° C. and preferably 0° C. to 25° C.

The reaction time varies depending on the reaction temperature, the raw compound, the reaction reagent, and the kind of the solvent used and is usually 10 minutes to 24 hours and preferably 1 to 12 hours.

After completion of the reaction, the target compound of this step is collected from the reaction mixture according to a method similar to Step A1 of Method A.

Step C2 is a step for producing a compound having General Formula (XIII) and is a step of amidating a compound having General Formula (XI) and a compound having General Formula (XII) by a condensation reaction performed by a method similar to Step A2'-1 of Method A.

The condensing agent used in the above reaction is, for example, an azodicarboxylic acid di-lower alkyl ester-triphenylphosphine such as azodicarboxylic acid diethyl ester-triphenylphosphine; a carbodiimide derivative such as N,N'-dicyclohexylcarbodiimide (DCC) or 1-ethyl-3-(3-dimethylaminopropyl)carbodiimide (EDCI); a 2-halo-1-lower alkylpyridinium halide such as 2-chloro-1-methylpyridinium iodide; a diarylphosphoryl azide such as diphenylphosphoryl azide (DPPA); a chloroformic acid ester such as ethyl chloroformate or isobutyl chloroformate; a phosphoryl chloride such as diethylphosphoryl chloride; an imidazole derivative such as N,N'-carbodiimidazole (CDI); a benzotriazole derivative such as O-(7-azabenzotriazol-1-yl)-N,N,N',N'-tetramethyluronium hexafluorophosphate (HATU) or (1H-benzotriazol-1-yloxy)tripyrrolidinophosphonium hexafluorophosphate (PyBOP); or cyanophosphoric acid dialkyl ester such as 4-(4,6-dimethoxy-1,3,5-triazin-2-yl)-4-methylmorphorinium chloride (DMT-MM) or diethyl cyanophosphate (DEPC), and is preferably DEPC.

The base used in the above reaction is, for example, an organic base such as imidazole, pyridine, triethylamine, N-methylimidazole, or diisopropylethylamine and is preferably triethylamine.

The solvent used in the above reaction is, for example, a halogenated hydrocarbon such as dichloromethane or 1,2-dichloroethane; an ether such as diethyl ether, diisopropyl ether, tetrahydrofuran, dioxane, dimethoxyethane, or diethylene glycol dimethyl ether; or an amide such as N,N-dimethylformamide, and is preferably an ether or an amide and more preferably N,N-dimethylformamide.

The reaction temperature varies depending on the raw compound, the reagent used, and the kind of the solvent, for example, and is usually −20° C. to 100° C. and preferably 0° C. to 50° C.

The reaction time varies depending on the reaction temperature, the raw compound, the reaction reagent, and the kind of the solvent used and is usually 10 minutes to 24 hours and preferably 1 to 12 hours.

After completion of the reaction, the target compound of this step is collected from the reaction mixture according to a method similar to Step A1 of Method A.

Step C3 is a step for producing a compound having General Formula (XIV) and for deprotecting the amino protecting group of a compound having General Formula (XIII). The method for deprotecting an amino group is described in Greene and Wuts, "Protective Groups in Organic Synthesis", 3rd edition, JOHN WILEY & SONS, INC., (1999), pp. 494-653. In this step, the deprotecting is preferably performed using a metal catalyst under a hydrogen atmosphere or using an acid and is more preferably performed using an acid.

Step Using Metal Catalyst Under Hydrogen Atmosphere

The metal catalyst used in this reaction is, for example, a supported palladium catalyst such as palladium-carbon, palladium-alumina, or palladium-zeolite; a nickel catalyst such as Raney nickel; a platinum catalyst such as platinum oxide or platinum-carbon; a rhodium catalyst such as rhodium-aluminum oxide, rhodium-carbon, or triphenylphosphine-rhodium chloride; or a noble metal catalyst other than the above, such as ruthenium-carbon, and is preferably palladium-carbon.

The hydrogen pressure of the above reaction is usually 0.1 to 50 atmospheres and preferably 1 to 10 atmospheres.

The inert solvent used in the above reaction is, for example, an aliphatic hydrocarbon such as hexane or heptane; an aromatic hydrocarbon such as toluene or xylene; an ester such as ethyl acetate or butyl acetate; an ether such as tetrahydrofuran, diethyl ether, or t-butylmethyl ether; an alcohol such as methanol, ethanol, or n-propanol; or an organic acid such as formic acid or acetic acid, and is preferably an alcohol or an ether.

The above reaction temperature varies depending on the raw compound, the reagent used, and the kind of the solvent, for example, and is usually −20° C. to 100° C. and preferably 0° C. to 80° C.

The above reaction time varies depending on the reaction temperature, the raw compound, the reaction reagent, and the kind of the solvent used and is usually 5 minutes to 48 hours and preferably 30 minutes to 10 hours.

(2) Step Using Acid

The acid used in the above reaction is, for example, an inorganic acid such as hydrofluoric acid, hydrochloric acid, hydrobromic acid, sulfuric acid, perchloric acid, or phosphoric acid; or an organic acid such as acetic acid, formic acid, oxalic acid, citric acid, methanesulfonic acid, p-toluenesulfonic acid, camphorsulfonic acid, trifluoroacetic acid, or trifluoromethanesulfonic acid, and is preferably an acetic acid solution of hydrobromic acid.

The solvent used in the above reaction is, for example, an aliphatic hydrocarbon such as hexane or heptane; an aromatic hydrocarbon such as toluene or xylene; a halogenated hydrocarbon such as dichloromethane or 1,2-dichloroethane; or an organic acid such as acetic acid, and is preferably acetic acid.

The above reaction temperature varies depending on the raw compound, the reagent used, and the kind of the solvent, for example, and is usually −20° C. to 100° C. and preferably 0° C. to 50° C.

The above reaction time varies depending on the reaction temperature, the raw compound, the reaction reagent, and the kind of the solvent used and is usually 5 minutes to 2 weeks and preferably 1 to 10 hours.

After completion of the reaction, the target compound of this step is collected from the reaction mixture according to a method similar to Step A1 of Method A.

Step C4 is a step for producing a compound having General Formula (I'-s) and is a step of amidating a compound having General Formula (XIV) and a compound having General Formula (II'-c) by a condensation reaction performed by a method similar to Step C2 of this method.

Method D is a method for producing a compound having General Formula (VIII) used in Step B1 of Method B.

Method D

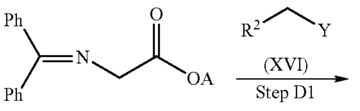

(XV)

-continued

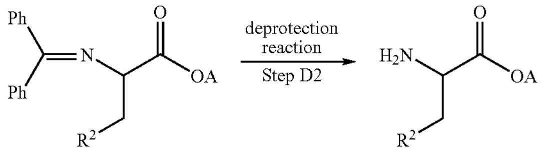

(XVII) (VIII)

In the above formula, $R^2$ and Y represent the same meanings as those described above. A represents a $C_1$-$C_6$ alkyl group and is preferably a t-butyl group.

This method is performed in accordance with the method described in The Journal of Organic Chemistry, 1982, 47, 2663-2666.

Step D1 is a step for producing a compound having General Formula (XVII) and is performed by the reaction of a compound having General Formula (XV) and a compound having General Formula (XVI) in the presence of a base. In addition, a phase transfer catalyst may be added for accelerating the reaction. This method may be performed in accordance with the method described in The Journal of Organic Chemistry, 1995, 60, 601.

The base used in the above reaction is, for example, an alkali metal carbonate such as lithium carbonate, sodium carbonate, or potassium carbonate; an alkali metal bicarbonate such as lithium bicarbonate, sodium bicarbonate, or potassium bicarbonate; an alkali metal hydride such as lithium hydride, sodium hydride, or potassium hydride; an alkali metal hydroxide such as lithium hydroxide, sodium hydroxide, or potassium hydroxide; or an alkali metal alkoxide such as lithium methoxide, sodium methoxide, sodium ethoxide, or potassium t-butoxide, and is preferably an alkali metal hydroxide and more preferably sodium hydroxide or potassium hydroxide, which is used as an aqueous solution.

The phase transfer catalyst (hereinafter abbreviated to as PTC) used in the above reaction is, for example, a PTC described in R. NOYORI, et al., ed. "Daigakuin Kogi Yuki Kagaku (Graduate Seminar in Organic Chemistry)", Tokyo Kagaku Dojin, published in 1998 and is a quaternary alkyl ammonium such as tetrabutylammonium chloride or tetrabutylammonium sulfate, a phosphonium salt, a crown ether, a pyridinium salt, or a viologen, for example, and is preferably a halogenated quaternary alkyl ammonium and more preferably tetrabutylammonium sulfate.

The solvent used in the above reaction is, for example, an aliphatic hydrocarbon such as hexane or heptane; an aromatic hydrocarbon such as toluene or xylene; a halogenated hydrocarbon such as dichloromethane or 1,2-dichloroethane; or an ether such as tetrahydrofuran, diethyl ether, or t-butylmethyl ether, and is preferably an aromatic hydrocarbon, an ether, or a halogenated hydrocarbon, more preferably an aromatic hydrocarbon or a halogenated hydrocarbon, and particularly preferably toluene or dichloromethane.

The above reaction temperature varies depending on the raw compound, the reagent used, and the kind of the solvent, for example, and is usually −100° C. to 100° C. and preferably 0° C. to 40° C.

The above reaction time varies depending on the reaction temperature, the raw compound, the reaction reagent, and the kind of the solvent used and is usually 5 minutes to 2 days and preferably 30 minutes to 5 hours.

In the above reaction, an optically active compound having General Formula (XVII-s) or General Formula (XVII-r) can be selectively produced by using an optically active PTC.

Such a step using an optically active PTC can be performed in accordance with the method described in Chemical Reviews, 2003, 103, 3013-3028.

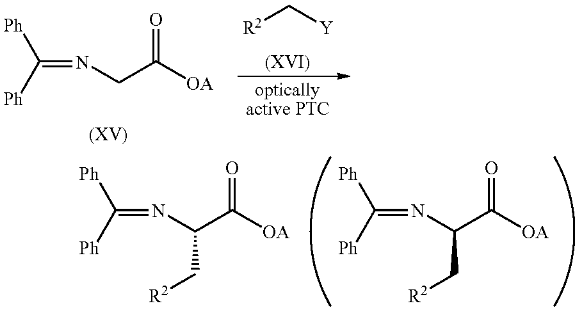

(XV)

(XVII-s)

(XVII-r)

The optically active PTC used in the above reaction is, for example, a chiral quaternary ammonium salt such as a quaternary ammonium salt derivative of which chiral sauce is cinchonidine described in the aforementioned document, a quaternary ammonium salt derivative of which chiral source is cinchonine, a quaternary ammonium salt derivative of which chiral source is binaphthyl, a chiral cyclic guanidine derivative having C2-symmetry planes, a quaternary ammonium salt derivative of which chiral source is tartaric acid, or a quaternary ammonium salt derivative of which chiral source is a salen skeleton; or a combination of a quaternary ammonium salt derivative of which chiral source is cinchonidine and a palladium catalyst. Preferably, the optically active PTCs are as follows: N-benzylcinchoninium bromide, N-benzylcinchonidinium bromide, N-(4-trifluoromethylbenzyl)cinchoninium bromide, N-(4-trifluoromethylbenzyl)cinchonidinium bromide, N-(9-anthracenylmethyl)cinchoninium chloride, N-(9-anthracenylmethyl)cinchonidinium chloride, (+)-O-(9)-allyl-N-(9-anthracenylmethyl)cinchoninium bromide, (−)-O-(9)-allyl-N-(9-anthracenylmethyl) cinchonidinium bromide, compounds (i-a), (i-b), (ii-a), and (ii-b), and Maruoka catalysts (for example, (S,S)-(iii-a), (S,S)-(iii-b), (S,S)-(iii-c), (R,R)-(iii-a), (R,R)-(iii-b), and (R,R)-(iii-c)). In addition, in the case that an S-isomer is selectively produced, N-benzylcinchonidinium bromide, N-(4-trifluoromethylbenzyl)cinchonidinium bromide, N-(9-anthracenylmethyl)cinchonidinium chloride, (−)-O-(9)-allyl-N-(9-anthracenylmethyl)cinchonidinium bromide, compounds (ii-a), (ii-b), (R,R)-(iii-a), (R,R)-(iii-b), and (R,R)-(iii-c) are preferred.

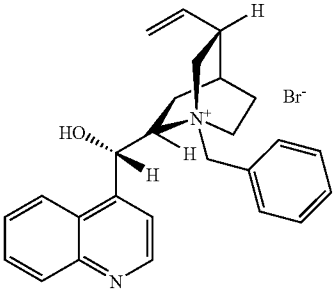

N-benzylcinchoninium bromide

-continued

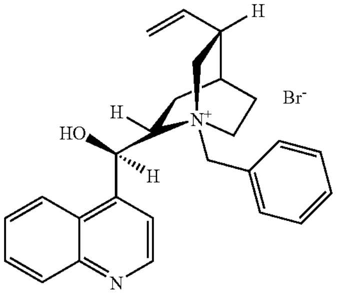

N-benzylcinchonidinium bromide

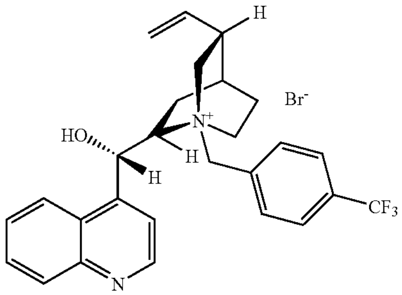

N-(4-trifluoromethylbenzyl)cinchoninium bromide

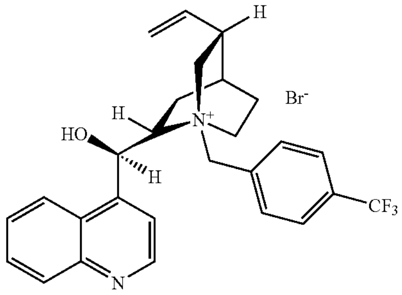

N-(4-trifluoromethylbenzyl)cinchonidinium bromide

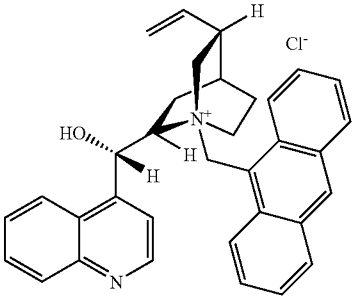

N-(9-anthracenylmethyl)cinchoninium chloride

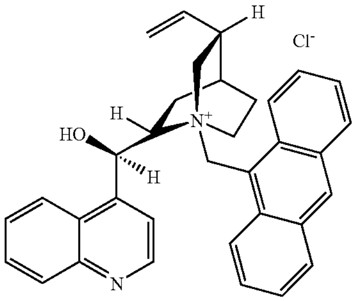

N-(9-anthracenylmethyl)cinchonidinium chloride

-continued

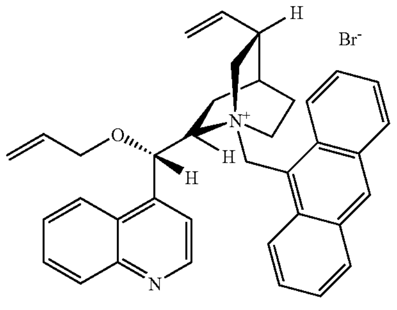

(-)-O-(9)-allyl-N-(9-anthracenylmethyl)cinchoninium bromide

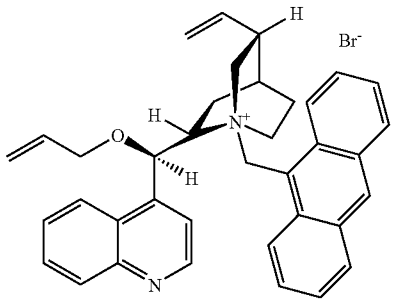

(-)-O-(9)-allyl-N-(9-anthracenylmethyl)cinchonidinium bromide

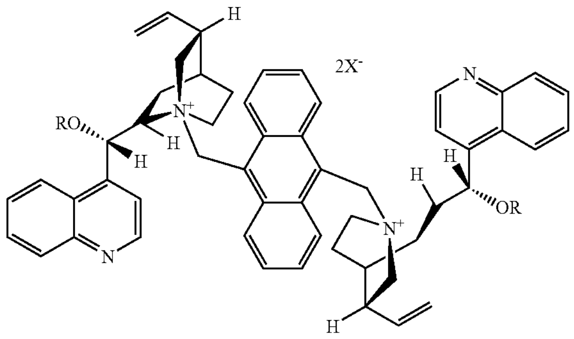

(i-a) R = H, X = Cl
(i-b) R = allyl, X = Br

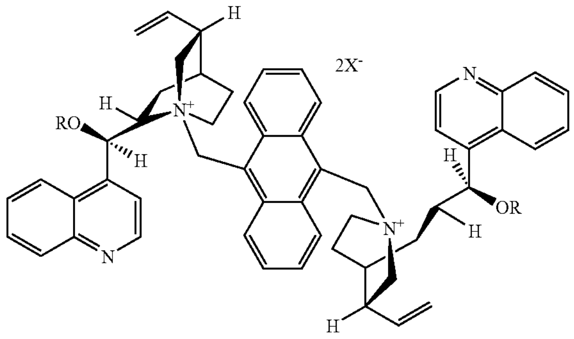

(ii-a) R = H, X = Cl
(ii-b) R = allyl, X = Br

-continued

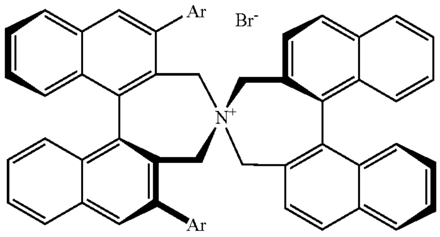

(S,S)-(iii-a) Ar = 3,4,5-trifluorophenyl
(S,S)-(iii-b) Ar = 3,5-bis(trifluoromethyl)phenyl
(S,S)-(iii-c) Ar = β-naphthyl

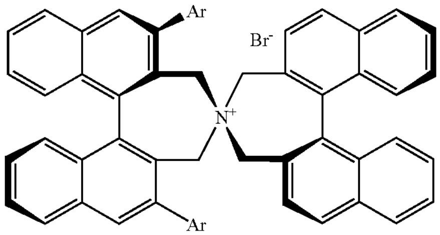

(R,R)-(iii-a) Ar = 3,4,5-trifluorophenyl
(R,R)-(iii-b) Ar = 3,5-bis(trifluoromethyl)phenyl
(R,R)-(iii-c) Ar = β-naphthyl The compound having General Formula (XVI) used in the above reaction is preferably a compound having General Formula (XVI) in which Y is bromine or iodine.

The base used in the above reaction is, for example, an alkali metal carbonate such as lithium carbonate, sodium carbonate, or potassium carbonate; an alkali metal bicarbonate such as lithium bicarbonate, sodium bicarbonate, or potassium bicarbonate; an alkali metal hydroxide such as lithium hydroxide, sodium hydroxide, potassium hydroxide, or cesium hydroxide; a combination of an alkali metal carbonate and an alkali metal hydroxide; or a phosphazene base, and is preferably sodium hydroxide, potassium hydroxide, cesium hydroxide, a combination of potassium carbonate and potassium hydroxide, or a phosphazene base.

The solvent used in the above reaction is, for example, an aromatic hydrocarbon such as toluene or xylene; or a halogenated hydrocarbon such as dichloromethane or 1,2-dichloroethane, and is preferably toluene, dichloromethane, or chloroform.

The above reaction temperature varies depending on the raw compound, the reagent used, and the kind of the solvent, for example, and is usually −100° C. to 50° C. and preferably −78° C. to 40° C.

The above reaction time varies depending on the reaction temperature, the raw compound, the reaction reagent, and the kind of the solvent used and is usually 5 minutes to 5 days and preferably 30 minutes to 2 days.

After completion of the reaction, the target compound of this step is collected from the reaction mixture according to a method similar to Step A1 of Method A.

Step D2 is a step for producing a compound having General Formula (VIII) and is performed by treating a compound having General Formula (XVII) in the presence of an acid.

This step can be performed in accordance with the method described in Journal of the American Chemical Society, 2003, 125, 5139.

The acid used in the above reaction is, for example, a Bronsted acid, e.g., an inorganic acid such as hydrochloric acid, hydrobromic acid, sulfuric acid, perchloric acid, or phosphoric acid, or an organic acid such as acetic acid, formic acid, oxalic acid, citric acid, methanesulfonic acid, p-toluenesulfonic acid, camphorsulfonic acid, trifluoroacetic acid, or trifluoromethanesulfonic acid; a Lewis acid such as zinc chloride, tin tetrachloride, boron trichloride, boron trifluoride, or boron tribromide; or an acidic ion-exchange resin, and is preferably an inorganic acid or an organic acid and more preferably hydrochloric acid or citric acid, which is used as an aqueous solution.

The solvent used in the above reaction is, for example, an aliphatic hydrocarbon such as hexane or heptane; an aromatic hydrocarbon such as toluene or xylene; or an ether such as tetrahydrofuran, diethyl ether, or t-butylmethyl ether, and is preferably an ether and more preferably tetrahydrofuran.

The above reaction temperature varies depending on the raw compound, the reagent used, and the kind of the solvent, for example, and is usually −20° C. to 100° C. and preferably 0° C. to 40° C.

The above reaction time varies depending on the reaction temperature, the raw compound, the reaction reagent, and the kind of the solvent used and is usually 5 minutes to 24 hours and preferably 1 to 10 hours.

After completion of the reaction, the target compound of this step is collected from the reaction mixture according to a method similar to Step A1 of Method A.

Method E is a method for producing a compound having General Formula (VIII'-s) used in Step C1 of Method C.

Method E

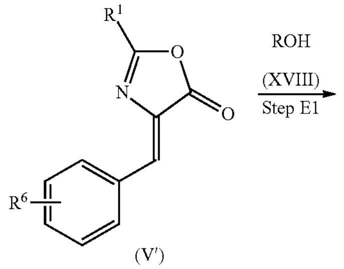

(V')

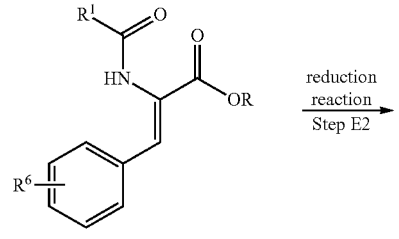

(XIX)

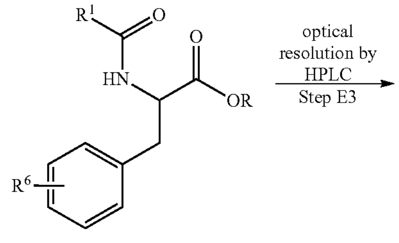

(XX)

-continued

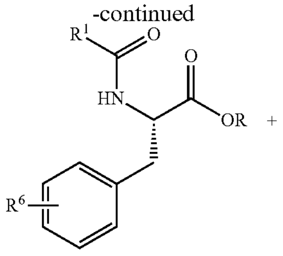

(XX-s)

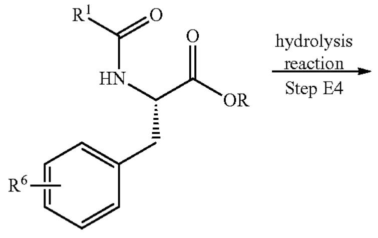

(XX-r)

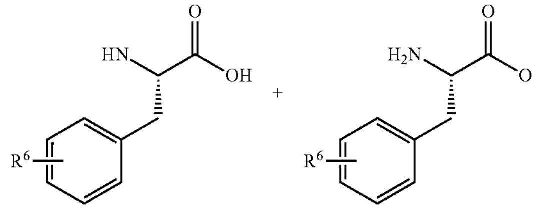

(VIII'-s) (VIII'-r)

$R^1$ and $R^6$ represent the same meanings as those described above, and $R^1$ is preferably a $C_1$-$C_6$ alkyl group. R represents a $C_1$-$C_6$ alkyl group and preferably a methyl group or an ethyl group. A compound having General Formula (V') is produced in accordance with Step A3 of Method A.

Step E1 is a step of producing a compound having General Formula (XIX) and is performed by treating a compound having General Formula (V') with a compound having General Formula (XVIII) in the presence of a base.

The base used in the above reaction is, for example, an organic base such as imidazole, pyridine, triethylamine, N-methylimidazole, or diisopropylethylamine, and is preferably a tertiary amine and more preferably triethylamine.

The solvent used in the above reaction is, for example, an ether such as tetrahydrofuran, diethyl ether, or t-butylmethyl ether; or an alcohol such as methanol or ethanol, and is preferably methanol.

The reaction temperature varies depending on the raw compound, the reagent used, and the kind of the solvent, for example, and is usually −20° C. to 80° C. and preferably 0° C. to 50° C.

The reaction time varies depending on the reaction temperature, the raw compound, the reaction reagent, and the kind of the solvent used and is usually 10 minutes to 12 hours and preferably 1 to 3 hours.

Step E2 is a step for producing a compound having General Formula (XX) and is performed by reducing a compound having General Formula (XIX).

This step is performed as in Step A5 of Method A.

Step E3 is a step of obtaining a compound having General Formula (XX-s) and a compound having General Formula (XX-r) by resolution of a compound having General Formula (XX) by a chiral column method.

The chiral column method is a method of separating a racemic mixture or salts thereof by an optical isomer separation column (chiral column). For example, in the case of liquid chromatography, a mixture of the optical isomers is applied to a chiral column such as ENANTIO-OVM (manufactured by Tosoh Corp.) or CHIRAL Series (manufactured by Daicel Co.) and is developed with water, various buffers (e.g., phosphate buffer), or organic solvents (e.g., ethanol, methanol, isopropanol, acetonitrile, trifluoroacetic acid, and diethylamine) alone or as a solution mixture to separate optical isomers.

Step E4 is a step for hydrolyzing a compound having General Formula (XX-s) and a compound having General Formula (XX-r) to convert them into a compound having General Formula (VIII'-s) and a compound having General Formula (VIII'-r), respectively.

The hydrolysis reaction of this step is performed as in Step A1 of the above Method A.

Method F is a method for producing a compound having General Formula (II'-f) that can be used in Method A or Method B as a compound having General Formula (II').

Method F

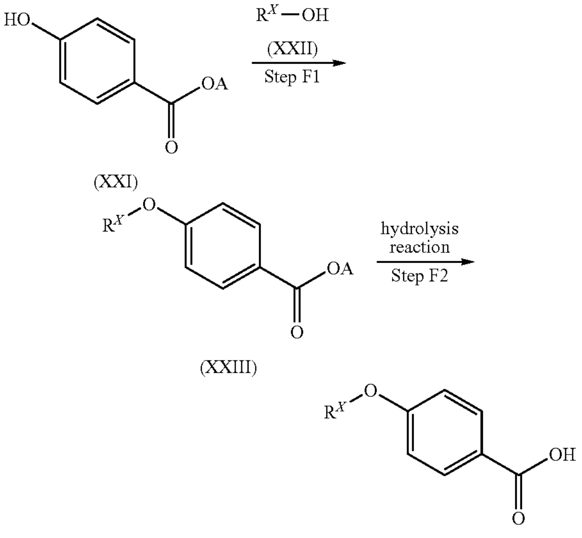

(XXI)
(XXIII)
(II'-f)

In the above formula, A represents a protecting group for a carboxyl group, and $R^X$ represents a group selected from the group consisting of $C_1$-$C_6$ alkyl groups that may be substituted by groups selected from Substituent Group β, $C_1$-$C_6$ haloalkyl groups, and $C_3$-$C_6$ cycloalkyl groups, among groups selected from the aforementioned Substituent Group α.

Step F1 is a method for producing General Formula (XXIII) and is performed by the reaction of a compound having General Formula (XXI) and a compound having General Formula (XXII) using a Mitsunobu reagent or the like in a solvent.

The Mitsunobu reagent or the like used in the above reaction is preferably a combination of an azo compound and a phosphine, or a tributyl phosphoranylidene acetonitrile. The azo compound is a diazodicarboxylic acid lower alkyl ester such as diethyl azodicarboxylate or diisopropyl azodicarboxylate or an azodicarbonyl such as 1,1'-(azodicarbonyl) dipiperidine, and the phosphine is a triarylphosphine such as triphenylphosphine or a tri-lower-alkyl phosphine such as tributylphosphine. The Mitsunobu reagent is more preferably a combination of a diazodicarboxylic acid lower alkyl ester and a triarylphosphine, or tributyl phosphoranylidene acetonitrile, and particularly preferably a combination of diethyl azodicarboxylate and triphenylphosphine, or tributyl phosphoranylidene acetonitrile.

In the case that tributyl phosphoranylidene acetonitrile is used as Mitsunobu reagent or the like The solvent used is, for example, an aliphatic hydrocarbon such as hexane, heptane, ligroin, or petroleum ether; an aromatic hydrocarbon such as toluene, benzene, or xylene; a halogenated hydrocarbon such as dichloromethane or 1,2-dichloroethane; or an ether such as diethyl ether, diisopropyl ether, tetrahydrofuran, dioxane, dimethoxyethane, or diethylene glycol dimethyl ether, and is preferably an aromatic hydrocarbon and more preferably toluene.

The reaction temperature varies depending on the raw compound, the reagent used, and the kind of the solvent, for example, and is usually 0° C. to 150° C. and preferably 50° C. to 120° C.

The reaction time varies depending on the reaction temperature, the raw compound, the reaction reagent, and the kind of the solvent used and is usually 30 minutes to 12 hours and preferably 2 to 5 hours.

(2) In the case that a combination of an azo compound and a phosphine is used as the Mitsunobu reagent or the like The solvent used is, for example, an aliphatic hydrocarbon such as hexane, heptane, ligroin, or petroleum ether; an aromatic hydrocarbon such as toluene, benzene, or xylene; a halogenated hydrocarbon such as dichloromethane or 1,2-dichloroethane; or an ether such as diethyl ether, diisopropyl ether, tetrahydrofuran, dioxane, dimethoxyethane, or diethylene glycol dimethyl ether, and is preferably an ether and more preferably tetrahydrofuran.

The reaction temperature varies depending on the raw compound, the reagent used, and the kind of the solvent, for example, and is usually −20° C. to 80° C. and preferably 0° C. to 50° C.

The reaction time varies depending on the reaction temperature, the raw compound, the reaction reagent, and the kind of the solvent used and is usually 30 minutes to 24 hours and preferably 1 to 3 hours.

After completion of the reaction, the target compound of this step is collected from the reaction mixture according to a method similar to Step A1 of Method A.

Step F2 is a method for producing General Formula (II'-f) and is performed by hydrolyzing a compound having General Formula (XXIII) in a solvent in the presence of a base or an acid, as in Step A1 of Method A.

Method G is an alternate method for producing a compound having General Formula (XXIII) in Method F.

Method G

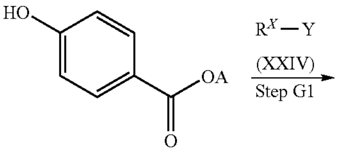

(XXI)

-continued

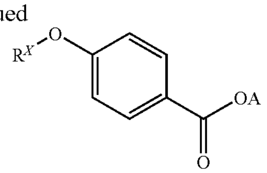

(XXIII)

In the above formula, A represents a protecting group for a carboxyl group, and $R^x$ and Y are the same meanings as those described above.

Step G1 is a method for producing General Formula (XXIII) and is performed by the reaction of a compound having General Formula (XXI) and a compound having General Formula (XXIV) in the presence of a base in a solvent. A catalyst may be added for accelerating the reaction, if necessary.

The base used in the above reaction is, for example, an alkali metal carbonate such as lithium carbonate, sodium carbonate, potassium carbonate, or cesium carbonate; an alkali metal bicarbonate such as lithium bicarbonate, sodium bicarbonate, or potassium bicarbonate; an alkali metal hydride such as lithium hydride, sodium hydride, or potassium hydride; an alkali metal hydroxide such as lithium hydroxide, sodium hydroxide, or potassium hydroxide; or an alkali metal alkoxide such as lithium methoxide, sodium methoxide, sodium ethoxide, or potassium t-butoxide. In the case that Y is a halogen atom, the base is preferably an alkali metal carbonate. In the case that Y is a group represented by the general formula —O—$S(O)_2R^C$ ($R^C$ represents a phenyl group that may be substituted by one to three groups selected from the group consisting of $C_1$-$C_6$ alkyl groups that may be each substituted by a $C_1$-$C_6$ alkyl group that may be substituted by one to three halogen atoms, a methoxy group, or one to three halogen atoms; and halogen atoms), the base is preferably an alkali metal carbonate, an alkali metal hydroxide, an alkali metal bicarbonate, or an alkali metal alkoxide. In both cases, an alkali metal carbonate is more preferred, and potassium carbonate is particularly preferred.

The catalyst used in the above reaction is, for example, a salt containing a halogen ion, such as potassium iodide or tetrabutylammonium iodide.

The solvent used in the above reaction is, for example, a ketone such as acetone or butanone; an ether such as diethyl ether, diisopropyl ether, tetrahydrofuran, dioxane, dimethoxyethane, diethylene glycol dimethyl ether; a lower alkylnitrile such as acetonitrile or propionitrile; an amide such as formamide, N,N-dimethylformamide, N,N-dimethylacetamide, or hexamethylphosphoric acid triamide; or a sulfoxide such as dimethylsulfoxide, and is preferably a ketone or an amide and more preferably acetone, 2-butanone, or N,N-dimethylacetamide.

The reaction temperature varies depending on the raw compound, the reagent used, and the kind of the solvent, for example, and is usually 0° C. to 150° C. and preferably 50° C. to 120° C.

The reaction time varies depending on the reaction temperature, the raw compound, the reaction reagent, and the kind of the solvent used and is usually 10 minutes to 7 days and preferably 1 hour to 2 days.

After completion of the reaction, the target compound of this step is collected from the reaction mixture according to a method similar to Step A1 of Method A.

Method H is a method for producing a compound having General Formula (II'-h) used as a compound having General Formula (II') in Method A or Method B.

Method H

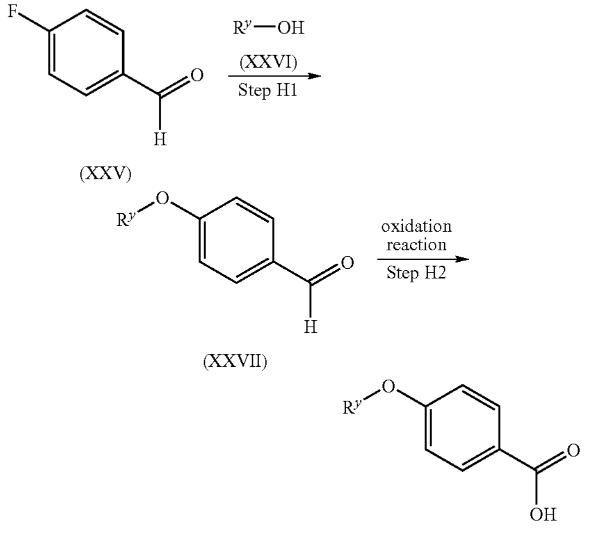

In the above formula, $R^y$ represents a group selected from the group consisting of $C_1$-$C_6$ alkyl groups that may be substituted by groups selected from Substituent Group β, $C_1$-$C_6$ haloalkyl groups, $C_3$-$C_6$ cycloalkyl groups, $C_6$-$C_{10}$ aryl groups that may be substituted by groups selected from Substituent Group γ, and 5- to 10-membered heteroaryl groups that may be substituted by groups selected from Substituent Group γ, among groups selected from the aforementioned Substituent Group α.

Step H1 is a method for producing General Formula (XXVII) and is performed by the reaction of a compound having General Formula (XXV) and a compound having General Formula (XXVI) in the presence of a base in a solvent.

This step is performed in accordance with the method described in Bioorganic & Medicinal Chemistry Letters, 2003, 13, 1801-1804 or Journal of Medicinal Chemistry, 1994, 37, 3977-3985.

The base used in the above reaction is, for example, an alkali metal carbonate such as lithium carbonate, sodium carbonate, potassium carbonate, or cesium carbonate; an alkali metal bicarbonate such as lithium bicarbonate, sodium bicarbonate, or potassium bicarbonate; an alkali metal hydride such as lithium hydride, sodium hydride, or potassium hydride; an alkali metal hydroxide such as lithium hydroxide, sodium hydroxide, or potassium hydroxide; or an alkali metal alkoxide such as lithium methoxide, sodium methoxide, sodium ethoxide, or potassium t-butoxide, and is preferably an alkali metal hydride and more preferably sodium hydride.

The solvent used in the above reaction is, for example, an ether such as diethyl ether, diisopropyl ether, tetrahydrofuran, dioxane, dimethoxyethane, diethylene glycol dimethyl ether; an amide such as formamide, N,N-dimethylformamide, N,N-dimethylacetamide, or hexamethylphosphoric acid triamide; or a sulfoxide such as dimethylsulfoxide, and is preferably an amide and more preferably N,N-dimethylacetamide.

The reaction temperature varies depending on the raw compound, the reagent used, and the kind of the solvent, for example, and is usually 0° C. to 150° C. and preferably 0° C. to 50° C.

The reaction time varies depending on the reaction temperature, the raw compound, the reaction reagent, and the kind of the solvent used and is usually 10 minutes to 7 days and preferably 1 hour to 2 days.

After completion of the reaction, the target compound of this step is collected from the reaction mixture according to a method similar to Step A1 of Method A.

Step H2 is a method for producing General Formula (II'-h) and is performed by the reaction of a compound having General Formula (XXVII) with an oxidizing agent in a solvent.

The oxidizing agent used in this reaction is usually an oxidizing agent described in, for example, the aforementioned "Comprehensive Organic Transformations", VCH Publishers Inc., (1989). The oxidizing agent is, for example, oxygen used together with a metal catalyst such as a manganese salt; a permanganate such as potassium permanganate or sodium permanganate; a peroxide, such as t-butyl peroxide, used together with a metal catalyst such as molybdate; a peroxide, such as sodium periodate, used together with a ruthenium salt; a chromate such as potassium bichromate; a silver salt such as silver oxide; N-bromosuccinic acid imide; a chlorite such as sodium chlorite; a hypochlorite such as potassium hypochlorite; or nickel peroxide, and is preferably a chlorite and more preferably sodium chlorite. In addition, side reactions can be suppressed and the yield can be improved by simultaneously using a radical-trapping agent such as 2-methyl-2-butane and a buffer solution such as a sodium dihydrogenphosphate aqueous solution.

The solvent used in the above reaction is, for example, an aliphatic hydrocarbon such as hexane, heptane, ligroin, or petroleum ether; an aromatic hydrocarbon such as toluene, benzene, or xylene; a halogenated hydrocarbon such as dichloromethane or 1,2-dichloroethane; or an ether such as diethyl ether, diisopropyl ether, tetrahydrofuran, dioxane, dimethoxyethane, or diethylene glycol dimethyl ether, and is preferably an ether and more preferably diethyl ether.

The reaction temperature varies depending on the raw compound, the reagent used, and the kind of the solvent, for example, and is usually 0° C. to 50° C. and preferably 0° C. to 40° C.

The reaction time varies depending on the reaction temperature, the raw compound, the reaction reagent, and the kind of the solvent used and is usually 10 minutes to 10 hours and preferably 30 minutes to 5 hours.

After completion of the reaction, the target compound of this step is collected from the reaction mixture according to a method similar to Step A1 of Method A.

Method I is an alternative method for producing a compound of General Formula (XXIII-i) having a difluorocyclopropylalkyl group as the substituent Rx of a compound having General Formula (XXIII) in Method F.

Method I

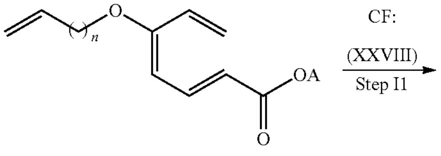

(XXIII')

-continued

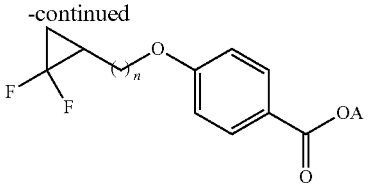

(XXIII-i)

In the above formula, n represents an integer of 1 to 3, and A is the same meaning as that described above.

Step I1 is a method for producing a compound of General Formula (XXIII-i) and is performed by difluorocyclopropanating a compound having General Formula (XXIII') in the presence or absence of a solvent in a reaction solution with a reagent producing difluorocarbene. This step is performed in accordance with the method described in Journal of Fluorine Chemistry, 2001, 112, 63-68.

The reagent producing difluorocarbene in this reaction is, for example, a combination of phenyl(trifluoromethyl)mercury and sodium iodide; a combination of trimethyl(trifluoromethyl)tin and sodium iodide; sodium chlorodifluoroacetate; hexafluoropropylene oxide; or a combination of trimethylsilyl fluorosulfonyldifluoroacetate (TFDA) and (a catalytic amount of) an alkali metal fluoride, and is preferably a combination of trimethylsilyl fluorosulfonyldifluoroacetate (TFDA) and (a catalytic amount of an alkali metal fluoride and more preferably a combination of trimethylsilyl fluorosulfonyldifluoroacetate (TFDA) and (a catalytic amount of) sodium fluoride.

The solvent used in the above reaction is, for example, an aromatic hydrocarbon such as toluene, benzene, or xylene; or an ether such as diethyl ether, diisopropyl ether, tetrahydrofuran, dioxane, dimethoxyethane, or diethylene glycol dimethyl ether, and is preferably an aromatic hydrocarbon and more preferably toluene. In addition, in some cases, the reaction is performed in the absence of solvent, as appropriate conditions.

The reaction temperature varies depending on the raw compound, the reagent used, and the kind of the solvent, for example, and is usually 50° C. to 300° C. and preferably 70° C. to 150° C.

The reaction time varies depending on the reaction temperature, the raw compound, the reaction reagent, and the kind of the solvent used and is usually 30 minutes to 2 days and preferably 1 to 24 hours.

After completion of the reaction, the target compound of this step is collected from the reaction mixture according to a method similar to Step A1 of Method A.

(Administration Route, Dosage, and so on)

When the compound having General Formula (I) or a pharmacologically acceptable salt thereof according to the present invention is used for the aforementioned prophylaxis or treatment (in particular treatment), the compound or the salt itself or a mixture with an optional pharmacologically acceptable filler, diluent, or the like is administered, for example, orally as a tablet, a capsule, granules, powder, or syrup or parenterally as an injection or a suppository.

These drugs are prepared by widely known methods using additives such as fillers (for example, organic fillers: sugar derivatives such as lactose, white sugar, glucose, mannitol, and sorbitol; starch derivatives such as corn starch, potato starch, α-starch, and dextrin; cellulose derivatives such as crystal cellulose; gum arabic; dextran; and pullulan, and inorganic fillers: silicate derivatives such as light anhydrous silicic acid, synthetic aluminum silicate, calcium silicate, and magnesium aluminometasilicate; phosphates such as calcium hydrogen phosphate; carbonates such as calcium carbonate; and sulfates such as calcium sulfate), lubricants (for example, stearic acid, stearic acid metal salts such as calcium stearate and magnesium stearate; talc; colloidal silica; waxes such as bee gum and spermaceti; boric acid; adipic acid; sulfates such as sodium sulfate; glycol; fumaric acid; sodium benzoate; D,L-leucine; fatty acid sodium salts; laurylsulfates such as sodium laurylsulfate and magnesium laurylsulfate; silic acids such as silica and silicate hydrate; and the aforementioned starch derivatives), binders (for example, hydroxypropyl cellulose, hydroxypropylmethyl cellulose, polyvinylpyrrolidone, macrogol, and the same compounds as the aforementioned fillers), disintegrating agents (for example, cellulose derivatives such as low-substituted hydroxypropyl cellulose, carboxylmethyl cellulose, carboxylmethyl cellulose calcium, and internally-crosslinked carboxylmethyl cellulose sodium; and chemically modified starch/cellulose such as carboxylmethyl starch, carboxylmethyl starch sodium, and crosslinked polyvinylpyrrolidone), stabilizers (for example, paraoxybenzoic acid esters such as methylparabene and propylparabene; alcohols such as chlorobutanol, benzyl alcohol, and phenylethyl alcohol; benzalkonium chloride; phenols such as phenol and cresol; thimerosal; dehydroacetic acid; and sorbic acid), flavoring agents (for example, sweeteners, acidifiers, and flavors that are usually used), and diluents.

The dosage and administration route vary depending on the symptom and the age, for example, and are usually as follows:

For oral administration, the dose of each administration is 0.001 to 100 mg/kg and preferably 0.01 to 10 mg/kg.

For intravenous administration, the dose of each administration is 0.0001 to 10 mg/kg and preferably 0.001 to 1 mg/kg.

The administration frequency and the administration interval vary depending on the disease to be treated and its severity or the purpose, i.e., therapeutic use or prophylactic use, and are usually one to three times a day, one to six times a week, or one to four times a month.

The above drugs are used as pharmaceutical compositions for prophylaxis or treatment (in particular, treatment) characterized by administering to mammals (such as human, ape, dog, cat, horse, and hog, in particular, human).

The compounds according to the present invention are low in toxicity, show favorable pharmacokinetics, and have an excellent bone resorption-suppressing activity and a blood calcium concentration-decreasing activity and a bone mass decrease-suppressing activity associated therewith, and thereby can be used for prophylaxis or treatment (in particular, treatment) of the aforementioned bone metabolic diseases. Thus, the compounds are useful.

BEST MODE FOR CARRYING OUT THE INVENTION

The present invention will now be further specifically described in detail with reference to Examples and Test Examples, but is not limited thereto.

EXAMPLES

Example 1

4-(2-Cyclopropylethoxy)-N-[2-[(2-hydroxyethyl)amino]-2-oxo-1-(4-propylbenzyl)ethyl]benzamide (Exemplary Compound No. 47)

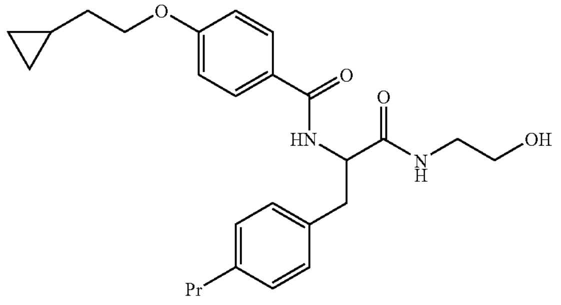

(1a) 4-(2-Cyclopropylethoxy)benzoic acid

Methyl 4-hydroxybenzoate (8.83 g, 58.0 mmol), 2-cyclopropylethanol (5.13 g, 59.6 mmol), and triphenylphosphine (15.7 g, 59.9 mmol) were dissolved in tetrahydrofuran (THF, 250 mL), and then diethyl azodicarboxylate (29.8 mL, 40% toluene solution, 59.6 mmol) was added thereto under ice-cooling with stirring. The mixture was stirred at room temperature for two days, and then to the reaction solution was added water (200 mL). The resulting mixture was extracted with ethyl acetate twice. The organic layers were combined, washed with saturated brine, and dried over anhydrous magnesium sulfate. Then, the solvent was evaporated. The obtained residue was dissolved in diethyl ether, the resulting precipitate was removed by filtration, and diethyl ether was evaporated. This filtration procedure was repeated twice, and the residue was purified by silica gel column chromatography (n-hexane:ethyl acetate, 20:1, V/V) to give an oily substance (13.2 g). All this substance was dissolved in ethanol (200 mL), and a 2 M lithium hydroxide aqueous solution (60 mL, 120 mmol) was added thereto. The mixture was stirred at 60° C. for 50 min, and then 10% hydrochloric acid (40 mL) was added thereto under ice-cooling. The mixture was extracted with ethyl acetate twice. The organic layers were combined, washed with saturated brine, and dried over anhydrous magnesium sulfate. Then, the solvent was evaporated. The obtained residue was suspended in diisopropyl ether, and the precipitate was collected by filtration and dried under reduced pressure to give 9.28 g of the title compound (powder, yield: 78%).

$^1$H-Nuclear Magnetic Resonance Spectra (400 MHz, DMSO-$d_6$) δ ppm:

12.6 (1H, s), 7.88 (2H, d, J=9 Hz), 7.02 (2H, d, J=9 Hz), 4.10 (2H, t, J=7 Hz), 1.64 (2H, q, J=7 Hz), 0.88-0.79 (1H, m), 0.46-0.42 (2H, m), 0.15-0.11 (2H, m).

(1b) N-[4-(2-Cyclopropylethoxy)benzoyl]glycine

Oxalyl chloride (8.64 mL, 99.0 mmol) and one drop of N,N-dimethylformamide (DMF) were added to a methylene chloride (30 mL) solution of 4-(2-cyclopropylethoxy)benzoic acid (9.28 g, 45.0 mmol) prepared in Example 1 (1a), under ice-cooling. The mixture was stirred at room temperature for 1.75 hours, and then the solvent was evaporated. Then, the obtained residue was suspended in THF (3 mL). This suspension was dropwise added to a 50% THF aqueous solution (120 mL) of glycine (4.41 g, 58.7 mmol) and triethylamine (15.7 mL, 112 mmol) under ice-cooling. The resulting mixture was stirred at room temperature for 1.5 hours, and the solvents (mainly THF) were evaporated. Then, 10% hydrochloric acid (40 mL) was added to the residue under ice-cooling. The resulting precipitate was collected by filtration, washed with water, and dried by heating under reduced pressure to give 11.4 g of the title compound (powder, yield: 97%).

MS (FAB) m/z: 264 $[M+H]^+$;

$^1$H-Nuclear Magnetic Resonance Spectra (400 MHz, DMSO-$d_6$) δ ppm:

12.5 (1H, brs), 8.64 (1H, brt, J=6 Hz), 7.81 (2H, d, J=9 Hz), 6.98 (2H, d, J=9 Hz), 4.07 (2H, t, J=7 Hz), 3.88 (2H, d, J=6 Hz), 1.63 (2H, q, J=7 Hz), 0.88-0.78 (1H, m), 0.46-0.42 (2H, m), 0.15-0.11 (2H, m).

(1c) (4Z)-4-(4-Cyclopropylbenzylidene)-2-[4-(2-cyclopropylethoxy)phenyl]-1,3-oxazol-5(4H)-one A mixture of N-[4-(2-cyclopropylethoxy)benzoyl]glycine (184 mg, 0.699 mmol) prepared in Example 1 (1b), 4-cyclopropylbenzaldehyde (compound described in Tetrahedron Lett., (2002), 43, 6987-6990, 113 mg, 0.773 mmol), sodium acetate (75 mg, 0.914 mmol), and acetic anhydride (660 μL, 6.99 mmol) was stirred at 120° C. for 30 minutes and then allowed to cool to room temperature. The solidified product was ultrasonically washed with n-hexane (2 mL) and water (4 mL). Then, the precipitate was collected by filtration, washed with water and n-hexane, and dried by heating under reduced pressure to give 196 mg of the title compound (yellow powder, yield 74%). Hereinafter, the compound obtained by this cyclizing reaction is called oxazolone.

$^1$H-Nuclear Magnetic Resonance Spectra (400 MHz, $CDCl_3$) δ ppm:

8.12 (2H, d, J=9 Hz), 8.10 (2H, d, J=8 Hz), 7.16 (1H, s), 7.15 (2H, d, J=8 Hz), 7.03 (2H, d, J=9 Hz), 4.14 (2H, t, J=7 Hz), 1.99-1.93 (1H, m), 1.73 (2H, q, J=6 Hz), 1.10-1.05 (2H, m), 0.93-0.83 (1H, m), 0.83-0.79 (2H, m), 0.55-0.50 (2H, m), 0.17-0.14 (2H, m).

(1d) 4-(2-Cyclopropylethoxy)-N-((Z)-2-(4-cyclopropylphenyl)-1-{[(2-hydroxyethyl)amino]carbonyl}vinyl)benzamide To an ethanol (1.6 mL) solution of (4Z)-4-(4-cyclopropylbenzylidene)-2-[4-(2-cyclopropylethoxy)phenyl]-1,3-oxazol-5(4H)-one (95 mg, 0.25 mmol) prepared in Example 1 (1c) was added 2-aminoethanol (20 μL, 0.33 mmol), and the mixture was stirred at 60° C. for one hour. The solvent was evaporated, and the residue was washed with n-hexane:ethyl acetate (3:1, V/V). The precipitate was collected by filtration and dried under reduced pressure to give 95 mg of the title compound (white powder, yield: 86%).

MS (FAB) m/z: 435 $[M+H]^+$;

$^1$H-Nuclear Magnetic Resonance Spectra (400 MHz, DMSO-$d_6$) δ ppm:

9.67 (1H, brs), 7.95-7.91 (3H, m), 7.39 (2H, d, J=8 Hz), 7.15 (1H, brs), 7.02 (2H, d, J=9 Hz), 7.00 (2H, d, J=9 Hz), 4.62 (1H, t, J=5 Hz), 4.10 (2H, t, J=7 Hz), 3.43 (2H, q, J=6 Hz), 3.22 (2H, q, J=6 Hz), 1.90-1.83 (1H, m), 1.65 (2H, q, J=7 Hz), 0.95-0.91 (2H, m), 0.89-0.80 (1H, m), 0.68-0.64 (2H, m), 0.47-0.43 (2H, m), 0.16-0.12 (2H, m).

(1e) 4-(2-Cyclopropylethoxy)-N-[2-[(2-hydroxyethyl)amino]-2-oxo-1-(4-propylbenzyl)ethyl]benzamide To a methanol:THF (2:1, V/V, 6 mL) solution of 4-(2-cyclopropylethoxy)-N-((Z)-2-(4-cyclopropylphenyl)-1-{[(2-hydroxyethyl)amino]carbonyl}vinyl)benzamide (215 mg, 0.495 mmol) prepared in Example (1 (1d) was added 10% palladium-carbon (wet, 100 mg). The mixture was stirred under a hydrogen atmosphere (rubber balloon) at room temperature for 2 hours. To the reaction solution was added ethyl acetate (10 mL), and the mixture was filtered. The solvent was evaporated, and the residue was purified by thin layer chromatography for separation (ethyl acetate, developed once) to give a white solid. This solid was suspended in acetonitrile:water (1:1, V/V, 4 mL), and the insoluble substance was collected by filtration, washed with water, and dried under reduced pressure to give 104 mg of the title compound (white powder, yield: 48%).

MS (FAB) m/z: 439 $[M+H]^+$;

$^1$H-Nuclear Magnetic Resonance Spectra (500 MHz, $CDCl_3$) δ ppm:

7.69 (2H, d, J=9 Hz), 7.18 (2H, d, J=8 Hz), 7.13 (2H, d, J=8 Hz), 6.91 (2H, d, J=9 Hz), 6.78 (1H, d, J=7 Hz), 6.28 (1H, t, J=6 Hz), 4.76 (1H, td, J=8 Hz, 6 Hz), 4.07 (2H, t, J=6 Hz), 3.62-3.52 (2H, m), 3.41-3.35 (1H, m), 3.30-3.25 (1H, m), 3.22 (1H, dd, J=14 Hz, 6 Hz), 3.05 (1H, dd, J=14 Hz, 8 Hz), 2.54 (2H, t, J=8 Hz), 2.33 (1H, t, J=6 Hz), 1.70 (2H, q, J=7 Hz), 1.64-1.56 (2H, m), 0.92 (3H, t, J=7 Hz), 0.89-0.79 (1H, m), 0.52-0.48 (2H, m), 0.14-0.11 (2H, m).

Example 2

N-{1-(4-Cyclopropylbenzyl)-2-[(2-hydroxyethyl)amino]-2-oxoethyl}-4-(2-cyclopropylethoxy)benzamide (Exemplary Compound No. 37)

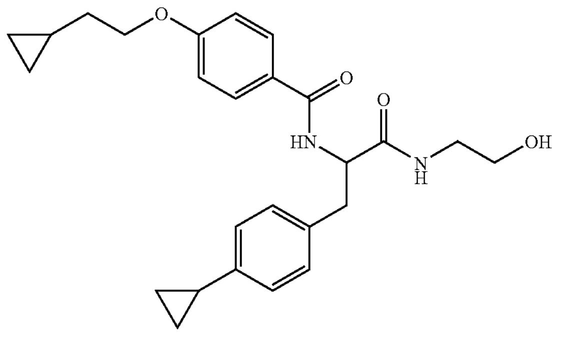 [SMILES: O=C(NC(Cc1ccc(C2CC2)cc1)C(=O)NCCO)c1ccc(OCCC2CC2)cc1]

To an ethanol:THF (4:1, V/V, 7.5 mL) solution of 4-(2-cyclopropylethoxy)-N-((Z)-2-(4-cyclopropylphenyl)-1-{[(2-hydroxyethyl)amino]carbonyl}vinyl)benzamide (165 mg, 0.380 mmol) prepared in Example 1 (1d) was added tris(triphenylphosphine)rhodium(I) chloride (71 mg, 0.076 mmol). The mixture was stirred under a hydrogen atmosphere (rubber balloon) at 60° C. for 5 hours. The reaction solution was cooled to room temperature, and the solvent was evaporated. The residue was purified by alumina column chromatography (ethyl acetate to ethyl acetate:methanol, 10:1, V/V) to give 89 mg of the title compound (white powder, yield: 54%).

MS (FAB) m/z: 437 $[M+H]^+$;

[1]H-Nuclear Magnetic Resonance Spectra (500 MHz, DMSO-$d_6$) δ ppm:

8.34 (1H, d, J=8 Hz), 8.02 (1H, t, J=6 Hz), 7.78 (2H, d, J=8 Hz), 7.19 (2H, d, J=8 Hz), 6.97 (2H, d, J=8 Hz), 6.93 (2H, d, J=8 Hz), 4.67 (1H, t, J=5 Hz), 4.62-4.58 (1H, m), 4.07 (2H, t, J=7 Hz), 3.39 (2H, q, J=6 Hz), 3.16-3.12 (2H, m), 3.00 (1H, dd, J=14 Hz, 4 Hz), 2.92 (1H, dd, J=14 Hz, 11 Hz), 1.84-1.79 (1H, m), 1.63 (2H, q, J=7 Hz), 0.89-0.85 (2H, m), 0.86-0.80 (1H, m), 0.60-0.57 (2H, m), 0.45-0.42 (2H, m), 0.14-0.11 (2H, m).

Example 3

4-(2-Cyclopropylethoxy)-N-{1-[4-(difluoromethoxy)benzyl]-2-[(2-hydroxyethyl)amino]-2-oxoethyl}benzamide (Exemplary Compound No. 38)

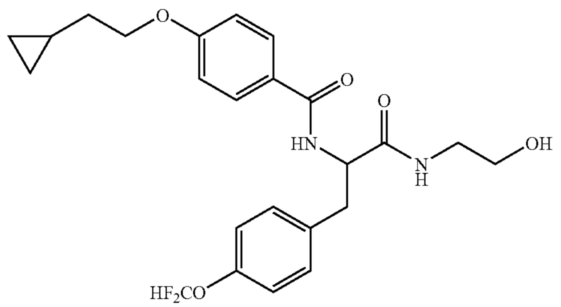

A reaction similar to that described in Example (1 (1 c) was conducted using N-[4-(2-cyclopropylethoxy)benzoyl]glycine (150 mg) prepared in Example 1 (1b) and 4-(difluoromethoxy)benzaldehyde (83 μL) to give the corresponding oxazolone (188 mg). A reaction similar to that described in Example 1 (1d) was conducted using 90 mg of this oxazolone to give 76 mg of 4-(2-cyclopropylethoxy)-N-((Z)-2-[4-(difluoromethoxy)phenyl]-1-{[(2-hydroxyethyl)amino]carbonyl}vinyl)benzamide (white powder).

MS (FAB) m/z: 461 $[M+H]^+$;

[1]H-Nuclear Magnetic Resonance Spectra (400 MHz, DMSO-$d_6$) δ ppm:

9.72 (1H, brs), 8.00 (1H, brt, J=6 Hz), 7.93 (2H, d, J=9 Hz), 7.56 (2H, d, J=9 Hz), 7.23 (1H, t, J=74 Hz), 7.16 (1H, s), 7.12 (2H, d, J=9 Hz), 7.02 (2H, d, J=9 Hz), 4.62 (1H, t, J=5 Hz), 4.10 (2H, t, J=7 Hz), 3.43 (2H, q, J=6 Hz), 3.22 (2H, q, J=6 Hz), 1.64 (2H, q, J=7 Hz), 0.88-0.81 (1H, m), 0.47-0.43 (2H, m), 0.16-0.12 (2H, m).

A reaction similar to that described in Example 1 (1e) was conducted using 4-(2-cyclopropylethoxy)-N-((Z)-2-[4-(difluoromethoxy)phenyl]-1-{[(2-hydroxyethyl)amino]carbonyl}vinyl)benzamide (196 mg) to give 147 mg of the title compound (white powder).

MS (FAB) m/z: 463 $[M+H]^+$;

[1]H-Nuclear Magnetic Resonance Spectra (500 MHz, $CDCl_3$) δ ppm:

7.68 (2H, d, J=9 Hz), 7.26 (2H, d, J=9 Hz), 7.06 (2H, d, J=8 Hz), 6.92 (2H, d, J=9 Hz), 6.74 (1H, d, J=7 Hz), 6.48 (1H, t, J=74 Hz), 6.36 (1H, t, J=5 Hz), 4.78 (1H, dt, J=8 Hz, 6 Hz), 4.07 (2H, t, J=7 Hz), 3.66-3.56 (2H, m), 3.40-3.30 (2H, m), 3.20 (1H, dd, J=14 Hz, 6 Hz), 3.12 (1H, dd, J=14 Hz, 8 Hz), 2.33 (1H, t, J=5 Hz), 1.69 (2H, q, J=7 Hz), 0.89-0.81 (1H, m), 0.52-0.48 (2H, m), 0.14-0.11 (2H, m).

Example 4

4-(2-Cyclopropylethoxy)-N-{2-[(2-hydroxyethyl)amino]-2-oxo-1-[4-(trifluoromethoxy)benzyl]ethyl}benzamide (Exemplary Compound No. 39)

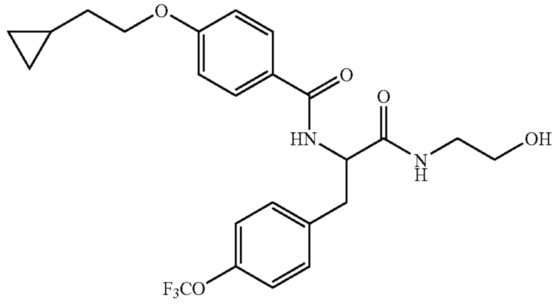

A reaction similar to that described in Example 1 (1c) was conducted using N-[4-(2-cyclopropylethoxy)benzoyl]glycine (150 mg) prepared in Example 1 (1b) and 4-(trifluoromethoxy)benzaldehyde (90 μL) to give (4Z)-2-[4-(2-cyclopropylethoxy)phenyl]-4-[4-(trifluoromethoxy)benzylidene]-1,3-oxazol-5(4H)-one (176 mg). A reaction similar to that described in Example 1 (1d) was conducted using 80 mg of this given compound to give 74 mg of 4-(2-cyclopropylethoxy)-N-{(Z)-1-{[(2-hydroxyethyl)amino]carbonyl}-2-[4-(trifluoromethoxy)phenyl]vinyl}benzamide (white powder).

MS (FAB) m/z: 479 $[M+H]^+$;

[1]H-Nuclear Magnetic Resonance Spectra (400 MHz, DMSO-$d_6$) δ ppm:

9.75 (1H, brs), 8.04 (1H, t, J=6 Hz), 7.93 (2H, d, J=9 Hz), 7.62 (2H, d, J=9 Hz), 7.32 (2H, d, J=8 Hz), 7.14 (1H, brs), 7.02 (2H, d, J=9 Hz), 4.62 (1H, t, J=5 Hz), 4.10 (2H, t, J=7 Hz), 3.43 (2H, q, J=6 Hz), 3.22 (2H, q, J=6 Hz), 1.64 (2H, q, J=7 Hz), 0.89-0.79 (1H, m), 0.47-0.42 (2H, m), 0.16-0.12 (2H, m).

A reaction similar to that described in Example 1 (1e) was conducted using 4-(2-cyclopropylethoxy)-N-{(Z)-1-{[(2-hydroxyethyl)amino]carbonyl}-2-[4-(trifluoromethoxy)phenyl]vinyl}benzamide (110 mg) to give 82 mg of the title compound (white powder).

MS (FAB) m/z: 481 $[M+H]^+$;

[1]H-Nuclear Magnetic Resonance Spectra (400 MHz, DMSO-$d_6$) δ ppm:

8.42 (1H, d, J=9 Hz), 8.09 (1H, t, J=5 Hz), 7.77 (2H, d, J=9 Hz), 7.44 (2H, d, J=8 Hz), 7.24 (2H, d, J=8 Hz), 6.97 (2H, d, J=8 Hz), 4.71-4.64 (2H, m), 4.07 (2H, t, J=7 Hz), 3.38 (2H, q,

J=6 Hz), 3.17-2.97 (4H, m), 1.62 (2H, q, J=7 Hz), 0.88-0.77 (1H, m), 0.46-0.41 (2H, m), 0.14-0.11 (2H, m).

Example 5

4-(2-Cyclopropylethoxy)-N-{1-[4-(cyclopropyloxy)benzyl]-2-[(2-hydroxyethyl)amino]-2-oxoethyl}benzamide (Exemplary Compound No. 36)

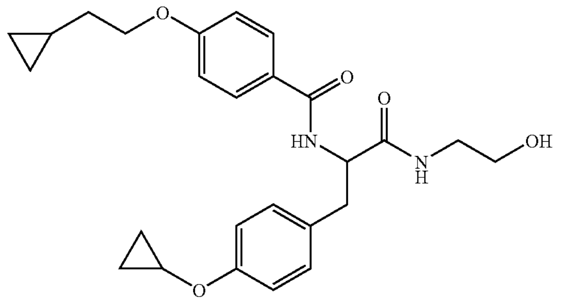 [SMILES: O=C(NC(Cc1ccc(OC2CC2)cc1)C(=O)NCCO)c1ccc(OCCC2CC2)cc1]

(5a) 1-Bromo-4-(2-chloroethoxy)benzene

The preparation was conducted according to the description in the document (J. Org. Chem., (2002), 67, 1093-1101). Potassium carbonate (83.0 g, 600 mmol) was added to an N,N-dimethylformamide (DMF, 500 mL) solution of 4-bromophenol (50.4 g, 291 mmol) at room temperature. The mixture was stirred at the same temperature for 30 minutes, and then 2-chloroethyl p-toluenesulfonate (70.2 g, 299 mmol) was added thereto. The resulting mixture was stirred at 50° C. for 24 hours. The reaction solution was cooled to 110° C., and water (500 mL) was added thereto to precipitate a white solid. The solid was collected by filtration, washed with water (500 mL), and dried under reduced pressure to give 58.6 g of the title compound (white powder, yield: 86%).

$^1$H-Nuclear Magnetic Resonance Spectra (400 MHz, $CDCl_3$) δ ppm:

7.39 (2H, d, J=9 Hz), 6.81 (2H, d, J=9 Hz), 4.20 (2H, t, J=6 Hz), 3.80 (2H, t, J=6 Hz).

(5b) 1-Bromo-4-(vinyloxy)benzene

To a THF (250 mL) solution of 1-bromo-4-(2-chloroethoxy)benzene (58.6 g, 249 mmol) prepared in Example 5 (5a) was added tert-butoxy potassium (33.7 g, 300 mmol) at −10° C. over 10 minutes. The resulting mixture was stirred at room temperature for 21 hours. Water (500 mL) was added thereto, and the mixture was extracted with methyl tert-butyl ether (200 mL, 150 mL) twice. The organic layers were combined, washed with saturated brine (100 mL) twice, and dried over anhydrous magnesium sulfate. Then, the solvent was evaporated. The resulting residue was dissolved in n-hexane (100 mL), and the precipitated insoluble substance was removed by filtration, and this insoluble substance was further washed with n-hexane (5 mL) five times. These filtrates were combined and concentrated, and then purified by silica gel column chromatography (n-hexane) to give 39.0 g of the title compound (colorless oil, yield: 79%).

$^1$H-Nuclear Magnetic Resonance Spectra (400 MHz, $CDCl_3$) δ ppm:

7.43 (2H, d, J=9 Hz), 6.89 (2H, d, J=9 Hz), 6.59 (1H, dd, J=14 Hz, 6 Hz), 4.78 (1H, dd, J=14 Hz, 2 Hz), 4.47 (1H, dd, J=6 Hz, 2 Hz).

(5c) 4-(Cyclopropyloxy)benzaldehyde

The following cyclopropanation was conducted according to the description in the document (Tetrahedron Lett., (1998), 39, 8621-8624). Diethylzinc (1.0 M n-hexane solution, 250 mL, 250 mmol) was added to methylene chloride (250 mL), and a methylene chloride (120 mL) solution of trifluoroacetic acid (19.2 mL, 249 mmol) was added thereto under ice-cooling over 100 minutes. The mixture was further stirred for 1 hour. Then, a methylene chloride (100 mL) solution of chloroiodomethane (20.1 mL, 250 mmol) was added thereto under ice-cooling over 40 minutes. At the same temperature, a methylene chloride (120 mL) solution of 1-bromo-4-(vinyloxy)benzene (32.8 g, 165 mmol) prepared in Example 5 (5b) was added thereto over 20 minutes. The resulting mixture was stirred at room temperature for 1.5 hours. To the reaction solution was added 0.1 N hydrochloric acid (400 mL). The mixture was stirred for 30 minutes, filtered through Celite, and further washed with n-hexane (200 mL). The filtrate and the n-hexane washing solution were combined, and the organic layer was washed with 0.1 N hydrochloric acid (100 mL) and saturated brine (100 mL) containing about 1 g of sodium sulfite twice. This organic layer was dried over anhydrous magnesium sulfate, and then the solvent was evaporated to give 36.0 g of 1-bromo-4-(cyclopropyloxy)benzene (yellow oil).

$^1$H-Nuclear Magnetic Resonance Spectra (400 MHz, $CDCl_3$) δ ppm:

7.37 (2H, d, J=9 Hz), 6.93 (2H, d, J=9 Hz), 3.72-3.68 (1H, m), 0.79-0.73 (4H, m).

To a THF (350 mL) solution of this crude product (36.0 g, 165 mmol) was added n-butyllithium (116 mL, 1.56 M n-hexane solution, 181 mmol) under a nitrogen atmosphere at −66° C. over 40 minutes, and the mixture was further stirred at the same temperature for 1 hour. Then, DMF (23.6 g, 323 mmol) was dropwise added to the reaction solution over 12 minutes. The mixture was stirred at the same temperature for 30 minutes and then left standing at room temperature overnight, and then a saturated ammonium chloride aqueous solution (150 mL) was dropwise added thereto over 5 minutes. The organic layer was separated and washed with saturated ammonium chloride aqueous solution (100 mL) and saturated brine (110 mL). The washing solutions were combined and extracted with n-hexane (200 mL). All the organic layer was collected and dried over anhydrous magnesium sulfate. The solvent was evaporated, and the obtained residue was purified by silica gel column chromatography (hexane:ethyl acetate, 9:1, V/V) to give 23.3 g of the title compound (light yellow oil, yield: 87%).

MS (EI) m/z: 162 $[M]^+$;

$^1$H-Nuclear Magnetic Resonance Spectra (400 MHz, $CDCl_3$) δ ppm:

9.87 (1H, s), 7.82 (2H, d, J=9 Hz), 7.14 (2H, d, J=9 Hz), 3.83-3.79 (1H, m), 0.87-0.81 (4H, m).

(5d) 4-(2-Cyclopropylethoxy)-N-{1-[4-(cyclopropyloxy)benzyl]-2-[(2-hydroxyethyl)amino]-2-oxoethyl}benzamide A reaction similar to that described in Example 1 (1c) was conducted using N-[4-(2-cyclopropylethoxy)benzoyl]glycine (263 mg) prepared in Example 1 (1b) and 4-(cyclopropyloxy)benzaldehyde (170 mg) prepared in Example 5 (5c) to give the corresponding oxazolone (235 mg). A reaction similar to that described in Example 1 (1d) was conducted using 156 mg of this oxazolone to give 157 mg of 4-(2-cyclopropylethoxy)-N-((Z)-2-[4-(cyclopropyloxy)phenyl]-1-{[(2-hydroxyethyl)amino]carbonyl}vinyl)benzamide (white powder).

MS (FAB) m/z: 451 $[M+H]^+$;

$^1$H-Nuclear Magnetic Resonance Spectra (500 MHz, $CDCl_3$) δ ppm:

7.88 (1H, brs), 7.82 (2H, d, J=9 Hz), 7.34 (2H, d, J=8 Hz), 7.06 (1H, s), 6.98 (2H, d, J=9 Hz), 6.93 (2H, d, J=8 Hz), 6.79

(1H, brt, J=6 Hz), 4.08 (2H, t, J=6 Hz), 3.75 (2H, t, J=5 Hz), 3.70 (1H, sept, J=3 Hz), 3.47 (2H, q, J=5 Hz), 1.71 (2H, q, J=6 Hz), 0.89-0.82 (1H, m), 0.78-0.73 (4H, m), 0.52-0.49 (2H, m), 0.15-0.12 (2H, m).

A reaction similar to that described in Example (1 (1e) was conducted using 4-(2-cyclopropylethoxy)-N-((Z)-2-[4-(cyclopropyloxy)phenyl]-1-{[(2-hydroxyethyl)amino]carbonyl}vinyl)benzamide (193 mg) to give 117 mg of the title compound (white powder).

MS (FAB) m/z: 453 $[M+H]^+$;

$^1$H-Nuclear Magnetic Resonance Spectra (500 MHz, DMSO-$d_6$) δ ppm:

8.35 (1H, d, J=8 Hz), 8.02 (1H, t, J=6 Hz), 7.79 (2H, d, J=9 Hz), 7.23 (2H, d, J=8 Hz), 6.97 (2H, d, J=9 Hz), 6.91 (2H, d, J=8 Hz), 4.67 (1H, t, J=5 Hz), 4.61-4.57 (1H, m), 4.07 (2H, t, J=6 Hz), 3.76-3.72 (1H, m), 3.39 (2H, q, J=6 Hz), 3.18-3.11 (2H, m), 3.00 (1H, dd, J=14 Hz, 4 Hz), 2.91 (1H, dd, J=14 Hz, 10 Hz), 1.63 (2H, q, J=6 Hz), 0.87-0.79 (1H, m), 0.74-0.70 (2H, m), 0.60-0.57 (2H, m), 0.45-0.42 (2H, m), 0.14-0.11 (2H, m).

Example 6

4-(2-Cyclopropylethoxy)-N-{1-(4-ethoxybenzyl)-2-[(2-hydroxyethyl)amino]-2-oxoethyl}benzamide (Exemplary Compound No. 45)

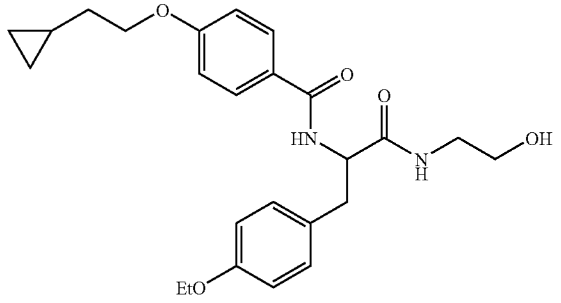 [SMILES: CCOc1ccc(CC(NC(=O)c2ccc(OCCC3CC3)cc2)C(=O)NCCO)cc1]

A reaction similar to that described in Example 1 (1c) was conducted using N-[4-(2-cyclopropylethoxy)benzoyl]glycine (210 mg) prepared in Example 1 (1b) and 4-ethoxybenzaldehyde (122 μL) to give the corresponding oxazolone (180 mg). A reaction similar to that described in Example 1 (1d) was conducted using all this oxazolone to give 154 mg of 4 (2 cyclopropylethoxy)-N-((Z)-2-(4-ethoxyphenyl)-1-{[(2-hydroxyethyl)amino]carbonyl}vinyl)benzamide (white amorphous solid).

MS (FAB) m/z: 439 $[M+H]^+$;

$^1$H-Nuclear Magnetic Resonance Spectra (400 MHz, DMSO-$d_6$) δ ppm:

9.64 (1H, s), 7.95 (2H, d, J=9 Hz), 7.87 (1H, brt, J=5 Hz), 7.46 (2H, d, J=9 Hz), 7.17 (1H, s), 7.02 (2H, d, J=9 Hz), 6.85 (2H, d, J=9 Hz), 4.61 (1H, t, J=6 Hz), 4.10 (2H, t, J=7 Hz), 3.99 (2H, q, J=7 Hz), 3.42 (2H, q, J=6 Hz), 3.21 (2H, q, J=6 Hz), 1.65 (2H, q, J=7 Hz), 1.29 (3H, t, J=7 Hz), 0.88-0.81 (1H, m), 0.47-0.43 (2H, m), 0.16-0.12 (2H, m).

A reaction similar to that described in Example (1 (1e) was conducted using 4-(2-cyclopropylethoxy)-N-((Z)-2-(4-ethoxyphenyl)-1-{[(2-hydroxyethyl)amino]carbonyl}vinyl)benzamide (197 mg) to give 58 mg of the title compound (white powder).

MS (FAB) m/z: 441 $[M+H]^+$;

$^1$H-Nuclear Magnetic Resonance Spectra (400 MHz, DMSO-$d_6$) δ ppm:

8.30 (1H, d, J=9 Hz), 7.99 (1H, t, J=6 Hz), 7.75 (2H, d, J=9 Hz), 7.19 (2H, d, J=9 Hz), 6.94 (2H, d, J=9 Hz), 6.76 (2H, d, J=9 Hz), 4.86 (1H, t, J=5 Hz), 4.60-4.55 (1H, m), 4.05 (2H, t, J=7 Hz), 3.92 (2H, q, J=7 Hz), 3.37 (2H, q, J=6 Hz), 3.16-3.11 (2H, m), 2.98 (1H, dd, J=14 Hz, 4 Hz), 2.88 (1H, dd, J=14 Hz, 11 Hz), 1.62 (2H, q, J=7 Hz), 1.27 (3H, t, J=7 Hz), 0.86-0.79 (1H, m), 0.46-0.41 (2H, m), 0.14-0.11 (2H, m).

Example 7

4-(2-Cyclopropylethoxy)-N-{2-[(2-hydroxyethyl)amino]-2-oxo-1-[4-(trifluoromethyl)benzyl]ethyl}benzamide (Exemplary Compound No. 40)

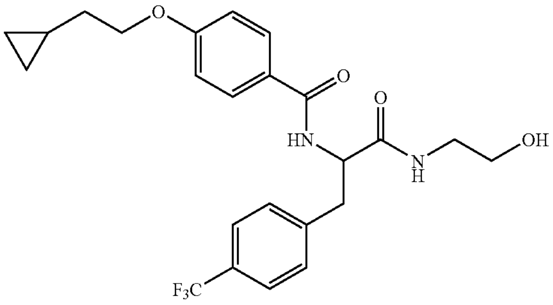

A reaction similar to that described in Example 1 (1c) was conducted using N-[4-(2-cyclopropylethoxy)benzoyl]glycine (212 mg) prepared in Example 1 (1b) and 4(trifluoromethyl)benzaldehyde (122 μL) to give the corresponding oxazolone (235 mg). A reaction similar to that described in Example 1 (1d) was conducted using all this oxazolone to give 163 mg of 4-(2 cyclopropylethoxy)-N-{(Z)-1-{[(2hydroxyethyl)amino]carbonyl}-2-[4-(trifluoromethyl)phenyl]vinyl} benzamide (white powder).

MS (FAB) m/z: 463 $[M+H]^+$;

$^1$H-Nuclear Magnetic Resonance Spectra (400 MHz, DMSO-$d_6$) δ ppm:

9.80 (1H, s), 8.13 (1H, brt, J=6 Hz), 7.92 (2H, d, J=9 Hz), 7.69 (2H, d, J=9 Hz), 7.64 (2H, d, J=9 Hz), 7.14 (1H, s), 7.02 (2H, d, J=9 Hz), 4.63 (1H, t, J=5 Hz), 4.10 (2H, t, J=7 Hz), 3.45 (2H, q, J=6 Hz), 3.23 (2H, q, J=6 Hz), 1.64 (2H, q, J=7 Hz), 0.87-0.81 (1H, m), 0.47-0.42 (2H, m), 0.16-0.12 (2H, m).

A reaction similar to that described in Example (1 (1e) was conducted using 4-(2-cyclopropylethoxy)-N-{(Z)-1-{[(2-hydroxyethyl)amino]carbonyl}-2-[4-(trifluoromethyl)phenyl]vinyl}benzamide (212 mg) to give 185 mg of the title compound (white powder).

MS (FAB) m/z: 465 $[M+H]^+$;

$^1$H-Nuclear Magnetic Resonance Spectra (500 MHz, DMSO-$d_6$) δ ppm:

8.44 (1H, d, J=8 Hz), 8.11 (1H, t, J=5 Hz), 7.77 (2H, d, J=9 Hz), 7.62 (2H, d, J=8 Hz), 7.55 (2H, d, J=8 Hz), 6.97 (2H, d, J=9 Hz), 4.74-4.69 (2H, m), 4.06 (2H, t, J=6 Hz), 3.41-3.38

(2H, m), 3.18-3.14 (3H, m), 3.07 (1H, dd, J=13 Hz, 11 Hz), 1.63 (2H, q, J=6 Hz), 0.86-0.79 (1H, m), 0.45-0.42 (2H, m), 0.14-0.11 (2H, m).

Example 8

2-({2-{[4-(2-Cyclopropylethoxy)benzoyl]amino}-3-[4-(trifluoromethoxy)phenyl]propanoyl}amino)ethyl acetate (Exemplary Compound No. 559)

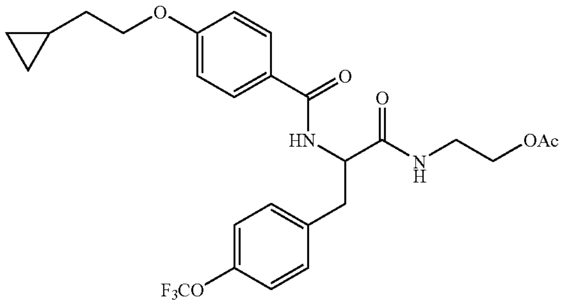 [SMILES: CC(=O)OCCNC(=O)C(Cc1ccc(OC(F)(F)F)cc1)NC(=O)c1ccc(OCCC2CC2)cc1]

Acetic anhydride (50 μL, 0.526 mmol) and N-ethyl-N,N-diisopropylamine (84 μL, 0.479 mmol) were added to a methylene chloride:THF (1:1, V/V, 4 mL) solution of 4-(2-cyclopropylethoxy)-N-{2-[(2-hydroxyethyl)amino]-2-oxo-1-[4-(trifluoromethoxy)benzyl]ethyl}benzamide (116 mg, 0.239 mmol) prepared in Example 4. The mixture was stirred at room temperature for 65 hours. The reaction solution was evaporated, and the residue was purified by thin layer chromatography for separation (ethyl acetate, developed once) to give 65 mg of the title compound (white powder, yield: 52%).

MS (FAB) m/z: 523 $[M+H]^+$;

$^1$H-Nuclear Magnetic Resonance Spectra (500 MHz, $CDCl_3$) δ ppm:

7.69 (2H, d, J=9 Hz), 7.29 (2H, d, J=9 Hz), 7.15 (2H, d, J=8 Hz), 6.93 (2H, d, J=9 Hz), 6.66 (1H, d, J=7 Hz), 6.23 (1H, t, J=5 Hz), 4.79 (1H, td, J=8 Hz, 6 Hz), 4.13-4.08 (1H, m), 4.08 (2H, t, J=7 Hz), 4.00 (1H, ddd, J=11 Hz, 6 Hz, 4 Hz), 3.51-3.42 (2H, m), 3.20 (1H, dd, J=14 Hz, 6 Hz), 3.16 (1H, dd, J=14 Hz, 8 Hz), 1.99 (3H, s), 1.69 (2H, q, J=7 Hz), 0.87-0.82 (1H, m), 0.52-0.48 (2H, m), 0.14-0.11 (2H, m).

Example 9

4-(2-Cyclopropylethoxy)-N-{2-{[(1-hydroxycyclopropyl)methyl]amino}-2-oxo-1-[4-(trifluoromethoxy)benzyl]ethyl}benzamide (Exemplary Compound No. 399)

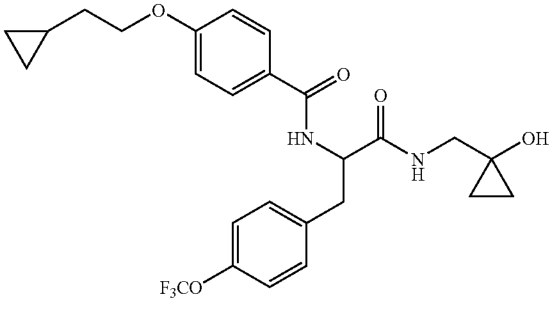 [SMILES: O=C(NC(Cc1ccc(OC(F)(F)F)cc1)C(=O)NCC1(O)CC1)c1ccc(OCCC2CC2)cc1]

A reaction similar to that described in Example (1 (1d) was conducted using (4Z)-2-[4-(2-cyclopropylethoxy)phenyl]-4-[4-(trifluoromethoxy)benzylidene]-1,3-oxazol-5(4H)-one (417 mg) obtained in the preparation process of Example 4 and 1-(aminomethyl)cyclopropanol (compound described in Russ. J. Org. Chem., (2001), 37, 1238-1243, 131 mg) to give 434 mg of 4-(2-cyclopropylethoxy)-N-{(Z)-1-({[(1-hydroxycyclopropyl)methyl]amino}carbonyl)-2-[4-(trifluoromethoxy)phenyl]vinyl}benzamide (white powder).

MS (FAB) m/z: 505 $[M+H]^+$;

$^1$H-Nuclear Magnetic Resonance Spectra (500 MHz, DMSO-$d_6$) δ ppm:

9.83 (1H, s), 8.04 (1H, t, J=6 Hz), 7.97 (2H, d, J=8 Hz), 7.67 (2H, d, J=9 Hz), 7.35 (2H, d, J=8 Hz), 7.16 (1H, s), 7.05 (2H, d, J=9 Hz), 5.34 (1H, s), 4.11 (2H, t, J=6 Hz), 3.37 (2H, d, J=6 Hz), 1.65 (2H, q, J=7 Hz), 0.89-0.81 (1H, m), 0.56-0.49 (4H, m), 0.47-0.43 (2H, m), 0.15-0.13 (2H, m).

A reaction similar to that described in Example 1 (1e) was conducted using 4-(2-cyclopropylethoxy)-N-{(Z)-1-({[(1-hydroxycyclopropyl)methyl]amino}carbonyl)-2-[4-(trifluoromethoxy)phenyl]vinyl}benzamide (202 mg) to give 98 mg of the title compound (white powder).

MS (FAB) m/z: 507 $[M+H]^+$;

$^1$H-Nuclear Magnetic Resonance Spectra (500 MHz, DMSO-$d_6$) δ ppm:

8.43 (1H, d, J=8 Hz), 8.12 (1H, t, J=6 Hz), 7.77 (2H, d, J=9 Hz), 7.46 (2H, d, J=9 Hz), 7.24 (2H, d, J=9 Hz), 6.96 (2H, d, J=9 Hz), 5.35 (1H, s), 4.74-4.69 (1H, m), 4.06 (2H, t, J=6 Hz), 3.26-3.25 (2H, m), 3.10 (1H, dd, J=14 Hz, 4 Hz), 3.01 (1H, dd, J=14 Hz, 11 Hz), 1.63 (2H, q, J=7 Hz), 0.86-0.80 (1H, m), 0.51-0.49 (2H, m), 0.45-0.42 (4H, m), 0.14-0.11 (2H, m).

Example 10

4-(2-Cyclopropylethoxy)-N-{(1S)-2-[(2-hydroxyethyl)amino]-2-oxo-1-[4-(trifluoromethoxy)benzyl]ethyl}benzamide (Exemplary Compound No. 39)

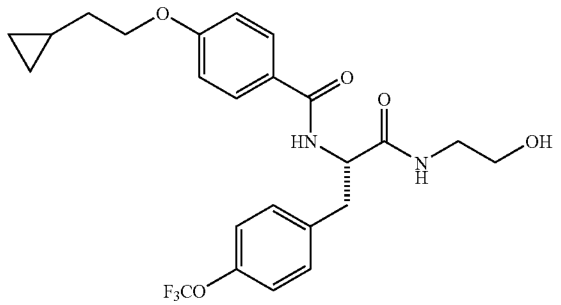 [SMILES: O=C(N[C@@H](Cc1ccc(OC(F)(F)F)cc1)C(=O)NCCO)c1ccc(OCCC2CC2)cc1]

The title compound was obtained using 4-(2-cyclopropylethoxy)-N-{2-[(2-hydroxyethyl)amino]-2-oxo-1-[4-(trifluoromethoxy)benzyl]ethyl}benzamide prepared in Example 4 by fractionation under the following conditions:

[Fractionation conditions] column: CHIRALPAK AD-H (manufactured by Daicel Chemical Industries, Ltd., internal diameter: 2 cm, length: 25 cm), mobile phase: methanol, flow rate: 5.0 mL/min, temperature: room temperature, detection: 254 nm (UV), retention time: S-isomer 30 min, R-isomer 21 min.

No R-isomer was recognized by HPLC analysis of this compound under the following conditions, and thereby it was confirmed that the optical purity was 99% or higher.

[Analysis conditions] column: CHIRALCEL OD-H (manufactured by Daicel Chemical Industries, Ltd., internal diameter: 0.46 cm, length: 25 cm), mobile phase: n-hexane/isopropanol=9/1, flow rate: 1.0 mL/min, temperature: 40° C., detection: 254 nm (UV), retention time: S-isomer 7.9 min, R-isomer 12.4 min.

Example 11

4-(2-Cyclopropylethoxy)-N-{2-[(3-hydroxypropyl)amino]-2-oxo-1-[4-(trifluoromethoxy)benzyl]ethyl}benzamide (Exemplary Compound No. 219)

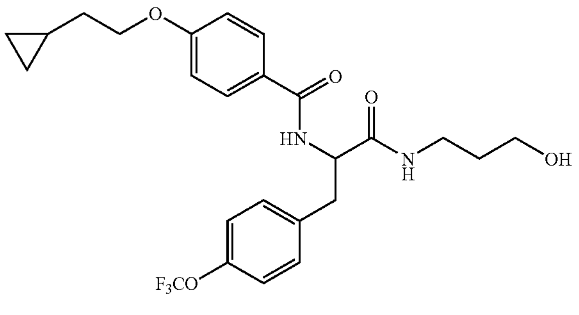 [SMILES: O=C(NC(Cc1ccc(OC(F)(F)F)cc1)C(=O)NCCCO)c1ccc(OCCC2CC2)cc1]

A reaction similar to that described in Example 1 (1d) was conducted using (4Z)-2-[4-(2-cyclopropylethoxy)phenyl]-4-[4-(trifluoromethoxy)benzylidene]-1,3-oxazol-5(4H)-one (417 mg) obtained in the preparation process of Example 4 and 3-amino-1-propanol (115 μL) to give 169 mg of 4-(2-cyclopropylethoxy)-N-{(Z)-1-{[(3-hydroxypropyl)amino]carbonyl}-2-[4-(trifluoromethoxy)phenyl]vinyl}benzamide (white powder).

MS (FAB) m/z: 493 $[M+H]^+$;

$^1$H-Nuclear Magnetic Resonance Spectra (500 MHz, DMSO-$d_6$) δ ppm:

9.78 (1H, s), 8.14 (1H, t, J=6 Hz), 7.96 (2H, d, J=9 Hz), 7.65 (2H, d, J=9 Hz), 7.34 (2H, d, J=9 Hz), 7.14 (1H, s), 7.04 (2H, d, J=9 Hz), 4.43 (1H, t, J=5 Hz), 4.11 (2H, t, J=6 Hz), 3.44 (2H, q, J=6 Hz), 3.22 (2H, q, J=6 Hz), 1.67-1.59 (4H, m), 0.89-0.81 (1H, m), 0.47-0.43 (2H, m), 0.15-0.12 (2H, m).

A reaction similar to that described in Example (1 (1e) was conducted using 4-(2-cyclopropylethoxy)-N-{(Z)-1-{[(3-hydroxypropyl)amino]carbonyl}-2-[4-(trifluoromethoxy)phenyl]vinyl}benzamide (197 mg) to give 169 mg of the title compound (white powder).

MS (FAB) m/z: 495 $[M+H]^+$;

$^1$H-Nuclear Magnetic Resonance Spectra (500 MHz, DMSO-$d_6$) δ ppm:

8.42 (1H, d, J=8 Hz), 8.05 (1H, t, J=5 Hz), 7.78 (2H, d, J=9 Hz), 7.43 (2H, d, J=8 Hz), 7.25 (2H, d, J=8 Hz), 6.96 (2H, d, J=9 Hz), 4.66-4.61 (1H, m), 4.42 (1H, t, J=5 Hz), 4.07 (2H, t, J=6 Hz), 3.38 (2H, q, J=6 Hz), 3.16-3.06 (2H, m), 3.08 (1H, dd, J=14 Hz, 4 Hz), 3.01 (1H, dd, J=14 Hz, 11 Hz), 1.63 (2H, q, J=7 Hz), 1.56-1.50 (2H, m), 0.86-0.79 (1H, m), 0.45-0.42 (2H, m), 0.14-0.11 (2H, m).

Example 12

N-{2-[(2-Hydroxyethyl)amino]-2-oxo-1-[4-(trifluoromethoxy)benzyl]ethyl}-4-[2-(4-methoxyphenyl)ethoxy]benzamide (Exemplary Compound No. 84)

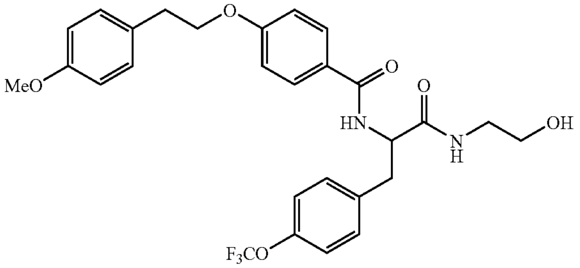 [SMILES: COc1ccc(CCOc2ccc(C(=O)NC(Cc3ccc(OC(F)(F)F)cc3)C(=O)NCCO)cc2)cc1]

(12a) N-{4-[2-(4-Methoxyphenyl)ethoxy]benzoyl}glycine

Reactions similar to those described in Example 1 (1a) and (1b) were conducted using methyl 4-hydroxybenzoate (4.56 g, 30.0 mmol) and 2-(4-methoxyphenyl)ethanol (5.03 g, 33.0 mmol) to give 7.80 g of the title compound (white powder, yield: 79%).

MS (FAB) m/z: 330 $[M+H]^+$;

$^1$H-Nuclear Magnetic Resonance Spectra (400 MHz, DMSO-$d_6$) δ ppm:

12.50 (1H, brs), 8.67 (1H, t, J=5 Hz), 7.83 (2H, d, J=8 Hz), 7.24 (2H, d, J=8 Hz), 7.00 (2H, d, J=8 Hz), 6.87 (2H, d, J=8 Hz), 4.20 (2H, t, J=6 Hz), 3.89 (2H, d, J=5 Hz), 3.72 (3H, s), 2.98 (2H, t, J=6 Hz).

(12b) N-{2-[(2-Hydroxyethyl)amino]-2-oxo-1-[4-(trifluoromethoxy)benzyl]ethyl}-4-[2-(4-methoxyphenyl)ethoxy]benzamide A reaction similar to that described in Example (1 (1c) was conducted using N-[4-(methoxyphenylethoxybenzoyl)]glycine (329 mg) prepared in Example 12 (12a) and 4-(trifluoromethoxy)benzaldehyde (150 μL) to give the corresponding oxazolone (366 mg). A reaction similar to that described in Example 1 (1d) was conducted using 160 mg of this oxazolone to give 126 mg of N-{(Z)-1-{[(2-hydroxyethyl)amino]carbonyl}-2-[4-(trifluoromethoxy)phenyl]vinyl}-4-[2-(4-methoxyphenyl)ethoxy]benzamide (white powder).

MS (FAB) m/z: 545 $[M+H]^+$;

$^1$H-Nuclear Magnetic Resonance Spectra (400 MHz, DMSO-$d_6$) δ ppm:

9.80 (1H, brs), 8.08 (1H, t, J=5 Hz), 7.95 (2H, d, J=8 Hz), 7.64 (2H, d, J=7 Hz), 7.33 (2H, d, J=8 Hz), 7.25 (2H, d, J=7 Hz), 7.17 (1H, s), 7.04 (2H, d, J=8 Hz), 6.88 (2H, d, J=8 Hz), 4.64 (1H, t, J=5 Hz), 4.23 (2H, t, J=6 Hz), 3.73 (3H, s), 3.46 (2H, q, J=6 Hz), 3.24 (2H, q, J=6 Hz), 3.00 (2H, t, J=6 Hz).

A reaction similar to that described in Example 1 (1e) was conducted using N-{(Z)-1-{[(2-hydroxyethyl)amino]carbonyl}-2-[4-(trifluoromethoxy)phenyl]vinyl}-4-[2-(4-methoxyphenyl)ethoxy]benzamide (162 mg) to give 98 mg of the title compound (white powder).

MS (FAB) m/z: 547 $[M+H]^+$;

$^1$H-Nuclear Magnetic Resonance Spectra (500 MHz, $CDCl_3$) δ ppm:

7.67 (2H, d, J=8 Hz), 7.29 (2H, d, J=9 Hz), 7.20 (2H, d, J=9 Hz), 7.16 (2H, d, J=8 Hz), 6.90 (2H, d, J=9 Hz), 6.87 (2H, d, J=8 Hz), 6.72 (1H, d, J=7 Hz), 6.33 (1H, t, J=6 Hz), 4.77 (1H, td, J=8 Hz, 6 Hz), 4.17 (2H, t, J=7 Hz), 3.80 (3H, s), 3.66-3.55 (2H, m), 3.39-3.31 (2H, m), 3.21 (1H, dd, J=14 Hz, 6 Hz), 3.14 (1H, dd, J=14 Hz, 8 Hz), 3.05 (2H, t, J=7 Hz), 2.29 (1H, t, J=5).

Example 13

N-{1-[4-(2,2-Difluoroethoxy)benzyl]-2-[(2-hydroxyethyl)amino]-2-oxoethyl}-4-[2-(4-methoxyphenyl)ethoxy]benzamide (Exemplary Compound No. 82)

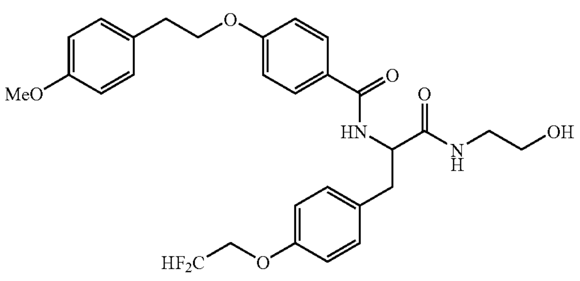

(13a) 4-(2,2-Difluoroethoxy)benzaldehyde

The preparation was conducted according to the description in the document (J. Med. Chem., (1994), 37, 3977-3985). Sodium hydride (3.36 g, 55%, 77.0 mmol) was added to a DMF (100 mL) solution of 2,2-difluoroethanol (5.75 g, 70.0 mmol) under ice-cooling over 5 minutes under a nitrogen gas flow. The resulting mixture was stirred at the same temperature for 10 minutes, and then to the reaction solution was dropwise added a DMF (40 mL) solution of 4-fluorobenzaldehyde (9.56 g, 77.0 mmol) over 5 minutes. The mixture was stirred at room temperature for 4 hours, and the reaction solution was poured into ice water (500 mL). The resulting mixture was extracted with ether:n-hexane (300 mL, 1:1, V/V) three times. The extracted organic layer was washed with water (300 mL) three times and with saturated brine and dried over anhydrous magnesium sulfate. The solvent was evaporated to give a crude product. A solution mixture of ether:n-hexane (20 mL, 1:10, V/V) was added to this crude product, and the supernatant was removed. This procedure was repeated four times in total to wash the crystalline product to give 10.1 g of the title compound (colorless crystal, yield: 77%).

MS (FAB) m/z: 187 $[M+H]^+$;

$^1$H-Nuclear Magnetic Resonance Spectra (500 MHz, $CDCl_3$) δ ppm:

9.92 (1H, s), 7.87 (2H, d, J=8 Hz), 7.04 (2H, d, J=8 Hz), 6.13 (1H, tt, J=55 Hz, 4 Hz), 4.27 (2H, td, J=13 Hz, 4 Hz).

(13b) N-{1-[4-(2,2-Difluoroethoxy)benzyl]-2-[(2-hydroxyethyl)amino]-2-oxoethyl}-4-[2-(4-methoxyphenyl)ethoxy]benzamide A reaction similar to that described in Example 1 (1c) was conducted using N-[4-(methoxyphenylethoxybenzoyl)]glycine (329 mg) prepared in Example 12 (12a) and 4-(2,2-difluoroethoxy)benzaldehyde (196 mg) prepared in Example 13 (13a) to give the corresponding oxazolone (306 mg). A reaction similar to that described in Example 1 (1d) was conducted using 138 mg of this oxazolone to give 145 mg of N-((Z)-2-[4-(2,2-difluoroethoxy)phenyl]-1-{[(2-hydroxyethyl)amino]carbonyl}vinyl)-4-[2-(4-methoxyphenyl)ethoxy]benzamide (white powder).

MS (FAB) m/z: 541 $[M+H]^+$;

$^1$H-Nuclear Magnetic Resonance Spectra (400 MHz, DMSO-$d_6$) δ ppm:

9.69 (1H, brs), 7.96 (2H, d, J=8 Hz), 7.93 (1H, t, J=5 Hz), 7.51 (2H, d, J=8 Hz), 7.25 (2H, d, J=7 Hz), 7.20 (1H, s), 7.04 (2H, d, J=8 Hz), 6.97 (2H, d, J=8 Hz), 6.88 (2H, d, J=7 Hz), 6.36 (1H, tt, J=55 Hz, 3 Hz), 4.63 (1H, t, J=7 Hz), 4.30 (2H, td, J=14 Hz, 3 Hz), 4.23 (2H, t, J=7 Hz), 3.73 (3H, s), 3.43 (2H, q, J=6 Hz), 3.22 (2H, q, J=6 Hz), 3.00 (2H, t, J=7 Hz).

A reaction similar to that described in Example (1 (1e) was conducted using N-((Z)-2-[4-(2,2-difluoroethoxy)phenyl]-1-{[(2-hydroxyethyl)amino]carbonyl}vinyl)-4-[2-(4-methoxyphenyl)ethoxy]benzamide (200 mg) to give 146 mg of the title compound (white powder).

MS (FAB) m/z: 543 $[M+H]^+$;

$^1$H-Nuclear Magnetic Resonance Spectra (500 MHz, DMSO-$d_6$) δ ppm:

8.35 (1H, d, J=8 Hz), 8.03 (1H, t, J=5 Hz), 7.78 (2H, d, J=8 Hz), 7.26 (2H, d, J=8 Hz), 7.24 (2H, d, J=8 Hz), 6.96 (2H, d, J=8 Hz), 6.87 (2×2H, d, J=8 Hz), 6.33 (1H, tt, J=54 Hz, 3 Hz), 4.67 (1H, t, J=5 Hz), 4.63-4.58 (1H, m), 4.26-4.17 (4H, m), 3.40 (2H, q, J=6 Hz), 3.33 (3H, s), 3.17-3.13 (2H, m), 3.03-2.96 (3H, m), 2.91 (1H, dd, J=14 Hz, 11 Hz).

Example 14

N-{1-[4-(Cyclopropyloxy)benzyl]-2-[(2-hydroxy-ethyl)amino]-2-oxoethyl}-4-[2-(4-methoxyphenyl)ethoxy]benzamide (Exemplary Compound No. 81)

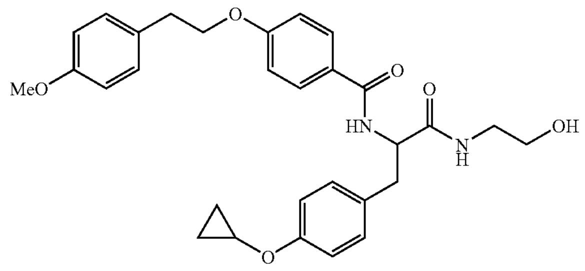 [SMILES: COc1ccc(CCOc2ccc(C(=O)NC(Cc3ccc(OC4CC4)cc3)C(=O)NCCO)cc2)cc1]

A reaction similar to that described in Example 1 (1c) was conducted using N-{4-[2-(4-methoxyphenyl)ethoxy]benzoyl}glycine (329 mg) prepared in Example 12 (12a) and 4-(cyclopropyloxy)benzaldehyde (170 mg) prepared in Example 5 (5c) to give the corresponding oxazolone (304 mg). A reaction similar to that described in Example 1 (1d) was conducted using 140 mg of this oxazolone to give 144 mg of N-((Z)-2-[4-(cyclopropyloxy)phenyl]-1-{[(2-hydroxy-ethyl)amino]carbonyl}vinyl)-4-[2-(4-methoxyphenyl)ethoxy]benzamide (white amorphous solid).

MS (FAB) m/z: 517 $[M+H]^+$;

$^1$H-Nuclear Magnetic Resonance Spectra (400 MHz, $CDCl_3$) δ ppm:

7.81 (2H, d, J=9 Hz), 7.68 (1H, brs), 7.35 (2H, d, J=9 Hz), 7.21 (2H, d, J=8 Hz), 7.10 (1H, s), 7.00 (2H, d, J=9 Hz), 6.94 (2H, d, J=9 Hz), 6.87 (2H, d, J=8 Hz), 6.64 (1H, t, J=6 Hz), 4.19 (2H, t, J=7 Hz), 3.80 (3H, s), 3.78 (2H, t, J=5 Hz), 3.71 (1H, sept, J=3 Hz), 3.51 (2H, q, J=5 Hz), 3.06 (2H, t, J=7 Hz), 0.78-0.75 (4H, m).

A reaction similar to that described in Example 1 (1e) was conducted using N-((Z)-2-[4-(cyclopropyloxy)phenyl]-1-{[(2-hydroxyethyl)amino]carbonyl}vinyl)-4-[2-(4-methoxyphenyl)ethoxy]benzamide (207 mg) to give 134 mg of the title compound (white amorphous solid).

MS (ESI) m/z: 519 $[M+H]^+$;

$^1$H-Nuclear Magnetic Resonance Spectra (500 MHz, DMSO-$d_6$) δ ppm:

8.34 (1H, d, J=8 Hz), 8.02 (1H, t, J=6 Hz), 7.78 (2H, d, J=9 Hz), 7.23 (2×2H, d, J=8 Hz), 6.97 (2H, d, J=9 Hz), 6.91 (2H, d, J=8 Hz), 6.87 (2H, d, J=9 Hz), 4.67 (1H, t, J=5 Hz), 4.62-4.57 (1H, m), 4.19 (2H, t, J=7 Hz), 3.76-3.72 (1H, m), 3.39 (2H, q, J=6 Hz), 3.33 (3H, s), 3.19-3.11 (2H, m), 3.02-2.96 (3H, m), 2.91 (1H, dd, J=14 Hz, 10 Hz), 0.74-0.70 (2H, m), 0.60-0.57 (2H, m).

Example 15

4-[2-(4-Chlorophenyl)ethoxy]-N-{2-[(2-hydroxy-ethyl)amino]-2-oxo-1-[4-(trifluoromethoxy)benzyl]ethyl}benzamide (Exemplary Compound No. 89)

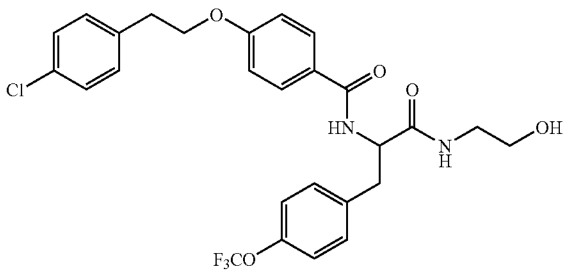 [SMILES: O=C(NC(Cc1ccc(OC(F)(F)F)cc1)C(=O)NCCO)c1ccc(OCCc2ccc(Cl)cc2)cc1]

(15a) 4-[2-(4-Chlorophenyl)ethoxy]benzoic acid

Potassium carbonate (54.9 g, 397 mmol) was added to a N,N-dimethylacetamide (330 mL) solution of methyl 4-hydroxybenzoate (25.2 g, 165 mmol) and 2-(4-chlorophenyl)ethyl p-toluenesulfonate (compound described in J. Am. Chem. Soc., (1978), 100, 228-246, 61.7 g, 199 mmol) at room temperature. The mixture was stirred at 120° C. for 1.5 hours. The reaction solution was cooled to room temperature, and water (1 L) was added thereto. The resulting mixture was extracted with ethyl acetate three times. The organic layers were combined, washed with water (three times) and saturated brine, and dried over anhydrous magnesium sulfate. The solvent was evaporated, and the residue was purified by silica gel column chromatography (n-hexane:ethyl acetate, 10:1, V/V) to give 43.2 g of methyl 4-[2-(4-chlorophenyl)ethoxy]benzoate (white solid). All this solid was dissolved in ethanol (430 mL), and a 2 M lithium hydroxide aqueous solution (148 mL, 297 mmol) was added thereto. The mixture was stirred at 60° C. for 2 hours, and the solvents (mainly ethanol) were evaporated. The residue was suspended in water (300 mL), and 2 N hydrochloric acid (160 mL) was added thereto under ice-cooling with stirring. The precipitated white solid was collected by filtration, washed with water and n-hexane, and dried under reduced pressure to give 41.0 g of the title compound (white solid, yield: 90%).

$^1$H-Nuclear Magnetic Resonance Spectra (400 MHz, DMSO-$d_6$) δ ppm:

12.67 (1H, brs), 7.87 (2H, d, J=9 Hz), 7.38 (2H, d, J=9 Hz), 7.36 (2H, d, J=9 Hz), 7.01 (2H, d, J=9 Hz), 4.26 (2H, t, J=7 Hz), 3.05 (2H, t, J=7 Hz).

(15b) N-{4-[2-(4-Chlorophenyl)ethoxy]benzoyl}glycine

A reaction similar to that described in Example (1b) was conducted using 4-[2-(4-chlorophenyl)ethoxy]benzoic acid (40.9 g, 148 mmol) prepared in Example 15 (15a) to give 48.3 g of the title compound (light yellow powder, yield: 98%).

$^1$H-Nuclear Magnetic Resonance Spectra (500 MHz, DMSO-$d_6$) δ ppm:

12.54 (1H, brs), 8.66 (1H, t, J=6 Hz), 7.82 (2H, d, J=9 Hz), 7.38 (2H, d, J=9 Hz), 7.36 (2H, d, J=9 Hz), 7.01 (2H, d, J=9 Hz), 4.25 (2H, t, J=7 Hz), 3.88 (2H, d, J=6 Hz), 3.05 (2H, t, J=7 Hz).

(15c) 4-[2-(4-Chlorophenyl)ethoxy]-N-{2-[(2-hydroxy-ethyl)amino]-2-oxo-1-[4-(trifluoromethoxy)benzyl]ethyl}benzamide A reaction similar to that described in Example 1 (1c) was conducted using N-{4-[2-(4-chlorophenyl)ethoxy]benzoyl}glycine (234 mg) prepared in Example 15 (15b) and 4-(trifluoromethoxy)benzaldehyde (110 μL) to give the corresponding oxazolone (208 mg). A reaction similar to that described in Example 1 (1d) was conducted using all this oxazolone to give 160 mg of 4-[2-(4-chlorophenyl)ethoxy]-N-{(Z)-1-{[(2-hydroxyethyl)amino]carbonyl}-2-[4-(trifluoromethoxy)phenyl]vinyl}benzamide (white powder).

MS (FAB) m/z: 549 $[M+H]^+$;

$^1$H-Nuclear Magnetic Resonance Spectra (400 MHz, DMSO-$d_6$) δ ppm:

9.76 (1H, s), 8.04 (1H, brt, J=5 Hz), 7.92 (2H, d, J=9 Hz), 7.61 (2H, d, J=9 Hz), 7.35 (4H, s), 7.31 (2H, d, J=9 Hz), 7.14 (1H, s), 7.02 (2H, d, J=9 Hz), 4.62 (1H, t, J=5 Hz), 4.26 (2H, t, J=7 Hz), 3.43 (2H, q, J=6 Hz), 3.22 (2H, q, J=6 Hz), 3.06 (2H, t, J=7 Hz).

A reaction similar to that described in Example 2 was conducted using 4-[2-(4-chlorophenyl)ethoxy]-N-{(Z)-1-{[(2-hydroxyethyl)amino]carbonyl}-2-[4-(trifluoromethoxy)phenyl]vinyl}benzamide (110 mg) to give 55 mg of the title compound (white powder).

MS (ESI) m/z: 551 $[M+H]^+$;

$^1$H-Nuclear Magnetic Resonance Spectra (500 MHz, DMSO-$d_6$) δ ppm:

8.41 (1H, d, J=9 Hz), 8.07 (1H, t, J=6 Hz), 7.76 (2H, d, J=9 Hz), 7.43 (2H, d, J=8 Hz), 7.37 (2H, d, J=9 Hz), 7.35 (2H, d, J=9 Hz), 7.23 (2H, d, J=8 Hz), 6.96 (2H, d, J=9 Hz), 4.69-4.64 (2H, m), 4.23 (2H, t, J=6 Hz), 3.40-3.37 (2H, m), 3.17-3.12 (2H, m), 3.08 (1H, dd, J=14 Hz, 4 Hz), 3.04 (2H, t, J=7 Hz), 3.00 (1H, dd, J=14 Hz, 11 Hz).

Example 16

N-[2-[(2-Hydroxyethyl)amino]-1-(4-isopropoxybenzyl)-2-oxoethyl]-4-isobutoxybenzamide (Exemplary Compound No. 7)

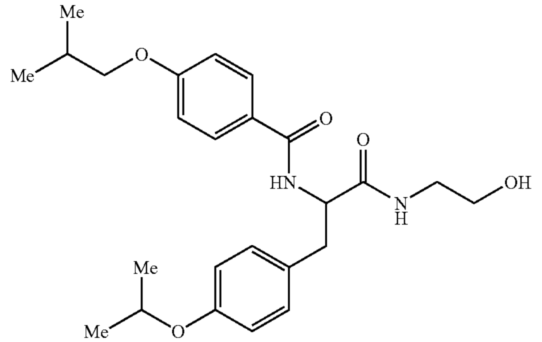 [SMILES: CC(C)COc1ccc(C(=O)NC(Cc2ccc(OC(C)C)cc2)C(=O)NCCO)cc1]

A reaction similar to that described in Example 1 (1b) was conducted using 4-isobutoxybenzoic acid (compound described in J. Am. Chem. Soc., (1939), 61, 3050, 55.0 g) to give 50.2 g of N-(4-isobutoxybenzoyl)glycine (colorless crystal). A reaction similar to that described in Example (1 (1c) was conducted using this N-(4-isobutoxybenzoyl)glycine (5.00 g) and 4-isopropoxybenzaldehyde (3.59 g) to give the corresponding oxazolone (3.86 g). A reaction similar to that described in Example 1 (1d) was conducted using 2.70 g of this oxazolone to give 1.60 g of N-[(Z)-1-{[(2-hydroxyethyl)amino]carbonyl}-2-(4-isopropoxyphenyl)vinyl]-4-isobutoxybenzamide (white powder). A reaction similar to that described in Example 1 (1e) was conducted using 46 mg of this white powder to give 35 mg of the title compound (white powder).

MS (FAB) m/z: 443 $[M+H]^+$;

$^1$H-Nuclear Magnetic Resonance Spectra (500 MHz, $CDCl_3$) δ ppm:

7.68 (2H, d, J=9 Hz), 7.17 (2H, d, J=9 Hz), 6.90 (2H, d, J=9 Hz), 6.84 (2H, d, J=8 Hz), 6.70 (1H, d, J=7 Hz), 6.17 (1H, brs), 4.71 (1H, td, J=8 Hz, 6 Hz), 4.51 (1H, sept, J=6 Hz), 3.76 (2H, d, J=6 Hz), 3.63-3.41 (3H, m), 3.40-3.34 (1H, m), 3.33-3.27 (1H, m), 3.20 (1H, dd, J=14 Hz, 6 Hz), 3.02 (1H, dd, J=14 Hz, 8 Hz), 2.13-2.06 (1H, m), 1.32 (6H, d, J=6 Hz), 1.03 (6H, d, J=7 Hz).

Example 17

4-(Cyclobutylmethoxy)-N-{2-[(2-hydroxyethyl)amino]-2-oxo-1-[4-(trifluoromethoxy)benzyl]ethyl}benzamide (Exemplary Compound No. 14)

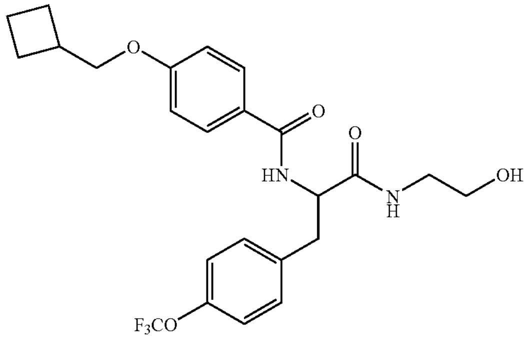 [SMILES: O=C(NC(Cc1ccc(OC(F)(F)F)cc1)C(=O)NCCO)c1ccc(OCC2CCC2)cc1]

(17a) N-[4-(Cyclobutylmethoxy)benzoyl]glycine

Reactions similar to those described in Example 1 (1a) and (1b) were conducted using methyl 4-hydroxybenzoate (3.81 g, 25.0 mmol) and cyclobutylmethanol (2.36 mL, 25.0 mmol) to give 6.41 g of the title compound (white powder, yield: 97%).

MS (EI) m/z: 263 $[M]^+$;

$^1$H-Nuclear Magnetic Resonance Spectra (400 MHz, DMSO-$d_6$) δ ppm:

12.50 (1H, brs), 8.65 (1H, t, J=6 Hz), 7.81 (2H, d, J=9 Hz), 6.98 (2H, d, J=9 Hz), 3.99 (2H, t, J=6 Hz), 3.89 (2H, d, J=6 Hz), 2.72 (1H, sept, J=7 Hz), 2.11-2.03 (2H, m), 1.94-1.78 (4H, m).

(17b) 4-(Cyclobutylmethoxy)-N-{2-[(2-hydroxyethyl)amino]-2-oxo-1-[4-(trifluoromethoxy)benzyl]ethyl}benzamide A reaction similar to that described in Example 1 (1c) was conducted using N-[4-(cyclobutylmethoxy)benzoyl]glycine (263 mg) prepared in Example 17 (17a) and 4-(trifluoromethoxy)benzaldehyde (150 μL) to give the corresponding oxazolone (238 mg). A reaction similar to that described in Example 1 (1d) was conducted using all this oxazolone to give 219 mg of 4-(cyclobutylmethoxy)-N-{(Z)-1-{[(2-hydroxyethyl)amino]carbonyl}-2-[4-(trifluoromethoxy)phenyl]vinyl}benzamide (white powder).

MS (FAB) m/z: 479 $[M+H]^+$;

$^1$H-Nuclear Magnetic Resonance Spectra (400 MHz, DMSO-$d_6$) δ ppm:

9.75 (1H, brs), 8.04 (1H, t, J=6 Hz), 7.92 (2H, d, J=9 Hz), 7.62 (2H, d, J=9H), 7.32 (2H, d, J=8 Hz), 7.14 (1H, brs), 7.02 (2H, d, J=9 Hz), 4.62 (1H, brt, J=6 Hz), 4.02 (2H, d, J=7 Hz), 3.43 (2H, q, J=6 Hz), 3.22 (2H, q, J=6 Hz), 2.73 (1H, sept, J=7 Hz), 2.12-2.04 (2H, m), 1.96-1.79 (4H, m).

A reaction similar to that described in Example 1 (1e) was conducted using all this 4-(cyclobutylmethoxy)-N-{(Z)-1-{[(2-hydroxyethyl)amino]carbonyl}-2-[4-(trifluoromethoxy)phenyl]vinyl}benzamide to give 187 mg of the title compound (white powder).

MS (FAB) m/z: 481 $[M+H]^+$;

$^1$H-Nuclear Magnetic Resonance Spectra (500 MHz, DMSO-$d_6$) δ ppm:

8.41 (1H, d, J=8 Hz), 8.08 (1H, t, J=5 Hz), 7.77 (2H, d, J=9 Hz), 7.44 (2H, d, J=8 Hz), 7.24 (2H, d, J=8 Hz), 6.96 (2H, d, J=9 Hz), 4.69-4.65 (2H, m), 3.99 (2H, d, J=7 Hz), 3.39 (2H, q, J=6 Hz), 3.19-3.13 (2H, m), 3.10 (1H, dd, J=13 Hz, 4 Hz), 3.00 (1H, dd, J=13 Hz, 11 Hz), 2.71 (1H, sept, J=7 Hz), 2.10-2.04 (2H, m), 1.94-1.87 (2H, m), 1.86-1.78 (2H, m).

Example 18

4-(Cyclopropylmethoxy)-N-{1-[4-(difluoromethoxy)benzyl]-2-[(2-hydroxyethyl)amino]-2-oxoethyl}benzamide (Exemplary Compound No. 18)

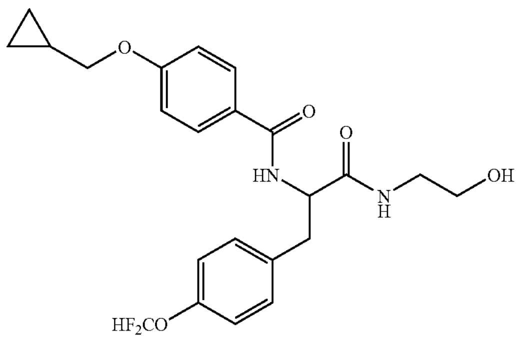

(18a) 4-(Cyclopropylmethoxy)benzoic acid

Potassium carbonate (114 g, 827 mmol) and potassium iodide (0.5 g) were added to a 2-butanone (535 mL) solution of methyl 4-hydroxybenzoate (52.4 g, 345 mmol) and cyclopropylmethyl bromide (72.7 g, 517 mmol) at room temperature. The mixture was stirred at 75° C. for 4 hours. The reaction solution was cooled to room temperature, and insoluble substances were separated by filtration. The insoluble substances were further washed with 2-butanone, and the filtrate was concentrated. The residue was dissolved in ethyl acetate (1 L), washed with water and saturated brine, and dried over anhydrous magnesium sulfate. The solvent was evaporated, and the obtained residue was dried under reduced pressure to give 71.6 g of methyl 4-(cyclopropylmethoxy)benzoate (colorless crystal). All this crystal was dissolved in methanol (715 mL), and a 2 N sodium hydroxide aqueous solution (345 mL, 690 mmol) was added thereto. The resulting mixture was stirred at 60° C. for 3 hours, and the solvents (mainly methanol) were evaporated. The residue was suspended in water (500 mL), and 2 N hydrochloric acid (360 mL) was added thereto under ice-cooling with stirring. The precipitated white solid was collected by filtration, washed with water and n-hexane, and dried under reduced pressure to give 64.6 g of the title compound (white powder, yield: 97%).

$^1$H-Nuclear Magnetic Resonance Spectra (400 MHz, DMSO-$d_6$) δ ppm:

12.60 (1H, brs), 7.87 (2H, d, J=9 Hz), 7.00 (2H, d, J=9 Hz), 3.89 (2H, d, J=7 Hz), 1.27-1.19 (1H, m), 0.60-0.56 (2H, m), 0.36-0.32 (2H, m).

(18b) N-[4-(Cyclopropylmethoxy)benzoyl]glycine

A reaction similar to that described in Example 1 (1b) was conducted using 4-(cyclopropylmethoxy)benzoic acid (23.0 g, 120 mmol) prepared in Example 18 (18a) to give 22.8 g of the title compound (colorless crystal, yield: 76%).

MS (FAB) m/z: 250 $[M+H]^+$;

$^1$H-Nuclear Magnetic Resonance Spectra (400 MHz, DMSO-$d_6$) δ ppm:

12.55 (1H, brs), 8.66 (1H, t, J=6 Hz), 7.82 (2H, d, J=9 Hz), 6.99 (2H, d, J=9 Hz), 3.99-3.87 (4H, m), 1.29-1.18 (1H, m), 0.60-0.56 (2H, m), 0.35-0.32 (2H, m).

(18c) 4-(Cyclopropylmethoxy)-N-{1-[4-(difluoromethoxy)benzyl]-2-[(2-hydroxyethyl)amino]-2-oxoethyl}benzamide A reaction similar to that described in Example 1 (1c) was conducted using N-[4-(cyclopropylmethoxy)benzoyl]glycine (300 mg) prepared in Example 18 (18b) and 4-(difluoromethoxy)benzaldehyde (167 μL) to give the corresponding oxazolone (305 mg). A reaction similar to that described in Example (1 (1d) was conducted using 300 mg of this oxazolone to give 341 mg of 4-(cyclopropylmethoxy)-N-((Z)-2-[4-(difluoromethoxy)phenyl]-1-{[(2-hydroxyethyl)amino]carbonyl}vinyl)benzamide (white amorphous solid).

MS (FAB) m/z: 447 $[M+H]^+$;

$^1$H-Nuclear Magnetic Resonance Spectra (400 MHz, DMSO-$d_6$) δ ppm:

9.71 (1H, s), 8.00 (1H, t, J=6 Hz), 7.92 (2H, d, J=9 Hz), 7.56 (2H, d, J=9 Hz), 7.23 (1H, t, J=74 Hz), 7.16 (1H, s), 7.11 (2H, d, J=9 Hz), 7.01 (2H, d, J=9 Hz), 4.62 (1H, t, J=5 Hz), 3.89 (2H, d, J=7 Hz), 3.43 (2H, q, J=6 Hz), 3.22 (2H, q, J=6 Hz), 1.29-1.21 (1H, m), 0.61-0.57 (2H, m), 0.36-0.33 (2H, m).

A reaction similar to that described in Example (1 (1e) was conducted using 4-(cyclopropylmethoxy)-N-((Z)-2-[4-(difluoromethoxy)phenyl]-1-{[(2-hydroxyethyl)amino]carbonyl}vinyl)benzamide (279 mg) to give 227 mg of the title compound (white powder).

MS (FAB) m/z: 449 $[M+H]^+$;

$^1$H-Nuclear Magnetic Resonance Spectra (400 MHz, DMSO-$d_6$) δ ppm:

8.42 (1H, d, J=8 Hz), 8.11 (1H, t, J=5 Hz), 7.81 (2H, d, J=9 Hz), 7.40 (2H, d, J=9 Hz), 7.19 (1H, t, J=74 Hz), 7.09 (2H, d, J=8 Hz), 6.99 (2H, d, J=9 Hz), 4.73 (1H, t, J=5 Hz), 4.72-4.65 (1H, m), 3.90 (2H, d, J=7 Hz), 3.44 (2H, q, J=6 Hz), 3.21 (2H, q, J=5 Hz), 3.11 (1H, dd, J=10 Hz, 4 Hz), 3.02 (1H, dd, J=13 Hz, 11 Hz), 1.32-1.21 (1H, m), 0.65-0.60 (2H, m), 0.40-0.36 (2H, m).

Example 19

4-(Cyclopropylmethoxy)-N-{2-[(2-hydroxyethyl)amino]-2-oxo-1-[4-(trifluoromethoxy)benzyl]ethyl}benzamide (Exemplary Compound No. 19)

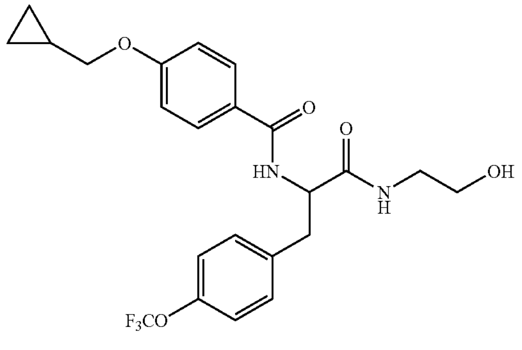 [SMILES: O=C(NC(Cc1ccc(OC(F)(F)F)cc1)C(=O)NCCO)c1ccc(OCC2CC2)cc1]

A reaction similar to that described in Example 1 (1c) was conducted using N-[4-(cyclopropylmethoxy)benzoyl]glycine (499 mg) prepared in Example 18 (18b) and 4-(trifluoromethoxy)benzaldehyde (300 μL) to give the corresponding oxazolone (668 mg). A reaction similar to that described in Example (1 (1d) was conducted using all this oxazolone to give 698 mg of 4-(cyclopropylmethoxy)-N-{(Z)-1-{[(2-hydroxyethyl)amino]carbonyl}-2-[4-(trifluoromethoxy)phenyl]vinyl}benzamide (white solid).

MS (FAB) m/z: 465 $[M+H]^+$;

$^1$H-Nuclear Magnetic Resonance Spectra (400 MHz, DMSO-$d_6$) δ ppm:

9.80 (1H, brs), 8.08 (1H, t, J=5 Hz), 7.94 (2H, d, J=8 Hz), 7.64 (2H, d, J=8 Hz), 7.34 (2H, d, J=8 Hz), 7.16 (1H, s), 7.02 (2H, d, J=8 Hz), 4.64 (1H, brs), 3.90 (2H, d, J=7 Hz), 3.44 (2H, brs), 3.23 (2H, q, J=6 Hz), 1.29-1.19 (1H, m), 0.61-0.57 (2H, m), 0.36-0.32 (2H, m).

A reaction similar to that described in Example 1 (1e) was conducted using 4-(cyclopropylmethoxy)-N-{(Z)-1-{[(2-hydroxyethyl)amino]carbonyl}-2-[4-(trifluoromethoxy)phenyl]vinyl}benzamide (232 mg) to give 153 mg of the title compound (white powder).

MS (ESI) m/z: 467 $[M+H]^+$;

$^1$H-Nuclear Magnetic Resonance Spectra (400 MHz, DMSO-$d_6$) δ ppm:

8.38 (1H, d, J=8 Hz), 8.05 (1H, t, J=6 Hz), 7.74 (2H, d, J=9 Hz), 7.41 (2H, d, J=9 Hz), 7.21 (2H, d, J=9 Hz), 6.93 (2H, d, J=9 Hz), 4.68-4.62 (2H, m), 3.85 (2H, d, J=7 Hz), 3.37 (2H, q, J=6 Hz), 3.16-3.11 (2H, m), 3.06 (1H, dd, J=14 Hz, 4 Hz), 2.98 (1H, dd, J=14 Hz, 11 Hz), 1.26-1.17 (1H, m), 0.59-0.55 (2H, m), 0.34-0.30 (2H, m).

Example 20

4-(Cyclopropylmethoxy)-N-{1-[4-(cyclopropyloxy)benzyl]-2-[(2-hydroxyethyl)amino]-2-oxoethyl}benzamide (Exemplary Compound No. 16)

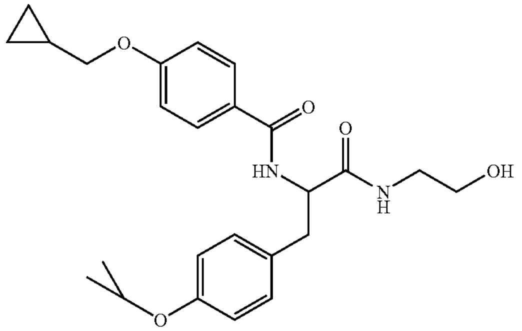 [SMILES: CC(C)Oc1ccc(CC(NC(=O)c2ccc(OCC3CC3)cc2)C(=O)NCCO)cc1]

A reaction similar to that described in Example 1 (1c) was conducted using N-[4-(cyclopropylmethoxy)benzoyl]glycine (249 mg) prepared in Example 18 (18b) and 4-(cyclopropyloxy)benzaldehyde (170 mg) prepared in Example 5 (5c) to give the corresponding oxazolone (291 mg). A reaction similar to that described in Example 1 (1d) was conducted using all this oxazolone to give 313 mg of 4-(cyclopropylmethoxy)-N-((Z)-2-[4-(cyclopropyloxy)phenyl]-1-{[(2-hydroxyethyl)amino]carbonyl}vinyl)benzamide (light yellow amorphous solid).

MS (FAB) m/z: 437 $[M+H]^+$;

$^1$H-Nuclear Magnetic Resonance Spectra (500 MHz, DMSO-$d_6$) δ ppm:

9.67 (1H, s), 7.97 (2H, d, J=9 Hz), 7.90 (1H, t, J=5 Hz), 7.50 (2H, d, J=9 Hz), 7.20 (1H, s), 7.03 (2H, d, J=9 Hz), 7.00 (2H, d, J=9 Hz), 4.63 (1H, t, J=5 Hz), 3.90 (2H, d, J=7 Hz), 3.84-3.81 (1H, m), 3.44 (2H, q, J=6 Hz), 3.23 (2H, q, J=6 Hz), 1.29-1.19 (1H, m), 0.78-0.74 (2H, m), 0.63-0.57 (4H, m), 0.36-0.33 (2H, m).

A reaction similar to that described in Example 1 (1e) was conducted using 4-(cyclopropylmethoxy)-N-((Z)-2-[4-(trifluoromethoxy)phenyl]-1-{[(2-hydroxyethyl)amino]carbonyl}vinyl)benzamide (257 mg) to give 176 mg of the title compound (white powder).

MS (FAB) m/z: 439 $[M+H]^+$;

$^1$H-Nuclear Magnetic Resonance Spectra (500 MHz, DMSO-$d_6$) δ ppm:

8.34 (1H, d, J=8 Hz), 8.02 (1H, t, J=6 Hz), 7.78 (2H, d, J=8 Hz), 7.24 (2H, d, J=8 Hz), 6.95 (2H, d, J=8 Hz), 6.91 (2H, d, J=8 Hz), 4.67 (1H, t, J=5 Hz), 4.62-4.57 (1H, m), 3.86 (2H, d, J=7 Hz), 3.74 (1H, brs), 3.39 (2H, q, J=6 Hz), 3.19-3.12 (2H, m), 3.00 (1H, dd, J=14 Hz, 4 Hz), 2.91 (1H, dd, J=14 Hz, 11 Hz), 1.25-1.17 (1H, m), 0.74-0.70 (2H, m), 0.60-0.55 (4H, m), 0.33-0.31 (2H, m).

Example 21

4-(Cyclopropylmethoxy)-N-{1-(4-ethoxybenzyl)-2-[(2-hydroxyethyl)amino]-2-oxoethyl}benzamide (Exemplary Compound No. 25)

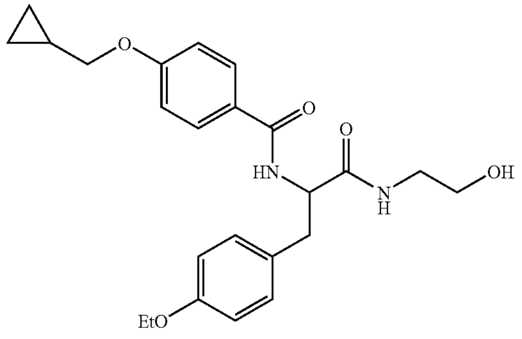 [SMILES: CCOc1ccc(CC(NC(=O)c2ccc(OCC3CC3)cc2)C(=O)NCCO)cc1]

A reaction similar to that described in Example 1 (1c) was conducted using N-[4-(cyclopropylmethoxy)benzoyl]glycine (300 mg) prepared in Example 18 (18b) and 4-ethoxybenzaldehyde (190 mg) to give the corresponding oxazolone (293 mg). A reaction similar to that described in Example (1 (1d) was conducted using 290 mg of this oxazolone to give 315 mg of 4-(cyclopropylmethoxy)-N-((Z)-2-(4-ethoxyphenyl)-1-{[(2-hydroxyethyl)amino]carbonyl}vinyl)benzamide (white amorphous solid).

MS (FAB) m/z: 425 $[M+H]^+$;

$^1$H-Nuclear Magnetic Resonance Spectra (400 MHz, DMSO-$d_6$) δ ppm:

9.66 (1H, s), 7.97 (2H, d, J=9 Hz), 7.89 (1H, t, J=5 Hz), 7.48 (2H, d, J=9 Hz), 7.19 (1H, s), 7.03 (2H, d, J=9 Hz), 6.87 (2H, d, J=9 Hz), 4.63 (1H, t, J=6 Hz), 4.01 (2H, q, J=7 Hz), 3.91 (2H, d, J=7 Hz), 3.43 (2H, q, J=6 Hz), 3.22 (2H, q, J=6 Hz), 1.29 (3H, t, J=7 Hz), 1.29-1.21 (1H, m), 0.61-0.57 (2H, m), 0.37-0.33 (2H, m).

A reaction similar to that described in Example (1 (1e) was conducted using 4-(cyclopropylmethoxy)-N-((Z)-2-(4-ethoxyphenyl)-1-{[(2-hydroxyethyl)amino]carbonyl}vinyl)benzamide (255 mg) to give 41 mg of the title compound (white powder).

MS (FAB) m/z: 427 $[M+H]^+$;

$^1$H-Nuclear Magnetic Resonance Spectra (400 MHz, DMSO-$d_6$) δ ppm:

8.29 (1H, d, J=8 Hz), 7.99 (1H, t, J=5 Hz), 7.74 (2H, d, J=9 Hz), 7.19 (2H, d, J=9 Hz), 6.93 (2H, d, J=9 Hz), 6.76 (2H, d, J=9 Hz), 4.65 (1H, t, J=5 Hz), 4.60-4.54 (1H, m), 3.92 (2H, q, J=7 Hz), 3.85 (2H, d, J=7 Hz), 3.37 (2H, q, J=6 Hz), 3.15-3.11 (2H, m), 2.98 (1H, dd, J=14 Hz, 4 Hz), 2.88 (1H, dd, J=14 Hz, 11 Hz), 1.27 (3H, t, J=7 Hz), 1.30-1.15 (1H, m), 0.59-0.55 (2H, m), 0.34-0.31 (2H, m).

Example 22

4-(Cyclopropylmethoxy)-N-{2-[(2-hydroxyethyl)amino]-2-oxo-1-[4-(trifluoromethyl)benzyl]ethyl}benzamide (Exemplary Compound No. 20)

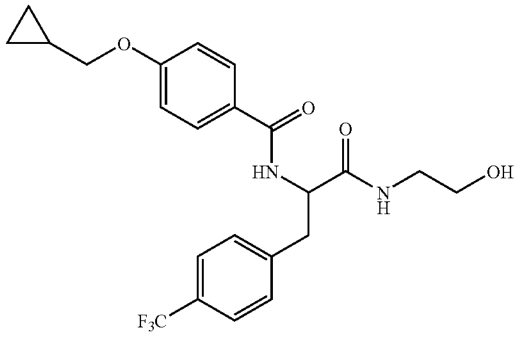 [SMILES: O=C(NC(Cc1ccc(C(F)(F)F)cc1)C(=O)NCCO)c1ccc(OCC2CC2)cc1]

A reaction similar to that described in Example (1c) was conducted using N-[4-(cyclopropylmethoxy)benzoyl]glycine (300 mg) prepared in Example 18 (18b) and 4-trifluoromethylbenzaldehyde (169 mg) to give the corresponding oxazolone (242 mg). A reaction similar to that described in Example 1 (1d) was conducted using 240 mg of this oxazolone to give 267 mg of 4-(cyclopropylmethoxy)-N-{(Z)-1-{[(2-hydroxyethyl)amino]carbonyl}-2-[4-(trifluoromethyl)phenyl]vinyl}benzamide (white powder).

MS (FAB) m/z: 449 $[M+H]^+$;

$^1$H-Nuclear Magnetic Resonance Spectra (400 MHz, DMSO-$d_6$) δ ppm:

9.82 (1H, s), 8.15 (1H, t, J=5 Hz), 7.93 (2H, d, J=9 Hz), 7.70 (4H, s), 7.16 (1H, s), 7.03 (2H, d, J=9 Hz), 4.64 (1H, t, J=6 Hz), 3.90 (2H, d, J=7 Hz), 3.45 (2H, q, J=6 Hz), 3.23 (2H, q, J=6 Hz), 1.28-1.19 (1H, m), 0.61-0.57 (2H, m), 0.36-0.32 (2H, m).

A reaction similar to that described in Example 1 (1e) was conducted using 4-(cyclopropylmethoxy)-N-{(Z)-1-{[(2-hydroxyethyl)amino]carbonyl}-2-[4-(trifluoromethyl)phenyl]vinyl}benzamide (200 mg) to give 150 mg of the title compound (white powder).

MS (FAB) m/z: 451 $[M+H]^+$;

$^1$H-Nuclear Magnetic Resonance Spectra (400 MHz, DMSO-$d_6$) δ ppm:

8.45 (1H, d, J=9 Hz), 8.12 (1H, t, J=5 Hz), 7.77 (2H, d, J=9 Hz), 7.62 (2H, d, J=8 Hz), 7.55 (2H, d, J=8 Hz), 6.95 (2H, d,

J=9 Hz), 4.74-4.86 (2H, m), 3.86 (2H, d, J=7 Hz), 3.39 (2H, q, J=5 Hz), 3.18-3.03 (4H, m), 1.27-1.17 (1H, m), 0.59-0.54 (2H, m), 0.34-0.30 (2H, m).

Example 23

N-{1-(4-Cyclopropylbenzyl)-2-[(2-hydroxyethyl)amino]-2-oxoethyl}-4-(cyclopropylmethoxy)benzamide (Exemplary Compound No. 17)

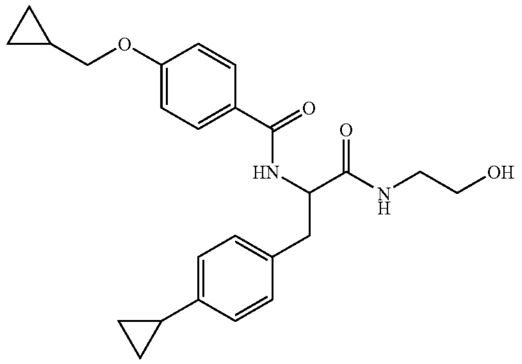 [SMILES: O=C(NC(Cc1ccc(C2CC2)cc1)C(=O)NCCO)c1ccc(OCC2CC2)cc1]

A reaction similar to that described in Example 1 (1c) was conducted using N-[4-(cyclopropylmethoxy)benzoyl]glycine (299 mg) prepared in Example 18 (18b) and 4-cyclopropylbenzaldehyde (184 mg) to give the corresponding oxazolone (366 mg). A reaction similar to that described in Example (1 (1d) was conducted using all this oxazolone to give 385 mg of 4-(cyclopropylmethoxy)-N-((Z)-2-(4-cyclopropylphenyl)-1-{[(2-hydroxyethyl)amino]carbonyl}vinyl)benzamide (white powder).

MS (FAB) m/z: 421 $[M+H]^+$;

$^1$H-Nuclear Magnetic Resonance Spectra (500 MHz, DMSO-$d_6$) δ ppm:

9.71 (1H, s), 7.97-7.95 (3H, m), 7.41 (2H, d, J=9 Hz), 7.17 (1H, s), 7.03 (2H, d, J=9 Hz), 7.02 (2H, d, J=9 Hz), 4.65 (1H, brs), 3.91 (2H, d, J=7 Hz), 3.42 (2H, q, J=6 Hz), 3.22 (2H, q, J=6 Hz), 1.90-1.85 (1H, m), 1.28-1.22 (1H, m), 0.95-0.91 (2H, m), 0.67-0.64 (2H, m), 0.61-0.57 (2H, m), 0.36-0.33 (2H, m).

A reaction similar to that described in Example 2 was conducted using 4-(cyclopropylmethoxy)-N-((Z)-2-(4-cyclopropylphenyl)-1-{[(2-hydroxyethyl)amino]carbonyl}vinyl)benzamide (296 mg) to give 172 mg of the title compound (white powder).

MS (FAB) m/z: 423 $[M+H]^+$;

$^1$H-Nuclear Magnetic Resonance Spectra (400 MHz, DMSO-$d_6$) δ ppm:

8.31 (1H, d, J=9 Hz), 7.99 (1H, t, J=6 Hz), 7.74 (2H, d, J=8 Hz), 7.16 (2H, d, J=8 Hz), 6.93 (2H, d, J=7 Hz), 6.91 (2H, d, J=7 Hz), 4.65 (1H, brs), 4.61-4.55 (1H, m), 3.85 (2H, d, J=7 Hz), 3.37 (2H, q, J=6 Hz), 3.16-3.10 (2H, m), 2.98 (1H, dd, J=13 Hz, 4 Hz), 2.90 (1H, dd, J=13 Hz, 10 Hz), 1.84-1.78 (1H, m), 1.25-1.18 (1H, m), 0.89-0.84 (2H, m), 0.60-0.55 (4H, m), 0.34-0.30 (2H, m).

Example 24

4-(Cyclopropylmethoxy)-N-{1-(4-ethylbenzyl)-2-[(2-hydroxyethyl)amino]-2-oxoethyl}benzamide (Exemplary Compound No. 26)

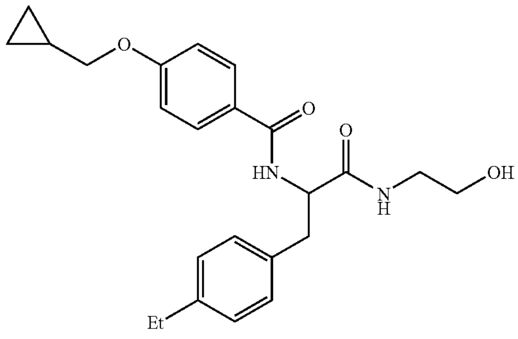

A reaction similar to that described in Example 1 (1c) was conducted using N-[4-(cyclopropylmethoxy)benzoyl]glycine (200 mg) prepared in Example 18 (18b) and 4-ethylbenzaldehyde (121 μL) to give the corresponding oxazolone (226 mg). A reaction similar to that described in Example 1 (1d) was conducted using 222 mg of this oxazolone to give 177 mg of 4-(cyclopropylmethoxy)-N-((Z)-2-(4-ethylphenyl)-1-{[(2-hydroxyethyl)amino]carbonyl}vinyl)benzamide (white powder).

MS (FAB) m/z: 409 $[M+H]^+$;

$^1$H-Nuclear Magnetic Resonance Spectra (500 MHz, DMSO-$d_6$) δ ppm:

9.70 (1H, s), 7.97-7.94 (3H, m), 7.45 (2H, d, J=8 Hz), 7.18 (1H, s), 7.17 (2H, d, J=8 Hz), 7.03 (2H, d, J=9 Hz), 4.63 (1H, t, J=6 Hz), 3.91 (2H, d, J=7 Hz), 3.43 (2H, q, J=6 Hz), 3.23 (2H, q, J=6 Hz), 2.56 (2H, q, J=7 Hz), 1.29-1.21 (1H, m), 1.14 (3H, t, J=7 Hz), 0.61-0.57 (2H, m), 0.36-0.33 (2H, m).

A reaction similar to that described in Example 1 (1e) was conducted using 4-(cyclopropylmethoxy)-N-((Z)-2-(4-ethylphenyl)-1-{[(2-hydroxyethyl)amino]carbonyl}vinyl)benzamide (146 mg) to give 148 mg of the title compound (colorless crystal).

MS (FAB) m/z: 411 $[M+H]^+$;

$^1$H-Nuclear Magnetic Resonance Spectra (400 MHz, DMSO-$d_6$) δ ppm:

8.35 (1H, d, J=9 Hz), 8.03 (1H, t, J=5 Hz), 7.77 (2H, d, J=9 Hz), 7.22 (2H, d, J=8 Hz), 7.07 (2H, d, J=8 Hz), 6.95 (2H, d, J=9 Hz), 4.67 (1H, t, J=5 Hz), 4.64-4.58 (1H, m), 3.86 (2H, d, J=7 Hz), 3.38 (2H, q, J=5 Hz), 3.17-3.12 (2H, m), 3.02 (1H, dd, J=14 Hz, 4 Hz), 2.93 (1H, dd, J=14 Hz, 10 Hz), 2.52 (2H, q, J=7 Hz), 1.26-1.16 (1H, m), 1.12 (3H, t, J=7 Hz), 0.59-0.55 (2H, m), 0.34-0.31 (2H, m).

Example 25

4-(3-Cyclopropylpropoxy)-N-{2-[(2-hydroxyethyl)amino]-2-oxo-1-[4-(trifluoromethoxy)benzyl]ethyl}benzamide (Exemplary Compound No. 54)

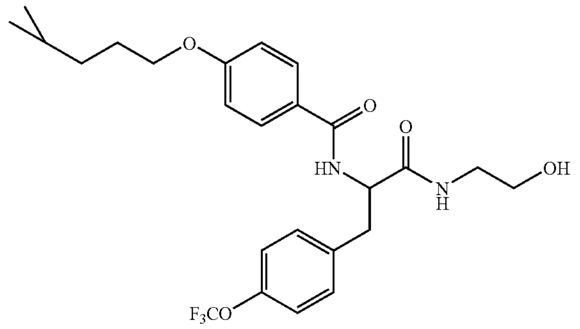 [SMILES: CC(C)CCCOc1ccc(C(=O)NC(Cc2ccc(OC(F)(F)F)cc2)C(=O)NCCO)cc1]

(25a) N-[4-(3-Cyclopropylpropoxy)benzoyl]glycine

Reactions similar to those described in Example 1 (1a) and (1b) were conducted using methyl 4-hydroxybenzoate (6.09 g, 40.0 mmol) and 3-cyclopropyl-1-propanol (compound described in Helv. Chim. Acta, (2003), 86, 865-893, 4.41 g, 44.0 mmol) to give 5.74 g of the title compound (white powder, yield: 51%).

MS (FAB) m/z: 278 $[M+H]^+$;

$^1$H-Nuclear Magnetic Resonance Spectra (400 MHz, DMSO-$d_6$) δ ppm:

12.55 (1H, brs), 8.66 (1H, t, J=6 Hz), 7.83 (2H, d, J=9 Hz), 7.00 (2H, d, J=9 Hz), 4.06 (2H, t, J=6 Hz), 3.89 (2H, d, J=6 Hz), 1.85-1.78 (2H, m), 1.33 (2H, q, J=7 Hz), 0.77-0.68 (1H, m), 0.42-0.38 (2H, m), 0.05-0.01 (2H, m).

(25b) 4-(3-Cyclopropylpropoxy)-N-{2-[(2-hydroxyethyl)amino]-2-oxo-1-[4-(trifluoromethoxy)benzyl]ethyl}benzamide A reaction similar to that described in Example 1 (1c) was conducted using N-[4-(3-cyclopropylpropoxy)benzoyl]glycine (277 mg) prepared in Example 25 (25a) and 4-(trifluoromethoxy)benzaldehyde (150 μL) to give the corresponding oxazolone (287 mg). A reaction similar to that described in Example 1 (1d) was conducted using all this oxazolone to give 261 mg of 4-(3-cyclopropylpropoxy)-N-{(Z)-1-{[(2-hydroxyethyl)amino]carbonyl}-2-[4-(trifluoromethoxy)phenyl]vinyl}benzamide (white solid).

MS (FAB) m/z: 493 $[M+H]^+$;

$^1$H-Nuclear Magnetic Resonance Spectra (500 MHz, $CDCl_3$) δ ppm:

7.91 (1H, brs), 7.78 (2H, d, J=9 Hz), 7.40 (2H, d, J=9 Hz), 7.16 (2H, d, J=8 Hz), 7.01 (1H, s), 6.92 (2H, d, J=9 Hz), 6.78 (1H, t, J=5 Hz), 4.05 (2H, t, J=6 Hz), 3.78 (2H, brq, J=4 Hz), 3.49 (2H, q, J=4 Hz), 3.05 (1H, brt, J=6 Hz), 1.92 (2H, quint, J=7 Hz), 1.39 (2H, q, J=7 Hz), 0.74-0.67 (1H, m), 0.47-0.43 (2H, m), 0.07-0.04 (2H, m).

A reaction similar to that described in Example 1 (1e) was conducted using 4-(3-cyclopropylpropoxy)-N-{(Z)-1-{[(2-hydroxyethyl)amino]carbonyl}-2-[4-(trifluoromethoxy)phenyl]vinyl}benzamide (261 mg) to give 215 mg of the title compound (white powder).

MS (FAB) m/z: 495 $[M+H]^+$;

$^1$H-Nuclear Magnetic Resonance Spectra (500 MHz, DMSO-$d_6$) δ ppm:

8.41 (1H, d, J=8 Hz), 8.08 (1H, t, J=6 Hz), 7.77 (2H, d, J=9 Hz), 7.44 (2H, d, J=9 Hz), 7.24 (2H, d, J=8 Hz), 6.96 (2H, d, J=8 Hz), 4.70-4.65 (2H, m), 4.04 (2H, t, J=6 Hz), 3.39 (2H, q, J=6 Hz), 3.18-3.13 (2H, m), 3.11 (1H, dd, J=13 Hz, 4 Hz), 3.01 (1H, dd, J=13 Hz, 10 Hz), 1.84-1.78 (2H, m), 1.35-1.31 (2H, m), 0.76-0.68 (1H, m), 0.42-0.38 (2H, m), 0.04-0.01 (2H, m).

Example 26

4-(3-Cyclopropylpropoxy)-N-{1-[4-(2,2-difluoroethoxy)benzyl]-2-[(2-hydroxyethyl)amino]-2-oxoethyl}benzamide (Exemplary Compound No. 58)

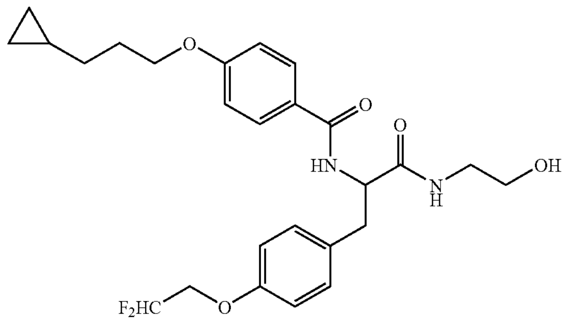 [SMILES: O=C(NC(Cc1ccc(OCC(F)F)cc1)C(=O)NCCO)c1ccc(OCCCC2CC2)cc1]

A reaction similar to that described in Example (1 (1c) was conducted using N-[4-(3-cyclopropylpropoxy)benzoyl]glycine (277 mg) prepared in Example 25 (25a) and 4-(2,2-difluoroethoxy)benzaldehyde (196 mg) prepared in Example 13 (13a) to give the corresponding oxazolone (298 mg). A reaction similar to that described in Example 1 (1d) was conducted using all this oxazolone to give 268 mg of 4-(3-cyclopropylpropoxy)-N-((Z)-2-[4-(2,2-difluoroethoxy)phenyl]-1-{[(2-hydroxyethyl)amino]carbonyl}vinyl)benzamide (light yellow powder).

MS (FAB) m/z: 489 $[M+H]^+$;

$^1$H-Nuclear Magnetic Resonance Spectra (500 MHz, $CDCl_3$) δ ppm:

7.81-7.79 (3H, m), 7.36 (2H, d, J=9 Hz), 7.06 (1H, s), 6.93 (2H, d, J=9 Hz), 6.86 (2H, d, J=8 Hz), 6.74 (1H, t, J=6 Hz), 6.07 (1H, tt, J=55 Hz, 4 Hz), 4.16 (2H, td, J=13 Hz, 4 Hz), 4.05 (2H, t, J=7 Hz), 3.77 (2H, t, J=5 Hz), 3.50 (2H, q, J=5 Hz), 1.92 (2H, quint, J=7 Hz), 1.39 (2H, q, J=7 Hz), 0.76-0.68 (1H, m), 0.47-0.44 (2H, m), 0.07-0.04 (2H, m).

A reaction similar to that described in Example 1 (1e) was conducted using 4-(3-cyclopropylpropoxy)-N-((Z)-2-[4-(2,2-difluoroethoxy)phenyl]-1-{[(2-hydroxyethyl)amino]carbonyl}vinyl)benzamide (268 mg) to give 207 mg of the title compound (white powder).

MS (FAB) m/z: 491 $[M+H]^+$;

$^1$H-Nuclear Magnetic Resonance Spectra (400 MHz, DMSO-$d_6$) δ ppm:

8.32 (1H, d, J=9 Hz), 8.01 (1H, t, J=6 Hz), 7.75 (2H, d, J=9 Hz), 7.24 (2H, d, J=9 Hz), 6.93 (2H, d, J=9 Hz), 6.85 (2H, d, J=9 Hz), 6.31 (1H, tt, J=54 Hz, 4 Hz), 4.67 (1H, t, J=5 Hz), 4.62-4.56 (1H, m), 4.22 (2H, td, J=14 Hz, 4 Hz), 4.03 (2H, t, J=7 Hz), 3.38 (2H, q, J=6 Hz), 3.14 (2H, q, J=6 Hz), 3.00 (1H, dd, J=14 Hz, 4 Hz), 2.90 (1H, dd, J=14 Hz, 11 Hz), 1.84-1.77 (2H, m), 1.32 (2H, q, J=7 Hz), 0.76-0.67 (1H, m), 0.42-0.38 (2H, m), 0.04-0.01 (2H, m).

Example 27

N-{1-[4-(Cyclopropyloxy)benzyl]-2-[(2-hydroxyethyl)amino]-2-oxoethyl}-4-(3-cyclopropylpropoxy)benzamide (Exemplary Compound No. 51)

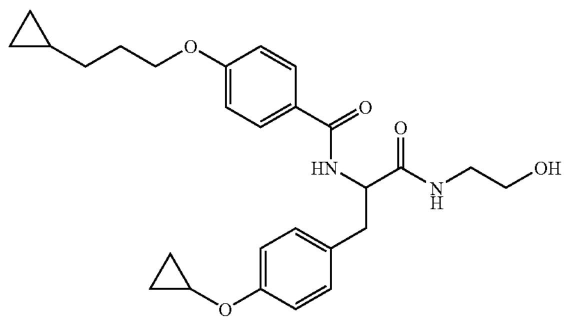 [SMILES: O=C(NC(Cc1ccc(OC2CC2)cc1)C(=O)NCCO)c1ccc(OCCCC2CC2)cc1]

A reaction similar to that described in Example (1c) was conducted using N-[4-(3-cyclopropylpropoxy)benzoyl]glycine (277 mg) prepared in Example 25 (25a) and 4-(cyclopropyloxy)benzaldehyde (170 mg) prepared in Example 5 (5a) to give the corresponding oxazolone (271 mg). A reaction similar to that described in Example 1 (1d) was conducted using all this oxazolone to give 278 mg of N-((Z)-2-[4-(cyclopropyloxy)phenyl]-1-{[(2-hydroxyethyl)amino]carbonyl}vinyl)-4-(3-cyclopropylpropoxy)benzamide (light yellow amorphous solid).

MS (FAB) m/z: 465 $[M+H]^+$;

$^1$H-Nuclear Magnetic Resonance Spectra (400 MHz, $CDCl_3$) δ ppm:

7.82 (2H, d, J=9 Hz), 7.71 (1H, brs), 7.35 (2H, d, J=9 Hz), 7.10 (1H, s), 7.00 (2H, d, J=9 Hz), 6.94 (2H, d, J=9 Hz), 6.67 (1H, brt, J=6 Hz), 4.06 (2H, t, J=6 Hz), 3.78 (2H, t, J=5 Hz), 3.74-3.69 (1H, m), 3.50 (2H, q, J=5 Hz), 1.92 (2H, quint, J=5 Hz), 1.39 (2H, q, J=8 Hz), 0.79-0.68 (5H, m), 0.47-0.43 (2H, m), 0.08-0.04 (2H, m).

A reaction similar to that described in Example 1 (1e) was conducted using N-((Z)-2-[4-(cyclopropyloxy)phenyl]-1-{[(2-hydroxyethyl)amino]carbonyl}vinyl)-4-(3-cyclopropylpropoxy)benzamide (278 mg) to give 96 mg of the title compound (white powder).

MS (FAB) m/z: 467 $[M+H]^+$;

$^1$H-Nuclear Magnetic Resonance Spectra (500 MHz, DMSO-$d_6$) δ ppm:

8.34 (1H, d, J=9 Hz), 8.02 (1H, t, J=6 Hz), 7.78 (2H, d, J=9 Hz), 7.23 (2H, d, J=9 Hz), 6.96 (2H, d, J=9 Hz), 6.91 (2H, d, J=9 Hz), 4.67 (1H, t, J=5 Hz), 4.61-4.57 (1H, m), 4.04 (2H, t, J=6 Hz), 3.74 (1H, sept, J=3 Hz), 3.39 (2H, q, J=6 Hz), 3.18-3.11 (2H, m), 3.00 (1H, dd, J=14 Hz, 4 Hz), 2.91 (1H, dd, J=14 Hz, 11 Hz), 1.84-1.78 (2H, m), 1.83 (2H, q, J=7 Hz), 0.74-0.70 (3H, m), 0.60-0.57 (2H, m), 0.42-0.38 (2H, m), 0.04-0.01 (2H, m).

Example 28

4-(2-Cyclopentylethoxy)-N-{2-[(2-hydroxyethyl)amino]-2-oxo-1-[4-(trifluoromethoxy)benzyl]ethyl}benzamide (Exemplary Compound No. 74)

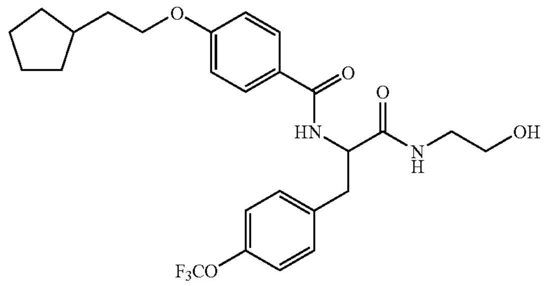 [SMILES: O=C(NC(Cc1ccc(OC(F)(F)F)cc1)C(=O)NCCO)c1ccc(OCCC2CCCC2)cc1]

(28a) N-[4-(2-Cyclopentylethoxy)benzoyl]glycine

Reactions similar to those described in Example 1 (1a) and (1b) were conducted using methyl 4-hydroxybenzoate (6.09 g, 40.0 mmol) and 2-cyclopentylethanol (4.57 g, 40.0 mmol) to give 9.20 g of the title compound (white solid, yield: 79%).

MS (FAB) m/z: 292 $[M+H]^+$;

$^1$H-Nuclear Magnetic Resonance Spectra (500 MHz, DMSO-$d_6$) δ ppm:

12.55 (1H, s), 8.66 (1H, t, J=6 Hz), 7.83 (2H, d, J=9 Hz), 7.00 (2H, d, J=9 Hz), 4.04 (2H, t, J=6 Hz), 3.89 (2H, d, J=6 Hz), 1.94 (1H, sept, J=8 Hz), 1.81-1.73 (4H, m), 1.64-1.55 (2H, m), 1.53-1.45 (2H, m), 1.19-1.12 (2H, m).

(28b) 4-(2-Cyclopentylethoxy)-N-{2-[(2-hydroxyethyl)amino]-2-oxo-1-[4-(trifluoromethoxy)benzyl]ethyl}benzamide A reaction similar to that described in Example 1 (1c) was conducted using N-[4-(2-cyclopentylethoxy)benzoyl]glycine (291 mg) prepared in Example 28 (28a) and 4-(trifluoromethoxy)benzaldehyde (150 μL) to give the corresponding oxazolone (377 mg). A reaction similar to that described in Example 1 (1d) was conducted using all this oxazolone to give 360 mg of 4-(2-cyclopentylethoxy)-N-{(Z)-1-{[(2-hydroxyethyl)amino]carbonyl}-2-[4-(trifluoromethoxy)phenyl]vinyl}benzamide (white powder).

MS (FAB) m/z: 507 $[M+H]^+$;

$^1$H-Nuclear Magnetic Resonance Spectra (500 MHz, DMSO-$d_6$) δ ppm:

9.78 (1H, s), 8.06 (1H, t, J=6 Hz), 7.95 (2H, d, J=9 Hz), 7.64 (2H, d, J=9 Hz), 7.34 (2H, d, J=9 Hz), 7.16 (1H, s), 7.03 (2H, d, J=9 Hz), 4.63 (1H, t, J=5 Hz), 4.07 (2H, t, J=6 Hz), 3.45 (2H, q, J=6 Hz), 3.23 (2H, q, J=6 Hz), 1.95 (1H, sept, J=7 Hz), 1.81-1.74 (4H, m), 1.64-1.56 (2H, m), 1.54-1.48 (2H, m), 1.20-1.12 (2H, m).

A reaction similar to that described in Example 1 (1e) was conducted using 4-(2-cyclopentylethoxy)-N-{(Z)-1-{[(2-hydroxyethyl)amino]carbonyl}-2-[4-(trifluoromethoxy)phenyl]vinyl}benzamide (360 mg) to give 252 mg of the title compound (white powder).

MS (FAB) m/z: 509 $[M+H]^+$;

$^1$H-Nuclear Magnetic Resonance Spectra (500 MHz, DMSO-$d_6$) δ ppm:

8.40 (1H, d, J=9 Hz), 8.08 (1H, t, J=6 Hz), 7.77 (2H, d, J=9 Hz), 7.44 (2H, d, J=8 Hz), 7.24 (2H, d, J=8 Hz), 6.95 (2H, d,

J=8 Hz), 4.69-4.65 (2H, m), 4.02 (2H, t, J=7 Hz), 3.39 (2H, q, J=6 Hz), 3.17-3.13 (2H, m), 3.10 (1H, dd, J=13 Hz, 4 Hz), 3.00 (1H, dd, J=13 Hz, 10 Hz), 1.93 (1H, sept, J=7 Hz), 1.80-1.71 (4H, m), 1.62-1.56 (2H, m), 1.53-1.46 (2H, m), 1.18-1.11 (2H, m).

Example 29

4-(Cyclopentylmethoxy)-N-{2-[(2-hydroxyethyl) amino]-2-oxo-1-[4-(trifluoromethoxy)benzyl] ethyl}benzamide (Exemplary Compound No. 69)

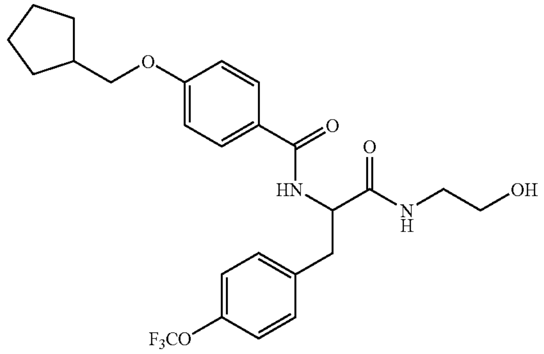 [SMILES: O=C(NC(Cc1ccc(OC(F)(F)F)cc1)C(=O)NCCO)c1ccc(OCC2CCCC2)cc1]

(29a) N-[4-(Cyclopentylmethoxy)benzoyl]glycine

Reactions similar to those described in Example 1 (1a) and (1b) were conducted using methyl 4-hydroxybenzoate (22.8 g, 150 mmol) and cyclopentylmethanol (10.0 g, 100 mmol) to give 9.3 g of the title compound (colorless crystal, yield: 35%).

MS (EI) m/z: 277 $[M]^+$;

$^1$H-Nuclear Magnetic Resonance Spectra (400 MHz, DMSO-$d_6$) δ ppm:

12.55 (1H, brs), 8.67 (1H, t, J=6 Hz), 7.82 (2H, d, J=9 Hz), 7.00 (2H, d, J=9 Hz), 3.90 (2H, d, J=7 Hz), 3.89 (2H, d, J=6 Hz), 2.31 (1H, sept, J=7 Hz), 1.81-1.73 (2H, m), 1.65-1.50 (4H, m), 1.37-1.29 (2H, m).

(29b) 4-(Cyclopentylmethoxy)-N-{2-[(2-hydroxyethyl) amino]-2-oxo-1-[4-(trifluoromethoxy)benzyl] ethyl}benzamide A reaction similar to that described in Example 1 (1c) was conducted using N-[4-(cyclopentylmethoxy)benzoyl]glycine (277 mg) prepared in Example 29 (29a) and 4-(trifluoromethoxy)benzaldehyde (150 μL) to give the corresponding oxazolone (377 mg). A reaction similar to that described in Example 1(1d) was conducted using all this oxazolone to give 327 mg of 4-(cyclopentylmethoxy)-N-{(Z)-1-{[(2-hydroxyethyl)amino]carbonyl}-2-[4-(trifluoromethoxy)phenyl] vinyl}benzamide (white powder).

MS (FAB) m/z: 493 $[M+H]^+$;

$^1$H-Nuclear Magnetic Resonance Spectra (500 MHz, DMSO-$d_6$) δ ppm:

9.78 (1H, s), 8.06 (1H, t, J=6 Hz), 7.95 (2H, d, J=9 Hz), 7.64 (2H, d, J=9 Hz), 7.34 (2H, d, J=9 Hz), 7.16 (1H, s), 7.03 (2H, d, J=9 Hz), 4.64 (1H, t, J=5 Hz), 3.93 (2H, d, J=7 Hz), 3.45 (2H, q, J=6 Hz), 3.23 (2H, q, J=6 Hz), 2.33 (1H, sept, J=7 Hz), 1.82-1.75 (2H, m), 1.66-1.51 (4H, m), 1.37-1.31 (2H, m).

A reaction similar to that described in Example 1 (1e) was conducted using 4-(cyclopentylmethoxy)-N-{(Z)-1-{[(2-hydroxyethyl)amino]carbonyl}-2-[4-(trifluoromethoxy)phenyl]vinyl}benzamide (258 mg) to give 180 mg of the title compound (white powder)

MS (FAB) m/z: 495 $[M+H]^+$; .

$^1$H-Nuclear Magnetic Resonance Spectra (500 MHz, DMSO-$d_6$) δ ppm:

8.41 (1H, d, J=8 Hz), 8.08 (1H, t, J=6 Hz), 7.77 (2H, d, J=9 Hz), 7.44 (2H, d, J=8 Hz), 7.24 (2H, d, J=8 Hz), 6.96 (2H, d, J=9 Hz), 4.69-4.65 (2H, m), 3.88 (2H, d, J=7 Hz), 3.39 (2H, q, J=6 Hz), 3.17-3.13 (2H, m), 3.10 (1H, dd, J=14 Hz, 4 Hz), 3.00 (1H, dd, J=14 Hz, 11 Hz), 2.30 (1H, sept, J=7 Hz), 1.80-1.74 (2H, m), 1.64-1.50 (4H, m), 1.35-1.29 (2H, m).

Example 30

N-{2-[(2-Hydroxyethyl)amino]-2-oxo-1-[4-(trifluoromethoxy)benzyl]ethyl}-4-propoxybenzamide (Exemplary Compound No. 144)

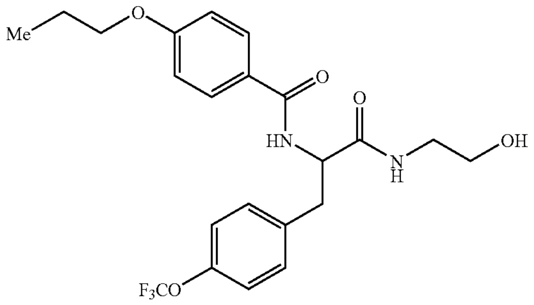 [SMILES: CCCOc1ccc(C(=O)NC(Cc2ccc(OC(F)(F)F)cc2)C(=O)NCCO)cc1]

A reaction similar to that described in Example 1 (1c) was conducted using N-(4-propoxybenzoyl)glycine (compound described in Arm. Khim. Zh., (1973), 26, 676-677, 300 mg) and 4-(trifluoromethoxy)benzaldehyde (264 mg) to give the corresponding oxazolone (260 mg). A reaction similar to that described in Example 1 (1d) was conducted using 257 mg of this oxazolone to give 257 mg of N-{(Z)-1-{[(2-hydroxyethyl)amino]carbonyl}-2-[4-(trifluoromethoxy)phenyl]vinyl}-4-propoxybenzamide (white amorphous solid).

MS (FAB) m/z: 453 $[M+H]^+$;

$^1$H-Nuclear Magnetic Resonance Spectra (400 MHz, DMSO-$d_6$) δ ppm:

9.76 (1H, s), 8.05 (1H, t, J=6 Hz), 7.92 (2H, d, J=9 Hz), 7.62 (2H, d, J=9 Hz), 7.32 (2H, d, J=8 Hz), 7.14 (1H, s), 7.01 (2H, d, J=9 Hz), 4.63 (1H, t, J=5 Hz), 4.00 (2H, t, J=7 Hz), 3.43 (2H, q, J=6 Hz), 3.22 (2H, q, J=6 Hz), 1.79-1.71 (2H, m), 0.99 (3H, t, J=7 Hz).

A reaction similar to that described in Example 1 (1e) was conducted using N-{(Z)-1-{[(2-hydroxyethyl)amino]carbonyl}-2-[4-(trifluoromethoxy)phenyl]vinyl}-4-propoxybenzamide (198 mg) to give 162 mg of the title compound (white powder).

MS (FAB) m/z: 455 $[M+H]^+$;

$^1$H-Nuclear Magnetic Resonance Spectra (400 MHz, DMSO-$d_6$) δ ppm:

8.39 (1H, d, J=7 Hz), 8.07 (1H, brs), 7.75 (2H, d, J=8 Hz), 7.42 (2H, d, J=8 Hz), 7.21 (2H, d, J=7 Hz), 6.93 (2H, d, J=8

Hz), 4.69 (2H, brs), 3.95 (2H, brt, J=5 Hz), 3.42-3.36 (2H, brs), 3.18-2.97 (4H, m), 1.72 (2H, brq, J=7 Hz), 0.96 (3H, t, J=7 Hz).

Example 31

4-(2,2-Difluoroethoxy)-N-{2-[(2-hydroxyethyl) amino]-2-oxo-1-[4-(trifluoromethoxy)benzyl] ethyl}benzamide (Exemplary Compound No. 109)

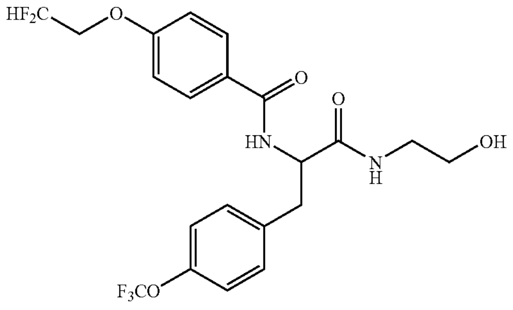

(31a) 4-(2,2-Difluoroethoxy)benzoic acid 4-(2,2-Difluoroethoxy)benzaldehyde (2.50 g, 13.4 mmol) prepared in Example 13 (13a) was dissolved in a solution mixture of tert-butanol:water (28 mL, 22:6, V/V). Then, to the resulting mixture were added sodium dihydrogen phosphate dihydrate (2.10 g, 13.4 mmol), 2-methyl-2-butene (6.26 mL, 59.1 mmol), and sodium chlorite (4.25 g, 37.6 mmol). The mixture was stirred at room temperature for 4 hours, and then 2-methyl-2-butene (2.85 mL, 26.9 mmol) and sodium chlorite (1.52 g, 13.4 mmol) were further added thereto. The resulting mixture was further stirred at room temperature for 20 hours, and then a saturated ammonium chloride aqueous solution was added to the reaction solution to terminate the reaction. The resulting mixture was extracted with ethyl acetate, and the organic layer was washed with saturated brine and dried over anhydrous sodium sulfate. The solvent was evaporated to give 2.71 g of the title compound (white solid, yield: quantitative).

$^1$H-Nuclear Magnetic Resonance Spectra (400 MHz, DMSO-$d_6$) δ ppm:

12.93 (1H, brs), 7.90 (2H, d, J=9 Hz), 7.08 (2H, d, J=9 Hz), 6.41 (1H, tt, J=54 Hz, 4 Hz), 4.40 (2H, td, J=15 Hz, 4 Hz).

(31b) N-[4-(2,2-Difluoroethoxy)benzoyl]glycine

A reaction similar to that described in Example 1 (1b) was conducted using 4-(2,2-difluoroethoxy)benzoic acid (2.71 g, 13.4 mmol) prepared in Example 31 (31a) to give 1.67 g of the title compound (yellow powder, yield: 48%).

$^1$H-Nuclear Magnetic Resonance Spectra (400 MHz, DMSO-$d_6$) δ ppm:

12.57 (1H, brs), 8.74 (1H, brt, J=5 Hz), 7.86 (2H, d, J=9 Hz), 7.10 (2H, d, J=9 Hz), 6.42 (1H, tt, J=54 Hz, 4 Hz), 4.39 (2H, t, J=15 Hz), 3.90 (2H, d, J=6 Hz).

(31c) 4-(2,2-Difluoroethoxy)-N-{2-[(2-hydroxyethyl) amino]-2-oxo-1-[4-(trifluoromethoxy)benzyl] ethyl}benzamide A reaction similar to that described in Example 1 (1c) was conducted using N-[4-(2,2-difluoroethoxy)benzoyl]glycine (300 mg) prepared in Example 31 (31b) and 4-(trifluoromethoxy)benzaldehyde (231 mg) to give the corresponding oxazolone (241 mg). A reaction similar to that described in Example (1 (1d) was conducted using 238 mg of this oxazolone to give 252 mg of 4-(2,2-difluoroethoxy)-N-{(Z)-1-{[(2-hydroxyethyl)amino]carbonyl}-2-[4-(trifluoromethoxy)phenyl]vinyl}benzamide (white amorphous solid).

MS (FAB) m/z: 475 [M+H]$^+$;

$^1$H-Nuclear Magnetic Resonance Spectra (400 MHz, DMSO-$d_6$) δ ppm:

9.81 (1H, s), 8.07 (1H, t, J=6 Hz), 7.95 (2H, d, J=9 Hz), 7.62 (2H, d, J=9 Hz), 7.32 (2H, d, J=8 Hz), 7.15 (1H, s), 7.11 (2H, d, J=9 Hz), 6.41 (1H, tt, J=54 Hz, 3 Hz), 4.63 (1H, t, J=6 Hz), 4.41 (2H, td, J=15 Hz, 4 Hz), 3.43 (2H, q, J=6 Hz), 3.22 (2H, q, J=6 Hz).

A reaction similar to that described in Example (1 (1e) was conducted using 4-(2,2-difluoroethoxy)-N-{(Z)-1-{[(2-hydroxyethyl)amino]carbonyl}-2-[4-(trifluoromethoxy)phenyl]vinyl}benzamide (190 mg) to give 140 mg of the title compound (white powder).

MS (FAB) m/z: 477 [M+H]$^+$;

$^1$H-Nuclear Magnetic Resonance Spectra (400 MHz, DMSO-$d_6$) δ ppm:

8.45 (1H, d, J=9 Hz), 8.07 (1H, t, J=5 Hz), 7.77 (2H, d, J=9 Hz), 7.42 (2H, d, J=9 Hz), 7.22 (2H, d, J=9 Hz), 7.03 (2H, d, J=9 Hz), 6.38 (1H, tt, J=54 Hz, 4 Hz), 4.69-4.63 (2H, m), 4.36 (2H, td, J=15 Hz, 4 Hz), 3.37 (2H, q, J=6 Hz), 3.17-3.07 (3H, m), 2.99 (1H, dd, J=13 Hz, 11 Hz).

Example 32

4-[(2E)-But-2-en-1-yloxy]-N-{2-[(2-hydroxyethyl) amino]-2-oxo-1-[4-(trifluoromethoxy)benzyl] ethyl}benzamide (Exemplary Compound No. 124)

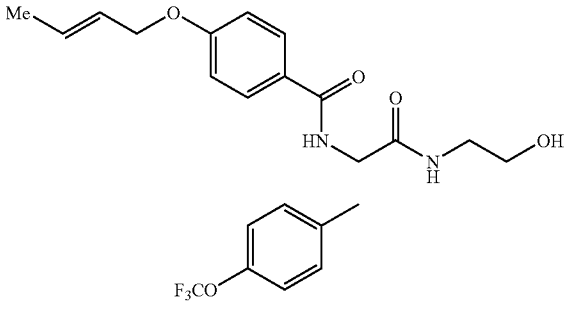

(32a) 4-[(2E)-But-2-en-1-yloxy]benzoic acid

A reaction similar to that described in Example 1 (1a) was conducted using methyl 4-hydroxybenzoate (5.00 g, 32.9 mmol) and trans-crotyl alcohol (manufactured by Fluka, 2.37 g, 32.9 mmol) to give 5.78 g of the title compound (white powder, yield: 91%).

MS (EI) m/z: 192 [M]$^+$;

$^1$H-Nuclear Magnetic Resonance Spectra (400 MHz, $CDCl_3$) δ ppm:

8.02 (2H, d, J=9 Hz), 6.93 (2H, d, J=9 Hz), 5.91-5.84 (1H, m), 5.75-5.68 (1H, m), 4.52 (2H, d, J=6 Hz), 1.77 (3H, dd, J=6 Hz, 1 Hz).

(32b) 2-({4-[(2E)-But-2-en-1-yloxy]benzoyl}amino)-3-[4-(trifluoromethoxy)phenyl]propanoic acid 4-(4,6-Dimethoxy-1,3,5-triazin-2-yl)-4-methylmorphorinium chloride (DMT-MM, 332 mg, 1.20 mmol) was added to a methanol (6 mL) solution of tert-butyl 2-amino-3-[4-(trifluoromethoxy)phenyl]propanoate (305 mg, 1.00 mmol) and 4-[(2E)-buten-2-yloxy]benzoic acid (192 mg, 1.00 mmol) prepared in Example 32 (32a). The mixture was stirred at room temperature for 4 hours and 50 minutes. The solvent was evaporated, and the residue was purified by silica gel column chromatography (n-hexane:ethyl acetate, 19:1 and 4:1, V/V) to give 421 mg of tert-butyl 2-({4-[(2E)-but-2-en-1-yloxy]benzoyl}amino)-3-[4-(trifluoromethoxy)phenyl]propanoate (colorless oil). This oily compound (492 mg, 1.03 mmol) was dissolved in methylene chloride (20 mL), and trifluoroacetic acid (4 mL) was added thereto at room temperature. The resulting mixture was stirred at the same temperature for 4.5 hours. The solvent was evaporated, and the residue was suspended in diisopropyl ether. The insoluble substance was collected by filtration, washed with diisopropyl ether, and dried to give 284 mg of the title compound (white powder, yield: 57%).

MS (FAB) m/z: 424 $[M+H]^+$;

$^1$H-Nuclear Magnetic Resonance Spectra (400 MHz, DMSO-$d_6$) δ ppm:

12.72 (1H, brs), 8.54 (1H, d, J=8 Hz), 7.73 (2H, d, J=9 Hz), 7.40 (2H, d, J=9 Hz), 7.24 (2H, d, J=9 Hz), 6.95 (2H, d, J=9 Hz), 5.88-5.80 (1H, m), 5.70-5.63 (1H, m), 4.61-4.55 (1H, m), 4.52 (2H, brd, J=6 Hz), 3.20 (1H, dd, J=14 Hz, 5 Hz), 3.08 (1H, dd, J=14 Hz, 11 Hz), 1.70 (3H, dd, J=7 Hz, 2 Hz).

(32c) 4-[(2E)-Buten-2-yloxy]-N-{2-[(2-hydroxyethyl)amino]-2-oxo-1-[4-(trifluoromethoxy)benzyl]ethyl}benzamide DMT-MM (278 mg, 1.01 mmol) was added to a methanol (4 mL) solution of 2-({4-[(2E)-buten-2-yloxy]benzoyl}amino)-3-[4-(trifluoromethoxy)phenyl]propanoic acid (284 mg, 0.67 mmol) prepared in Example 32 (32b) and 2-aminoethanol (49 μL, 0.80 mmol) at room temperature. The mixture was stirred at the same temperature for 20 hours. The solvent was evaporated, and the residue was purified by silica gel column chromatography (n-hexane:ethyl acetate of 1:1 to ethyl acetate, V/V) to give a white powder. This powder was washed with water and dried to give 114 mg of the title compound (white powder, yield: 36%).

MS (FAB) m/z: 467 $[M+H]^+$;

$^1$H-Nuclear Magnetic Resonance Spectra (400 MHz, DMSO-$d_6$) δ ppm:

8.38 (1H, d, J=8 Hz), 8.05 (1H, t, J=6 Hz), 7.73 (2H, d, J=9 Hz), 7.41 (2H, d, J=9 Hz), 7.22 (2H, d, J=9 Hz), 6.93 (2H, d, J=9 Hz), 5.87-5.81 (1H, m), 5.70-5.63 (1H, m), 4.68-4.62 (2H, m), 4.51 (2H, d, J=6 Hz), 3.37 (2H, q, J=5 Hz), 3.16-3.12 (2H, m), 3.09 (1H, dd, J=14 Hz, 4 Hz), 2.99 (1H, dd, J=14 Hz, 11 Hz), 1.70 (3H, dd, J=7 Hz, 1 Hz).

Example 33

N-{1-[4-(Difluoromethoxy)benzyl]-2-[(2-hydroxyethyl)amino]-2-oxoethyl}-4-(3,3,3-trifluoropropoxy)benzamide (Exemplary Compound No. 93)

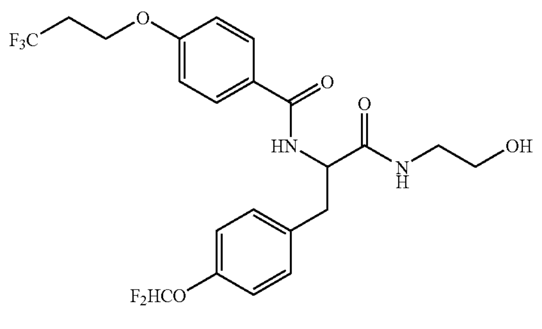

(33a) N-[4-(3,3,3-Trifluoropropoxy)benzoyl]glycine

Reactions similar to those described in Example 1 (1a) and (1b) were conducted using methyl 4-hydroxybenzoate (1.52 g, 10.0 mmol) and 3,3,3-trifluoropropan-1-ol (1.14 g, 10.0 mmol) to give 385 mg of the title compound (white powder, yield: 14%).

MS (FAB) m/z: 292 $[M+H]^+$;

$^1$H-Nuclear Magnetic Resonance Spectra (400 MHz, DMSO-$d_6$) δ ppm:

12.52 (1H, brs), 8.68 (1H, t, J=6 Hz), 7.83 (2H, d, J=9 Hz), 7.02 (2H, d, J=9 Hz), 4.26 (2H, t, J=6 Hz), 3.88 (2H, d, J=6 Hz), 2.86-2.75 (2H, m).

(33b) N-{1-[4-(Difluoromethoxy)benzyl]-2-[(2-hydroxyethyl)amino]-2-oxoethyl}-4-(3,3,3-trifluoropropoxy)benzamide A reaction similar to that described in Example 1 (1c) was conducted using N-[4-(3,3,3-trifluoropropoxy)benzoyl]glycine (350 mg) prepared in Example 33 (33a) and 4-(difluoromethoxy)benzaldehyde (167 μL) to give the corresponding oxazolone (304 mg). A reaction similar to that described in Example 1 (1d) was conducted using 300 mg of this oxazolone to give 284 mg of N-((Z)-2-[4-(difluoromethoxy)phenyl]-1-{[(2-hydroxyethyl)amino]carbonyl}vinyl)-4-(3,3,3-trifluoropropoxy)benzamide (white powder).

MS (FAB) m/z: 489 $[M+H]^+$;

$^1$H-Nuclear Magnetic Resonance Spectra (400 MHz, DMSO-$d_6$) δ ppm:

9.77 (1H, s), 8.03 (1H, t, J=5 Hz), 7.98 (2H, d, J=9 Hz), 7.59 (2H, d, J=9 Hz), 7.25 (1H, t, J=74 Hz), 7.19 (1H, s), 7.13 (2H, d, J=9 Hz), 7.08 (2H, d, J=9 Hz), 4.63 (1H, t, J=5 Hz), 4.30 (2H, t, J=6 Hz), 3.44 (2H, q, J=6 Hz), 3.23 (2H, q, J=6 Hz), 2.88-2.77 (2H, m).

A reaction similar to that described in Example (1 (1e) was conducted using N-((Z)-2-[4-(difluoromethoxy)phenyl]-1-{[(2-hydroxyethyl)amino]carbonyl}vinyl)-4-(3,3,3-trifluoropropoxy)benzamide (204 mg) to give 140 mg of the title compound (white powder).

MS (FAB) m/z: 491 $[M+H]^+$;

$^1$H-Nuclear Magnetic Resonance Spectra (400 MHz, DMSO-$d_6$) δ ppm:

8.43 (1H, d, J=8 Hz), 8.08 (1H, t, J=6 Hz), 7.80 (2H, d, J=9 Hz), 7.37 (2H, d, J=9 Hz), 7.16 (1H, t, J=74 Hz), 7.05 (2H, d, J=9 Hz), 7.01 (2H, d, J=9 Hz), 4.69 (1H, t, J=5 Hz), 4.68-4.62 (1H, m), 4.26 (2H, t, J=6 Hz), 3.39 (2H, q, J=6 Hz), 3.18-3.13 (2H, m), 3.06 (1H, dd, J=14 Hz, 4 Hz), 2.97 (1H, dd, J=14 Hz, 11 Hz), 2.86-2.75 (2H, m).

Example 34

N-{2-[(2-Hydroxyethyl)amino]-2-oxo-1-[4-(trifluoromethoxy)benzyl]ethyl}-4-(3,3,3-trifluoropropoxy)benzamide (Exemplary Compound No. 94)

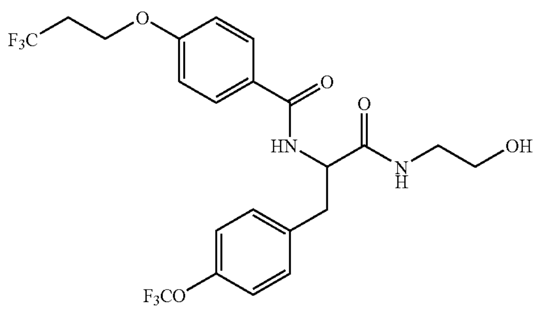 [SMILES: O=C(NC(Cc1ccc(OC(F)(F)F)cc1)C(=O)NCCO)c1ccc(OCCC(F)(F)F)cc1]

A reaction similar to that described in Example (1 (1c) was conducted using N-[4-(3,3,3-trifluoropropoxy)benzoyl]glycine (291 mg) prepared in Example 33 (33a) and 4-(trifluoromethoxy)benzaldehyde (150 μL) to give the corresponding oxazolone (390 mg). A reaction similar to that described in Example 1 (1d) was conducted using all this oxazolone to give 349 mg of N-{(Z)-1-{[(2-hydroxyethyl)amino]carbonyl}-2-[4-(trifluoromethoxy)phenyl]vinyl}-4-(3,3,3-trifluoropropoxy)benzamide (white powder).

MS (FAB) m/z: 507 $[M+H]^+$;

$^1$H-Nuclear Magnetic Resonance Spectra (500 MHz, DMSO-$d_6$) δ ppm:

9.82 (1H, s), 8.08 (1H, t, J=6 Hz), 7.97 (2H, d, J=9 Hz), 7.64 (2H, d, J=9 Hz), 7.34 (2H, d, J=9 Hz), 7.17 (1H, s), 7.08 (2H, d, J=9 Hz), 4.64 (1H, t, J=5 Hz), 4.30 (2H, t, J=6 Hz), 3.45 (2H, q, J=6 Hz), 3.23 (2H, q, J=6 Hz), 2.87-2.78 (2H, m).

A reaction similar to that described in Example 1 (1e) was conducted using N-{(Z)-1-{[(2-hydroxyethyl)amino]carbonyl}-2-[4-(trifluoromethoxy)phenyl]vinyl}-4-(3,3,3-trifluoropropoxy)benzamide (273 mg) to give 210 mg of the title compound (white powder).

MS (FAB) m/z: 509 $[M+H]^+$;

$^1$H-Nuclear Magnetic Resonance Spectra (400 MHz, DMSO-$d_6$) δ ppm:

8.43 (1H, d, J=9 Hz), 8.07 (1H, t, J=6 Hz), 7.77 (2H, d, J=9 Hz), 7.41 (2H, d, J=9 Hz), 7.21 (2H, d, J=9 Hz), 6.98 (2H, d, J=9 Hz), 4.69-4.63 (2H, m), 4.24 (2H, t, J=6 Hz), 3.38 (2H, q, J=6 Hz), 3.16-3.12 (2H, m), 3.09 (1H, dd, J=14 Hz, 4 Hz), 2.99 (1H, dd, J=14 Hz, 11 Hz), 2.86-2.73 (2H, m).

Example 35

N-{1-[4-(Cyclopropyloxy)benzyl]-2-[(2-hydroxyethyl)amino]-2-oxoethyl}-4-(3,3,3-trifluoropropoxy)benzamide (Exemplary Compound No. 91)

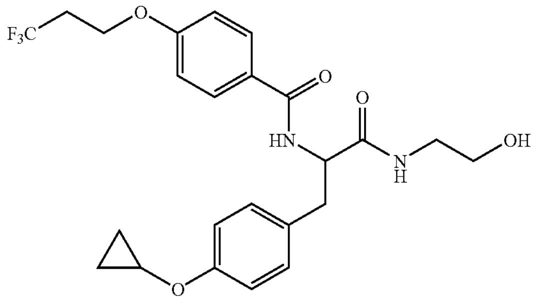 [SMILES: O=C(NC(Cc1ccc(OC2CC2)cc1)C(=O)NCCO)c1ccc(OCCC(F)(F)F)cc1]

A reaction similar to that described in Example (1 (1c) was conducted using N-[4-(3,3,3-trifluoropropoxy)benzoyl]glycine (291 mg) prepared in Example 33 (33a) and 4-(cyclopropyloxy)benzaldehyde (170 mg) prepared in Example 5 (5c) to give the corresponding oxazolone (384 mg). A reaction similar to that described in Example 1 (1d) was conducted using all this oxazolone to give 374 mg of N-((Z)-2-[4-(cyclopropyloxy)phenyl]-1-{[(2-hydroxyethyl)amino]carbonyl}vinyl)-4-(3,3,3-trifluoropropoxy)benzamide (yellow solid).

MS (FAB) m/z: 479 $[M+H]^+$;

$^1$H-Nuclear Magnetic Resonance Spectra (400 MHz, DMSO-$d_6$) δ ppm:

9.71 (1H, s), 8.00 (2H, d, J=9 Hz), 7.92 (1H, t, J=6 Hz), 7.50 (2H, d, J=9 Hz), 7.20 (1H, s), 7.09 (2H, d, J=9 Hz), 7.00 (2H, d, J=9 Hz), 4.63 (1H, t, J=5 Hz), 4.31 (2H, t, J=6 Hz), 3.85-3.81 (1H, m), 3.44 (2H, q, J=6 Hz), 3.22 (2H, q, J=6 Hz), 2.89-2.77 (2H, m), 0.78-0.74 (2H, m), 0.64-0.60 (2H, m).

A reaction similar to that described in Example 1 (1e) was conducted using all this N-((Z)-2-[4-(cyclopropyloxy)phenyl]-1-{[(2-hydroxyethyl)amino]carbonyl}vinyl)-4-(3,3,3-trifluoropropoxy)benzamide to give 176 mg of the title compound (white powder).

MS (FAB) m/z: 481 $[M+H]^+$;

$^1$H-Nuclear Magnetic Resonance Spectra (500 MHz, DMSO-$d_6$) δ ppm:

8.38 (1H, d, J=8 Hz), 8.03 (1H, t, J=5 Hz), 7.80 (2H, d, J=9 Hz), 7.23 (2H, d, J=9 Hz), 7.01 (2H, d, J=9 Hz), 6.91 (2H, d, J=9 Hz), 4.67 (1H, t, J=5 Hz), 4.62-4.57 (1H, m), 4.26 (2H, t, J=6 Hz), 3.76-3.72 (1H, m), 3.38 (2H, q, J=6 Hz), 3.17-3.12 (2H, m), 3.00 (1H, dd, J=14 Hz, 4 Hz), 2.91 (1H, dd, J=14 Hz, 11 Hz), 2.85-2.76 (2H, m), 0.74-0.71 (2H, m), 0.60-0.57 (2H, m).

Example 36

N-{1-(4-Ethoxybenzyl)-2-[(2-hydroxyethyl)amino]-2-oxoethyl}-4-(3,3,3-trifluoropropoxy)benzamide (Exemplary Compound No. 100)

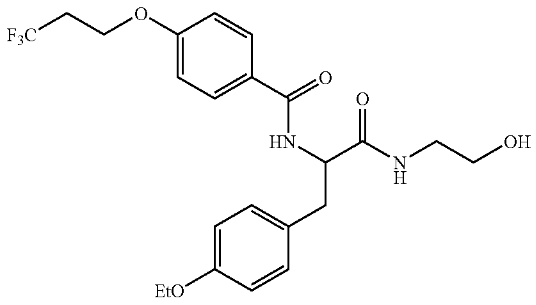 [SMILES: CCOc1ccc(CC(NC(=O)c2ccc(OCCC(F)(F)F)cc2)C(=O)NCCO)cc1]

A reaction similar to that described in Example 1 (1c) was conducted using N-[4-(3,3,3-trifluoropropoxy)benzoyl]glycine (350 mg) prepared in Example 33 (33a) and 4-ethoxybenzaldehyde (190 mg) to give the corresponding oxazolone (285 mg). A reaction similar to that described in Example 1 (1d) was conducted using 282 mg of this oxazolone to give 324 mg of N-((Z)-2-(4-ethoxyphenyl)-1-{[(2-hydroxyethyl)amino]carbonyl}vinyl)-4-(3,3,3-trifluoropropoxy)benzamide (light yellow amorphous solid).

MS (FAB) m/z: 467 $[M+H]^+$;

$^1$H-Nuclear Magnetic Resonance Spectra (400 MHz, DMSO-$d_6$) δ ppm:

9.70 (1H, s), 7.99 (2H, d, J=9 Hz), 7.91 (1H, t, J=5 Hz), 7.48 (2H, d, J=9 Hz), 7.20 (1H, s), 7.09 (2H, d, J=9 Hz), 6.88 (2H, d, J=9 Hz), 4.62 (1H, t, J=5 Hz), 4.31 (2H, t, J=6 Hz), 4.01 (2H, q, J=7 Hz), 3.43 (2H, q, J=6 Hz), 3.22 (2H, q, J=6 Hz), 2.89-2.78 (2H, m), 1.29 (3H, t, J=7 Hz).

A reaction similar to that described in Example 1 (1e) was conducted using N-((Z)-2-(4-ethoxyphenyl)-1-{[(2-hydroxyethyl)amino]carbonyl}vinyl)-4-(3,3,3-trifluoropropoxy)benzamide (244 mg) to give 182 mg of the title compound (white powder).

MS (FAB) m/z: 469 $[M+H]^+$;

$^1$H-Nuclear Magnetic Resonance Spectra (400 MHz, DMSO-$d_6$) δ ppm:

8.37 (1H, d, J=7 Hz), 8.03 (1H, t, J=6 Hz), 7.80 (2H, d, J=9 Hz), 7.21 (2H, d, J=9 Hz), 7.01 (2H, d, J=9 Hz), 6.78 (2H, d, J=9 Hz), 4.67 (1H, t, J=5 Hz), 4.62-4.57 (1H, m), 4.26 (2H, t,

J=6 Hz), 3.92 (2H, q, J=7 Hz), 3.39 (2H, q, J=9 Hz), 3.17-3.12 (2H, m), 2.99 (1H, dd, J=14 Hz, 4 Hz), 2.89 (1H, dd, J=13 Hz, 11 Hz), 2.85-2.75 (2H, m), 1.27 (3H, t, J=7 Hz).

Example 37

N-{2-[(2-Hydroxyethyl)amino]-2-oxo-1-[4-(trifluoromethyl)benzyl]ethyl}-4-(3,3,3-trifluoropropoxy)benzamide (Exemplary Compound No. 95)

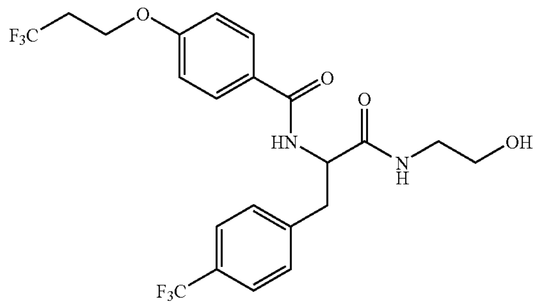

A reaction similar to that described in Example 1 (1c) was conducted using N-[4-(3,3,3-trifluoropropoxy)benzoyl]glycine (291 mg) prepared in Example 33 (33a) and 4-(trifluoromethyl)benzaldehyde (183 mg) to give the corresponding oxazolone (378 mg). A reaction similar to that described in Example 1 (1d) was conducted using all this oxazolone to give 357 mg of N-{(Z)-1-{[(2-hydroxyethyl)amino]carbonyl}-2-[4-(trifluoromethyl)phenyl]vinyl}-4-(3,3,3-trifluoropropoxy)benzamide (white powder).

MS (FAB) m/z: 491 $[M+H]^+$;

$^1$H-Nuclear Magnetic Resonance Spectra (400 MHz, DMSO-$d_6$) δ ppm:

9.86 (1H, s), 8.16 (1H, t, J=5 Hz), 7.96 (2H, d, J=9 Hz), 7.70 (4H, s), 7.17 (1H, s), 7.08 (2H, d, J=9 Hz), 4.64 (1H, t, J=5 Hz), 4.30 (2H, t, J=6 Hz), 3.46 (2H, q, J=6 Hz), 3.24 (2H, q, J=6 Hz), 2.88-2.77 (2H, m).

A reaction similar to that described in Example 1 (1e) was conducted using N-{(Z)-1-{[(2-hydroxyethyl)amino]carbonyl}-2-[4-(trifluoromethyl)phenyl]vinyl}-4-(3,3,3-trifluoropropoxy)benzamide (256 mg) to give 163 mg of the title compound (white powder).

MS (FAB) m/z: 493 $[M+H]^+$;

$^1$H-Nuclear Magnetic Resonance Spectra (500 MHz, DMSO-$d_6$) δ ppm:

8.48 (1H, d, J=8 Hz), 8.12 (1H, t, J=6 Hz), 7.79 (2H, d, J=9 Hz), 7.62 (2H, d, J=8 Hz), 7.55 (2H, d, J=8 Hz), 7.00 (2H, d, J=9 Hz), 4.75-4.69 (2H, m), 4.26 (2H, t, J=6 Hz), 3.43-3.38 (2H, m), 3.19-3.14 (3H, m), 3.07 (1H, dd, J=14 Hz, 11 Hz), 2.85-2.76 (2H, m).

Example 38

N-{1-(4-Cyclopropylbenzyl)-2-[(2-hydroxyethyl)amino]-2-oxoethyl}-4-(3,3,3-trifluoropropoxy)benzamide (Exemplary Compound No. 92)

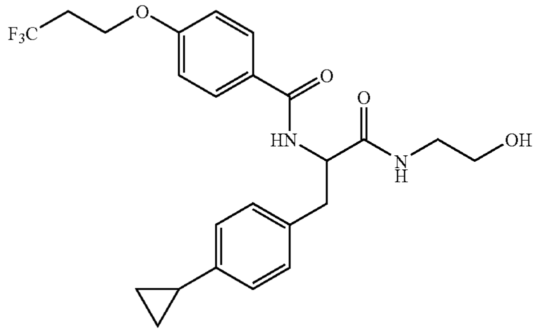 [SMILES: O=C(NC(Cc1ccc(C2CC2)cc1)C(=O)NCCO)c1ccc(OCCC(F)(F)F)cc1]

A reaction similar to that described in Example 1 (1c) was conducted using N-[4-(3,3,3-trifluoropropoxy)benzoyl]glycine (1.46 g) prepared in Example 33 (33a) and 4-cyclopropylbenzaldehyde (768 mg) to give the corresponding oxazolone (1.72 g). A reaction similar to that described in Example 1 (1d) was conducted using all this oxazolone to give 1.22 g of N-((Z)-2-(4-cyclopropylphenyl)-1-{[(2-hydroxyethyl)amino]carbonyl}vinyl)-4-(3,3,3-trifluoropropoxy)benzamide (white powder).

MS (FAB) m/z: 463 $[M+H]^+$;

$^1$H-Nuclear Magnetic Resonance Spectra (400 MHz, DMSO-$d_6$) δ ppm:

9.69 (1H, brs), 7.96 (2H, d, J=9 Hz), 7.93 (1H, brt, J=5 Hz), 7.39 (2H, d, J=8 Hz), 7.15 (1H, s), 7.06 (2H, d, J=9 Hz), 7.00 (2H, d, J=8 Hz), 4.61 (1H, t, J=5 Hz), 4.29 (2H, t, J=6 Hz), 3.43 (2H, q, J=6 Hz), 3.22 (2H, q, J=6 Hz), 2.88-2.77 (2H, m), 1.90-1.83 (1H, m), 0.95-0.91 (2H, m), 0.67-0.64 (2H, m).

A reaction similar to that described in Example 2 was conducted using N-((Z)-2-(4-cyclopropylphenyl)-1-{[(2-hydroxyethyl)amino]carbonyl}vinyl)-4-(3,3,3-trifluoropropoxy)benzamide (185 mg) to give 109 mg of the title compound (white powder).

MS (FAB) m/z: 465 $[M+H]^+$;

$^1$H-Nuclear Magnetic Resonance Spectra (400 MHz, DMSO-$d_6$) δ ppm:

8.38 (1H, d, J=8 Hz), 8.03 (1H, t, J=6 Hz), 7.80 (2H, d, J=9 Hz), 7.18 (2H, d, J=8 Hz), 7.01 (2H, d, J=9 Hz), 6.93 (2H, d, J=8 Hz), 4.66 (1H, t, J=6 Hz), 4.63-4.57 (1H, m), 4.26 (2H, t, J=6 Hz), 3.39 (2H, q, J=6 Hz), 3.17-3.12 (2H, m), 3.00 (1H, dd, J=14 Hz, 4 Hz), 2.91 (1H, dd, J=14 Hz, 11 Hz), 2.85-2.76 (2H, m), 1.85-1.78 (1H, m), 0.89-0.85 (2H, m), 0.60-0.56 (2H, m).

Example 39

N-{1-(4-Ethylbenzyl)-2-[(2-hydroxyethyl)amino]-2-oxoethyl}-4-(3,3,3-trifluoropropoxy)benzamide (Exemplary Compound No. 101)

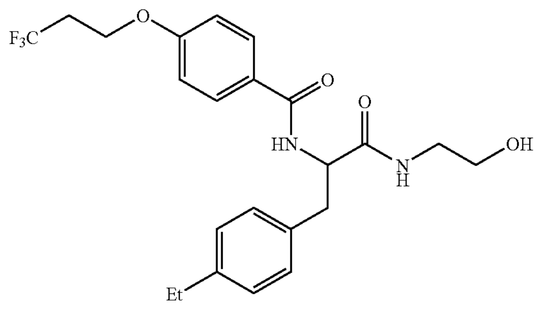 [SMILES: CCc1ccc(CC(NC(=O)c2ccc(OCCC(F)(F)F)cc2)C(=O)NCCO)cc1]

A reaction similar to that described in Example 1 (1c) was conducted using N-[4-(3,3,3-trifluoropropoxy)benzoyl]glycine (350 mg) prepared in Example 33 (33a) and 4-ethylbenzaldehyde (173 μL) to give the corresponding oxazolone (281 mg). A reaction similar to that described in Example 1 (1d) was conducted using 278 mg of this oxazolone to give 257 mg of N-((Z)-2-(4-ethylphenyl)-1-{[(2-hydroxyethyl)amino]carbonyl}vinyl)-4-(3,3,3-trifluoropropoxy)benzamide (white powder).

MS (FAB) m/z: 451 $[M+H]^+$;

$^1$H-Nuclear Magnetic Resonance Spectra (400 MHz, DMSO-$d_6$) δ ppm:

9.74 (1H, s), 7.99 (2H, d, J=9 Hz), 7.97 (1H, t, J=5 Hz), 7.46 (2H, d, J=8 Hz), 7.19 (1H, s), 7.17 (2H, d, J=8 Hz), 7.09 (2H, d, J=9 Hz), 4.63 (1H, t, J=5 Hz), 4.31 (2H, t, J=6 Hz), 4.01 (2H, q, J=7 Hz), 3.43 (2H, q, J=6 Hz), 3.22 (2H, q, J=6 Hz), 2.89-2.78 (2H, m), 1.29 (3H, t, J=7 Hz).

A reaction similar to that described in Example (1e) was conducted using N-((Z)-2-(4-ethylphenyl)-1-{[(2-hydroxyethyl)amino]carbonyl}vinyl)-4-(3,3,3-trifluoropropoxy)benzamide (177 mg) to give 67 mg of the title compound (white powder).

MS (FAB) m/z: 453 $[M+H]^+$;

$^1$H-Nuclear Magnetic Resonance Spectra (400 MHz, DMSO-$d_6$) δ ppm:

8.40 (1H, d, J=9 Hz), 8.03 (1H, t, J=5 Hz), 7.80 (2H, d, J=9 Hz), 7.22 (2H, d, J=8 Hz), 7.07 (2H, d, J=8 Hz), 7.01 (2H, d, J=9 Hz), 4.67 (1H, t, J=5 Hz), 4.64-4.58 (1H, m), 4.26 (2H, t, J=6 Hz), 3.38 (2H, q, J=6 Hz), 3.17-3.12 (2H, m), 3.02 (1H, dd, J=14 Hz, 4 Hz), 2.94 (1H, dd, J=13 Hz, 11 Hz), 2.86-2.76 (2H, m), 2.53 (2H, q, J=8), 1.12 (3H, t, J=7 Hz).

Example 40

4-[(2,2-Difluorocyclopropyl)methoxy]-N-{2-[(2-hydroxyethyl)amino]-2-oxo-1-[4-(trifluoromethoxy)benzyl]ethyl}benzamide (Exemplary Compound No. 129)

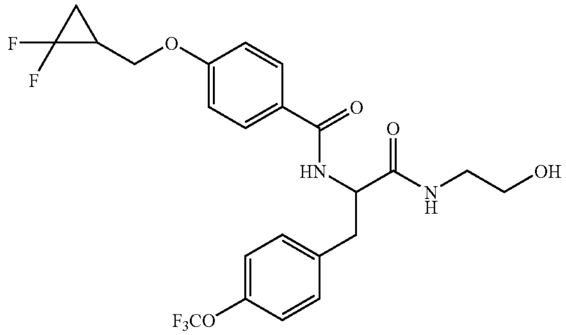 [SMILES: O=C(NC(Cc1ccc(OC(F)(F)F)cc1)C(=O)NCCO)c1ccc(OCC2CC2(F)F)cc1]

(40a) Methyl 4-[(2,2-difluorocyclopropyl)methoxy]benzoate

Trimethylsilyl fluorosulfonyldifluoroacetate (9.46 mL, 48.0 mmol) was slowly added to a mixture of methyl 4-(allyloxy)benzoate (compound described in J. Org. Chem., (2004), 69, 4482-4486, 3.69 g, 19.0 mmol) and sodium fluoride (7.9 mg, 0.19 mmol) at 100° C. over 4 hours according to the method described in the document (J. Fluorine Chem., (2001), 112, 63-68). The resulting mixture was stirred at the same temperature for 4.5 hours. The reaction solution was cooled to room temperature and purified by silica gel column chromatography (n-hexane to n-hexane:ethyl acetate, 97:3, 95:5, 90:10, and 85:15, V/V) to give 3.80 g of the title compound (white solid, yield: 83%).

MS (FAB) m/z 243 $[M+H]^+$;

$^1$H-Nuclear Magnetic Resonance Spectra (400 MHz, $CDCl_3$) δ ppm:

7.97 (2H, d, J=9 Hz), 6.90 (2H, d, J=9 Hz), 4.14-4.09 (1H, m), 4.07-4.02 (1H, m), 3.88 (3H, s), 2.12-2.02 (1H, m), 1.66-1.57 (1H, m), 1.34-1.26 (1H, m).

(40b) 4-[(2,2-Difluorocyclopropyl)methoxy]benzoic acid

Methyl 4-[(2,2-difluorocyclopropyl)methoxy]benzoate (1.94 g, 8.01 mmol) prepared in Example 40 (40a) was dissolved in ethanol (24 mL), and a 2 M lithium hydroxide aqueous solution (8 mL, 16 mmol) was added thereto at room temperature. The resulting mixture was stirred at the same temperature for 18 hours. The solvents (mainly ethanol) were evaporated, and water was added to the obtained residue. Then, the resulting mixture was changed to weak acidic by adding 2 N hydrochloric acid under ice-cooling with stirring. The precipitated insoluble substance was collected by filtration, washed with water and n-hexane, and dried under reduced pressure to give 1.73 g of the title compound (white powder, yield: 95%).

MS (EI) m/z: 228 $[M]^+$;

$^1$H-Nuclear Magnetic Resonance Spectra (400 MHz, DMSO-$d_6$) δ ppm:

12.62 (1H, brs), 7.86 (2H, d, J=9 Hz), 7.02 (2H, d, J=9 Hz), 4.24-4.19 (1H, m), 4.07-4.02 (1H, m), 2.31-2.19 (1H, m), 1.78-1.69 (1H, m), 1.54-1.46 (1H, m).

(40c) 2-({4-[(2,2-Difluorocyclopropyl)methoxy]benzoyl}amino)-3-[4-(trifluoromethoxy)phenyl]propanoic acid A reaction similar to that described in Example 32 (32b) was conducted using tert-butyl 2-amino-3-[4-(trifluoromethoxy)phenyl]propanoate (366 mg, 1.20 mmol) and 4-[(2,2-difluorocyclopropyl)methoxy]benzoic acid (274 mg, 1.20 mmol) prepared in Example 40 (40b) to give 360 mg of the title compound (white powder, yield: 66%).

MS (FAB) m/z: 460 [M+H];

$^1$H-Nuclear Magnetic Resonance Spectra (500 MHz, DMSO-$d_6$) δ ppm:

12.76 (1H, brs), 8.59 (1H, d, J=8 Hz), 7.78 (2H, d, J=9 Hz), 7.42 (2H, d, J=9 Hz), 7.26 (2H, d, J=9 Hz), 7.01 (2H, d, J=9 Hz), 4.63-4.58 (1H, m), 4.23-4.19 (1H, m), 4.03 (1H, t, J=10 Hz), 3.21 (1H, dd, J=14 Hz, 4 Hz), 3.10 (1H, dd, J=14 Hz, 11 Hz), 2.29-2.19 (1H, m), 1.77-1.70 (1H, m), 1.52-1.46 (1H, m).

(40d) 4-[(2,2-Difluorocyclopropyl)methoxy]-N-{2-[(2-hydroxyethyl)amino]-2-oxo-1-[4-(trifluoromethoxy)benzyl]ethyl}benzamide A reaction similar to that described in Example 32 (32c) was conducted using 2-({4-[(2,2-difluorocyclopropyl)methoxy]benzoyl}amino)-3-[4-(trifluoromethoxy)phenyl]propanoic acid (352 mg, 0.766 mmol) prepared in Example 40 (40c) and 2-aminoethanol (55 μL, 0.919 mmol) to give 243 mg of the title compound (white powder, yield: 63%).

MS (FAB) m/z: 503 $[M+H]^+$;

$^1$H-Nuclear Magnetic Resonance Spectra (500 MHz, DMSO-$d_6$) δ ppm:

8.42 (1H, d, J=8 Hz), 8.07 (1H, t, J=5 Hz), 7.78 (2H, d, J=9 Hz), 7.43 (2H, d, J=9 Hz), 7.23 (2H, d, J=8 Hz), 7.00 (2H, d, J=8 Hz), 4.70-4.65 (2H, m), 4.22-4.18 (1H, m), 4.03 (1H, t, J=9 Hz), 3.38 (2H, q, J=6 Hz), 3.17-3.13 (2H, m), 3.10 (1H, dd, J=14 Hz, 4 Hz), 3.00 (1H, dd, J=14 Hz, 11 Hz), 2.28-2.19 (1H, m), 1.77-1.69 (1H, m), 1.52-1.45 (1H, m).

Example 41

N-{1-[4-(Difluoromethoxy)benzyl]-2-[(2-hydroxyethyl)amino]-2-oxoethyl}-4-[4-(trifluoromethyl)phenoxy]benzamide (Exemplary Compound No. 148)

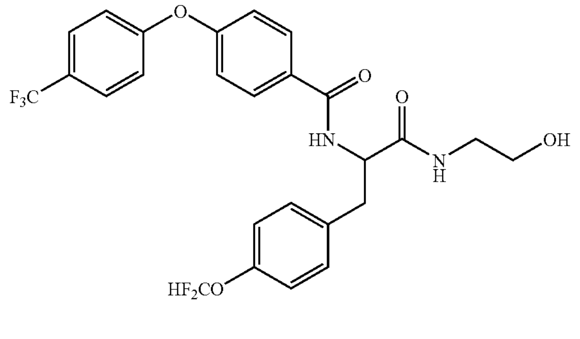

(41a) N-{4-[4-(Trifluoromethyl)phenoxy]benzoyl}glycine

A reaction similar to that described in Example 1 (1b) was conducted using 4-[4-(trifluoromethyl)phenoxy]benzoic acid (compound described in International Publication No. WO 04/14844, 7.06 g, 25.0 mmol) and glycine (1.88 g, 25.0 mmol) to give 8.38 g of the title compound (white powder, yield: 99%)

MS (FAB) m/z: 340 $[M+H]^+$; .

$^1$H-Nuclear Magnetic Resonance Spectra (400 MHz, DMSO-$d_6$) δ ppm:

12.53 (1H, brs), 8.82 (1H, t, J=6 Hz), 7.93 (2H, d, J=9 Hz), 7.76 (2H, d, J=9 Hz), 7.21 (2H, d, J=9 Hz), 7.18 (2H, d, J=9 Hz), 3.91 (2H, d, J=6 Hz).

(41b) N-{1-[4-(Difluoromethoxy)benzyl]-2-[(2-hydroxyethyl)amino]-2-oxoethyl}-4-[4-(trifluoromethyl)phenoxy]benzamide A reaction similar to that described in Example 1 (1c) was conducted using N-{4-[4-(trifluoromethyl)phenoxy]benzoyl}glycine (350 mg) prepared in Example 41 (41a) and 4-(difluoromethoxy)benzaldehyde (151 μL) to give the corresponding oxazolone (218 mg). A reaction similar to that described in Example 1 (1d) was conducted using 215 mg of this oxazolone to give 222 mg of N-((Z)-2-[4-(difluoromethoxy)phenyl]-1-{[(2-hydroxyethyl)amino]carbonyl}vinyl)-4-[4-(trifluoromethyl)phenoxy]benzamide (white amorphous solid).

MS (FAB) m/z: 537 $[M+H]^+$;

$^1$H-Nuclear Magnetic Resonance Spectra (400 MHz, DMSO-$d_6$) δ ppm:

9.92 (1H, s), 8.10-8.07 (3H, m), 7.81 (2H, d, J=9 Hz), 7.62 (2H, d, J=9 Hz), 7.27 (1H, t, J=74 Hz), 7.25 (1H, s), 7.24 (2H, d, J=9 Hz), 7.23 (2H, d, J=9 Hz), 7.16 (2H, d, J=9 Hz), 4.65 (1H, t, J=5 Hz), 3.46 (2H, q, J=6 Hz), 3.25 (2H, q, J=6 Hz).

A reaction similar to that described in Example 1 (1e) was conducted using N-((Z)-2-[4-(difluoromethoxy)phenyl]-1-{[(2-hydroxyethyl)amino]carbonyl}vinyl)-4-[4-(trifluoromethyl)phenoxy]benzamide (148 mg) to give 138 mg of the title compound (white powder).

MS (FAB) m/z: 539 $[M+H]^+$;

$^1$H-Nuclear Magnetic Resonance Spectra (400 MHz, DMSO-$d_6$) δ ppm:

8.59 (1H, d, J=8 Hz), 8.11 (1H, t, J=5 Hz), 7.90 (2H, d, J=9 Hz), 7.77 (2H, d, J=9 Hz), 7.38 (2H, d, J=8 Hz), 7.21 (2H, d, J=9 Hz), 7.17 (2H, d, J=9 Hz), 7.17 (1H, t, J=75 Hz), 7.07 (2H, d, J=9 Hz), 4.71-4.65 (2H, m), 3.40 (2H, q, J=6 Hz), 3.16 (2H, q, J=6 Hz), 3.08 (1H, dd, J=13 Hz, 4 Hz), 2.97 (1H, dd, J=13 Hz, 11 Hz).

Example 42

N-{2-[(2-Hydroxyethyl)amino]-2-oxo-1-[4-(trifluoromethoxy)benzyl]ethyl}-4-[4-(trifluoromethyl)phenoxy]benzamide (Exemplary Compound No. 149)

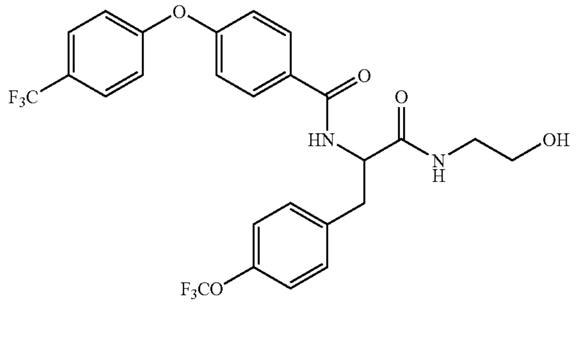 [SMILES: O=C(NC(Cc1ccc(OC(F)(F)F)cc1)C(=O)NCCO)c1ccc(Oc2ccc(C(F)(F)F)cc2)cc1]

A reaction similar to that described in Example 1 (1c) was conducted using N-{4-[4-(trifluoromethyl)phenoxy]benzoyl}glycine (382 mg) prepared in Example 41 (41a) and 4-(trifluoromethoxy)benzaldehyde (225 mg) to give the corresponding oxazolone (256 mg). A reaction similar to that described in Example 1 (1d) was conducted using all this oxazolone to give 256 mg of N-{(Z)-1-{[(2-hydroxyethyl) amino]carbonyl}-2-[4-(trifluoromethoxy)phenyl]vinyl}-4-[4-(trifluoromethyl)phenoxy]benzamide (white powder).

MS (FAB) m/z: 555 $[M+H]^+$;

$^1$H-Nuclear Magnetic Resonance Spectra (400 MHz, DMSO-$d_6$) δ ppm:

9.93 (1H, s), 8.10 (1H, t, J=6 Hz), 8.04 (2H, d, J=9 Hz), 7.78 (2H, d, J=8 Hz), 7.64 (2H, d, J=9 Hz), 7.34 (2H, d, J=8 Hz), 7.23 (2H, d, J=8 Hz), 7.21 (2H, d, J=9 Hz), 7.17 (1H, s), 4.63 (1H, t, J=5 Hz), 3.44 (2H, q, J=6 Hz), 3.23 (2H, q, J=6 Hz).

A reaction similar to that described in Example 1 (1e) was conducted using N-{(Z)-1-{[(2-hydroxyethyl)amino]carbonyl}-2-[4-(trifluoromethoxy)phenyl]vinyl}-4-[4-(trifluoromethyl)phenoxy]benzamide (190 mg) to give 155 mg of the title compound (white powder).

MS (FAB) m/z: 557 $[M+H]^+$;

$^1$H-Nuclear Magnetic Resonance Spectra (400 MHz, DMSO-$d_6$) δ ppm:

8.58 (1H, d, J=8 Hz), 8.10 (1H, t, J=5 Hz), 7.87 (2H, d, J=9 Hz), 7.75 (2H, d, J=9 Hz), 7.43 (2H, d, J=9 Hz), 7.23 (2H, d, J=8 Hz), 7.19 (2H, d, J=8 Hz), 7.14 (2H, d, J=9 Hz), 4.73-4.67 (2H, m), 3.38 (2H, q, J=6 Hz), 3.18-3.09 (3H, m), 3.00 (1H, dd, J=13 Hz, 11 Hz).

Example 43

N-{1-[4-(Cyclopropyloxy)benzyl]-2-[(2-hydroxyethyl)amino]-2-oxoethyl}-4-[4-(trifluoromethyl) phenoxy]benzamide (Exemplary Compound No. 146)

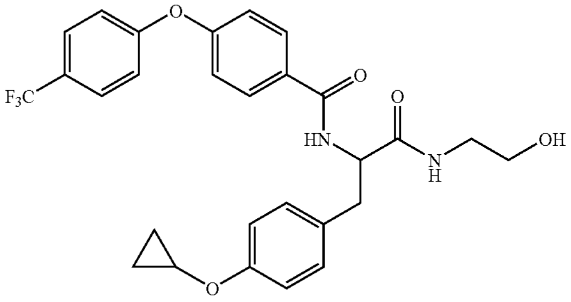 [SMILES: O=C(NC(Cc1ccc(OC2CC2)cc1)C(=O)NCCO)c1ccc(Oc2ccc(C(F)(F)F)cc2)cc1]

A reaction similar to that described in Example 1 (1c) was conducted using N-{4-[4-(trifluoromethyl)phenoxy] benzoyl}glycine (339 mg) prepared in Example 41 (41a) and 4-(cyclopropyloxy)benzaldehyde (170 mg) prepared in Example 5 (5c) to give the corresponding oxazolone. This oxazolone was directly used for a reaction similar to that described in Example 1 (1d) to give 217 mg of N-((Z)-2-[4-(cyclopropyloxy)phenyl]-1-{[(2-hydroxyethyl)amino] carbonyl}vinyl)-4-[4-(trifluoromethyl)phenoxy]benzamide (white powder).

MS (ESI) m/z: 527 $[M+H]^+$;

$^1$H-Nuclear Magnetic Resonance Spectra (500 MHz, DMSO-$d_6$) δ ppm:

9.85 (1H, s), 8.09 (2H, d, J=8 Hz), 7.96 (1H, t, J=6 Hz), 7.80 (2H, d, J=9 Hz), 7.52 (2H, d, J=9 Hz), 7.26-7.22 (5H, m), 7.02 (2H, d, J=9H), 4.63 (1H, t, J=6 Hz), 3.86-3.82 (1H, m), 3.44 (2H, q, J=6 Hz), 3.23 (2H, q, J=6 Hz), 0.79-0.75 (2H, m), 0.64-0.61 (2H, m).

A reaction similar to that described in Example 1 (1e) was conducted using N-((Z)-2-[4-(cyclopropyloxy)phenyl]-1-{[(2-hydroxyethyl)amino]carbonyl}vinyl)-4-[4-(trifluoromethyl)phenoxy]benzamide (193 mg) to give 64 mg of the title compound (white powder).

MS (FAB) m/z: 529 $[M+H]^+$;

$^1$H-Nuclear Magnetic Resonance Spectra (500 MHz, DMSO-$d_6$) δ ppm:

8.54 (1H, d, J=8 Hz), 8.07 (1H, t, J=5 Hz), 7.91 (2H, d, J=9 Hz), 7.77 (2H, d, J=8 Hz), 7.26 (2H, d, J=8 Hz), 7.21 (2H, d, J=8 Hz), 7.17 (2H, d, J=9 Hz), 6.93 (2H, d, J=8 Hz), 4.68 (1H, t, J=5 Hz), 4.67-4.62 (1H, m), 3.76-3.74 (1H, m), 3.41 (2H, q, J=6 Hz), 3.19-3.15 (2H, m), 3.03 (1H, dd, J=14 Hz, 4 Hz), 2.93 (1H, dd, J=14 Hz, 11 Hz), 0.75-0.71 (2H, m), 0.61-0.58 (2H, m).

Example 44

N-{1-(4-Ethoxybenzyl)-2-[(2-hydroxyethyl)amino]-2-oxoethyl}-4-[4-(trifluoromethyl)phenoxy]benzamide (Exemplary Compound No. 155)

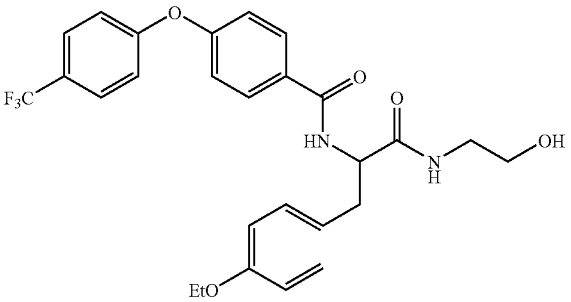 [SMILES: C=C/C(=C\C=C\CC(NC(=O)c1ccc(Oc2ccc(C(F)(F)F)cc2)cc1)C(=O)NCCO)OCC]

A reaction similar to that described in Example 1 (1c) was conducted using N-{4-[4-(trifluoromethyl)phenoxy] benzoyl}glycine (350 mg) prepared in Example 41 (41a) and 4-ethoxybenzaldehyde (151 μL) to give the corresponding oxazolone (281 mg). A reaction similar to that described in Example 1 (1d) was conducted using 278 mg of this oxazolone to give 204 mg of N-((Z)-2-(4-ethoxyphenyl)-1-{[(2-hydroxyethyl)amino]carbonyl}vinyl)-4-[4-(trifluoromethyl)phenoxy]benzamide (white amorphous solid).

MS (FAB) m/z: 515 $[M+H]^+$;

$^1$H-Nuclear Magnetic Resonance Spectra (400 MHz, DMSO-$d_6$) δ ppm:

9.85 (1H, s), 8.10 (2H, d, J=9 Hz), 7.96 (1H, t, J=5 Hz), 7.81 (2H, d, J=9 Hz), 7.51 (2H, d, J=9 Hz), 7.27-7.22 (5H, m), 6.90 (2H, d, J=9 Hz), 4.63 (1H, t, J=5 Hz), 4.02 (2H, q, J=7 Hz), 3.44 (2H, q, J=6 Hz), 3.23 (2H, q, J=6 Hz), 1.30 (3H, t, J=7 Hz).

A reaction similar to that described in Example 1 (1e) was conducted using N-((Z)-2-(4-ethoxyphenyl)-1-{[(2-hydroxyethyl)amino]carbonyl}vinyl)-4-[4-(trifluoromethyl) phenoxy]benzamide (134 mg) to give 135 mg of the title compound (white powder).

MS (FAB) m/z: 517 $[M+H]^+$;

$^1$H-Nuclear Magnetic Resonance Spectra (400 MHz, DMSO-$d_6$) δ ppm:

8.49 (1H, d, J=8 Hz), 8.03 (1H, t, J=5 Hz), 7.87 (2H, d, J=9 Hz), 7.74 (2H, d, J=9 Hz), 7.20 (2H, d, J=9 Hz), 7.18 (2H, d, J=9 Hz), 7.14 (2H, d, J=9 Hz), 6.77 (2H, d, J=9 Hz), 4.66 (1H, t, J=5 Hz), 4.65-4.59 (1H, m), 3.93 (2H, q, J=7 Hz), 3.38 (2H, q, J=5 Hz), 3.15 (2H, q, J=5 Hz), 3.00 (1H, dd, J=13 Hz, 5 Hz), 2.89 (1H, dd, J=13 Hz, 11 Hz), 1.27 (3H, t, J=7 Hz).

Example 45

N-{2-[(2-Hydroxyethyl)amino]-2-oxo-1-[4-(trifluoromethyl)benzyl]ethyl}-4-[4-(trifluoromethyl)phenoxy]benzamide (Exemplary Compound No. 150)

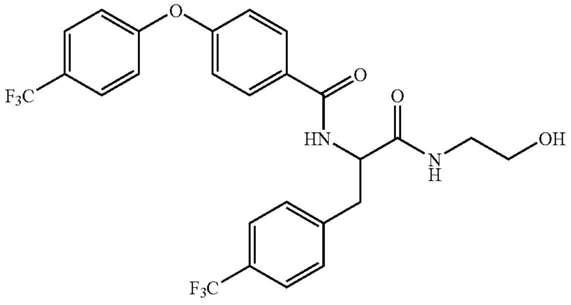

A reaction similar to that described in Example 1 (1c) was conducted using N-{4-[4-(trifluoromethyl)phenoxy]benzoyl}glycine (339 mg) prepared in Example 41 (41a) and 4-(trifluoromethyl)benzaldehyde (141 μL) to give the corresponding oxazolone (274 mg). A reaction similar to that described in Example 1 (1d) was conducted using all this oxazolone to give 196 mg of N-{(Z)-1-{[(2-hydroxyethyl)amino]carbonyl}-2-[4-(trifluoromethyl)phenyl]vinyl}-4-[4-(trifluoromethyl)phenoxy]benzamide (white amorphous solid).

MS (FAB) m/z: 539 $[M+H]^+$;

$^1$H-Nuclear Magnetic Resonance Spectra (500 MHz, DMSO-$d_6$) δ ppm:

10.00 (1H, s), 8.20 (1H, t, J=6 Hz), 8.05 (2H, d, J=9 Hz), 7.81 (2H, d, J=9 Hz), 7.73 (2H, d, J=9 Hz), 7.71 (2H, d, J=9 Hz), 7.25 (2H, d, J=9 Hz), 7.24 (1H, s), 7.21 (2H, d, J=9 Hz), 4.64 (1H, brs), 3.46 (2H, t, J=6 Hz), 3.25 (2H, q, J=6 Hz).

A reaction similar to that described in Example (1 (1e) was conducted using N-{(Z)-1-{[(2-hydroxyethyl)amino]carbonyl}-2-[4-(trifluoromethyl)phenyl]vinyl}-4-[4-(trifluoromethyl)phenoxy]benzamide (172 mg) to give 154 mg of the title compound (white powder).

MS (FAB) m/z: 541 $[M+H]^+$;

$^1$H-Nuclear Magnetic Resonance Spectra (500 MHz, DMSO-$d_6$) δ ppm:

8.63 (1H, d, J=9 Hz), 8.14 (1H, t, J=5 Hz), 7.89 (2H, d, J=9 Hz), 7.77 (2H, d, J=9 Hz), 7.63 (2H, d, J=8 Hz), 7.56 (2H, d, J=8 Hz), 7.21 (2H, d, J=9 Hz), 7.16 (2H, d, J=9 Hz), 4.77-4.73 (1H, m), 4.69 (1H, t, J=5 Hz), 3.41 (2H, q, J=6 Hz), 3.20-3.15 (3H, m), 3.08 (1H, dd, J=14 Hz, 11 Hz).

Example 46

N-{1-(4-Ethylbenzyl)-2-[(2-hydroxyethyl)amino]-2-oxoethyl}-4-[4-(trifluoromethyl)phenoxy]benzamide (Exemplary Compound No. 156)

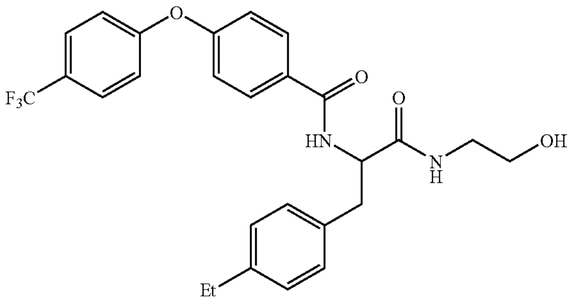 [SMILES: CCc1ccc(CC(NC(=O)c2ccc(Oc3ccc(C(F)(F)F)cc3)cc2)C(=O)NCCO)cc1]

A reaction similar to that described in Example 1 (1c) was conducted using N-{4-[4-(trifluoromethyl)phenoxy]benzoyl}glycine (339 mg) prepared in Example 41 (41a) and 4-ethylbenzaldehyde (144 μL) to give the corresponding oxazolone (235 mg). A reaction similar to that described in Example (1 (1d) was conducted using all this oxazolone to give 238 mg of N-((Z)-2-(4-ethylphenyl)-1-{[(2-hydroxyethyl)amino]carbonyl}vinyl)-4-[4-(trifluoromethyl)phenoxy]benzamide (white amorphous solid).

MS (ESI) m/z: 499 $[M+H]^+$;

$^1$H-Nuclear Magnetic Resonance Spectra (500 MHz, DMSO-$d_6$) δ ppm:

9.88 (1H, s), 8.08 (2H, d, J=9 Hz), 8.01 (1H, t, J=6 Hz), 7.80 (2H, d, J=9 Hz), 7.48 (2H, d, J=9 Hz), 7.26 (2H, d, J=9 Hz), 7.25 (1H, s), 7.22 (2H, d, J=9 Hz), 7.19 (2H, d, J=9 Hz), 4.63 (1H, t, J=5 Hz), 3.45 (2H, q, J=6 Hz), 3.23 (2H, q, J=6 Hz), 2.58 (2H, q, J=7 Hz), 1.15 (3H, t, J=7 Hz).

A reaction similar to that described in Example 1 (1e) was conducted using N-((Z)-2-(4-ethylphenyl)-1-{[(2-hydroxyethyl)amino]carbonyl}vinyl)-4-[4-(trifluoromethyl)phenoxy]benzamide (213 mg) to give 189 mg of the title compound (white powder).

MS (FAB) m/z: 501 $[M+H]^+$;

$^1$H-Nuclear Magnetic Resonance Spectra (500 MHz, DMSO-$d_6$) δ ppm:

8.54 (1H, d, J=8 Hz), 8.05 (1H, t, J=5 Hz), 7.90 (2H, d, J=9 Hz), 7.77 (2H, d, J=9 Hz), 7.24 (2H, d, J=8 Hz), 7.20 (2H, d, J=9 Hz), 7.16 (2H, d, J=9 Hz), 7.09 (2H, d, J=8 Hz), 4.68-4.63 (2H, m), 3.40 (2H, q, J=6 Hz), 3.19-3.12 (2H, m), 3.05 (1H, dd, J=14 Hz, 4 Hz), 2.95 (1H, dd, J=14 Hz, 11 Hz), 2.53 (2H, q, J=8 Hz), 1.13 (3H, t, J=8 Hz).

Example 47

4-(4-Fluorophenoxy)-N-{2-[(2-hydroxyethyl) amino]-2-oxo-1-[4-(trifluoromethoxy)benzyl] ethyl}benzamide (Exemplary Compound No. 174)

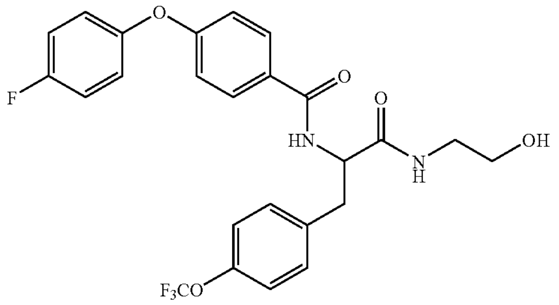 [SMILES: O=C(NC(Cc1ccc(OC(F)(F)F)cc1)C(=O)NCCO)c1ccc(Oc2ccc(F)cc2)cc1]

(47a) 2-{[4-(4-Fluorophenoxy)benzoyl]amino}-3-[4-(trifluoromethoxy)phenyl]propanoic acid Oxalyl chloride (192 μL, 2.21 mmol) and a drop of DMF were added to a methylene chloride (3 mL) solution of 4-(4-fluorophenoxy)benzoic acid (compound described in Pharmazie, (1999), 54, 260-262, 244 mg, 1.05 mmol) under ice-cooling. The mixture was stirred at room temperature for 1 hour. Then, the solvent was evaporated to give the corresponding acid chloride. Separately, 1 N sodium hydroxide (2 mL) was added to a water:THF (2:1, V/V, 1.5 mL) solution of 2-amino-3-[4-(trifluoromethoxy)phenyl]propanoic acid hydrochloride (286 mg, 1.00 mmol) under ice-cooling. To this mixture were dropwise added a THF (1 mL) solution of the above-prepared acid chloride and 1 N sodium hydroxide (1 mL) at the same time. The resulting mixture was stirred at room temperature for 3.75 hours. The solvents (mainly THF) were evaporated, and the liquid property was changed to acidic by adding 2 N hydrochloric acid under ice-cooling. After extraction with ethyl acetate, the organic layer was collected, washed with water and saturated brine, and dried over anhydrous sodium sulfate. The solvent was evaporated to give 444 mg of the title compound (white powder, yield: 96%).

MS (FAB) m/z: 464 $[M+H]^+$;

$^1$H-Nuclear Magnetic Resonance Spectra (400 MHz, DMSO-$d_6$) δ ppm:

12.77 (1H, brs), 8.68 (1H, d, J=8 Hz), 7.82 (2H, d, J=8 Hz), 7.43 (2H, d, J=8 Hz), 7.30-7.25 (4H, m), 7.16-7.13 (2H, m), 7.00 (2H, d, J=9 Hz), 4.65-4.58 (1H, m), 3.22 (1H, dd, J=14 Hz, 5 Hz), 3.10 (1H, dd, J=14 Hz, 11 Hz).

(47b) 4-(4-Fluorophenoxy)-N-{2-[(2-hydroxyethyl) amino]-2-oxo-1-[4-(trifluoromethoxy)benzyl] ethyl}benzamide A reaction similar to that described in Example 32 (32c) was conducted using 2-{[4-(4-fluorophenoxy)benzoyl] amino}-3-[4-(trifluoromethoxy)phenyl]propanoic acid (438 mg, 0.945 mmol) prepared in Example 47 (47a) and 2-aminoethanol (103 μL, 1.70 mmol) to give 396 mg of the title compound (white powder, yield: 82%).

MS (FAB) m/z: 507 $[M+H]^+$;

$^1$H-Nuclear Magnetic Resonance Spectra (400 MHz, DMSO-$d_6$) δ ppm:

8.50 (1H, d, J=8 Hz), 8.07 (1H, t, J=5 Hz), 7.80 (2H, d, J=9 Hz), 7.41 (2H, d, J=9 Hz), 7.27-7.21 (4H, m), 7.13-7.09 (2H, m), 6.96 (2H, d, J=9 Hz), 4.70-4.64 (2H, m), 3.38 (2H, q, J=6 Hz), 3.17-3.11 (2H, m), 3.10 (1H, dd, J=14 Hz, 4 Hz), 2.99 (1H, dd, J=14 Hz, 11 Hz).

Example 48

4-(4-Chlorophenoxy)-N-{2-[(2-hydroxyethyl) amino]-2-oxo-1-[4-(trifluoromethoxy)benzyl] ethyl}benzamide (Exemplary Compound No. 164)

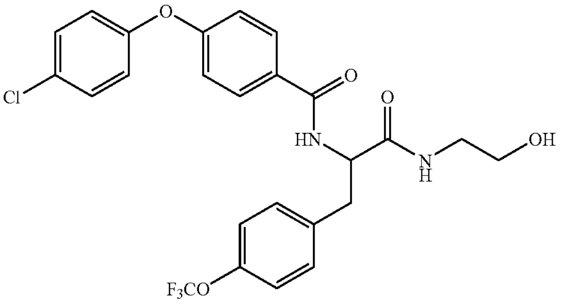 [SMILES: O=C(NC(Cc1ccc(OC(F)(F)F)cc1)C(=O)NCCO)c1ccc(Oc2ccc(Cl)cc2)cc1]

(48a) 2-{[4-(4-Chlorophenoxy)benzoyl]amino}-3-[4-(trifluoromethoxy)phenyl]propanoic acid A reaction similar to that described in Example 47 (47a) was conducted using 4-(4-chlorophenoxy)benzoic acid (compound described in Eur. J. Med. Chem., (1984), 19, 205-214, 261 mg, 1.05 mmol) to give 480 mg of the title compound (white powder, yield: quantitative).

MS (FAB) m/z: 480 $[M+H]^+$;

$^1$H-Nuclear Magnetic Resonance Spectra (500 MHz, DMSO-$d_6$) δ ppm:

12.85 (1H, brs), 8.63 (1H, brd, J=8 Hz), 7.83 (2H, d, J=9 Hz), 7.47 (2H, d, J=9 Hz), 7.41 (2H, d, J=9 Hz), 7.25 (2H, d, J=9 Hz), 7.10 (2H, d, J=9 Hz), 7.05 (2H, d, J=9 Hz), 4.62-4.56 (1H, m), 3.22 (1H, dd, J=14 Hz, 4 Hz), 3.09 (1H, dd, J=14 Hz, 10 Hz).

(48b) 4-(4-Chlorophenoxy)-N-{2-[(2-hydroxyethyl) amino]-2-oxo-1-[4-(trifluoromethoxy)benzyl] ethyl}benzamide A reaction similar to that described in Example 32 (32c) was conducted using 2-{[4-(4-chlorophenoxy)benzoyl] amino}-3-[4-(trifluoromethoxy)phenyl]propanoic acid (467 mg, 0.973 mmol) prepared in Example 48 (48a) and 2-aminoethanol (106 μL, 1.75 mmol) to give 420 mg of the title compound (white powder, yield: 83%).

MS (FAB) m/z: 523 $[M+H]^+$;

$^1$H-Nuclear Magnetic Resonance Spectra (400 MHz, DMSO-$d_6$) δ ppm:

8.53 (1H, d, J=9 Hz), 8.08 (1H, t, J=5 Hz), 7.82 (2H, d, J=9 Hz), 7.45 (2H, d, J=9 Hz), 7.42 (2H, d, J=9 Hz), 7.22 (2H, d,

J=8 Hz), 7.08 (2H, d, J=9 Hz), 7.02 (2H, d, J=9 Hz), 4.71-4.65 (2H, m), 3.38 (2H, q, J=6 Hz), 3.17-3.08 (3H, m), 2.98 (1H, dd, J=14 Hz, 11 Hz).

Example 49

N-{2-[(2-Hydroxyethyl)amino]-2-oxo-1-[4-(trifluoromethoxy)benzyl]ethyl}-4-(4-methoxyphenoxy) benzamide (Exemplary Compound No. 179)

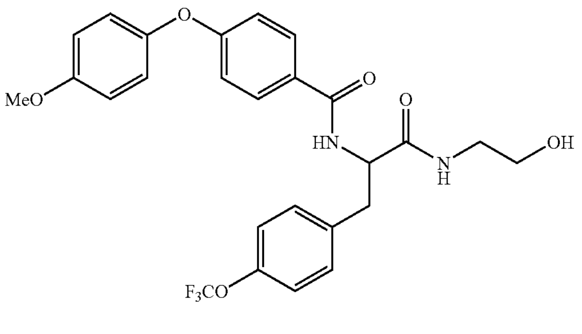 [SMILES: COc1ccc(Oc2ccc(C(=O)NC(Cc3ccc(OC(F)(F)F)cc3)C(=O)NCCO)cc2)cc1]

(49a) 2-{[4-(4-Methoxyphenoxy)benzoyl]amino}-3-[4-(trifluoromethoxy)phenyl]propanoic acid A reaction similar to that described in Example 47 (47a) was conducted using 4-(4-methoxyphenoxy)benzoic acid (compound described in J. Am. Chem. Soc., (1941), 63, 545-549, 300 mg, 1.23 mmol) to give 493 mg of the title compound (white amorphous solid, yield: 84%).

$^1$H-Nuclear Magnetic Resonance Spectra (400 MHz, DMSO-$d_6$) δ ppm:

12.7 (1H, brs), 8.61 (1H, d, J=8 Hz), 7.77 (2H, d, J=9 Hz), 7.40 (2H, d, J=9 Hz), 7.24 (2H, d, J=9 Hz), 7.03 (2H, d, J=9 Hz), 6.97 (2H, d, J=9 Hz), 6.91 (2H, d, J=9 Hz), 4.62-4.56 (1H, m), 3.75 (3H, s), 3.20 (1H, dd, J=14 Hz, 4 Hz), 3.08 (1H, dd, J=14 Hz, 10 Hz).

(49b) N-{2-[(2-Hydroxyethyl)amino]-2-oxo-1-[4-(trifluoromethoxy)benzyl]ethyl}-4-(4-methoxyphenoxy)benzamide A reaction similar to that described in Example 32 (32c) was conducted using 2-{[4-(4-methoxyphenoxy)benzoyl] amino}-3-[4-(trifluoromethoxy)phenyl]propanoic acid (490 mg, 1.03 mmol) prepared in Example 49 (49a) and 2-aminoethanol (112 μL, 1.86 mmol) to give 477 mg of the title compound (white powder, yield: 89%).

MS (FAB) m/z: 519 $[M+H]^+$;

$^1$H-Nuclear Magnetic Resonance Spectra (400 MHz, DMSO-$d_6$) δ ppm:

8.47 (1H, d, J=9 Hz), 8.07 (1H, t, J=5 Hz), 7.77 (2H, d, J=9 Hz), 7.41 (2H, d, J=9 Hz), 7.22 (2H, d, J=8 Hz), 7.02 (2H, d, J=9 Hz), 6.97 (2H, d, J=9 Hz), 6.90 (2H, d, J=9 Hz), 4.70-4.64 (2H, m), 3.75 (3H, s), 3.37 (2H, t, J=6 Hz), 3.16-3.07 (3H, m), 2.99 (1H, dd, J=13 Hz, 10 Hz).

Example 50

2-({(2S)-2-{[4-(Cyclopropylmethoxy)benzoyl] amino}-3-[4-(trifluoromethoxy)phenyl] propanoyl}amino)ethyl acetate (Exemplary Compound No. 544)

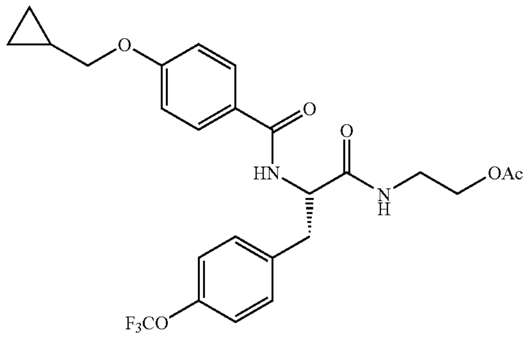

4-(Cyclopropylmethoxy)benzoic acid (1.52 g, 7.90 mmol) prepared in Example 18 (18a) was added to a DMF (53 mL) solution of 2-({(2S)-2-amino-3-[4-(trifluoromethoxy)phenyl]propanoyl}amino)ethyl acetate (2.64 g, 7.90 mmol). To the mixture was added diethyl cyanophosphate (1.54 mL, 9.78 mmol) under ice-cooling with stirring, and then triethylamine (1.32 mL, 9.78 mmol) was dropwise added thereto over 5 minutes. The resulting mixture was stirred at room temperature for 2.5 hours, and to this reaction solution was added ethyl acetate (380 mL). The resulting mixture was washed with water (380 mL, three times) and saturated brine, and dried over anhydrous sodium sulfate. The solvent was evaporated, and the obtained residue was washed with ethyl acetate and dried to give 1.47 g of the title compound. The ethyl acetate used for the washing was also concentrated, and the resulting residue was washed with methanol to give 0.82 g of the title compound. These compound fractions were combined to give 2.29 g of the title compound (white powder, yield: 57%).

MS (FAB) m/z: 509 $[M+H]^+$ $^1$H-Nuclear Magnetic Resonance Spectra (500 MHz, DMSO-$d_6$) δ ppm:

8.44 (1H, d, J=8 Hz), 8.23 (1H, t, J=6 Hz), 7.77 (2H, d, J=9 Hz), 7.43 (2H, d, J=9 Hz), 7.25 (2H, d, J=9 Hz), 6.95 (2H, d, J=9 Hz), 4.67-4.62 (1H, m), 4.04-3.95 (2H, m), 3.86 (2H, d, J=7 Hz), 3.39-3.25 (2H, m), 3.08 (1H, dd, J=14 Hz, 4 Hz), 3.01 (1H, dd, J=14 Hz, 10 Hz), 1.99 (3H, s), 1.25-1.20 (1H, m), 0.59-0.55 (2H, m), 0.34-0.31 (2H, m).

Example 51

4-(Cyclopropylmethoxy)-N-{(1S)-2-[(2-hydroxyethyl)amino]-2-oxo-1-[4-(trifluoromethoxy)benzyl]ethyl}benzamide (Exemplary Compound No. 19)

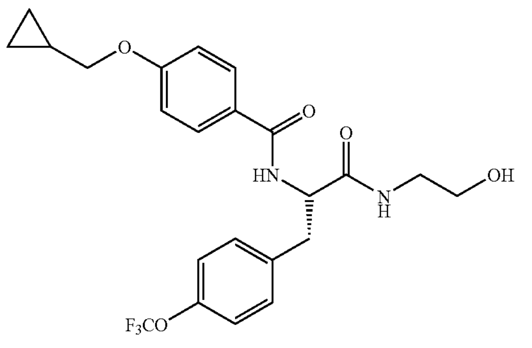

(51a) Potassium carbonate (32 mg, 0.23 mmol) was added at room temperature to a methanol (230 mL) suspension of 2-({(2S)-2-{[4-(cyclopropylmethoxy)benzoyl]amino}-3-[4-(trifluoromethoxy)phenyl]propanoyl}amino)ethyl acetate (1.17 g, 2.30 mmol) prepared in Example 50. The mixture was stirred for 1.5 hours, and then the reaction solution was evaporated. To the obtained residue was added ethyl acetate (200 mL). The mixture was washed with a saturated ammonium chloride aqueous solution (200 mL) and saturated brine and was dried over anhydrous sodium sulfate. The solvent was evaporated to give a crude crystalline solid, which was recrystallized with ethyl acetate (20 mL) to give 582 mg of the title compound (white powder, yield: 54%).

It was confirmed by HPLC analysis under conditions as in Example 10 that the compound was the S-isomer having an optical purity of 97%.

Retention time: S-isomer 8.9 min, R-isomer 13.2 min.

[It was confirmed as in Example 51 (51a) that compounds prepared in the following Example 53, Example 55, Example 57 (57a), Example 59 (59a), Example 61 (61a), Example 64 (64a), Example 66 (66a), and Example 68 (68a) were the S-isomers having an optical purity of 97% or higher.]

(51b) The title compound was also prepared by the following HPLC separation.

4-(Cyclopropylmethoxy)-N-{2-[(2-hydroxyethyl)amino]-2-oxo-1-[4-(trifluoromethoxy)benzyl]ethyl}benzamide prepared in Example 19 was subjected to HPLC separation under conditions as in Example 10 to give the title compound.

Retention time: S-isomer 38 min, R-isomer 24 min.

No R-isomer was recognized by HPLC analysis of this compound under conditions as in Example 10, and thereby it was confirmed that the optical purity was 99% or higher.

Example 52

2-({(2S)-2-{[4-(Cyclopropylmethoxy)benzoyl]amino}-3-[4-(difluoromethoxy)phenyl]propanoyl}amino)ethyl acetate (Exemplary Compound No. 543)

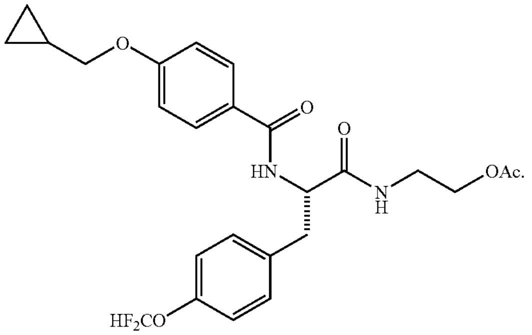

A reaction similar to that described in Example 50 was conducted using 2-({(2S)-2-amino-3-[4-(difluoromethoxy)phenyl]propanoyl}amino)ethyl acetate and 4-(cyclopropylmethoxy)benzoic acid prepared in Example 18 (18a) to give the title compound.

MS (FAB) m/z: 491 $[M+H]^+$ $^1$H-Nuclear Magnetic Resonance Spectra (400 MHz, DMSO-$d_6$) δ ppm:

8.42 (1H, d, J=8 Hz), 8.22 (1H, t, J=6 Hz), 7.78 (2H, d, J=9 Hz), 7.37 (2H, d, J=9 Hz), 7.16 (1H, t, J=74 Hz), 7.05 (2H, d, J=9 Hz), 6.95 (2H, d, J=9 Hz), 4.64-4.59 (1H, m), 4.05-3.90 (2H, m), 3.86 (2H, d, J=7 Hz), 3.38-3.25 (2H, m), 3.04 (1H, dd, J=14 Hz, 5 Hz), 2.98 (1H, dd, J=14 Hz, 10 Hz), 1.99 (3H, s), 1.26-1.18 (1H, m), 0.59-0.55 (2H, m), 0.34-0.31 (2H, m).

Example 53

4-(Cyclopropylmethoxy)-N-{(1S)-1-[4-(difluoromethoxy)benzyl]-2-[(2-hydroxyethyl)amino]-2-oxoethyl}benzamide (Exemplary Compound No. 18)

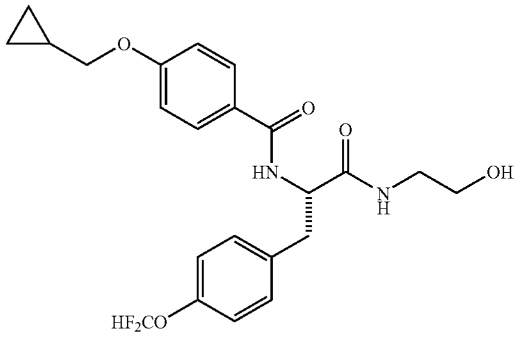

A reaction similar to that described in Example 51 (51a) was conducted using 2-({(2S)-2-{[4-(cyclopropylmethoxy)

benzoyl]amino}-3-[4-(difluoromethoxy)phenyl]propanoyl}amino)ethyl acetate prepared in Example 52 to give the title compound.

Retention time in HPLC analysis under conditions as in Example 10: S-isomer 16.4 min, R-isomer 24.1 min.

Example 54

2-({(2S)-2-{[4-(Cyclopropylmethoxy)benzoyl]amino}-3-[4-(trifluoromethyl)phenyl]propanoyl}amino)ethyl acetate (Exemplary Compound No. 545)

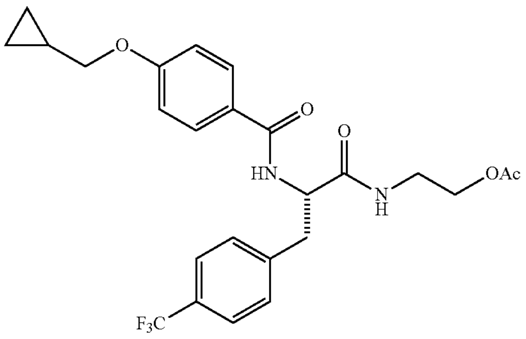 [SMILES: CC(=O)OCCNC(=O)[C@H](Cc1ccc(C(F)(F)F)cc1)NC(=O)c1ccc(OCC2CC2)cc1]

A reaction similar to that described in Example 50 was conducted using 2-({(2S)-2-amino-3-[4-(trifluoromethyl)phenyl]propanoyl}amino)ethyl acetate and 4-(cyclopropylmethoxy)benzoic acid prepared in Example 18 (18a) to give the title compound.

MS (FAB) m/z: 493 $[M+H]^+$;

$^1$H-Nuclear Magnetic Resonance Spectra (400 MHz, DMSO-$d_6$) δ ppm:

8.48 (1H, d, J=9 Hz), 8.26 (1H, t, J=5 Hz), 7.77 (2H, d, J=9 Hz), 7.62 (2H, d, J=8 Hz), 7.55 (2H, d, J=8 Hz), 6.95 (2H, d, J=9 Hz), 4.72-4.66 (1H, m), 4.05-3.95 (2H, m), 3.86 (2H, d, J=7 Hz), 3.39-3.25 (2H, m), 3.15 (1H, dd, J=14 Hz, 5 Hz), 3.08 (1H, dd, J=14 Hz, 11 Hz), 1.99 (3H, s), 1.26-1.16 (1H, m), 0.60-0.55 (2H, m), 0.35-0.31 (2H, m).

Example 55

4-(Cyclopropylmethoxy)-N-{(1S)-2-[(2-hydroxyethyl)amino]-2-oxo-1-[4-(trifluoromethyl)benzyl]ethyl}benzamide (Exemplary Compound No. 20)

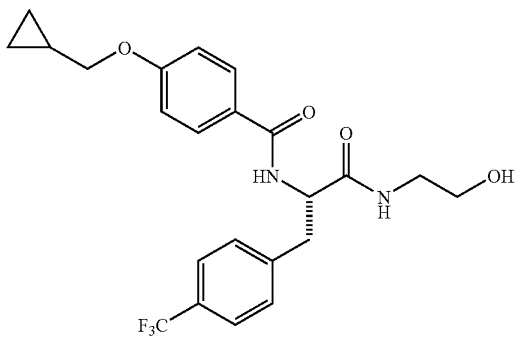

A reaction similar to that described in Example 51 (51a) was conducted using 2-({(2S)-2-{[4-(cyclopropylmethoxy)benzoyl]amino}-3-[4-(trifluoromethyl)phenyl]propanoyl}amino)ethyl acetate prepared in Example 54 to give the title compound.

Retention time in HPLC analysis under conditions as in Example 10: S-isomer 11.8 min, R-isomer 18.2 min.

Example 56

2-[((2S)-3-[4-(Trifluoromethoxy)phenyl]-2-{[4-(3,3,3-trifluoropropoxy)benzoyl]amino}propanoyl)amino]ethyl acetate (Exemplary Compound No. 589)

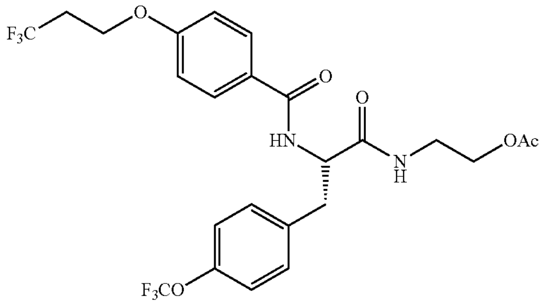

A reaction similar to that described in Example 50 was conducted using 2-({(2S)-2-amino-3-[4-(trifluoromethoxy)phenyl]propanoyl}amino)ethyl acetate and 4-(3,3,3-trifluoropropoxy)benzoic acid obtained in the preparation process of Example 33 (33a) to give the title compound.

MS (FAB) m/z: 551 $[M+H]^+$;

$^1$H-Nuclear Magnetic Resonance Spectra (400 MHz, DMSO-$d_6$) δ ppm:

8.46 (1H, d, J=8 Hz), 8.22 (1H, t, J=5 Hz), 7.77 (2H, d, J=9 Hz), 7.41 (2H, d, J=9 Hz), 7.22 (2H, d, J=9 Hz), 6.98 (2H, d, J=9 Hz), 4.67-4.61 (1H, m), 4.02-3.94 (2H, m), 3.37-3.25 (4H, m), 3.08 (1H, dd, J=14 Hz, 5 Hz), 3.00 (1H, dd, J=14 Hz, 10 Hz), 2.88-2.74 (2H, m), 1.98 (3H, s).

Example 57

N-{(1S)-2-[(2-Hydroxyethyl)amino]-2-oxo-1-[4-(trifluoromethoxy)benzyl]ethyl}-4-(3,3,3-trifluoropropoxy)benzamide (Exemplary Compound No. 94)

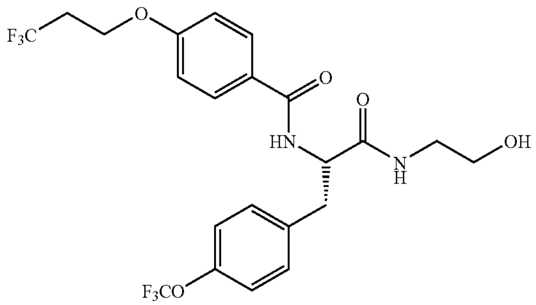

(57a) A reaction similar to that described in Example 51 (51a) was conducted using 2-[((2S)-3-[4-(trifluoromethoxy)

phenyl]-2-{[4-(3,3,3-trifluoropropoxy)benzoyl]amino}propanoyl)amino]ethyl acetate prepared in Example 56 to give the title compound.

Retention time in HPLC analysis under conditions as in Example 10: S-isomer 15.2 min, R-isomer 26.0 min.

(57b) The title compound was also prepared by the following HPLC separation.

N-{2-[(2-Hydroxyethyl)amino]-2-oxo-1-[4-(trifluoromethoxy)benzyl]ethyl}-4-(3,3,3-trifluoropropoxy)benzamide prepared in Example 34 was subjected to HPLC separation under conditions as in Example 10 to give the title compound.

Retention time: S-isomer 25 min, R-isomer 15 min.

No R-isomer was recognized by HPLC analysis of this compound under conditions as in Example 10, and thereby it was confirmed that the optical purity was 99% or higher.

Example 58

2-[((2S)-3-[4-(Difluoromethoxy)phenyl]-2-{[4-(3,3,3-trifluoropropoxy)benzoyl]amino}propanoyl)amino]ethyl acetate (Exemplary Compound No. 588)

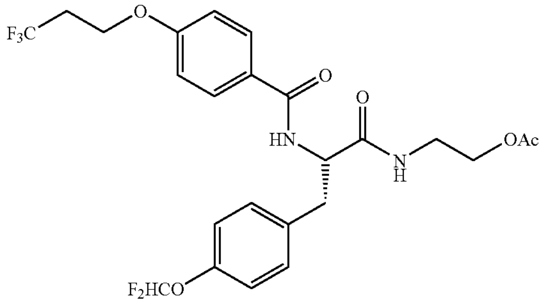

A reaction similar to that described in Example 50 was conducted using 2-({(2S)-2-amino-3-[4-(difluoromethoxy)phenyl]propanoyl}amino)ethyl acetate and 4-(3,3,3-trifluoropropoxy)benzoic acid obtained in the preparation process of Example 33 (33a) to give the title compound.

MS (ESI) m/z: 533 $[M+H]^+$, 531 $[M-H]^+$;

$^1$H-Nuclear Magnetic Resonance Spectra (400 MHz, DMSO-$d_6$) δ ppm:

8.43 (1H, d, J=8 Hz), 8.20 (1H, t, J=6 Hz), 7.78 (2H, d, J=9 Hz), 7.34 (2H, d, J=9 Hz), 7.13 (1H, t, J=74 Hz), 7.03 (2H, d, J=9 Hz), 6.99 (2H, d, J=9 Hz), 4.64-4.58 (1H, m), 4.25 (2H, t, J=6 Hz), 4.03-3.93 (2H, m), 3.37-3.26 (2H, m), 3.04 (1H, dd, J=14 Hz, 5 Hz), 2.96 (1H, dd, J=14 Hz, 10 Hz), 2.85-2.74 (2H, m), 1.98 (3H, s).

Example 59

N-{(1S)-1-[4-(Difluoromethoxy)benzyl]-2-[(2-hydroxyethyl)amino]-2-oxoethyl}-4-(3,3,3-trifluoropropoxy)benzamide (Exemplary Compound No. 93)

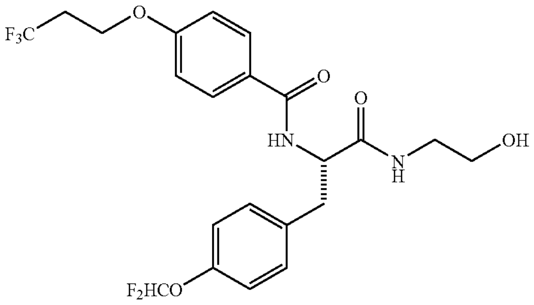

(59a) A reaction similar to that described in Example 51 (51a) was conducted using 2-[((2S)-3-[4-(difluoromethoxy)phenyl]-2-{[4-(3,3,3-trifluoropropoxy)benzoyl]amino}propanoyl)amino]ethyl acetate prepared in Example 58 to give the title compound.

Retention time in HPLC analysis under conditions as in Example 10: S-isomer 26.6 min, R-isomer 42.6 min.

(59b) The title compound was also prepared by the following HPLC separation.

N-{1-[4-(Difluoromethoxy)benzyl]-2-[(2-hydroxyethyl)amino]-2-oxoethyl}-4-(3,3,3-trifluoropropoxy)benzamide prepared in Example 33 was subjected to HPLC separation under conditions as in Example 10 to give the title compound.

Retention time: S-isomer 26 min, R-isomer 17 min.

No R-isomer was recognized by HPLC analysis of this compound under conditions as in Example 10, and thereby it was confirmed that the optical purity was 99% or higher.

Example 60

2-[((2S)-3-[4-(Trifluoromethyl)phenyl]-2-{[4-(3,3,3-trifluoropropoxy)benzoyl]amino}propanoyl)amino]ethyl acetate (Exemplary Compound No. 590)

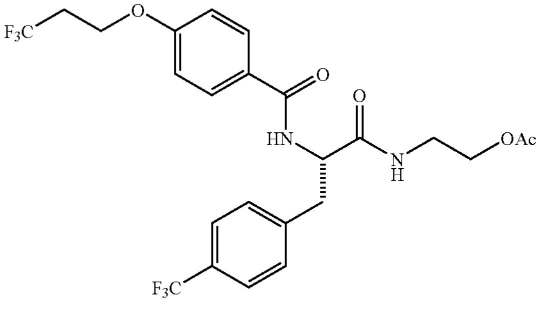 [SMILES: CC(=O)OCCNC(=O)[C@H](Cc1ccc(C(F)(F)F)cc1)NC(=O)c1ccc(OCCC(F)(F)F)cc1]

A reaction similar to that described in Example 50 was conducted using 2-({(2S)-2-amino-3-[4-(trifluoromethyl)phenyl]propanoyl}amino)ethyl acetate and 4-(3,3,3-trifluoropropoxy)benzoic acid obtained in the preparation process of Example 33 (33a) to give the title compound.

MS (FAB) m/z: 535 $[M+H]^+$ $^1$H-Nuclear Magnetic Resonance Spectra (400 MHz, DMSO-$d_6$) δ ppm:

8.52 (1H, d, J=9 Hz), 8.27 (1H, t, J=6 Hz), 7.80 (2H, d, J=9 Hz), 7.63 (2H, d, J=8 Hz), 7.55 (2H, d, J=8 Hz), 7.01 (2H, d, J=9 Hz), 4.73-4.67 (1H, m), 4.26 (2H, t, J=6 Hz), 4.06-3.95 (2H, m), 3.39-3.27 (2H, m), 3.15 (1H, dd, J=14 Hz, 5 Hz), 3.08 (1H, dd, J=14 Hz, 10 Hz), 2.87-2.75 (2H, m), 1.99 (3H, s).

Example 61

N-{(1S)-2-[(2-Hydroxyethyl)amino]-2-oxo-1-[4-(trifluoromethyl)benzyl]ethyl}-4-(3,3,3-trifluoropropoxy)benzamide (Exemplary Compound No. 95)

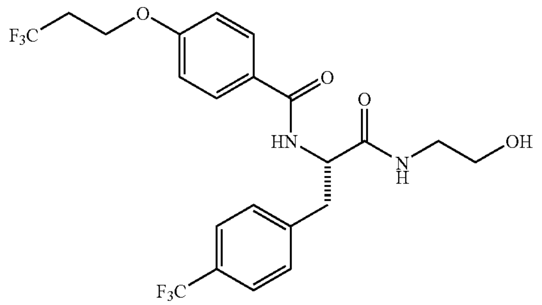

(61a) A reaction similar to that described in Example 51 (51a) was conducted using 2-[((2S)-3-[4-(trifluoromethyl)phenyl]-2-{[4-(3,3,3-trifluoropropoxy)benzoyl]amino}propanoyl)amino]ethyl acetate prepared in Example 60 to give the title compound.

Retention time in HPLC analysis under conditions as in Example 10: S-isomer 18.7 min, R-isomer 30.1 min.

(61b) The title compound was also prepared by the following HPLC separation.

N-{2-[(2-Hydroxyethyl)amino]-2-oxo-1-[4-(trifluoromethyl)benzyl]ethyl}-4-(3,3,3-trifluoropropoxy)benzamide prepared in Example 37 was subjected to HPLC separation under conditions as in Example 10 to give the title compound.

Retention time: S-isomer 26 min, R-isomer 16 min.

No R-isomer was recognized by HPLC analysis of this compound under conditions as in Example 10, and thereby it was confirmed that the optical purity was 99% or higher.

Example 62

4-[(2,2-Difluorocyclopropyl)methoxy]-N-{(1S)-2-[(2-hydroxyethyl)amino]-2-oxo-1-[4-(trifluoromethoxy)benzyl]ethyl}benzamide (Exemplary Compound No. 129)

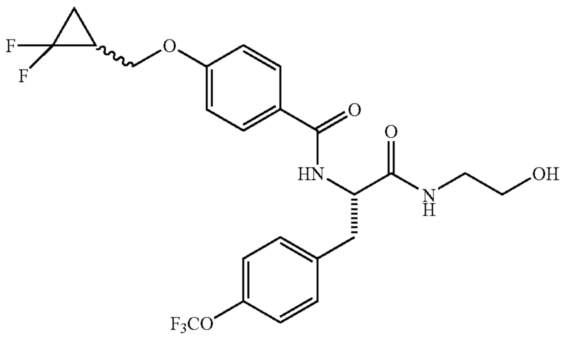 [SMILES: O=C(N[C@@H](Cc1ccc(OC(F)(F)F)cc1)C(=O)NCCO)c1ccc(OCC2CC2(F)F)cc1]

4-[(2,2-Difluorocyclopropyl)methoxy]-N-{2-[(2-hydroxyethyl)amino]-2-oxo-1-[4-(trifluoromethoxy)benzyl]ethyl}benzamide prepared in Example 40 was separated into three stereoisomers A, B, and C by HPLC under conditions as in Example 10 to give the title compound (referred to as Isomer A). Isomer A was estimated to be a mixture of 4-{[(1R)-2,2-difluorocyclopropyl]methoxy}-N-{(1S)-2-[(2-hydroxyethyl)amino]-2-oxo-1-[4-(trifluoromethoxy)benzyl]ethyl}benzamide and 4-{[(1S)-2,2-difluorocyclopropyl]methoxy}-N-{(1S)-2-[(2-hydroxyethyl)amino]-2-oxo-1-[4-(trifluoromethoxy)benzyl]ethyl}benzamide. Isomer B and Isomer C were estimated to be 4-{[(1R or S)-2,2-difluorocyclopropyl]methoxy}-N-{(1R)-2-[(2-hydroxyethyl)amino]-2-oxo-1-[4-(trifluoromethoxy)benzyl]ethyl}benzamide and 4-{[(1S or R)-2,2-difluorocyclopropyl]methoxy}-N-{(1R)-2-[(2-hydroxyethyl)amino]-2-oxo-1-[4-(trifluoromethoxy)benzyl]ethyl}benzamide, respectively.

Fractionation conditions retention time: Isomer A 25 min, Isomer B 16 min, Isomer C 18 min.

Isomers B and C were not observed by the HPLC analysis of the separated Isomer A under conditions as in Example 10.

Retention time Isomer A 12.8 min and 13.5 min, Isomer B 18.9 min, Isomer C 22.4 min.

Example 63

2-{[(2S)-3-[4-(Trifluoromethoxy)phenyl]-2-({4-[4-(trifluoromethyl)phenoxy]benzoyl}amino)propanoyl]amino}ethyl acetate (Exemplary Compound No. 634)

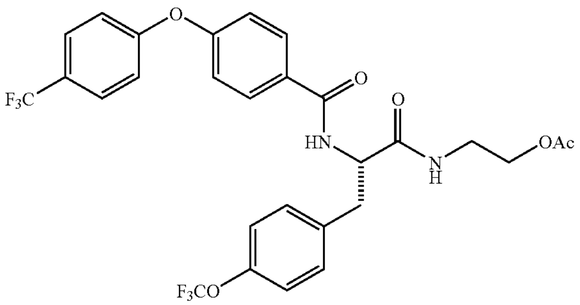 [SMILES: CC(=O)OCCNC(=O)[C@H](Cc1ccc(OC(F)(F)F)cc1)NC(=O)c1ccc(Oc2ccc(C(F)(F)F)cc2)cc1]

A reaction similar to that described in Example 50 was conducted using 2-({(2S)-2-amino-3-[4-(trifluoromethoxy)phenyl]propanoyl}amino)ethyl acetate and 4-[4-(trifluoromethyl)phenoxy]benzoic acid used in Example 41 (41a) to give the title compound.

MS (ESI) m/z: 599 $[M+H]^+$, 597$[M-H]^+$;

$^1$H-Nuclear Magnetic Resonance Spectra (400 MHz, DMSO-$d_6$) δ ppm:

8.61 (1H, d, J=8 Hz), 8.24 (1H, t, J=6 Hz), 7.87 (2H, d, J=9 Hz), 7.75 (2H, d, J=9 Hz), 7.43 (2H, d, J=9 Hz), 7.24 (2H, d, J=9 Hz), 7.18 (2H, d, J=9 Hz), 7.14 (2H, d, J=9 Hz), 4.70-4.64 (1H, m), 4.04-3.94 (2H, m), 3.38-3.26 (2H, m), 3.10 (1H, dd, J=14 Hz, 4 Hz), 3.01 (1H, dd, J=14 Hz, 11 Hz), 1.99 (3H, s).

Example 64

N-{(1S)-2-[(2-Hydroxyethyl)amino]-2-oxo-1-[4-(trifluoromethoxy)benzyl]ethyl}-4-[4-(trifluoromethyl)phenoxy]benzamide (Exemplary Compound No. 149)

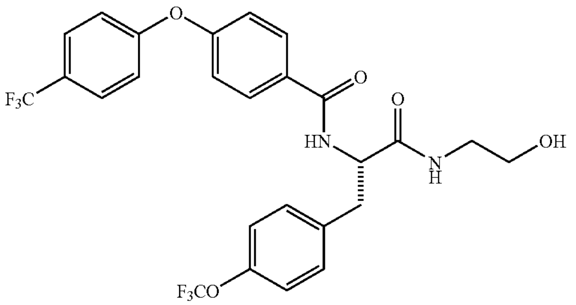 [SMILES: O=C(N[C@@H](Cc1ccc(OC(F)(F)F)cc1)C(=O)NCCO)c1ccc(Oc2ccc(C(F)(F)F)cc2)cc1]

(64a) A reaction similar to that described in Example 51 (51a) was conducted using 2-{[(2S)-3-[4-(trifluoromethoxy)phenyl]-2-({4-[4-(trifluoromethyl)phenoxy]benzoyl}amino)propanoyl]amino}ethyl acetate prepared in Example 63 to give the title compound.

Retention time in HPLC analysis under conditions as in Example 10: S-isomer 10.1 min, R-isomer 11.7 min.

(64b) The title compound was also prepared by the following HPLC separation.

The title compound was obtained using N-{2-[(2-hydroxyethyl)amino]-2-oxo-1-[4-(trifluoromethoxy)benzyl]ethyl}-4-[4-(trifluoromethyl)phenoxy]benzamide prepared in Example 42 by separation under the following conditions:

[Fractionation conditions] column: CHIRALPAK AD-H (manufactured by Daicel Chemical Industries, Ltd., internal diameter: 2 cm, length: 25 cm), mobile phase: ethanol/n-hexane=1/4, flow rate: 5.0 mL/min, temperature: room temperature, detection: 254 nm (UV), retention time: S-isomer 31 min, R-isomer 80 min.

No R-isomer was recognized by HPLC analysis of this compound under conditions as in Example 10, and thereby it was confirmed that the optical purity was 99% or higher.

Example 65

2-{[(2S)-3-[4-(Difluoromethoxy)phenyl]-2-({4-[4-(trifluoromethyl)phenoxy]benzoyl}amino)propanoyl]amino}ethyl acetate (Exemplary Compound No. 633)

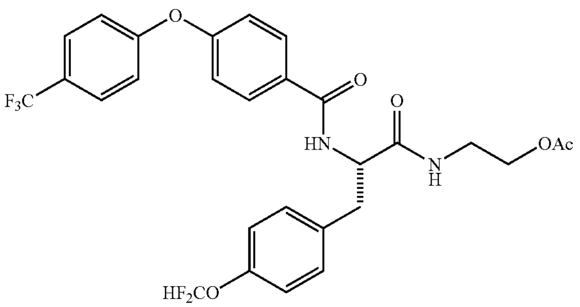

A reaction similar to that described in Example 50 was conducted using 2-({(2S)-2-amino-3-[4-(difluoromethoxy)phenyl]propanoyl}amino)ethyl acetate and 4-[4-(trifluoromethyl)phenoxy]benzoic acid used in Example 41 (41a) to give the title compound.

MS (FAB) m/z: 581 $[M+H]^+$;

$^1$H-Nuclear Magnetic Resonance Spectra (400 MHz, DMSO-$d_6$) δ ppm:

8.63 (1H, d, J=9 Hz), 8.27 (1H, t, J=6 Hz), 7.91 (2H, d, J=9 Hz), 7.78 (2H, d, J=9 Hz), 7.38 (2H, d, J=9 Hz), 7.21 (2H, d, J=9 Hz), 7.17 (2H, d, J=9 Hz), 7.17 (1H, t, J=74 Hz), 7.07 (2H, d, J=9 Hz), 4.68-4.63 (1H, m), 4.06-3.95 (2H, m), 3.41-3.26 (2H, m), 3.07 (1H, dd, J=14 Hz, 5 Hz), 2.99 (1H, dd, J=14 Hz, 11 Hz), 2.00 (3H, s).

Example 66

N-{(1S)-1-[4-(Difluoromethoxy)benzyl]-2-[(2-hydroxyethyl)amino]-2-oxoethyl}-4-[4-(trifluoromethyl)phenoxy]benzamide (Exemplary Compound No. 148)

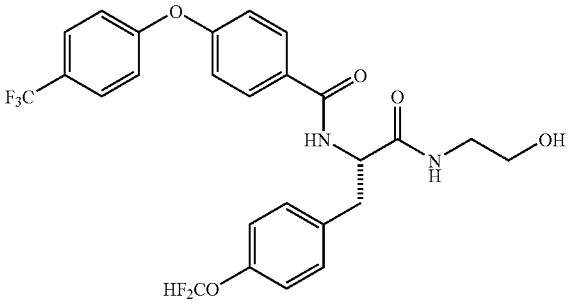

(66a) A reaction similar to that described in Example 51 (51a) was conducted using 2-{[(2S)-3-[4-(difluoromethoxy)phenyl]-2-({4-[4-(trifluoromethyl)phenoxy]benzoyl}amino)propanoyl]amino}ethyl acetate prepared in Example 65 to give the title compound.

Retention time in HPLC analysis under conditions as in Example 10: S-isomer 19.0 min, R-isomer 23.5 min.

(66b) The title compound was also prepared by the following HPLC separation.

The title compound was obtained using N-{1-[4-(difluoromethoxy)benzyl]-2-[(2-hydroxyethyl)amino]-2-oxoethyl}-4-[4-(trifluoromethyl)phenoxy]benzamide prepared in Example 41 by fractionation under the following conditions: [Fractionation conditions] column: CHIRALPAK AD-H (manufactured by Daicel Chemical Industries, Ltd., internal diameter: 2 cm, length: 25 cm), mobile phase: ethanol/n-hexane=1/4, flow rate: 15.0 mL/min, temperature: room temperature, detection: 254 nm (UV), retention time: S-isomer 15 min, R-isomer 23 min.

No R-isomer was recognized by HPLC analysis of this compound under conditions as in Example 10, and thereby it was confirmed that the optical purity was 99% or higher.

Example 67

2-({(2S)-2-({4-[4-(Trifluoromethyl)phenoxy]benzoyl}amino)-3-[4-(trifluoromethyl)phenyl]propanoyl}amino)ethyl acetate (Exemplary Compound No. 635)

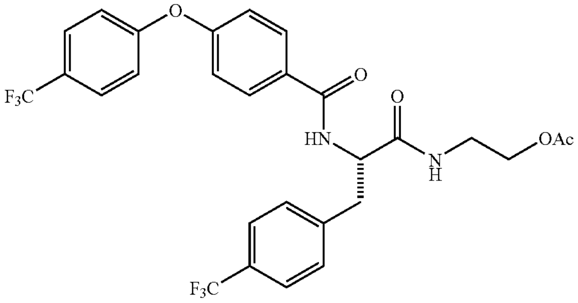 [SMILES: CC(=O)OCCNC(=O)[C@H](Cc1ccc(C(F)(F)F)cc1)NC(=O)c1ccc(Oc2ccc(C(F)(F)F)cc2)cc1]

A reaction similar to that described in Example 50 was conducted using 2-({(2S)-2-amino-3-[4-(trifluoromethyl)phenyl]propanoyl}amino)ethyl acetate and 4-[1-(trifluoromethyl)phenoxy]benzoic acid used in Example 41 (41a) to give the title compound.

MS (FAB) m/z: 583 $[M+H]^+$ $^1$H-Nuclear Magnetic Resonance Spectra (400 MHz, DMSO-$d_6$) δ ppm:

8.65 (1H, d, J=9 Hz), 8.28 (1H, t, J=6 Hz), 7.88 (2H, d, J=9 Hz), 7.75 (2H, d, J=9 Hz), 7.62 (2H, d, J=8 Hz), 7.54 (2H, d, J=8 Hz), 7.19 (2H, d, J=9 Hz), 7.15 (2H, d, J=9 Hz), 4.74-4.68 (1H, m), 4.05-3.95 (2H, m), 3.40-3.27 (2H, m), 3.16 (1H, dd, J=13 Hz, 5 Hz), 3.08 (1H, dd, J=13 Hz, 11 Hz), 1.99 (3H, s).

Example 68

N-{(1S)-2-[(2-Hydroxyethyl)amino]-2-oxo-1-[4-(trifluoromethyl)benzyl]ethyl}-4-[4-(trifluoromethyl)phenoxy]benzamide (Exemplary Compound No. 150)

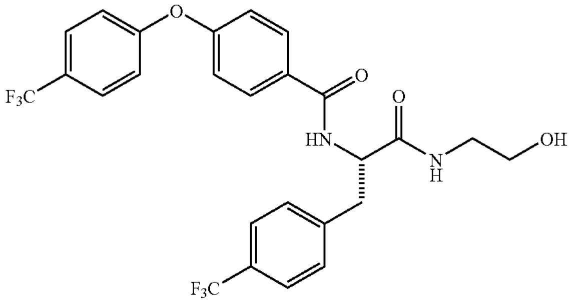 [SMILES: O=C(N[C@@H](Cc1ccc(C(F)(F)F)cc1)C(=O)NCCO)c1ccc(Oc2ccc(C(F)(F)F)cc2)cc1]

(68a) A reaction similar to that described in Example 51 (51a) was conducted using 2-({(2S)-2-({4-[4-(trifluoromethyl)phenoxy]benzoyl}amino)-3-[4-(trifluoromethyl)phenyl]propanoyl}amino)ethyl acetate prepared in Example 67 to give the title compound.

Retention time in HPLC analysis under conditions as in Example 10: S-isomer 14.8 min, R-isomer 18.0 min.

(68b) The title compound was also prepared by the following HPLC separation.

N-{2-[(2-Hydroxyethyl)amino]-2-oxo-1-[4-(trifluoromethyl)benzyl]ethyl}-4-[4-(trifluoromethyl)phenoxy]benzamide prepared in Example 45 was subjected to HPLC separation under conditions as in Example 66 to give the title compound.

Retention time: S-isomer 14 min, R-isomer 20 min.

No R-isomer was recognized by HPLC analysis of this compound under conditions as in Example 10, and thereby it was confirmed that the optical purity was 99% or higher.

Example 69

N-{2-(Methylamino)-2-oxo-1-[4-(trifluoromethoxy)benzyl]ethyl}-4-(3,3,3-trifluoropropoxy)benzamide (Exemplary Compound No. 959)

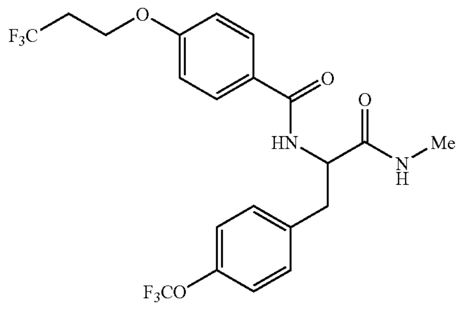 [SMILES: CNC(=O)C(Cc1ccc(OC(F)(F)F)cc1)NC(=O)c1ccc(OCCC(F)(F)F)cc1]

A reaction similar to that described in Example 1 (1d) was conducted using oxazolone (223 mg) obtained in the preparation process of Example 34 and methylamine (0.3 mL, 2 M methanol solution) to give 193 mg of N-{(Z)-1-[(methylamino)carbonyl]-2-[4-(trifluoromethoxy)phenyl]vinyl}-4-(3,3,3-trifluoropropoxy)benzamide (white powder).

MS (ESI) m/z: 477 $[M+H]^+$, 475 $[M-H]^+$;

$^1$H-Nuclear Magnetic Resonance Spectra (500 MHz, DMSO-$d_6$) δ ppm:

9.81 (1H, s), 8.09 (1H, q, J=4 Hz), 7.97 (2H, d, J=9 Hz), 7.64 (2H, d, J=9 Hz), 7.33 (2H, d, J=9 Hz), 7.17 (1H, s), 7.08 (2H, d, J=9 Hz), 4.30 (2H, t, J=6 Hz), 2.87-2.78 (2H, m), 2.68 (3H, d, J=4 Hz).

A reaction similar to that described in Example 1 (1e) was conducted using N-{(Z)-1-[(methylamino)carbonyl]-2-[4-(trifluoromethoxy)phenyl]vinyl}-4-(3,3,3-trifluoropropoxy)benzamide (159 mg) to give 146 mg of the title compound (white powder).

MS (ESI) m/z: 479 $[M+H]^+$, 477 $[M-H]^+$;

$^1$H-Nuclear Magnetic Resonance Spectra (400 MHz, DMSO-$d_6$) δ ppm:

8.48 (1H, d, J=8 Hz), 8.00 (1H, q, J=4 Hz), 7.80 (2H, d, J=9 Hz), 7.42 (2H, d, J=9 Hz), 7.24 (2H, d, J=9 Hz), 7.00 (2H, d, J=9 Hz), 4.65-4.59 (1H, m), 4.26 (2H, t, J=6 Hz), 3.11 (1H, dd, J=14 Hz, 5 Hz), 3.00 (1H, dd, J=14 Hz, 10 Hz), 2.86-2.74 (2H, m), 2.61 (3H, d, J=4 Hz).

Example 70

N-{2-(Ethylamino)-2-oxo-1-[4-(trifluoromethoxy)benzyl]ethyl}-4-(3,3,3-trifluoropropoxy)benzamide (Exemplary Compound No. 964)

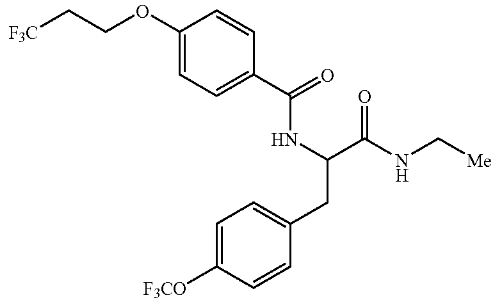 [SMILES: CCNC(=O)C(Cc1ccc(OC(F)(F)F)cc1)NC(=O)c1ccc(OCCC(F)(F)F)cc1]

(70a) 3-[4-(Trifluoromethoxy)phenyl]-2-{[4-(3,3,3-trifluoropropoxy)benzoyl]amino}propanoic acid DMF (three drops) and oxalyl chloride (3.50 mL, 40.0 mmol) were added to a methylene chloride (35 mL) solution of 4-(3,3,3-trifluoropropoxy)benzoic acid (4.68 g, 20.0 mmol) obtained in preparation process of Example 33 (33a), under ice-cooling with stirring. The mixture was stirred at room temperature for 3.5 hours, and then the solvent was evaporated. The obtained residue was dissolved in THF (20 mL). This solution and a 1 M sodium hydroxide aqueous solution (20 mL) were added dropwise simultaneously under ice-cooling with stirring to a solution mixture of a 1 M sodium hydroxide aqueous solution (40 mL) of 2-amino-3-[4-(trifluoromethoxy)phenyl]propanoic acid hydrochloride (5.71 g, 20.0 mmol) prepared in Reference Example 2, water (20 mL), and THF (15 mL). The resulting mixture was stirred under ice-cooling for 70 minutes, and then the solvents (mainly THF) were evaporated. Water was added to the residue, and the resulting mixture was changed to acidic by adding 2 M hydrochloric acid thereto. The precipitated crystalline solid was collected by filtration, washed with water and n-hexane, and dried under reduced pressure to give 8.75 g of the title compound (white powder, yield: 94%).

MS (ESI) m/z: 466 $[M+H]^+$, 464 $[M-H]^+$;

$^1$H-Nuclear Magnetic Resonance Spectra (500 MHz, DMSO-$d_6$) δ ppm:

12.87 (1H, brs), 8.51 (1H, d, J=8 Hz), 7.77 (2H, d, J=9 Hz), 7.40 (2H, d, J=8 Hz), 7.24 (2H, d, J=8 Hz), 7.01 (2H, d, J=9 Hz), 4.58-4.53 (1H, m), 4.26 (2H, t, J=6 Hz), 3.21 (1H, dd, J=14 Hz, 4 Hz), 3.09 (1H, dd, J=14 Hz, 11 Hz), 2.85-2.76 (2H, m).

(70b) N-{2-(Ethylamino)-2-oxo-1-[4-(trifluoromethoxy)benzyl]ethyl}-4-(3,3,3-trifluoropropoxy)benzamide A reaction similar to that described in Example 32 (32c) was conducted using 3-[4-(trifluoromethoxy)phenyl]-2-{[4-(3,3,3-trifluoropropoxy)benzoyl]amino}propanoic acid (139 mg) prepared in Example 70 (70a) and ethylamine (30 μL, 70% aqueous solution) to give 106 mg of the title compound (white powder).

(In this case, DMF was used instead of methanol.)

MS (ESI) m/z: 493 $[M+H]^+$, 491 $[M-H]^+$;

$^1$H-Nuclear Magnetic Resonance Spectra (400 MHz, DMSO-$d_6$) δ ppm:

8.43 (1H, d, J=9 Hz), 8.04 (1H, t, J=5 Hz), 7.80 (2H, d, J=9 Hz), 7.42 (2H, d, J=9 Hz), 7.23 (2H, d, J=9 Hz), 7.00 (2H, d, J=9 Hz), 4.65-4.59 (1H, m), 4.26 (2H, t, J=6 Hz), 3.14-2.97 (4H, m), 2.86-2.74 (2H, m), 0.98 (3H, t, J=7 Hz).

Example 71

N-{2-[(3-Hydroxypropyl)amino]-2-oxo-1-[4-(trifluoromethoxy)benzyl]ethyl}-4-(3,3,3-trifluoropropoxy)benzamide (Exemplary Compound No. 274)

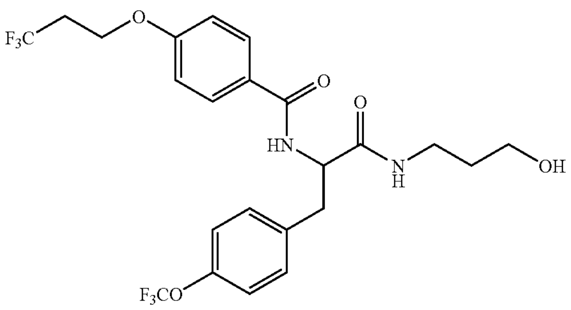 [SMILES: O=C(NC(Cc1ccc(OC(F)(F)F)cc1)C(=O)NCCCO)c1ccc(OCCC(F)(F)F)cc1]

A reaction similar to that described in Example 1 (1d) was conducted using oxazolone (223 mg) obtained in the preparation process of Example 34 and 3-aminopropanol (46 μL) to give 221 mg of N-{(Z)-1-{[(3-hydroxypropyl)amino]carbonyl}-2-[4-(trifluoromethoxy)phenyl]vinyl}-4-(3,3,3-trifluoropropoxy)benzamide (white powder).

MS (ESI) m/z: 521 $[M+H]^+$, 519 $[M-H]^+$;

[1]H-Nuclear Magnetic Resonance Spectra (500 MHz, DMSO-$d_6$) δ ppm:

9.80 (1H, s), 8.14 (1H, t, J=5 Hz), 7.97 (2H, d, J=8 Hz), 7.64 (2H, d, J=9 Hz), 7.34 (2H, d, J=8 Hz), 7.15 (1H, s), 7.08 (2H, d, J=9 Hz), 4.41 (1H, brs), 4.30 (2H, t, J=6 Hz), 3.43 (2H, brs), 3.21 (2H, q, J=6 Hz), 2.87-2.78 (2H, m), 1.61 (2H, quint, J=6 Hz).

A reaction similar to that described in Example 1 (1e) was conducted using N-{(Z)-1-{[(3-hydroxypropyl)amino]carbonyl}-2-[4-(trifluoromethoxy)phenyl]vinyl}-4-(3,3,3-trifluoropropoxy)benzamide (177 mg) to give 160 mg of the title compound (white powder).

MS (ESI) m/z: 523 $[M+H]^+$, 521 $[M-H]^+$;

[1]H-Nuclear Magnetic Resonance Spectra (400 MHz, DMSO-$d_6$) δ ppm:

8.45 (1H, d, J=8 Hz), 8.05 (1H, t, J=5 Hz), 7.80 (2H, d, J=8 Hz), 7.43 (2H, d, J=9 Hz), 7.24 (2H, d, J=8 Hz), 7.00 (2H, d, J=9 Hz), 4.67-4.61 (1H, m), 4.41 (1H, t, J=5 Hz), 4.26 (2H, t, J=6 Hz), 3.39 (2H, q, J=6 Hz), 3.17-3.06 (3H, m), 3.01 (1H, dd, J=13 Hz, 11 Hz), 2.86-2.75 (2H, m), 1.53 (2H, quint, J=7 Hz).

Example 72

N-{2-[(2-Methoxyethyl)amino]-2-oxo-1-[4-(trifluoromethoxy)benzyl]ethyl}-4-(3,3,3-trifluoropropoxy)benzamide (Exemplary Compound No. 969)

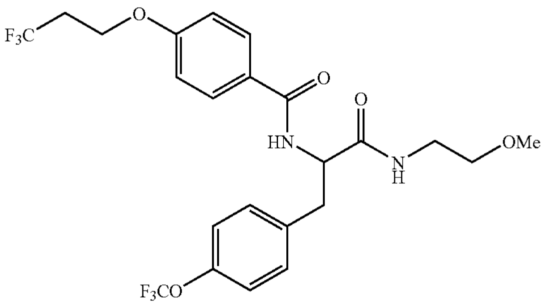 [SMILES: COCCNC(=O)C(Cc1ccc(OC(F)(F)F)cc1)NC(=O)c1ccc(OCCC(F)(F)F)cc1]

A reaction similar to that described in Example 1 (1d) was conducted using oxazolone (223 mg) obtained in the preparation process of Example 34 and 2-methoxyethylamine (52 μL) to give 227 mg of N-{(Z)-1-{[(2-methoxyethyl)amino]carbonyl}-2-[4-(trifluoromethoxy)phenyl]vinyl}-4-(3,3,3-trifluoropropoxy)benzamide (white powder).

MS (ESI) m/z: 521 $[M+H]^+$, 519 $[M-H]^+$;

[1]H-Nuclear Magnetic Resonance Spectra (400 MHz, DMSO-$d_6$) δ ppm:

9.78 (1H, s), 8.13 (1H, t, J=5 Hz), 7.95 (2H, d, J=9 Hz), 7.62 (2H, d, J=9 Hz), 7.32 (2H, d, J=9 Hz), 7.14 (1H, s), 7.06 (2H, d, J=9 Hz), 4.29 (2H, t, J=6 Hz), 3.38 (2H, t, J=6 Hz), 3.34-3.30 (2H, m), 3.23 (3H, s), 2.88-2.76 (2H, m).

A reaction similar to that described in Example 1 (1e) was conducted using N-{(Z)-1-{[(2-methoxyethyl)amino]carbonyl}-2-[4-(trifluoromethoxy)phenyl]vinyl}-4-(3,3,3-trifluoropropoxy)benzamide (190 mg) to give 167 mg of the title compound (white powder).

MS (ESI) m/z: 523 $[M+H]^+$, 521 $[M-H]^+$;

[1]H-Nuclear Magnetic Resonance Spectra (400 MHz, DMSO-$d_6$) δ ppm:

8.42 (1H, d, J=8 Hz), 8.13 (1H, t, J=5 Hz), 7.77 (2H, d, J=9 Hz), 7.42 (2H, d, J=9 Hz), 7.22 (2H, d, J=9 Hz), 6.98 (2H, d, J=9 Hz), 4.69-4.63 (1H, m), 4.24 (2H, t, J=6 Hz), 3.30-3.29

(2H, m), 3.26-3.20 (2H, m), 3.23 (3H, s), 3.07 (1H, dd, J=14 Hz, 5 Hz), 2.99 (1H, dd, J=14 Hz, 10 Hz), 2.85-2.74 (2H, m).

Example 73

N-{2-(Ethynylamino)-2-oxo-1-[4-(trifluoromethoxy)benzyl]ethyl}-4-(3,3,3-trifluoropropoxy)benzamide (Exemplary Compound No. 974)

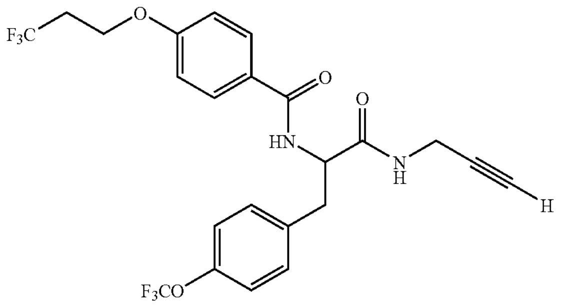 [SMILES: C#CCNC(=O)C(Cc1ccc(OC(F)(F)F)cc1)NC(=O)c1ccc(OCCC(F)(F)F)cc1]

A reaction similar to that described in Example 32 (32c) was conducted using 3-[4-(trifluoromethoxy)phenyl]-2-{[4-(3,3,3-trifluoropropoxy)benzoyl]amino}propanoic acid (140 mg) prepared in Example 70 (70a) and propargylamine (25 µL) to give 142 mg of the title compound (white powder).

(In this case, DMF was used instead of methanol.)

MS (ESI) m/z: 503 $[M+H]^+$, 501 $[M-H]^+$;

$^1$H-Nuclear Magnetic Resonance Spectra (400 MHz, DMSO-$d_6$) 5 ppm:

8.58 (1H, t, J=5 Hz), 8.52 (1H, d, J=9 Hz), 7.79 (2H, d, J=9 Hz), 7.45 (2H, d, J=9 Hz), 7.24 (2H, d, J=9 Hz), 7.01 (2H, d, J=9 Hz), 4.70-4.64 (1H, m), 4.26 (2H, t, J=6 Hz), 3.90-3.89 (2H, m), 3.14 (1 µl, t, J=2 Hz), 3.09 (1 µl, dd, J=14 Hz, 4 Hz), 3.00 (1H, dd, J=14 Hz, 11 Hz), 2.86-2.75 (2H, m).

Example 74

N-{2-{[(2R)-2-Hydroxypropyl]amino}-2-oxo-1-[4-(trifluoromethoxy)benzyl]ethyl}-4-(3,3,3-trifluoropropoxy)benzamide (Exemplary Compound No. 979)

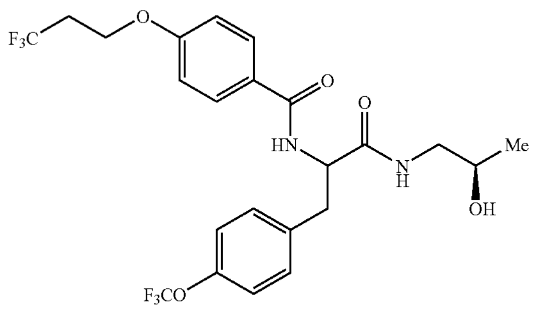 [SMILES: C[C@@H](O)CNC(=O)C(Cc1ccc(OC(F)(F)F)cc1)NC(=O)c1ccc(OCCC(F)(F)F)cc1]

A reaction similar to that described in Example 1 (1d) was conducted using oxazolone (500 mg) obtained in the preparation process of Example 34 and (R)-(−)-1-amino-2-propanol (106 µL) to give 540 mg of N-{(Z)-1-({[(2R)-2-hydroxypropyl]amino}carbonyl)-2-[4-(trifluoromethoxy)phenyl]vinyl}-4-(3,3,3-trifluoropropoxy)benzamide (white amorphous solid).

MS (FAB) m/z: 521 $[M+H]^+$;

$^1$H-Nuclear Magnetic Resonance Spectra (400 MHz, DMSO-$d_6$) δ ppm:

9.84 (1H, s), 8.01 (1H, t, J=6 Hz), 7.97 (2H, d, J=9 Hz), 7.65 (2H, d, J=9 Hz), 7.35 (2H, d, J=9 Hz), 7.16 (1H, s), 7.09 (2H, d, J=9 Hz), 4.62 (1H, d, J=4 Hz), 4.30 (2H, t, J=6 Hz), 3.75-3.70 (1H, m), 3.11 (2H, t, J=6 Hz), 2.89-2.77 (2H, m), 1.04 (3H, d, J=6 Hz).

A reaction similar to that described in Example 1 (1e) was conducted using N-{(Z)-1-({[(2R)-2-hydroxypropyl]amino}carbonyl)-2-[4-(trifluoromethoxy)phenyl]vinyl}-4-(3,3,3-trifluoropropoxy)benzamide (490 mg) to give 470 mg of the title compound (white powder).

MS (FAB) m/z: 523 $[M+H]^+$;

$^1$H-Nuclear Magnetic Resonance Spectra (400 MHz, DMSO-$d_6$) δ ppm:

8.46 (½H, d, J=9 Hz), 8.45 (½H, d, J=9 Hz), 8.03 (½H, t, J=6 Hz), 8.00 (½H, t, J=6 Hz), 7.80 (1H, d, J=9 Hz), 7.79 (1H, d, J=9 Hz), 7.44 (2H, d, J=8 Hz), 7.24 (2H, d, J=8 Hz), 7.00 (2H, d, J=9 Hz), 4.72-4.67 (1H, m), 4.66 (1H, d, J=5 Hz), 4.26 (2H, t, J=6 Hz), 3.66-3.58 (1H, m), 3.12-2.97 (4H, m), 2.86-2.74 (2H, m), 0.99 (3/2H, d, J=6 Hz), 0.96 (3/2H, d, J=6 Hz).

Example 75

N-{2-{[(2S)-2-Hydroxypropyl]amino}-2-oxo-1-[4-(trifluoromethoxy)benzyl]ethyl}-4-(3,3,3-trifluoropropoxy)benzamide (Exemplary Compound No. 984)

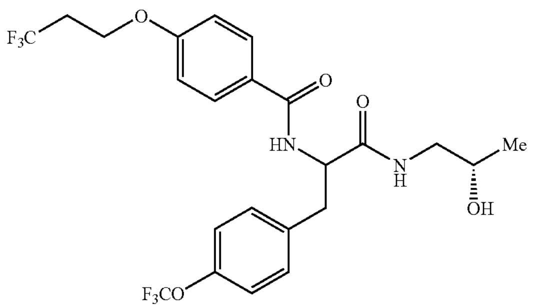

A reaction similar to that described in Example 1 (1d) was conducted using oxazolone (300 mg) obtained in the preparation process of Example 34 and (S)-(+)-1-amino-2-propanol (63 µL) to give 319 mg of N-{(Z)-1-({[(2S)-2-hydroxypropyl]amino}carbonyl)-2-[4-(trifluoromethoxy)phenyl]vinyl}-4-(3,3,3-trifluoropropoxy)benzamide (white amorphous solid).

MS (FAB) m/z: 521 $[M+H]^+$;

$^1$H-Nuclear Magnetic Resonance Spectra (400 MHz, DMSO-$d_6$) δ ppm:

9.83 (1H, s), 8.01 (1H, t, J=6 Hz), 7.97 (2H, d, J=9 Hz), 7.65 (2H, d, J=9 Hz), 7.34 (2H, d, J=9 Hz), 7.16 (1H, s), 7.08 (2H, d, J=9 Hz), 4.62 (1H, d, J=4 Hz), 4.30 (2H, t, J=6 Hz), 3.75-3.69 (1H, m), 3.11 (2H, t, J=6 Hz), 2.88-2.77 (2H, m), 1.04 (3H, d, J=6 Hz).

A reaction similar to that described in Example 1 (1e) was conducted using N-{(Z)-1-({[(2S)-2-hydroxypropyl]amino}carbonyl)-2-[4-(trifluoromethoxy)phenyl]vinyl}-4-(3,3,3-trifluoropropoxy)benzamide (270 mg) to give 251 mg of the title compound (white powder).

MS (FAB) m/z: 523 $[M+H]^+$;

[1]H-Nuclear Magnetic Resonance Spectra (400 MHz, DMSO-$d_6$) δ ppm:

8.46 (½H, d, J=9 Hz), 8.45 (½H, d, J=9 Hz), 8.03 (½H, t, J=6 Hz), 8.01 (½H, t, J=6 Hz), 7.80 (1H, d, J=9 Hz), 7.79 (1H, d, J=9 Hz), 7.45 (2H, d, J=8 Hz), 7.24 (2H, d, J=8 Hz), 7.01 (2H, d, J=9 Hz), 4.73-4.67 (1H, m), 4.66 (1H, d, J=5 Hz), 4.26 (2H, t, J=6 Hz), 3.67-3.59 (1H, m), 3.13-2.96 (4H, m), 2.86-2.75 (2H, m), 0.99 (3/2H, d, J=6 Hz), 0.97 (3/2H, d, J=6 Hz).

Example 76

N-{2-Oxo-2-[(2-oxo-propyl)amino]-1-[4-(trifluoromethoxy)benzyl]ethyl}-4-(3,3,3-trifluoropropoxy) benzamide (Exemplary Compound No. 989)

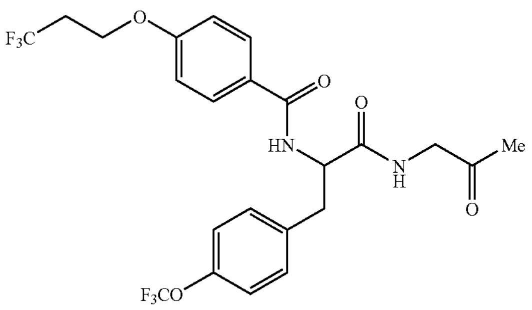 [SMILES: CC(=O)CNC(=O)C(Cc1ccc(OC(F)(F)F)cc1)NC(=O)c1ccc(OCCC(F)(F)F)cc1]

Pyridinium chlorochromate (266 mg, 1.23 mmol) and sodium acetate (20 mg, 0.247 mmol) were added to a methylene chloride (24 mL) solution of N-{2-{[(2R)-2-hydroxypropyl]amino}-2-oxo-1-[4-(trifluoromethoxy)benzyl] ethyl}-4-(3,3,3-trifluoropropoxy)benzamide (322 mg, 0.616 mmol) prepared in Example 74. The mixture was stirred at room temperature for 8 hours, and water (60 mL) was added thereto. The resulting mixture was extracted with methylene chloride (50 mL, three times). The organic layer was dried over anhydrous sodium sulfate, concentrated, and purified by alumina column chromatography (ethyl acetate:methanol, 9:1, V/V) to give 299 mg of the title compound (white powder, yield: 93%).

MS (ESI) m/z: 521 $[M+H]^+$, 519 $[M-H]^+$;

[1]H-Nuclear Magnetic Resonance Spectra (400 MHz, DMSO-$d_6$) δ ppm:

8.55 (1H, d, J=9 Hz), 8.39 (1H, t, J=6 Hz), 7.79 (2H, d, J=9 Hz), 7.47 (2H, d, J=9 Hz), 7.25 (2H, d, J=9 Hz), 7.01 (2H, d, J=9 Hz), 4.78-4.72 (1H, m), 4.26 (2H, t, J=6 Hz), 3.97 (1H, dd, J=18 Hz, 6 Hz), 3.93 (1H, dd, J=18 Hz, 6 Hz), 3.16 (1H, dd, J=14 Hz, 4 Hz), 3.04 (1H, dd, J=14 Hz, 11 Hz), 2.86-2.75 (2H, m), 2.06 (3H, s).

Example 77

N-{2-{[2-(Hydroxyimino)propyl]amino}-2-oxo-1-[4-(trifluoromethoxy)benzyl]ethyl}-4-(3,3,3-trifluoropropoxy)benzamide (Exemplary Compound No. 994)

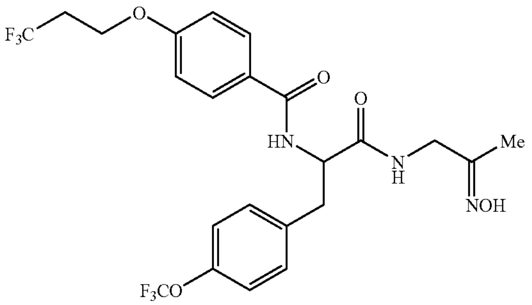

Hydroxyamine hydrochloride (20 mg, 0.288 mmol) was added to a solution mixture of ethanol:THF (2:1, V/V, 7.5 mL) containing N-{2-oxo-2-[(2-oxo-propyl)amino]-1-[4-(trifluoromethoxy)benzyl]ethyl}-4-(3,3,3-trifluoropropoxy) benzamide (100 mg, 0.192 mmol) prepared in Example 76. The mixture was stirred at room temperature for 6 hours, and the solvent was evaporated. The residue was purified by thin layer chromatography for separation (ethyl acetate:n-hexane, 2:1, V/V, developed once) to give 49 mg of the title compound (white powder, yield: 48%).

MS (FAB) m/z: 536 $[M+H]^+$;

[1]H-Nuclear Magnetic Resonance Spectra (400 MHz, DMSO-$d_6$) δ ppm:

10.58 (⅚H, s), 10.48 (⅙H, s), 8.58 (⅙H, d, J=9 Hz), 8.52 (⅚H, d, J=9 Hz), 8.39-8.34 (1H, m), 7.82-7.78 (2H, m), 7.47-7.43 (2H, m), 7.25 (2H, d, J=9 Hz), 7.01 (2H, d, J=9 Hz), 4.70-4.64 (1H, m), 4.26 (2H, t, J=6 Hz), 3.96 (⅓H, d, J=6 Hz), 3.82 (5/6H, dd, J=15 Hz, 6 Hz), 3.76 (5/6H, dd, J=15 Hz, 6 Hz), 3.16-3.00 (2H, m), 2.86-2.75 (2H, m), 1.65 (5/2H, s), 1.62 (½H, s).

Example 78

N-{2-[(2-Fluoroethyl)amino]-2-oxo-1-[4-(trifluoromethoxy)benzyl]ethyl}-4-(3,3,3-trifluoropropoxy)benzamide (Exemplary Compound No. 999)

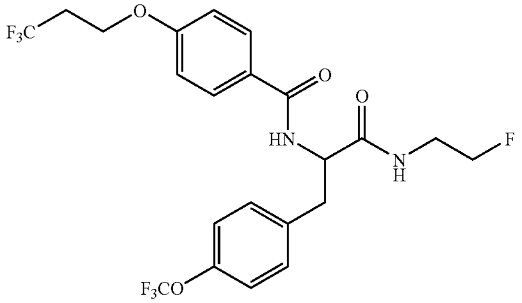

A reaction similar to that described in Example 32 (32c) was conducted using 3-[4-(trifluoromethoxy)phenyl]-2-{[4-(3,3,3-trifluoropropoxy)benzoyl]amino}propanoic acid (6.00 g) prepared in Example 70 (70a) and 2-fluoroethylamine hydrochloride (1.71 g) to give 7.67 g of the title compound (white powder).

MS (FAB) m/z: 511 $[M+H]^+$;

$^1$H-Nuclear Magnetic Resonance Spectra (400 MHz, DMSO-$d_6$) δ ppm:

8.47 (1H, d, J=8 Hz), 8.35 (1H, t, J=6 Hz), 7.80 (2H, d, J=9 Hz), 7.44 (2H, d, J=9 Hz), 7.24 (2H, d, J=9 Hz), 7.01 (2H, d, J=9 Hz), 4.72-4.66 (1H, m), 4.47 (1H, t, J=5 Hz), 4.35 (1H, t, J=5 Hz), 4.26 (2H, t, J=6 Hz), 3.44-3.40 (1H, m), 3.38-3.34 (1H, m), 3.10 (1H, dd, J=14 Hz, 5 Hz), 3.02 (1H, dd, J=14 Hz, 11 Hz), 2.86-2.75 (2H, m).

Example 79

N-{2-[(2,2-Difluoroethyl)amino]-2-oxo-1-[4-(trifluoromethoxy)benzyl]ethyl}-4-(3,3,3-trifluoropropoxy)benzamide (Exemplary Compound No. 1004)

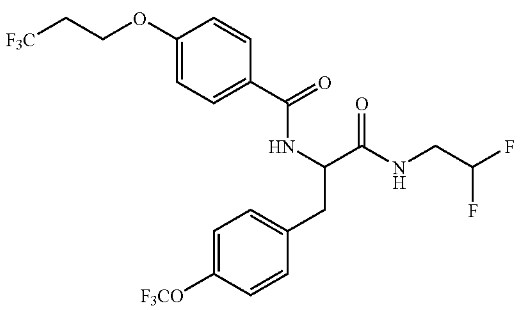

A reaction similar to that described in Example 32 (32c) was conducted using 3-[4-(trifluoromethoxy)phenyl]-2-{[4-(3,3,3-trifluoropropoxy)benzoyl]amino}propanoic acid (233 mg) prepared in Example 70 (70a) and 2,2-difluoroethylamine (49 mg) to give 214 mg of the title compound (white powder).

(In this case, DMF was used instead of methanol.)

MS (FAB) m/z: 529 $[M+H]^+$;

$^1$H-Nuclear Magnetic Resonance Spectra (400 MHz, DMSO-$d_6$) δ ppm:

8.52 (1H, d, J=9 Hz), 8.49 (1H, t, J=6 Hz), 7.80 (2H, d, J=9 Hz), 7.45 (2H, d, J=9 Hz), 7.25 (2H, d, J=9 Hz), 7.01 (2H, d, J=9 Hz), 5.98 (1H, tt, J=56 Hz, 4 Hz), 4.75-4.69 (1H, m), 4.26 (2H, t, J=6 Hz), 3.58-3.46 (2H, m), 3.10 (1H, dd, J=14 Hz, 5 Hz), 3.03 (1H, dd, J=14 Hz, 11 Hz), 2.86-2.74 (2H, m).

Example 80

N-{2-Amino-2-oxo-1-[4-(trifluoromethoxy)benzyl]ethyl}-4-(3,3,3-trifluoropropoxy)benzamide (Exemplary Compound No. 954)

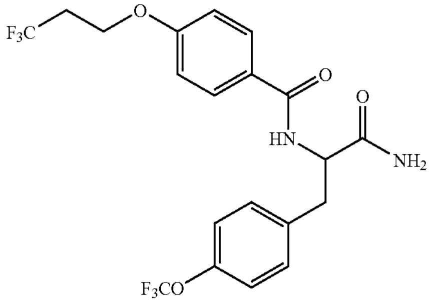

A reaction similar to that described in Example 32 (32c) was conducted using 3-[4-(trifluoromethoxy)phenyl]-2-{[4-(3,3,3-trifluoropropoxy)benzoyl]amino}propanoic acid (5.00 g) prepared in Example 70 (70a) and ammonia (16.1 mL, 2 M ethanol solution) to give 4.51 g of the title compound (white powder).

MS (FAB) m/z: 465 $[M+H]^+$;

$^1$H-Nuclear Magnetic Resonance Spectra (400 MHz, DMSO-$d_6$) δ ppm:

8.39 (1H, d, J=9 Hz), 7.78 (2H, d, J=9 Hz), 7.55 (1H, brs), 7.44 (2H, d, J=9 Hz), 7.24 (2H, d, J=9 Hz), 7.11 (1H, brs), 7.00 (2H, d, J=9 Hz), 4.65-4.59 (1H, m), 4.26 (2H, t, J=6 Hz), 3.12 (1H, dd, J=14 Hz, 4 Hz), 3.01 (1H, dd, J=14 Hz, 11 Hz), 2.86-2.73 (2H, m).

Example 81

N-{2-[(2-Hydroxyethyl)amino]-2-oxo-1-[4-(trifluoromethoxy)benzyl]ethyl}-4-(4,4,4-trifluorobutoxy)benzamide (Exemplary Compound No. 769)

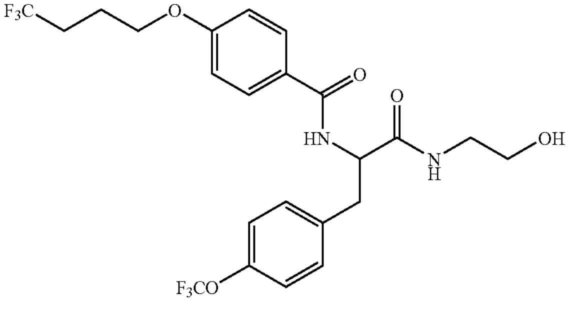 [SMILES: O=C(NC(Cc1ccc(OC(F)(F)F)cc1)C(=O)NCCO)c1ccc(OCCCC(F)(F)F)cc1]

(81a) 4-(4,4,4-Trifluorobutoxy)benzoic acid

A reaction similar to that described in Example 1 (1a) was conducted using methyl 4-hydroxybenzoate (1.19 g) and 4,4,4-trifluorobutan-1-ol (1.00 g) to give 1.29 g of the title compound (white powder).

MS (ESI) m/z: 249 $[M+H]^+$, 247 $[M-H]^+$;

$^1$H-Nuclear Magnetic Resonance Spectra (400 MHz, DMSO-$d_6$) δ ppm:

12.62 (1H, brs), 7.89 (2H, d, J=9 Hz), 7.03 (2H, d, J=9 Hz), 4.12 (2H, t, J=6 Hz), 2.50-2.37 (2H, m), 1.99-1.92 (2H, m).

(81b) N-[4-(4,4,4-Trifluorobutoxy)benzoyl]glycine

A reaction similar to that described in Example 1 (1b) was conducted using 4-(4,4,4-trifluorobutoxy)benzoic acid (1.00 g) prepared in Example 81 (81a) to give 849 mg of the title compound (white powder).

MS (ESI) m/z: 306 $[M+H]^+$, 304 $[M-H]^+$;

$^1$H-Nuclear Magnetic Resonance Spectra (400 MHz, DMSO-$d_6$) δ ppm:

12.54 (1H, brs), 8.68 (1H, t, J=6 Hz), 7.84 (2H, d, J=9 Hz), 7.02 (2H, d, J=9 Hz), 4.11 (2H, t, J=6 Hz), 3.89 (2H, d, J=9 Hz), 2.50-2.37 (2H, m), 1.99-1.92 (2H, m).

(81c) N-{2-[(2-Hydroxyethyl)amino]-2-oxo-1-[4-(trifluoromethoxy)benzyl]ethyl}-4-(4,4,4-trifluorobutoxy)benzamide A reaction similar to that described in Example 1 (1c) was conducted using N-[4-(4,4,4-trifluorobutoxy)benzoyl]glycine (350 mg) prepared in Example 81 (81b) and 4-(trifluoromethoxy)benzaldehyde (172 μL) to give the corresponding oxazolone (341 mg). A reaction similar to that described in Example 1 (1d) was conducted using 337 mg of this oxazolone to give 297 mg of N-{(Z)-1-{[(2-hydroxyethyl)amino]carbonyl}-2-[4-(trifluoromethoxy)phenyl]vinyl}-4-(4,4,4-trifluorobutoxy)benzamide (white amorphous solid).

MS (FAB) m/z: 521 $[M+H]^+$;

$^1$H-Nuclear Magnetic Resonance Spectra (400 MHz, DMSO-$d_6$) δ ppm:

9.79 (1H, s), 8.06 (1H, t, J=5 Hz), 7.95 (2H, d, J=9 Hz), 7.64 (2H, d, J=9 Hz), 7.34 (2H, d, J=9 Hz), 7.16 (1H, s), 7.06 (2H, d, J=9 Hz), 4.63 (1H, t, J=5 Hz), 4.13 (2H, t, J=6 Hz), 3.44 (2H, q, J=6 Hz), 3.23 (2H, t, J=6 Hz), 2.51-2.38 (2H, m), 2.00-1.93 (2H, m).

A reaction similar to that described in Example 1 (1e) was conducted using N-{(Z)-1-{[(2-hydroxyethyl)amino]carbonyl}-2-[4-(trifluoromethoxy)phenyl]vinyl}-4-(4,4,4-trifluorobutoxy)benzamide (230 mg) to give 194 mg of the title compound (white powder).

MS (FAB) m/z: 523 $[M+H]^+$;

$^1$H-Nuclear Magnetic Resonance Spectra (400 MHz, DMSO-$d_6$) δ ppm:

8.42 (1H, d, J=8 Hz), 8.07 (1H, t, J=5 Hz), 7.78 (2H, d, J=9 Hz), 7.43 (2H, d, J=9 Hz), 7.23 (2H, d, J=9 Hz), 6.98 (2H, d, J=9 Hz), 4.70-4.64 (2H, m), 4.09 (2H, t, J=6 Hz), 3.38 (2H, q, J=6 Hz), 3.18-3.08 (3H, m), 3.00 (1H, dd, J=14 Hz, 11 Hz), 2.47-2.36 (2H, m), 1.99-1.91 (2H, m).

Example 82

N-{2-Amino-2-oxo-1-[4-(trifluoromethoxy)benzyl]ethyl}-4-(4,4,4-trifluorobutoxy)benzamide (Exemplary Compound No. 1009)

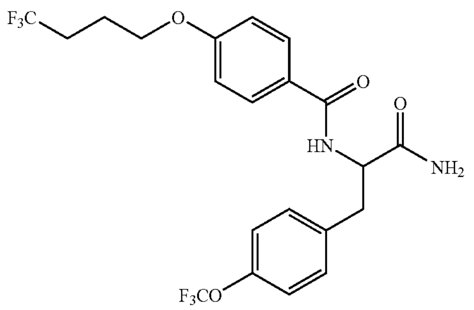 [SMILES: NC(=O)C(Cc1ccc(OC(F)(F)F)cc1)NC(=O)c1ccc(OCCCC(F)(F)F)cc1]

(82a) 2-{[4-(4,4,4-Trifluorobutoxy)benzoyl]amino}-3-[4-(trifluoromethoxy)phenyl]propanoic acid A reaction similar to that described in Example 70 (70a) was conducted using 4-(4,4,4-trifluorobutoxy)benzoic acid (6.21 g) prepared in Example 81 (81a) and 2-amino-3-[4-(trifluoromethoxy)phenyl]propanoic acid hydrochloride (7.20 g) prepared in Reference Example 2 to give 11.4 g of the title compound (white powder).

MS (ESI) m/z: 480 $[M+H]^+$, 478 $[M-H]^+$;

$^1$H-Nuclear Magnetic Resonance Spectra (400 MHz, DMSO-$d_6$) δ ppm:

12.79 (1H, brs), 8.54 (1H, d, J=8 Hz), 7.77 (2H, d, J=9 Hz), 7.41 (2H, d, J=9 Hz), 7.25 (2H, d, J=9 Hz), 6.99 (2H, d, J=9 Hz), 4.61-4.56 (1H, m), 4.09 (2H, t, J=6 Hz), 3.21 (1H, dd, J=14 Hz, 4 Hz), 3.09 (1H, dd, J=14 Hz, 11 Hz), 2.49-2.36 (2H, m), 1.98-1.91 (2H, m).

(82b) N-{2-Amino-2-oxo-1-[4-(trifluoromethoxy)benzyl]ethyl}-4-(4,4,4-trifluorobutoxy)benzamide A reaction similar to that described in Example 32 (32c) was conducted using 2-{[4-(4,4,4-trifluorobutoxy)benzoyl]amino}-3-[4-(trifluoromethoxy)phenyl]propanoic acid (360 mg) prepared in Example 82 (82a) and ammonia (600 μL, 2 M methanol solution) to give 122 mg of the title compound (white powder).

(In this case, DMF was used instead of methanol.)

MS (ESI) m/z: 479 $[M+H]^+$, 477 $[M-H]^+$;

$^1$H-Nuclear Magnetic Resonance Spectra (400 MHz, DMSO-$d_6$) δ ppm:

8.37 (1H, d, J=8 Hz), 7.77 (2H, d, J=9 Hz), 7.54 (1H, brs), 7.44 (2H, d, J=9 Hz), 7.24 (2H, d, J=9 Hz), 7.09 (1H, brs), 6.97 (2H, d, J=9 Hz), 4.65-4.59 (1H, m), 4.08 (2H, t, J=6 Hz), 3.12 (1H, dd, J=14 Hz, 4 Hz), 3.01 (1H, dd, J=14 Hz, 11 Hz), 2.47-2.36 (2H, m), 1.98-1.91 (2H, m).

Example 83

N-{2-(Methylamino)-2-oxo-1-[4-(trifluoromethoxy) benzyl]ethyl}-4-(4,4,4-trifluorobutoxy)benzamide (Exemplary Compound No. 1014)

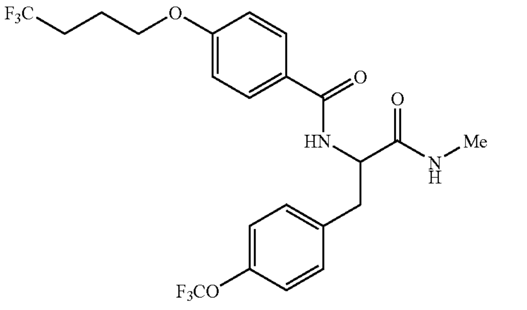 [SMILES: CNC(=O)C(Cc1ccc(OC(F)(F)F)cc1)NC(=O)c1ccc(OCCCC(F)(F)F)cc1]

A reaction similar to that described in Example 32 (32c) was conducted using 2-{[4-(4,4,4-trifluorobutoxy)benzoyl] amino}-3-[4-(trifluoromethoxy)phenyl]propanoic acid (360 mg) prepared in Example 82 (82a) and methylamine (450 μL, 2 M methanol solution) to give 270 mg of the title compound (white powder).

(In this case, DMF was used instead of methanol.)

MS (ESI) m/z: 493 $[M+H]^+$, 491 $[M-H]^+$;

$^1$H-Nuclear Magnetic Resonance Spectra (400 MHz, DMSO-$d_6$) δ ppm:

8.45 (1H, d, J=8 Hz), 8.00 (1H, q, J=4 Hz), 7.79 (2H, d, J=9 Hz), 7.42 (2H, d, J=9 Hz), 7.24 (2H, d, J=9 Hz), 6.98 (2H, d, J=9 Hz), 4.65-4.59 (1H, m), 4.09 (2H, t, J-6 Hz), 3.11 (1H, dd, J-14 Hz, 4 Hz), 3.00 (1H, dd, J-14 Hz, 11 Hz), 2.61 (3H, d, J=5 Hz), 2.48-2.36 (2H, m), 1.98-1.91 (2H, m).

Example 84

2-Fluoro-N-{2-[(2-hydroxyethyl)amino]-2-oxo-1-[4-(trifluoromethoxy)benzyl]ethyl}-4-(3,3,3-trifluoro-propoxy)benzamide

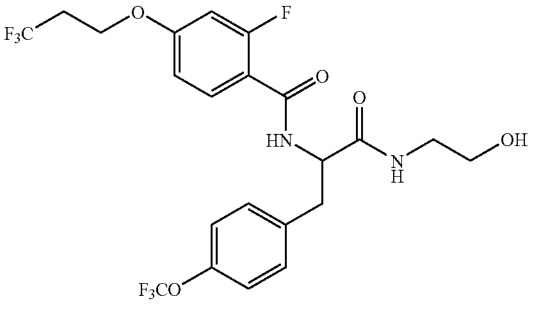

(84a) 2-Fluoro-4-(3,3,3-trifluoropropoxy)benzoic acid

Potassium carbonate (663 mg) was added to a 2-butanone (6 mL) solution of methyl 2-fluoro-4-hydroxybenzoate (compound described in U.S. Pat. No. 5,990,142 A1, 340 mg) and 3,3,3-trifluoropropyl trifluoromethanesulfonate (compound described in Tetrahedron, (1988), 44, 5375-5388, 590 mg). The mixture was stirred at 75° C. for 1.5 hours, and then the solvent was evaporated. To the obtained residue were added methanol (8 mL) and a 2 M sodium hydroxide aqueous solution (2 mL). The mixture was stirred at 60° C. for 1.5 hours, and the solvents (mainly methanol) were evaporated. To the residue was added water (15 mL), and the mixture was changed to acidic by adding 1 M hydrochloric acid thereto while stirring. The precipitated crystalline solid was collected by filtration, washed with water, and dried under reduced pressure to give 203 mg of the title compound (white crystal, yield: 40%).

MS (ESI) m/z: 251 $[M-H]^+$;

$^1$H-Nuclear Magnetic Resonance Spectra (400 MHz, DMSO-$d_6$) δ ppm:

12.91 (1H, brs), 7.83 (1H, t, J=9 Hz), 6.96 (1H, dd, J=13 Hz, 2 Hz), 6.89 (1H, dd, J=9 Hz, 2 Hz), 4.30 (2H, t, J=6 Hz), 2.88-2.76 (2H, m).

(84b) 2-{[2-Fluoro-4-(3,3,3-trifluoropropoxy)benzoyl] amino}-3-[4-(trifluoromethoxy)phenyl]propanoic acid A reaction similar to that described in Example 70 (70a) was conducted using 2-fluoro-4-(3,3,3-trifluoropropoxy) benzoic acid (177 mg) prepared in Example 84 (84a) and 2-amino-3-[4-(trifluoromethoxy)phenyl]propanoic acid hydrochloride (200 mg) prepared in Reference Example 2 to give 317 mg of the title compound (white powder).

MS (ESI) m/z: 484 $[M+H]^+$, 482 $[M-H]^+$;

$^1$H-Nuclear Magnetic Resonance Spectra (400 MHz, DMSO-$d_6$) δ ppm:

12.85 (1H, brs), 8.24 (1H, dd, J=8 Hz, 4 Hz), 7.49 (1H, t, J=9 Hz), 7.37 (2H, d, J=9 Hz), 7.24 (2H, d, J=8 Hz), 6.92 (1H, dd, J=13 Hz, 2 Hz), 6.84 (1H, dd, J=9 Hz, 2 Hz), 4.62-4.56 (1H, m), 4.26 (2H, t, J=6 Hz), 3.20 (1H, dd, J=14 Hz, 5 Hz), 3.07 (1H, dd, J=14 Hz, 10 Hz), 2.85-2.74 (2H, m).

(84c) 2-Fluoro-N-{2-[(2-hydroxyethyl)amino]-2-oxo-1-[4-(trifluoromethoxy)benzyl]ethyl}-4-(3,3,3-trifluoropropoxy)benzamide A reaction similar to that described in Example 32 (32c) was conducted using 2-{[2-fluoro-4-(3,3,3-trifluoropropoxy)benzoyl]amino}-3-[4-(trifluoromethoxy)phenyl]propanoic acid (145 mg) prepared in Example 84 (84b) and 2-aminoethanol (22 μL) to give 128 mg of the title compound (white powder).

(In this case, DMF was used instead of methanol.)

MS (ESI) m/z: 527 $[M+H]^+$, 525 $[M-H]^+$;

$^1$H-Nuclear Magnetic Resonance Spectra (400 MHz, DMSO-$d_6$) δ ppm:

8.12 (1H, t, J=5 Hz), 8.02 (1H, dd, J=8 Hz, 6 Hz), 7.53 (1H, t, J=9 Hz), 7.35 (2H, d, J=9 Hz), 7.22 (2H, d, J=8 Hz), 6.92 (1H, dd, J=13 Hz, 2 Hz), 6.84 (1H, dd, J=9 Hz, 3 Hz), 4.72-

4.66 (2H, m), 4.26 (2H, t, J=6 Hz), 3.38 (2H, q, J=6 Hz), 3.17-3.07 (3H, m), 2.96 (1H, dd, J=13 Hz, 9 Hz), 2.86-2.74 (2H, m).

Example 85

N-{2-[(2-Hydroxyethyl)amino]-2-oxo-1-[4-(trifluoromethoxy)benzyl]ethyl}-4-(2,2,2-trifluoroethoxy)benzamide (Exemplary Compound No. 754)

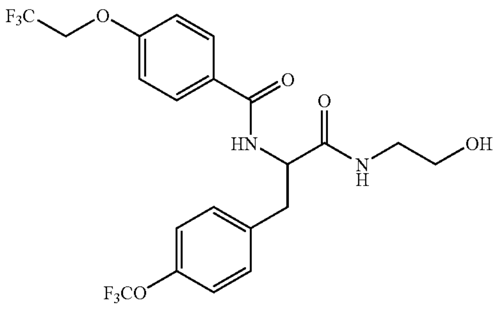 [SMILES: O=C(NC(Cc1ccc(OC(F)(F)F)cc1)C(=O)NCCO)c1ccc(OCC(F)(F)F)cc1]

(85a) N-[4-(2,2,2-Trifluoroethoxy)benzoyl]glycine

A reaction similar to that described in Example 1 (1b) was conducted using 4-(2,2,2-trifluoroethoxy)benzoic acid (compound described in Chem. Pharm. Bull., (1996), 44, 314-327, 2.00 g) to give 849 mg of the title compound (white powder).

MS (ESI) m/z: 278 $[M+H]^+$, 276 $[M-H]^+$;

$^1$H-Nuclear Magnetic Resonance Spectra (400 MHz, DMSO-$d_6$) δ ppm:

12.56 (1H, brs), 8.75 (1H, t, J=5 Hz), 7.87 (2H, d, J=9 Hz), 7.14 (2H, d, J=9 Hz), 4.85 (2H, q, J=9 Hz), 3.90 (2H, d, J=6 Hz).

(85b) N-{2-[(2-Hydroxyethyl)amino]-2-oxo-1-[4-(trifluoromethoxy)benzyl]ethyl}-4-(2,2,2-trifluoroethoxy)benzamide A reaction similar to that described in Example 1 (1c) was conducted using N-[4-(2,2,2-trifluoroethoxy)benzoyl]glycine (300 mg) prepared in Example 85 (85a) and 4-(trifluoromethoxy)benzaldehyde (162 μL) to give the corresponding oxazolone (270 mg). A reaction similar to that described in Example 1 (1d) was conducted using 265 mg of this oxazolone to give 303 mg of N-{(Z)-1-{[(2-hydroxyethyl)amino]carbonyl}-2-[4-(trifluoromethoxy)phenyl]vinyl}-4-(2,2,2-trifluoroethoxy)benzamide (white amorphous solid).

MS (FAB) m/z: 493 $[M+H]^+$;

$^1$H-Nuclear Magnetic Resonance Spectra (400 MHz, DMSO-$d_6$) δ ppm:

9.86 (1H, brs), 8.10 (1H, t, J=6 Hz), 7.99 (2H, d, J=9 Hz), 7.64 (2H, d, J=9 Hz), 7.34 (2H, d, J=9 Hz), 7.18 (2H, d, J=9 Hz), 7.18 (1H, s), 4.90 (1H, d, J=9 Hz), 4.86 (1H, d, J=9 Hz), 4.63 (1H, t, J=5 Hz), 3.44 (2H, q, J=6 Hz), 3.23 (2H, q, J=6 Hz).

A reaction similar to that described in Example 1 (1e) was conducted using N-{(Z)-1-{[(2-hydroxyethyl)amino]carbonyl}-2-[4-(trifluoromethoxy)phenyl]vinyl}-4-(2,2,2-trifluoroethoxy)benzamide (360 mg) to give 220 mg of the title compound (white powder).

MS (FAB) m/z: 495 $[M+H]^+$;

$^1$H-Nuclear Magnetic Resonance Spectra (400 MHz, DMSO-$d_6$) δ ppm:

8.49 (1H, d, J=9 Hz), 8.09 (1H, t, J=5 Hz), 7.81 (2H, d, J=9 Hz), 7.44 (2H, d, J=9 Hz), 7.24 (2H, d, J-9 Hz), 7.10 (2H, d, J-9 Hz), 4.81 (2H, 4, J-9 Hz), 4.71-4.62 (2H, m), 3.41-3.35 (2H, m), 3.18-3.08 (3H, m), 3.00 (1H, dd, J=14 Hz, 11 Hz).

Example 86

N-{1-[3-Fluoro-4-(trifluoromethyl)benzyl]-2-[(2-hydroxyethyl)amino]-2-oxoethyl}-4-(3,3,3-trifluoropropoxy)benzamide

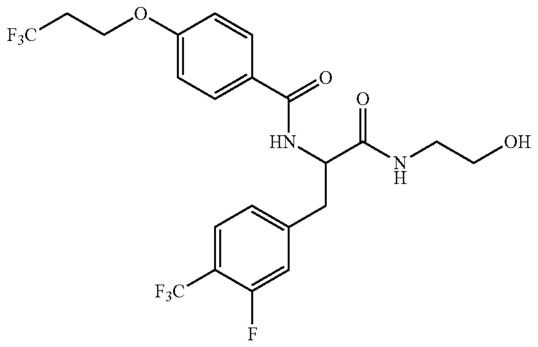 [SMILES: O=C(NC(Cc1ccc(C(F)(F)F)c(F)c1)C(=O)NCCO)c1ccc(OCCC(F)(F)F)cc1]

A reaction similar to that described in Example 1 (1c) was conducted using N-[4-(3,3,3-trifluoropropoxy)benzoyl]glycine (300 mg) prepared in Example 33 (33a) and 3-fluoro-4-(trifluoromethyl)benzaldehyde (208 mg) to give the corresponding oxazolone (274 mg). A reaction similar to that described in Example 1 (1d) was conducted using all this oxazolone to give 281 mg of N-((Z)-2-[3-fluoro-4-(trifluoromethyl)phenyl]-1-{[(2-hydroxyethyl)amino]carbonyl}vinyl)-4-(3,3,3-trifluoropropoxy)benzamide (yellow powder).

MS (FAB) m/z: 509 $[M+H]^+$;

$^1$H-Nuclear Magnetic Resonance Spectra (500 MHz, DMSO-$d_6$) δ ppm:

9.90 (1H, s), 8.23 (1H, t, J=6 Hz), 7.96 (2H, d, J=9 Hz), 7.76 (1H, t, J=8 Hz), 7.58 (1H, d, J=13 Hz), 7.52 (1H, d, J=8 Hz), 7.14 (1H, s), 7.09 (2H, d, J=9 Hz), 4.65 (1H, t, J=6 Hz), 4.30 (2H, t, J=6 Hz), 3.45 (2H, q, J=6 Hz), 3.24 (2H, q, J=6H), 2.89-2.77 (2H, m).

A reaction similar to that described in Example 1 (1e) was conducted using N-((Z)-2-[3-fluoro-4-(trifluoromethyl)phenyl]-1-{[(2-hydroxyethyl)amino]carbonyl}vinyl)-4-(3,3,3-trifluoropropoxy)benzamide (195 mg) to give 156 mg of the title compound (white powder).

MS (FAB) m/z: 511 $[M+H]^+$;

$^1$H-Nuclear Magnetic Resonance Spectra (500 MHz, DMSO-$d_6$) δ ppm:

8.48 (1H, d, J-9 Hz), 8.11 (1H, t, J-6 Hz), 7.79 (2H, d, J-9 Hz), 7.67 (1H, t, J=8 Hz), 7.46 (1H, d, J=12 Hz), 7.36 (1H, d, J=8 Hz), 7.01 (2H, d, J=9 Hz), 4.76-4.72 (1H, m), 4.69 (1H, t, J=5 Hz), 4.26 (2H, t, J=6 Hz), 3.39 (2H, d, J=6 Hz), 3.21-3.13 (3H, m), 3.07 (1H, dd, J=14 Hz, 11 Hz), 2.85-2.76 (2H, m).

Example 87

N-{2-Amino-2-oxo-1-[4-(trifluoromethoxy)benzyl]ethyl}-4-[4-(trifluoromethyl)phenoxy]benzamide (Exemplary Compound No. 1064)

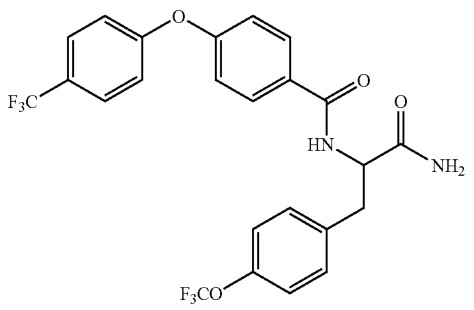 [SMILES: NC(=O)C(Cc1ccc(OC(F)(F)F)cc1)NC(=O)c1ccc(Oc2ccc(C(F)(F)F)cc2)cc1]

A reaction similar to that described in Example 1 (1d) was conducted using oxazolone (502 mg) obtained in the preparation process of Example 42 and ammonia (1.53 mL, 2 M ethanol solution) to give 286 mg of N-{(Z)-1-(aminocarbonyl)-2-[4-(trifluoromethoxy)phenyl]vinyl}-4-[4-(trifluoromethyl)phenoxy]benzamide (white amorphous solid).

MS (FAB) m/z: 511 $[M+H]^+$;

$^1$H-Nuclear Magnetic Resonance Spectra (400 MHz, DMSO-$d_6$) δ ppm:

9.92 (1H, s), 8.06 (2H, d, J=9 Hz), 7.79 (2H, d, J=9 Hz), 7.68-7.64 (3H, m), 7.36 (2H, d, J=9 Hz), 7.26-7.19 (6H, m).

A reaction similar to that described in Example 1 (1e) was conducted using N-{(Z)-1-(aminocarbonyl)-2-[4-(trifluoromethoxy)phenyl]vinyl}-4-[4-(trifluoromethyl)phenoxy]benzamide (172 mg) to give 159 mg of the title compound (white powder).

MS (FAB) m/z: 513 $[M+H]^+$;

$^1$H-Nuclear Magnetic Resonance Spectra (400 MHz, DMSO-$d_6$) δ ppm:

8.56 (1H, d, J=9 Hz), 7.89 (2H, d, J=9 Hz), 7.77 (2H, d, J=9 Hz), 7.58 (1H, brs), 7.45 (2H, d, J=9 Hz), 7.26 (2H, d, J=9 Hz), 7.21 (2H, d, J=9 Hz), 7.16 (2H, d, J=9 Hz), 7.13 (1H, brs), 4.69-4.63 (1H, m), 3.14 (1H, dd, J-14 Hz, 4 Hz), 3.02 (1H, dd, J=14 Hz, 11 Hz).

Example 88

N-{2-(Methylamino)-2-oxo-1-[4-(trifluoromethoxy)benzyl]ethyl}-4-[4-(trifluoromethyl)phenoxy]benzamide (Exemplary Compound No. 1069)

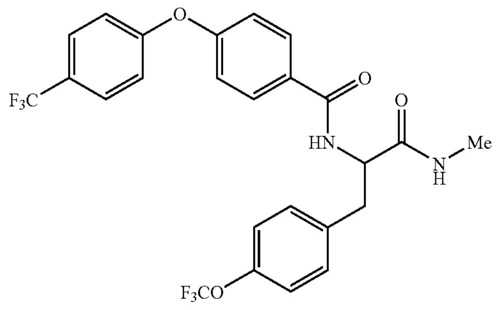 [SMILES: CNC(=O)C(Cc1ccc(OC(F)(F)F)cc1)NC(=O)c1ccc(Oc2ccc(C(F)(F)F)cc2)cc1]

(88a) 3-[4-(Trifluoromethoxy)phenyl]-2-({4-[4-(trifluoromethyl)phenoxy]benzoyl}amino)propanoic acid A reaction similar to that described in Example 70 (70a) was conducted using 4-[4-(trifluoromethyl)phenoxy]benzoic acid (compound described in International Publication No. WO 04/14844, 446 mg) to give 724 mg of the title compound (white powder).

$^1$H-Nuclear Magnetic Resonance Spectra (400 MHz, DMSO-$d_6$) δ ppm:

12.81 (1H, brs), 8.76 (1H, d, J=8 Hz), 7.88 (2H, d, J=9 Hz), 7.77 (2H, d, J=9 Hz), 7.44 (2H, d, J=9 Hz), 7.27 (2H, d, J=9 Hz), 7.22 (2H, d, J=9 Hz), 7.18 (2H, d, J=9 Hz), 4.67-4.61 (1H, m), 3.23 (1H, dd, J=14 Hz, 4 Hz), 3.11 (1H, dd, J=14 Hz, 11 Hz).

(88b) N-{2-(Methylamino)-2-oxo-1-[4-(trifluoromethoxy)benzyl]ethyl}-4-[4-(trifluoromethyl)phenoxy]benzamide A reaction similar to that described in Example 32 (32c) was conducted using 3-[4-(trifluoromethoxy)phenyl]-2-({4-[4-(trifluoromethyl)phenoxy]benzoyl}amino)propanoic acid (720 mg) prepared in Example 88 (88a) and methylamine (798 μL, 2 M methanol solution) to give 330 mg of the title compound (white powder).

(In this case, DMF was used instead of methanol.)

MS (FAB) m/z: 527 $[M+H]^+$;

$^1$H-Nuclear Magnetic Resonance Spectra (400 MHz, DMSO-$d_6$) δ ppm:

8.63 (1H, d, J=9 Hz), 8.03 (1H, q, J=4 Hz), 7.89 (2H, d, J=9 Hz), 7.77 (2H, d, J=9 Hz), 7.43 (2H, d, J=9 Hz), 7.25 (2H, d,

J=9 Hz), 7.20 (2H, d, J=9 Hz), 7.16 (2H, d, J=9 Hz), 4.68-4.62 (1H, m), 3.12 (1H, dd, J=14 Hz, 5 Hz), 3.01 (1H, dd, J=14 Hz, 11 Hz), 2.61 (3H, d, J=5 Hz).

Example 89

N-{(1S)-2-(Methylamino)-2-oxo-1-[4-(trifluoromethoxy)benzyl]ethyl}-4-(3,3,3-trifluoropropoxy) benzamide (Exemplary Compound No. 959)

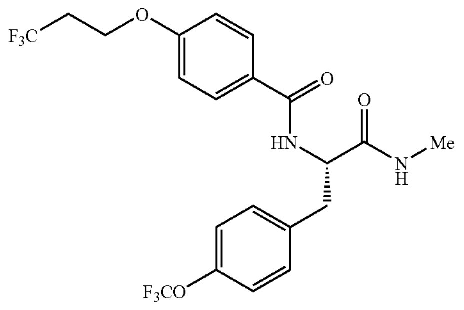

N-{2-(Methylamino)-2-oxo-1-[4-(trifluoromethoxy)benzyl]ethyl}-4-(3,3,3-trifluoropropoxy)benzamide prepared in Example 69 was subjected to HPLC separation under conditions as in Example 10 to give the title compound.

Retention time: S-isomer 17 min, R-isomer 64 min.

No R-isomer was recognized by HPLC analysis of this compound under the following conditions, and thereby it was confirmed that the optical purity was 99% or higher.

[Analysis conditions] column: CHIRALPAK AD-H (manufactured by Daicel Chemical Industries, Ltd., internal diameter: 0.46 cm, length: 25 cm), mobile phase: methanol, flow rate: 1.0 mL/min, temperature: 25° C., detection: 254 nm (UV), retention time: R-isomer 4.8 min, S-isomer 31.4 min.

Example 90

N-{(1S)-2-Amino-2-oxo-1-[4-(trifluoromethoxy) benzyl]ethyl}-4-(3,3,3-trifluoropropoxy)benzamide (Exemplary Compound No. 954)

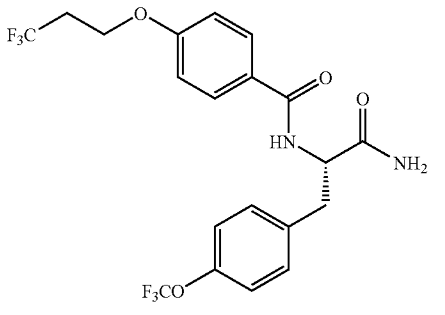 [SMILES: NC(=O)[C@H](Cc1ccc(OC(F)(F)F)cc1)NC(=O)c1ccc(OCCC(F)(F)F)cc1]

N-{2-Amino-2-oxo-1-[4-(trifluoromethoxy)benzyl] ethyl}-4-(3,3,3-trifluoropropoxy)benzamide prepared in Example 80 was subjected to HPLC separation under conditions as in Example 10 to give the title compound.

Retention time: S-isomer 22 min, R-isomer 147 min.

No R-isomer was recognized by HPLC analysis of this compound under conditions as in Example 10, and thereby it was confirmed that the optical purity was 99% or higher.

Retention time: S-isomer 17.9 min, R-isomer 29.7 min.

Example 91

N-{(1S)-2-[(2-Fluoroethyl)amino]-2-oxo-1-[4-(trifluoromethoxy)benzyl]ethyl}-4-(3,3,3-trifluoropropoxy)benzamide (Exemplary Compound No. 999)

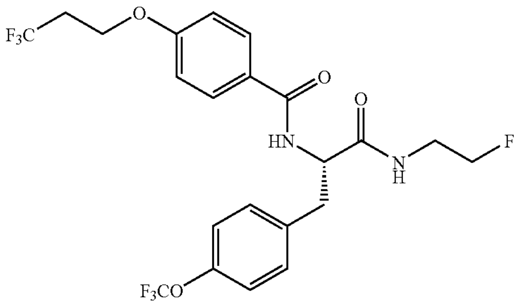 [SMILES: O=C(N[C@@H](Cc1ccc(OC(F)(F)F)cc1)C(=O)NCCF)c1ccc(OCCC(F)(F)F)cc1]

N-{2-[(2-Fluoroethyl)amino]-2-oxo-1-[4-(trifluoromethoxy)benzyl]ethyl}-4-(3,3,3-trifluoropropoxy)benzamide prepared in Example 78 was subjected to HPLC separation under conditions as in Example 10 to give the title compound.

Retention time: S-isomer 26 min, R-isomer 165 min.

No R-isomer was recognized by HPLC analysis of this compound under conditions as in Example 10, and thereby it was confirmed that the optical purity was 99% or higher.

Retention time: S-isomer 13.5 min, R-isomer 15.9 min.

Reference Example 1

Tert-Butyl 2-amino-3-[4-(trifluoromethoxy)phenyl]propanoate

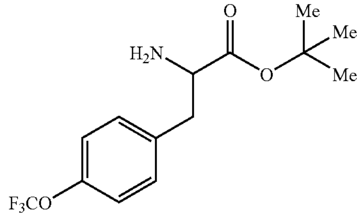 [SMILES: CC(C)(C)OC(=O)C(N)Cc1ccc(OC(F)(F)F)cc1]

(1a) Tert-Butyl 2-[(diphenylmethylene)amino]-3-[4-(trifluoromethoxy)phenyl]propanoate 1-(Bromomethyl)-4-(trifluoromethoxy)benzene (1.23 mL, 7.7 mmol) and tetrabutylammonium hydrogen sulfate (2.85 g, 8.4 mmol) were added to a methylene chloride (50 mL) solution of tert-butyl [(diphenylmethylene)amino]acetate (compound described in J. Org. Chem., (1982), 47, 2663-2666, 2.07 g, 7.0 mmol) at room temperature according to the method described in the document (J. Org. Chem., (1995), 60, 601-607), and subsequently a 10% sodium hydroxide aqueous solution (21 mL) was added thereto. The mixture was vigorously stirred for 1.5 hours, and then to the reaction solution was added water. The resulting mixture was extracted with methylene chloride. The organic layer was collected, washed with saturated brine, and dried over anhydrous magnesium sulfate. The solvent was evaporated, and the obtained residue was purified by silica gel column chromatography (n-hexane to n-hexane:ethyl acetate, 19:1 and 9:1, V/V) twice to give 2.55 g of the title compound (white powder, yield: 78%).

MS (FAB) m/z: 470 $[M+H]^+$;

$^1$H-Nuclear Magnetic Resonance Spectra (400 MHz, $CDCl_3$) δ ppm:

7.67 (2H, d, J=8 Hz), 7.40-7.27 (6H, m), 7.07 (2H, d, J=9 Hz), 7.04 (2H, d, J=9 Hz), 6.61 (2H, brd, J=6 Hz), 4.08 (1H, dd, J=9 Hz, 4 Hz), 3.22 (1H, dd, J=14 Hz, 4 Hz), 3.16 (1H, dd, J=14 Hz, 9 Hz), 1.44 (9H, s).

(1b) Tert-Butyl 2-amino-3-[4-(trifluoromethoxy)phenyl]propanoate

According to the method described in the document (J. Am. Chem. Soc., (2003), 125, 5139-5151), a 1 M citric acid aqueous solution (52 mL) was added to a THF (52 mL) solution of tert-butyl 2-[(diphenylmethylene)amino]-3-[4-(trifluoromethoxy)phenyl]propanoate (2.44 g, 5.21 mmol) prepared in Reference Example 1 (1a). The mixture was stirred at room temperature for 4 hours. The reaction solution (mainly THF) was evaporated, neutralized with a sodium bicarbonate aqueous solution, and then extracted with methylene chloride. The organic layer was dried over anhydrous sodium sulfate. The solvent was evaporated, and the obtained residue was purified by silica gel column chromatography (n-hexane:ethyl acetate, 94:6, 3:7, and 1:9, V/V) to give 1.5 g of the title compound (colorless oil, yield: 95%).

MS (FAB) m/z: 306 $[M+H]^+$;

$^1$H-Nuclear Magnetic Resonance Spectra (500 MHz, $CDCl_3$) δ ppm:

7.25 (2H, d, J=8 Hz), 7.15 (2H, d, J=8 Hz), 3.59 (1H, dd, J=7 Hz, 6 Hz), 3.01 (1H, dd, J=14 Hz, 6 Hz), 2.87 (1H, dd, J=14 Hz, 7 Hz), 1.41 (9H, s).

Reference Example 2

2-Amino-3-[4-(trifluoromethoxy)phenyl]propanoic acid hydrochloride

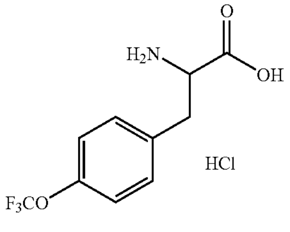 [SMILES: NC(Cc1ccc(OC(F)(F)F)cc1)C(=O)O ; Cl]

A 6 N hydrochloric acid (1 mL) solution of tert-butyl 2-[(diphenylmethylene)amino]-3-[4-(trifluoromethoxy)phenyl]propanoate (64 mg, 0.136 mmol) prepared in Reference Example 1 (1a) was heated under reflux for 6 hours and then cooled to room temperature. The reaction solution was concentrated under reduced pressure, and the residue was washed with diethyl ether to give 35 mg of the title compound (white powder, yield: 91%).

Reference Example 3

(2S)-2-Amino-3-[4-(trifluoromethoxy)phenyl]propanoic acid hydrochloride

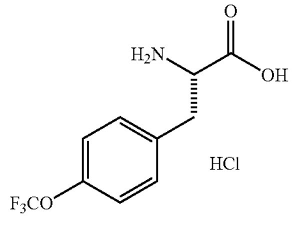

This compound was prepared according to the following two types methods, from (3a) to (3c) or from (3d) to (3g).

(3a) Tert-Butyl (2S)-2-[(diphenylmethylene)amino]-3-[4-(trifluoromethoxy)phenyl]propanoate 1-(Bromomethyl)-4-(trifluoromethoxy)benzene (28.1 g, 0.110 mol) and 50% potassium hydroxide (225 mL, 2.00 mol) were added to a toluene (1 L) suspension of tert-butyl [(diphenylmethylene)amino]acetate (29.5 g, 0.10 mol) and N-(9-anthracenylmethyl)cinchonidinium chloride (5.79 g, 0.01 mol) under ice-cooling with stirring. The mixture was vigorously stirred at the same temperature for 3.25 hours and then separated into an organic layer and an aqueous layer. The aqueous layer was extracted with ethyl acetate (200 mL), and the organic layers were combined, washed with saturated brine, and dried over anhydrous magnesium sulfate. The solvent was evaporated, and the obtained residue was purified by silica gel column chromatography (n-hexane:ethyl acetate, 20:1, 15:1, and 10:1, V/V) to give 41.2 g of the title compound (mixture of a yellow oil and a yellow solid, yield: 88%, optical purity: 88%).

[Analysis conditions] column: CHIRALCEL OD-H (manufactured by Daicel Chemical Industries, Ltd., internal diameter: 0.46 cm, length: 25 cm), mobile phase: n-hexane/isopropanol=99/1, flow rate: 1.0 mL/min, temperature: 40° C., detection: 254 nm (UV), retention time: S-isomer 4.2 min, R-isomer 5.8 min.

(3b) (2S)-2-Amino-3-[4-(trifluoromethoxy)phenyl]propanoic acid hydrochloride

A 6 N hydrochloric acid (400 mL) solution of tert-butyl (2S)-2-[(diphenylmethylene)amino]-3-[4-(trifluoromethoxy)phenyl]propanoate (41.2 g, 87.7 mmol) prepared in Reference Example 3 (3a) was heated under reflux for 3 hours and then cooled to room temperature. The reaction solution was concentrated under reduced pressure. The residue was washed with diethyl ether to give 23.8 g of a crude crystal (white powder, yield: 95%, optical purity: 84%). The crude crystalline solid (200 mg) was recrystallized from 1 N hydrochloric acid (1.5 mL) to give 120 mg of the title compound (colorless crystal, yield: 60%). No R-isomer was recognized in this compound by HPLC analysis according to the method described in Reference Example 3 (3c), and thereby it was confirmed that the optical purity was 99% or higher.

(3c) Determination of optical purity of (2S)-2-amino-3-[4-(trifluoromethoxy)phenyl]propanoic acid hydrochloride (2S)-2-Amino-3-[4-(trifluoromethoxy)phenyl]propanoic acid hydrochloride (3 mg) prepared in Reference Example 3

(3b) was dissolved in 0.5 N sodium hydroxide (100 μL), and then (benzyloxy)carbonyl chloride (ZCl, 5 μL) was added thereto. The resulting mixture was stirred, and then water (100 μL) was added thereto. The resulting mixture was changed to acidic with 1 N hydrochloric acid (50 μL) and extracted with ethyl acetate (300 μL) to obtain the corresponding (2S)-2-{[(benzyloxy)carbonyl]amino}-3-[4-(trifluoromethoxy)phenyl]propanoic acid. The optical purity was determined by HPLC under the following conditions.

[Analysis conditions] column: CHIRALPAK AD-H (manufactured by Daicel Chemical Industries, Ltd., internal diameter: 0.46 cm, length: 25 cm), mobile phase: n-hexane/isopropanol/trifluoroacetic acid ~90/10/0.1, flow rate: 0.5 mL/min, temperature: 25° C., detection: 254 nm (UV), retention time: S-isomer 28.9 min, R-isomer 31.9 min.

(3d) 2-Methyl-4-[4-(trifluoromethoxy)benzylidene]-1,3-oxazol-5(4H)-one

A mixture of N-acetylglycine (5.00 g, 42.7 mmol), 4-trifluoromethoxybenzaldehyde (9.30 g, 47.0 mmol), sodium acetate (4.55 g, 55.5 mmol), and acetic anhydride (20 mL, 213 mmol) was stirred at 120° C. for 1 hour, and then was cooled to room temperature. After further ice-cooling, the precipitated yellow solid was suspended in water. The insoluble substance was collected by filtration, washed with water, and dried by heating under reduced pressure to give 10.7 g of the title compound (yellowish brown crystal, yield: 92%).

MS (EI) m/z: 271 $[M]^+$;

$^1$H-Nuclear Magnetic Resonance Spectra (500 MHz, $CDCl_3$) δ ppm:

8.13 (2H, d, J=9 Hz), 7.28 (2H, d, J=9 Hz), 7.11 (1H, s), 2.42 (3H, s).

(3e) Methyl 2-(acetylamino)-3-[4-(trifluoromethoxy)phenyl]propanoate

N-Ethyl-N,N-diisopropylamine (2.50 g, 19.4 mmol) was added to a methanol (50 mL) solution of 2-methyl-4-[4-(trifluoromethoxy)benzylidene]-1,3-oxazol-5(4H)-one (5.00 g, 18.4 mmol) prepared in Reference Example 3 (3d), at room temperature. The mixture was stirred at 60° C. for 4 hours. The reaction solution was cooled to room temperature, and then 10% palladium-carbon (wet, 2.2 g) was added thereto. The resulting mixture was stirred under a hydrogen atmosphere (rubber balloon) at room temperature for 2 hours. The reaction solution was filtered, and the solvent was evaporated. The obtained residue was purified by silica gel column chromatography (n-hexane:ethyl acetate, 1:1 and 4:5, V/V) to give 4.56 g of the title compound (light yellow crystal, yield: 81%).

MS (FAB) m/z: 306 $[M+H]^+$;

$^1$H-Nuclear Magnetic Resonance Spectra (400 MHz, DMSO-$d_6$) δ ppm:

8.33 (1H, d, J=7 Hz), 7.32 (2H, d, J=9 Hz), 7.25 (2H, d, J=9 Hz), 4.48-4.42 (1H, m), 3.59 (3H, s), 3.04 (1H, dd, J=14 Hz, 5 Hz), 2.90 (1H, dd, J=14 Hz, 9 Hz), 1.78 (3H, s).

(3f) Methyl (2S)-2-(acetylamino)-3-[4-(trifluoromethoxy)phenyl]propanoate

Methyl 2-(acetylamino)-3-[4-(trifluoromethoxy)phenyl]propanoate (160 mg) prepared in Reference Example 3 (3e) was separated by HPLC under the following conditions to give 74.5 mg of the title compound.

[Fractionation conditions] column: CHIRALPAK AD-H (manufactured by Daicel Chemical Industries, Ltd., internal diameter: 2 cm, length: 25 cm), mobile phase: ethanol/n-hexane=1/4, flow rate: 5.0 mL/min, temperature: room temperature, detection: 210 nm (UV), retention time: S-isomer 50 min, R-isomer 19 min.

No R-isomer was recognized by HPLC analysis of this compound under the following conditions, and thereby it was confirmed that the optical purity was 99% or higher.

[Analysis conditions] column: CHIRALCEL OD-H (manufactured by Daicel Chemical Industries, Ltd., internal diameter: 0.46 cm, length: 25 cm), mobile phase: n-hexane/isopropanol=9/1, flow rate: 1.0 mL/min, temperature: 40° C., detection: 210 nm (UV), retention time: S-isomer 9.5 min, R-isomer 7.6 min.

(3g) (2S)-2-Amino-3-[4-(trifluoromethoxy)phenyl]propanoic acid hydrochloride

A 6 N hydrochloric acid (330 μL) solution of methyl (2S)-2-(acetylamino)-3-[4-(trifluoromethoxy)phenyl]propanoate (29.9 mg, 0.098 mmol) prepared in Reference Example 3 (3f) was stirred at 100° C. for 4 hours. The reaction solution was cooled to room temperature and then concentrated under reduced pressure. The obtained residue was azeotroped with toluene, washed with diethyl ether, and dried under reduced pressure to give 26 mg of the title compound (white powder, yield: 93%).

Reference Example 4

(2S)-2-Amino-3-[4-(difluoromethoxy)phenyl]propanoic acid hydrochloride

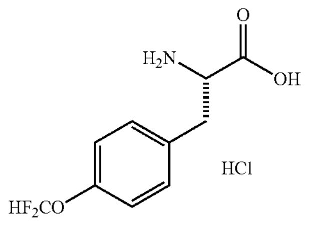

The preparation was conducted as in the methods described in Reference Example 3 (3a) to (3c).

(4a) Tert-Butyl (2S)-3-[4-(difluoromethoxy)phenyl]-2-[(diphenylmethylene)amino]propanoate MS (ESI) m/z: 452 $[M+H]^+$, 450 $[M-H]^+$;

$^1$H-Nuclear Magnetic Resonance Spectra (400 MHz, $CDCl_3$) δ ppm:

7.68-7.66 (2H, m), 7.40-7.27 (6H, m), 7.05 (2H, d, J=9 Hz), 6.95 (2H, d, J=9 Hz), 6.65 (2H, brd, J=8 Hz), 6.46 (1H, t, J=74 Hz), 4.09 (1H, dd, J=9 Hz, 4 Hz), 3.21 (1H, dd, J=13 Hz, 4 Hz), 3.14 (1H, dd, J=13 Hz, 9 Hz), 1.44 (9H, s).

[Analysis conditions] column: CHIRALCEL OD-H (manufactured by Daicel Chemical Industries, Ltd., internal diameter: 0.46 cm, length: 25 cm), mobile phase: n-hexane/isopropanol=99/1, flow rate: 0.5 mL/min, temperature: 40° C., detection: 254 nm (UV), retention time: S-isomer 28 min, R-isomer 43 min.

(4b) (2S)-2-Amino-3-[4-(difluoromethoxy)phenyl]propanoic acid hydrochloride

The corresponding N-benzyloxycarbonyl derivative was derived, and its optical purity was determined.

[Analysis conditions] column: CHIRALPAK AD-H (manufactured by Daicel Chemical Industries, Ltd., internal diameter: 0.46 cm, length: 25 cm), mobile phase: n-hexane/isopropanol/trifluoroacetic acid=90/10/0.1, flow rate: 0.5 mL/min, temperature: 25° C., detection: 210 nm (UV), retention time: S-isomer 63 min, R-isomer 59 min.

Reference Example 5

(2S)-2-Amino-3-[4-(trifluoromethyl)phenyl]propanoic acid hydrochloride

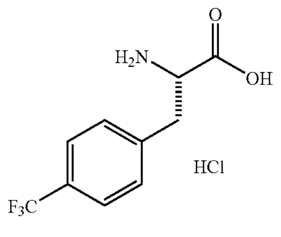

The preparation was conducted as in the methods described in Reference Example 3 (3a) to (3c).

(5a) Tert-Butyl (2S)-2-[(diphenylmethylene)amino]-3-[4-(trifluoromethyl)phenyl]propanoate

[Analysis conditions] the same as those in Reference Example 4 (4a), retention time: S-isomer 15 min, R-isomer 23 min.

(5b) (2S)-2-Amino-3-[4-(trifluoromethyl)phenyl]propanoic acid hydrochloride

The corresponding N-benzyloxycarbonyl derivative was derived, and its optical purity was determined.

[Analysis conditions] the same as those in Reference Example 4 (4b), retention time: S-isomer 35 min, R-isomer 39 min.

Reference Example 6

2-({(2S)-2-Amino-3-[4-(trifluoromethoxy)phenyl]propanoyl}amino)ethyl acetate

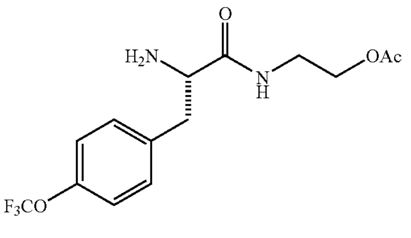

(6a) (2S)-2-{[(Benzyloxy)carbonyl]amino}-3-[4-(trifluoromethoxy)phenyl]propanoic acid ZCl (10.2 mL, 71.2 mmol) and 1 N sodium hydroxide (71.2 mL, 71.2 mmol) were simultaneously added dropwise over 10 minutes to a 1 N sodium hydroxide aqueous solution (135 mL, 135 mmol) of (2S)-2-amino-3-[4-(trifluoromethoxy)phenyl]propanoic acid hydrochloride (18.5 g, 64.8 mmol) under ice-cooling with stirring. The mixture was stirred at room temperature 1 hour. The reaction solution was washed with diethyl ether (100 mL), and to the aqueous layer was added 1 N hydrochloric acid (56 mL). The precipitated white precipitate was collected by filtration, washed with water, and dried by heating under reduced pressure to give 24.4 g of the title compound (white powder, yield: 98%).

MS (FAB) m/z: 384 $[M+H]^+$ $^1$H-Nuclear Magnetic Resonance Spectra (400 MHz, DMSO-$d_6$) δ ppm:

7.34-7.22 (10H, m), 4.97 (2H, s), 4.09-4.04 (1H, m), 3.11 (1H, dd, J=13 Hz, 4 Hz), 2.90 (1H, dd, J=13 Hz, 10 Hz).

(6b) Benzyl (1S)-2-[(2-hydroxyethyl)amino]-2-oxo-1-[4-(trifluoromethoxy)benzyl]ethylcarbamate 2-Aminoethanol (1.62 mL, 26.9 mmol) and diethyl cyanophosphate (4.37 mL, 26.9 mmol) were added to a DMF (82 mL) solution of (2S)-2-{[(benzyloxy)carbonyl]amino}-3-[4-(trifluoromethoxy)phenyl]propanoic acid (9.37 g, 24.4 mmol) prepared in Reference Example 6 (6a), at room temperature. Then, to the resulting mixture was dropwise added a DMF (10 mL) solution of triethylamine (3.75 mL, 26.9 mmol) under ice-cooling with stirring over 45 minutes. The mixture was stirred at room temperature for 3 hours, and ethyl acetate (480 mL) was added to this reaction solution. The mixture was sequentially washed with water (480 mL, four times), 1 N sodium hydroxide, water, and saturated brine. The organic layer was dried over anhydrous sodium sulfate, and the solvent was evaporated. The residue was dried under reduced pressure to give 9.36 g of the title compound (white powder, yield: 90%).

MS (FAB) m/z: 427 $[M+H]^+$ $^1$H-Nuclear Magnetic Resonance Spectra (400 MHz, DMSO-$d_6$) δ ppm:

8.02 (1H, t, J=6 Hz), 7.50 (1H, d, J=9 Hz), 7.36 (2H, d, J=9 Hz), 7.30-7.20 (7H, m), 4.93 (1H, d, J=13 Hz), 4.90 (1H, d, J=13 Hz), 4.68 (1H, t, J=5 Hz), 4.24-4.18 (1H, m), 3.36 (2H, q, J=6 Hz), 3.15-3.09 (2H, m), 2.98 (1H, dd, J=13 Hz, 4 Hz), 2.76 (1H, dd, J=13 Hz, 10 Hz).

(6c) 2-({(2S)-2-Amino-3-[4-(trifluoromethoxy)phenyl]propanoyl}amino)ethyl acetate A 30% hydrogen bromide acetic acid solution (13.1 mL, 65.9 mmol) was added to an acetic acid (4.4 mL) solution of benzyl (1S)-2-[(2-hydroxyethyl)amino]-2-oxo-1-[4-(trifluoromethoxy)benzyl]ethylcarbamate (9.36 g, 22.0 mmol) prepared in Reference Example 6 (6b) under ice-cooling with stirring. The mixture was stirred at room temperature for 4 hours, and then ice water (300 mL) was added thereto. The reaction solution was washed with diethyl ether (50 mL, three times), and subsequently the water layer was neutralized with sodium bicarbonate (about 40 g) and extracted with methylene chloride (300 mL, three times). The organic layer was dried over anhydrous sodium sulfate, and the solvent was evaporated. The residue was dried under reduced pressure to give 5.89 g of the title compound (yellow solid, yield: 80%).

MS (FAB) m/z: 335 $[M+H]^+$ $^1$H-Nuclear Magnetic Resonance Spectra (400 MHz, DMSO-$d_6$) δ ppm:

7.99 (1H, t, J=6 Hz), 7.30 (2H, d, J=9 Hz), 7.22 (2H, d, J=9 Hz), 4.03-3.92 (3H, m), 3.38-3.25 (4H, m), 2.91 (1H, dd, J=13 Hz, 5 Hz), 2.65 (1H, dd, J=13 Hz, 8 Hz), 1.98 (3H, s).

Reference Example 7

2-({(2S)-2-Amino-3-[4-(difluoromethoxy)phenyl] propanoyl}amino)ethyl acetate

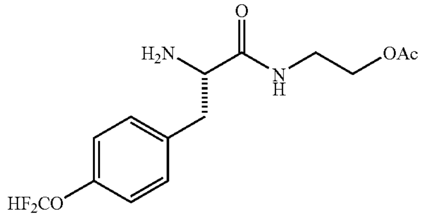

The preparation was conducted as in the methods described in Reference Example 6.

(7a) (2S)-2-{[(Benzyloxy)carbonyl]amino}-3-[4-(difluoromethoxy)phenyl]propanoic acid MS (ESI) m/z: 366 $[M+H]^+$ $^1$H-Nuclear Magnetic Resonance Spectra (400 MHz, DMSO-$d_6$) δ ppm:

7.51 (1H, d, J=8 Hz), 7.34-7.24 (7H, m), 7.17 (1H, t, J=74 Hz), 7.04 (2H, d, J=9 Hz), 4.95 (2H, s), 4.13-4.08 (1H, m), 3.05 (1H, dd, J=14 Hz, 4 Hz), 2.83 (1H, dd, J=14 Hz, 10 Hz).

(7b) Benzyl (1S)-1-[4-(difluoromethoxy)benzyl]-2-[(2-hydroxyethyl)amino]-2-oxoethylcarbamate MS (ESI) m/z: 409 $[M+H]^+$ $^1$H-Nuclear Magnetic Resonance Spectra (400 MHz, DMSO-$d_6$) δ ppm:

8.02 (1H, t, J=6 Hz), 7.48 (1H, d, J=9 Hz), 7.35-7.29 (5H, m), 7.24 (2H, d, J=9 Hz), 7.18 (1H, t, J=74 Hz), 7.07 (2H, d, J=9 Hz), 4.96 (1H, d, J=13 Hz), 4.92 (1H, d, J=13 Hz), 4.69 (1H, t, J=5 Hz), 4.23-4.17 (1H, m), 3.38 (2H, q, J=6 Hz), 3.18-3.09 (2H, m), 2.96 (1H, dd, J=13 Hz, 4 Hz), 2.73 (1H, dd, J=13 Hz, 11 Hz).

(7c) 2-({(2S)-2-Amino-3-[4-(difluoromethoxy)phenyl] propanoyl}amino)ethyl acetate MS (ESI) m/z: 317 $[M+H]^+$ $^1$H-Nuclear Magnetic Resonance Spectra (400 MHz, DMSO-$d_6$) δ ppm:

8.04 (1H, t, J=5 Hz), 7.22 (2H, d, J=9 Hz), 7.16 (1H, t, J=74 Hz), 7.05 (2H, d, J=9 Hz), 4.04-3.98 (1H, m), 3.39-3.35 (2H, m), 3.30-3.27 (2H, m), 2.89 (1H, dd, J=14 Hz, 6 Hz), 2.63 (1H, dd, J=14 Hz, 8 Hz), 1.99 (3H, s).

Reference Example 8

2-({(2S)-2-Amino-3-[4-(trifluoromethyl)phenyl] propanoyl}amino)ethyl acetate

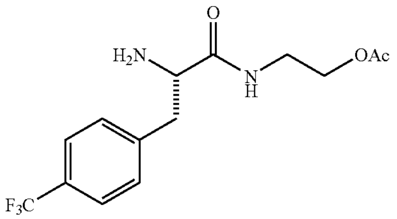

The preparation was conducted as in the methods described in Reference Example 6.

(8a) (2S)-2-{[(Benzyloxy)carbonyl]amino}-3-[4-(trifluoromethyl)phenyl]propanoic acid MS (FAB) m/z: 368 $[M+H]^+$ $^1$H-Nuclear Magnetic Resonance Spectra (400 MHz, DMSO-$d_6$) δ ppm:

7.59 (2H, d, J=8 Hz), 7.42 (2H, d, J=8 Hz), 7.33-7.25 (6H, m), 4.98 (1H, d, J=13 Hz), 4.95 (1H, d, J=13 Hz), 4.11-4.05 (1H, m), 3.17 (1H, dd, J=14 Hz, 5 Hz), 2.96 (1H, dd, J=14 Hz, 9 Hz).

(8b) Benzyl (1S)-2-[(2-hydroxyethyl)amino]-2-oxo-1-[4-(trifluoromethyl)benzyl]ethylcarbamate MS (FAB) m/z: 411 $[M+H]^+$ $^1$H-Nuclear Magnetic Resonance Spectra (400 MHz, DMSO-$d_6$) δ ppm:

8.07 (1H, t, J=6 Hz), 7.63 (2H, d, J=8 Hz), 7.55 (1H, d, J=9 Hz), 7.50 (2H, d, J=8 Hz), 7.34-7.26 (3H, m), 7.22 (2H, d, J=8 Hz), 4.95 (1H, d, J=13 Hz), 4.91 (1H, d, J=13 Hz), 4.30-4.24 (1H, m), 4.06-3.96 (1H, m), 3.40-3.35 (2H, m), 3.17-3.12 (2H, m), 3.06 (1H, dd, J=13 Hz, 4 Hz), 2.83 (1H, dd, J=13 Hz, 11 Hz).

(8c) 2-({(2S)-2-Amino-3-[4-(trifluoromethyl)phenyl] propanoyl}amino)ethyl acetate MS (FAB) m/z: 319 $[M+H]^+$ $^1$H-Nuclear Magnetic Resonance Spectra (400 MHz, DMSO-$d_6$) δ ppm:

8.00 (1H, t, J=6 Hz), 7.60 (2H, d, J=8 Hz), 7.41 (2H, d, J=8 Hz), 3.40 (1H, dd, J=8 Hz, 5 Hz), 3.31-3.22 (4H, m), 2.97 (1H, dd, J=13 Hz, 5 Hz), 2.72 (1H, dd, J=13 Hz, 8 Hz), 1.97 (3H, s).

Test Example 1

Evaluation of Bone Resorption-Suppressing Activity of Cultured Osteoclast

The bone resorption-suppressing activity of compounds according to the present invention was evaluated by observing the resorption lacuna formation-suppressing activity of mouse osteoclasts cultured on a bone tissue-like ivory section as an index of the activity.

Myelocytes containing osteoclast precursor cells were sampled from the femurs and the tibiae of 5 to 7-week old ddY male mice. The skull was extracted from a one-day old ddY mouse, and cells isolated by collagenase and dispase digestion were used as osteoblast-like cells. The myelocytes and the osteoblast-like cells were co-cultured for 7 days in the presence of active vitamin D or prostaglandin E2. The cells were cultured in a minimum essential medium containing 10% bovine fetal serum on a culture dish coated with collagen gel at 37° C. under 5% $CO_2$ concentration. The medium was exchanged on the second day and the fourth day. After the culture, multinuclear osteoclasts (osteoclasts and osteoblasts are included) were isolated by collagenase and dispase digestion and were seeded again on an ivory section. A compound to be tested was added to the culture at a concentration of from 10 to 1000 ng/mL, and the cells were cultured for two days. The cells on the ivory section were removed, and the section was stained in a hematoxylin solution for 20 minutes, washed, and dried. The number of the resorption lacunae on the ivory section visualized by the staining was counted under a microscope. A comparative test with a control example was conducted, and 50% inhibition concentration ($IC_{50}$) was calculated for evaluation.

The $IC_{50}$ for each of the compounds described in Examples was 100 ng/mL or less. Thus, it was confirmed that the compounds had high bone resorption-suppressing activity.

Test Example 2

Evaluation of Blood Calcium Concentration-Decreasing Activity

The blood calcium concentration in a living body is strictly controlled and constantly maintained by intestinal absorption and urinary excretion and release (bone resorption) and adhesion (bone formation) in bone tissues. In an immature rat, which is very active in bone resorption and bone formation, the blood calcium concentration is significantly decreased by strongly suppressing bone resorption. The bone resorption-suppressing activity of compounds according to the present invention was evaluated by observing decreases in blood calcium concentration in immature rats administered with the compounds as an index of the activity.

The test was conducted using 4-week old male Wistar rats fasted for 12 to 24 hours. Each compound to be tested was suspended in 0.5% methyl cellulose (MC). The suspension was orally administered to the rats at a dose of 5 mL/kg. Rats of a normal control group were similarly administered with 0.5% MC alone. Then, blood was drawn from rat jugular vein under ether anesthesia 6 hours after the administration of each test compound or 0.5% MC. The blood was immediately centrifuged (10000 rpm/revolutions per minute, 5 minutes) at room temperature to separate serum. The calcium concentration of each serum was measured by an autoanalyzer (JEOL, JCA-BM2250). Five rats were used for each test group.

The evaluation was conducted by a comparative test with the normal control group based on the serum calcium concentration-decreasing rate (%) calculated according to the following equation:

Serum calcium concentration-decreasing rate(%)=(([serum calcium concentration in normal control group]−[serum calcium concentration in test compound administration group]/[serum calcium concentration in normal control group])×100.

In general, a constant blood calcium concentration is strictly maintained. However, in the compounds described in Examples 3, 4, 7, 18, 19, 20, 22, 23, 25, 31, 34, 40, and 42, the serum calcium concentration-decreasing rate 6 hours after the oral administration of 10 mg/kg of the compound was 10% or more. Thus, the compounds showed significant efficacy. This result suggests that the blood calcium concentration-decreasing activity and the bone resorption-suppressing activity of the compounds according to the present invention are high.

Test Example 3

Bone Density Decrease-Suppressing Activity

In rheumatoid arthritis, not only swelling and pain caused by arthritis but also systemic bone mass decrease and articular destruction caused by a significant increase in bone resorption are observed. The effects of compounds according to the present invention for suppressing the bone mass decrease caused by arthritis were evaluated using adjuvant arthritis model rats, which exhibit arthritis similar to human rheumatoid arthritis.

The test was conducted using 8-week old female Lewis rats. Mycobacterium butyricum cells killed by heat were ground in an agate mortar, suspended in liquid paraffin sterilized by dry heat to a concentration of 2 mg/mL, and treated with ultrasonic to prepare an adjuvant. Under ether anesthesia, rats in a control group other than a normal control group and rats in test compound administration group were intradermally injected with 0.05 mL of the adjuvant each time (0.1 mL/rat in total) at two portions of the base of the tail. Starting from 14 days after the injection of the adjuvant, each rat was orally administered with 5 mL/kg of a test compound suspended in 0.5% MC once a day for 7 days. The rats of the control group were similarly administered with 0.5% MC alone. On the 21st day after the adjuvant injection, the femur was biopsied. The femur, after removing soft tissues, was sufficiently fixed, dehydrated, and dried with ethanol. The bone density of the femur was measured with a bone density analyzer (Aloka, DOS-600 EX-IIIR). Five rats were used for each group.

The test results are shown in Table 5 below. The evaluation was conducted by comparative tests with the normal control group and the control group based on the bone density decrease-suppressing rate (%) calculated according to the following equation:

Bone density decrease-suppressing rate(%)=((1−([femur bone density in normal control group]−[femur bone density in test compound administration group]))/([femur bone density in normal control group]−[femur bone density in control group]))×100

TABLE 5

| Test Compound | Dose (mg/kg) | Bone density decrease-suppressing rate (%) |
|---|---|---|
| Example 51 | 3 | 85 |
| Example 59 | 3 | 92 |
| Example 57 | 3 | 86 |
| Example 61 | 3 | 75 |
| Example 64 | 3 | 77 |

A significant suppression of the decrease in bone density was observed following the administration of the compounds according to the present invention. Thus, the efficacy of the compounds according to the present invention for prophylaxis and treatment of bone metabolic diseases and inflammation was demonstrated.

INDUSTRIAL APPLICABILITY

The compounds according to the present invention have low toxicity, show favorable pharmacokinetics, and have an excellent bone resorption-suppressing activity and a blood calcium concentration-decreasing activity and a bone mass decrease-suppressing activity associated therewith, and thereby can be used for prophylaxis or treatment (in particular, treatment) of the aforementioned bone metabolic diseases, for example, osteoporosis, hypercalcemia, bone metastasis of cancer, periodontal disease, bone Paget's disease, and osteoarthrosis. Thus, the compounds are useful.

The invention claimed is:

1. A compound having General Formula (I') or a pharmacologically acceptable salt thereof:

(I')

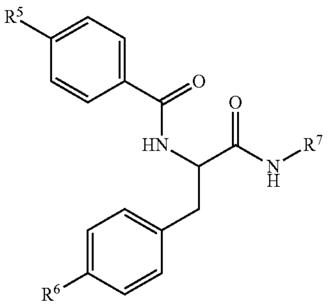

wherein, $R^5$ is selected from a propoxy, isobutyloxy, (cyclopropyl)methoxy, 2-(cyclopropyl)ethoxy, 3-(cyclopropyl)propoxy, (cyclobutyl)methoxy, (cyclopentyl)methoxy, 2-(cyclopentyl)ethoxy, 2-(phenyl)ethoxy, 2-(4-methoxyphenyl)ethoxy, 2-(4-chlorophenyl)ethoxy, (2,2-difluorocyclopropan-1-yl)methoxy, 2,2-difluoroethoxy, 2,2,2-trifluoroethoxy, 3,3,3-trifluoropropoxy, 4,4,4-trifluorobutoxy, 4-(trifluoromethyl)phenoxy, 4-methoxyphenoxy, 4-chlorophenoxy, or 4-fluorophenoxy group;

$R^6$ is selected from a $C_1$-$C_6$ haloalkyl group, a $C_1$-$C_6$ haloalkoxy group, a $C_3$-$C_6$ cycloalkyl group, or a $C_3$-$C_6$ cycloalkyloxy group; and $R^7$ represents a $C_1$-$C_6$ hydroxyalkyl group optionally protected by a hydroxyl protecting group.

2. The compound or a pharmacologically acceptable salt thereof according to claim 1, wherein, $R^6$ is a trifluoromethyl, cyclopropyl, cyclopropyloxy, difluoromethoxy, trifluoromethoxy, 2,2-difluoroethoxy, or 2,2,2-trifluoroethoxy.

3. The compound or a pharmacologically acceptable salt thereof according to claim 1, wherein, $R^7$ is a (1-hydroxycyclopropyl)methyl, 2-hydroxyethyl, 2 acetoxyethyl, 2-(morpholin-4-ylacetoxy)ethyl, or 2-(3-carboxypropionyloxy) ethyl group.

4. The compound or a pharmacologically acceptable salt thereof according to claim 1, wherein, General Formula (I') is General Formula (I'-a):

(I'-a)

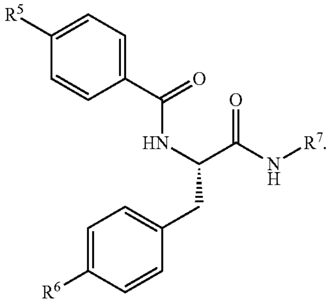

5. The compound or a pharmacologically acceptable salt thereof according to claim 1, wherein, the compound having General Formula (I') is anyone of the following compounds:

4-(cyclopropylmethoxy)-N-{1-[4-(cyclopropyloxy)benzyl]-2-[(2-hydroxyethyl)amino]-2-oxoethyl}benzamide, N-{1-(4-cyclopropylbenzyl)-2-[(2-hydroxyethyl)amino]-2-oxoethyl}-4-(cyclopropylmethoxy)benzamide, 4-(cyclopropylmethoxy)-N-{1-[4-(difluoromethoxy)benzyl]-2-[(2-hydroxyethyl)amino]-2-oxoethyl} benzamide, 4-(cyclopropylmethoxy)-N-{2-[(2-hydroxyethyl)amino]-2-oxo-1-[4-(trifluoromethoxy)benzyl]ethyl}benzamide, 4-(cyclopropylmethoxy)-N-{2-[(2-hydroxyethyl)amino]-2-oxo-1-[4-(trifluoromethyl)benzyl]ethyl}benzamide, 4-(2-cyclopropylethoxy)-N-{1-[4-(difluoromethoxy)benzyl]-2-[(2-hydroxyethyl)amino]-2-oxoethyl}benzamide, 4-(2-cyclopropylethoxy)-N-{2-[(2-hydroxyethyl)amino]-2-oxo-1-[4-(trifluoromethoxy)benzyl]ethyl}benzamide, 4-(2-cyclopropylethoxy)-N-{2-[(2-hydroxyethyl)amino]-2-oxo-1-[4-(trifluoromethyl)benzyl]ethyl}benzamide, 4-(3-cyclopropylpropoxy)-N-{2-[(2-hydroxyethyl)amino]-2-oxo-1-[4-(trifluoromethoxy)benzyl]ethyl}benzamide, N-{1-[4-(difluoromethoxy)benzyl]-2-[(2-hydroxyethyhamino]-2-oxoethyl}-4-(3,3,3-trifluoropropoxy)benzamide, N-{2-[(2-hydroxyethyl)amino]-2-oxo-1-[4-(trifluoromethoxy)benzyl]ethyl}-4-(3,3,3-trifluoropropoxy)benzamide, N-{2-[(2-hydroxyethyl)amino]-2-oxo-1-[4-(trifluoromethyl)benzyl]ethyl}-4-(3,3,3-trifluoropropoxy)benzamide, 4-(2,2-difluoroethoxy)-N-{2-[(2-hydroxyethyl)amino]-2-oxo-1-[4-(trifluoromethoxy)benzyl]ethyl} benzamide, 4-[(2,2-difluorocyclopropyl)methoxy]-N-{2-[(2-hydroxyethyl)amino]-2-oxo-1-[4-(trifluoromethoxy)benzyl]ethyl}benzamide, N-{1-[4-(difluoromethoxy)benzyl]-2-[(2-hydroxyethyhamino]-2-oxoethyl}-4-[4-(trifluoromethyl)phenoxy]benzamide, N-{2-[(2-hydroxyethyhamino]-2-oxo-1-[4-(trifluoromethoxy)benzyl]ethyl}-4-[4-(trifluoromethyl)phenoxy]benzamide, N-{2-[(2-hydroxyethyhamino]-2-oxo-1-[4-(trifluoromethyl)benzyl]ethyl}-4-[4-(trifluoromethyl)phenoxy]benzamide, N-{2-{[(2R)-2-hydroxypropyl]amino}-2-oxo-1-[4-(trifluoromethoxy)benzyl]ethyl}-4-(3,3,3-trifluoropropoxy)benzamide, N-{2-[(2-hydroxyethyl-amino]-2-oxo-1-[4-(trifluoromethoxy)benzyl]ethyl}-4-(4,4,4-trifluorobutoxy)benzamide, and N-{2-[(2-hydroxyethyl)amino]-2-oxo-1-[4-(trifluoromethoxy)benzyl]ethyl}-4-(2,2,2-trifluoroethoxy)benzamide.

6. The compound or a pharmacologically acceptable salt thereof according to claim 5, wherein, the absolute configuration is S.

7. A pharmaceutical composition comprising a compound or a pharmacologically acceptable salt thereof according to claim 1 as an active ingredient.

8. A method for improving bone metabolism in a mammal, comprising administering an amount of a pharmaceutical composition effective for improving bone metabolism according to claim 7 to a mammal in need thereof.

9. A method for prophylaxis or treatment of a bone metabolic disease in a mammal, comprising administering an amount of a pharmaceutical composition effective for prophylaxis or treatment of a bone metabolic disease according to claim 7 to a mammal in need thereof.

10. A method for prophylaxis or treatment of osteoporosis in a mammal, comprising administering an amount of a pharmaceutical composition effective for prophylaxis or treatment of osteoporosis according to claim 7 to a mammal in need thereof.

11. A method of suppressing bone resorption in a mammal, comprising administering an amount of a pharmaceutical composition effective for suppressing bone resorption according to claim 7 to a mammal in need thereof.

12. A method for decreasing blood calcium concentration in a mammal, comprising administering an amount of a pharmaceutical composition effective for decreasing blood calcium concentration according to claim 7 to a mammal in need thereof.

13. A method for suppressing a decrease in bone mass in a mammal, comprising administering an amount of a pharmaceutical composition effective for suppressing a decrease in bone mass according to claim 7 to a mammal in need thereof.

14. A method for suppressing bone metastasis of cancer in a mammal, comprising administering an amount of a pharmaceutical composition effective for suppressing bone metastasis of cancer according to claim 7 to a mammal in need thereof.

15. A method for prophylaxis or treatment of hypercalcemia in a mammal, comprising administering an amount of a pharmaceutical composition effective for prophylaxis or treatment for hypercalcemia according to claim 7 to a mammal in need thereof.

* * * * *

UNITED STATES PATENT AND TRADEMARK OFFICE

CERTIFICATE OF CORRECTION

PATENT NO. : 8,344,029 B2
APPLICATION NO. : 11/996268
DATED : January 1, 2013
INVENTOR(S) : Kazumasa Aoki et al.

It is certified that error appears in the above-identified patent and that said Letters Patent is hereby corrected as shown below:

In the Claims:

In column 191, at line 67, delete “anyone” and insert -- any one --;

In column 192, at lines 24-25, delete
“N-{1-[4-(difluoromethoxy)benzyl]-2-[(2-hydroxyethyhamino]-2-oxoethyl}-4-(3,3,3-trifluoropropoxy)benza-”
and insert
-- N-{1-[4-(difluoromethoxy)benzyl]-2-[(2-hydroxyethyl)amino]-2-oxoethyl}-4-(3,3,3-trifluoropropoxy)benza- --;

In column 192, at lines 37-38, delete
“N-{1-[4-(difluoromethoxy)benzyl]-2-[(2-hydroxyethyhamino]-2-oxoethyl}-4-[4-(trifluoromethyl)phenoxy]”
and insert
-- N-{1-[4-(difluoromethoxy)benzyl]-2-[(2-hydroxyethyl)amino]-2-oxoethyl}-4-[4-(trifluoromethyl)phenoxy] --;

In column 192, at line 40, delete “N-{2-[(2-hydroxyethyhamino]-2-oxo-1-[4-(trifluoro-” and insert -- N-{2-[(2-hydroxyethyl)amino]-2-oxo-1-[4-(trifluoro- --;

In column 192, at line 43, delete “N-{2-[(2-hydroxyethyhamino]-2-oxo-1-[4-(trifluorom-” and insert -- N-{2-[(2-hydroxyethyl)amino]-2-oxo-1-[4-(trifluorom- --; and In column 192, at line 48, delete “N-{2-[(2-hydroxyethyl-amino]-2-oxo-1-[4-(trifluoro-” and insert -- N-{2-[(2-hydroxyethyl)amino]-2-oxo-1-[4-(trifluoro- --.

Signed and Sealed this
Thirtieth Day of April, 2013

Teresa Stanek Rea
*Acting Director of the United States Patent and Trademark Office*